US011129410B2

(12) United States Patent
Barbaric et al.

(10) Patent No.: US 11,129,410 B2
(45) Date of Patent: Sep. 28, 2021

(54) VARIABLE-VISCOSITY CARRIER VAPORIZERS WITH ENHANCED THERMAL AND HYDRODYNAMIC PROPERTIES

(71) Applic

(56) References Cited

U.S. PATENT DOCUMENTS

| | | | |
|---|---|---|---|
| 5,044,550 A | 9/1991 | Lamm | |
| 5,135,009 A | 8/1992 | Muller et al. | |
| 5,564,442 A | 10/1996 | MacDonald et al. | |
| D449,404 S | 10/2001 | Emery | |
| 6,513,524 B1 | 2/2003 | Storz | |
| 6,532,965 B1 | 3/2003 | Abhulimen et al. | |
| 7,096,896 B2 | 8/2006 | Py | |
| D610,303 S | 2/2010 | Valle | |
| 7,832,410 B2 | 11/2010 | Hon | |
| D634,892 S | 3/2011 | Hein | |
| 7,997,280 B2 | 8/2011 | Rosenthal | |
| D677,000 S | 2/2013 | Liu | |
| D683,844 S | 6/2013 | Andrade et al. | |
| 8,499,766 B1 | 8/2013 | Newton | |
| D689,818 S | 9/2013 | Sasada | |
| 8,528,569 B1 | 9/2013 | Newton | |
| 8,733,346 B2 | 5/2014 | Rinker | |
| 8,897,628 B2 | 11/2014 | Conley et al. | |
| 8,991,402 B2 | 3/2015 | Bowen et al. | |
| 9,308,336 B2 | 4/2016 | Newton | |
| D762,003 S | 7/2016 | Lomeli | |
| 9,408,416 B2 | 8/2016 | Monsees et al. | |
| D765,908 S | 9/2016 | Zahr et al. | |
| D770,090 S | 10/2016 | Zahr et al. | |
| D770,091 S | 10/2016 | Zahr et al. | |
| D771,308 S | 11/2016 | Saydar et al. | |
| D776,338 S | 1/2017 | Lomeli | |
| 9,549,573 B2 | 1/2017 | Monsees et al. | |
| D778,235 S | 2/2017 | Geier et al. | |
| 9,596,887 B2 | 3/2017 | Newton | |
| 9,717,276 B2 | 8/2017 | Brammer et al. | |
| 9,820,509 B2 | 11/2017 | Newton et al. | |
| 9,894,938 B2 | 2/2018 | Vick et al. | |
| D812,289 S | 3/2018 | Ward et al. | |
| D816,267 S | 4/2018 | Fornarelli | |
| 9,999,250 B2 | 6/2018 | Minskoff et al. | |
| D825,102 S | 8/2018 | Bowen et al. | |
| D827,117 S | 8/2018 | Rigbi | |
| 10,045,567 B2 | 8/2018 | Monsees et al. | |
| 10,045,568 B2 | 8/2018 | Monsees et al. | |
| 10,058,124 B2 | 8/2018 | Monsees et al. | |
| 10,058,129 B2 | 8/2018 | Monsees et al. | |
| 10,058,130 B2 | 8/2018 | Monsees et al. | |
| 10,070,669 B2 | 9/2018 | Monsees et al. | |
| 10,076,139 B2 | 9/2018 | Monsees et al. | |
| 10,104,915 B2 | 10/2018 | Bowen et al. | |
| 10,111,470 B2 | 10/2018 | Monsees et al. | |
| 10,117,465 B2 | 11/2018 | Monsees et al. | |
| 10,117,466 B2 | 11/2018 | Monsees et al. | |
| 10,159,282 B2 | 12/2018 | Monsees et al. | |
| 10,201,190 B2 | 2/2019 | Monsees et al. | |
| D842,536 S | 3/2019 | Bowen et al. | |
| D844,235 S | 3/2019 | Cividi | |
| D844,240 S | 3/2019 | Kauss | |
| 10,231,486 B2 | 3/2019 | Bowen et al. | |
| 10,244,793 B2 | 4/2019 | Monsees et al. | |
| 10,264,823 B2 | 4/2019 | Monsees et al. | |
| D849,996 S | 5/2019 | Duque et al. | |
| 10,279,934 B2 | 5/2019 | Christensen et al. | |
| 10,405,582 B2 | 9/2019 | Hatton et al. | |
| 10,426,196 B2 | 10/2019 | Calfee et al. | |
| 10,440,989 B2 | 10/2019 | Gardella et al. | |
| 10,524,980 B2 | 1/2020 | Naing et al. | |
| 2011/0277761 A1* | 11/2011 | Terry | A61M 11/041 128/203.12 |
| 2013/0284192 A1 | 10/2013 | Peleg et al. | |
| 2013/0319439 A1 | 12/2013 | Gorelick et al. | |
| 2014/0366898 A1* | 12/2014 | Monsees | A24F 47/008 131/329 |
| 2014/0378790 A1 | 12/2014 | Cohen | |
| 2015/0090280 A1* | 4/2015 | Chen | A24F 40/42 131/329 |
| 2015/0150308 A1 | 6/2015 | Monsees et al. | |
| 2015/0181945 A1 | 7/2015 | Tremblay | |
| 2015/0224268 A1 | 8/2015 | Henry et al. | |
| 2015/0296887 A1* | 10/2015 | Zhu | H05B 1/0291 131/329 |
| 2015/0320116 A1 | 11/2015 | Bleloch et al. | |
| 2016/0200463 A1 | 1/2016 | Jang et al. | |
| 2016/0080535 A1 | 3/2016 | Stanimirovic et al. | |
| 2016/0128384 A1* | 5/2016 | Luciani | A24F 47/008 131/329 |
| 2016/0157524 A1 | 6/2016 | Bowen et al. | |
| 2016/0295917 A1 | 10/2016 | Malgat et al. | |
| 2016/0363917 A1 | 12/2016 | Blackley | |
| 2016/0366947 A1 | 12/2016 | Monsees et al. | |
| 2017/0208867 A1 | 7/2017 | Li et al. | |
| 2017/0238617 A1 | 8/2017 | Scatterday | |
| 2018/0037381 A1 | 2/2018 | White et al. | |
| 2018/0043114 A1 | 2/2018 | Bowen et al. | |
| 2018/0060873 A1 | 3/2018 | Chu | |
| 2018/0077967 A1* | 3/2018 | Hatton | A24F 47/008 |
| 2018/0093054 A1 | 4/2018 | Bowen et al. | |
| 2018/0117268 A1* | 5/2018 | Selby | A24F 47/008 |
| 2018/0177231 A1 | 6/2018 | Woodbine et al. | |
| 2019/0158938 A1 | 5/2019 | Bowen et al. | |
| 2019/0159519 A1 | 5/2019 | Bowen et al. | |
| 2019/0261689 A1 | 8/2019 | Bowen et al. | |

FOREIGN PATENT DOCUMENTS

| | | |
|---|---|---|
| CN | 107822208 | 3/2018 |
| CN | 110236228 A | 9/2019 |
| EP | 2592005 A1 | 5/2013 |
| FR | 3039039 A1 | 1/2017 |
| WO | WO 2017/139595 A1 | 8/2017 |
| WO | WO 2017/185051 | 10/2017 |
| WO | WO 2017/187148 A1 | 11/2017 |
| WO | WO 2018/024154 A1 | 2/2018 |
| WO | WO 2019/104227 A1 | 5/2019 |
| WO | WO 2019/126805 A1 | 6/2019 |
| WO | WO 2019/204812 A1 | 10/2019 |

OTHER PUBLICATIONS

International Search Report issued for PCT/CA2019/051469 dated Dec. 30, 2019.

International Search Report issued for PCT/CA2019/051326 dated Nov. 21, 2019.

* cited by examiner

SECTION A-A

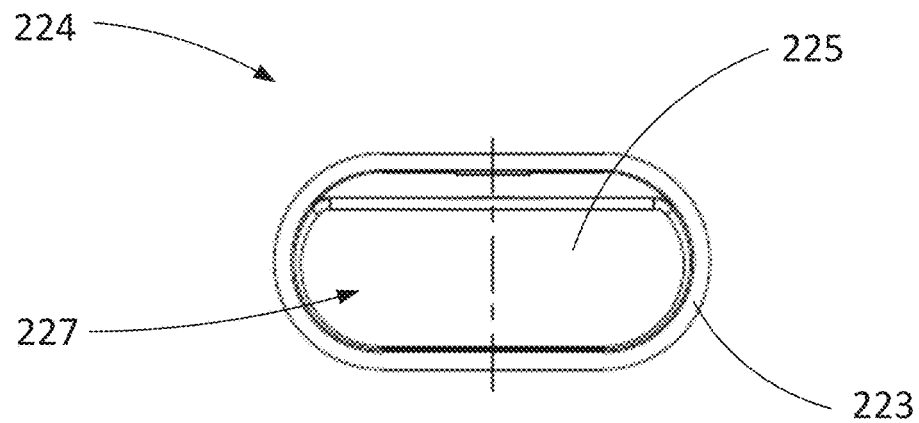
FIG. 6C
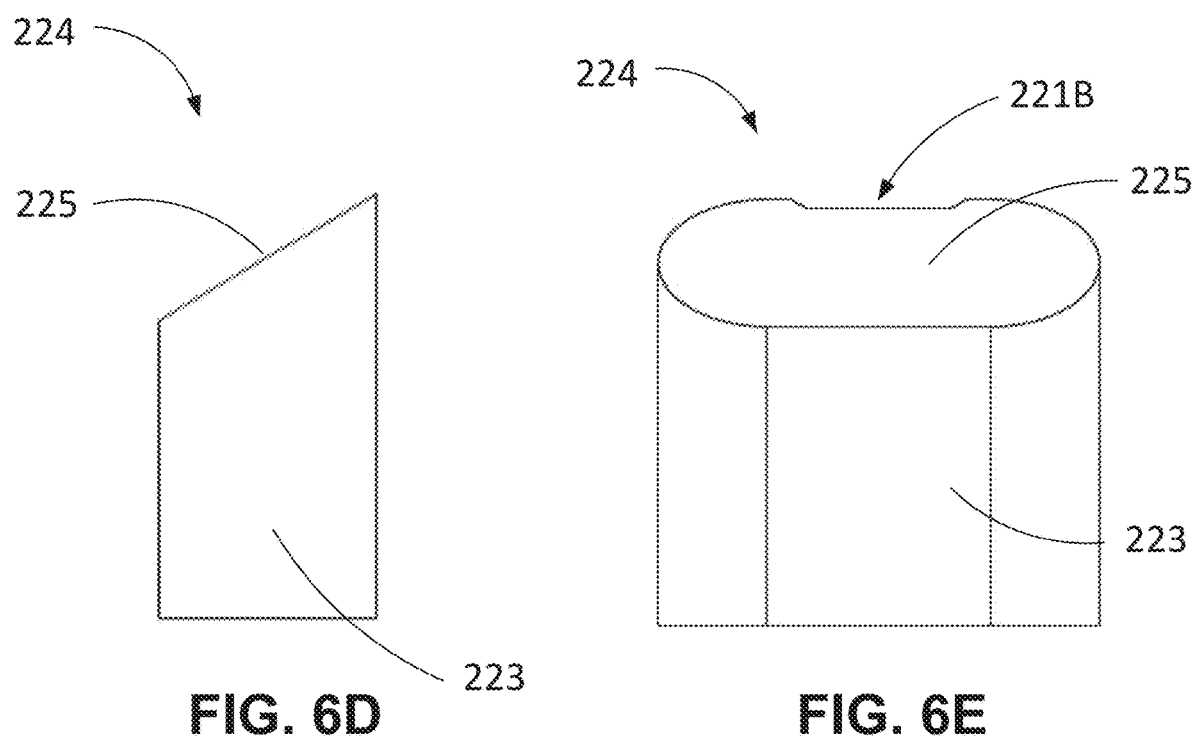
FIG. 6D
FIG. 6E

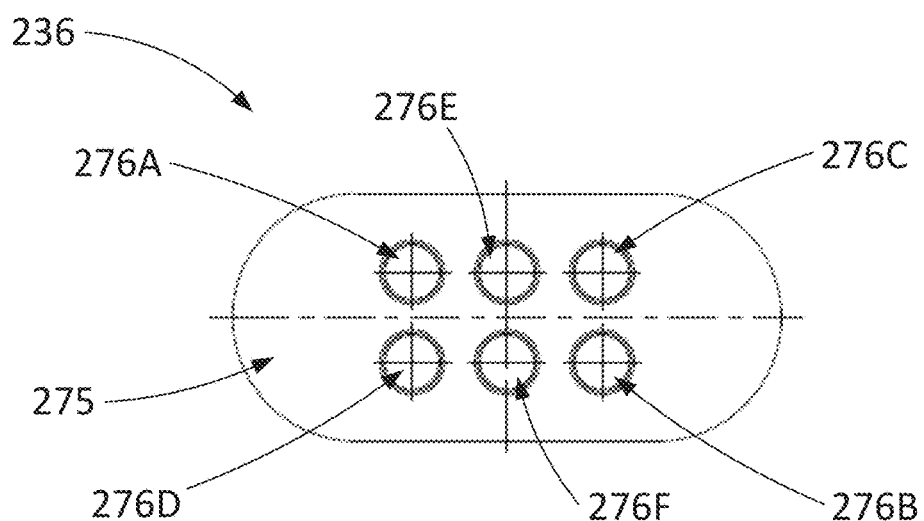
FIG. 11C
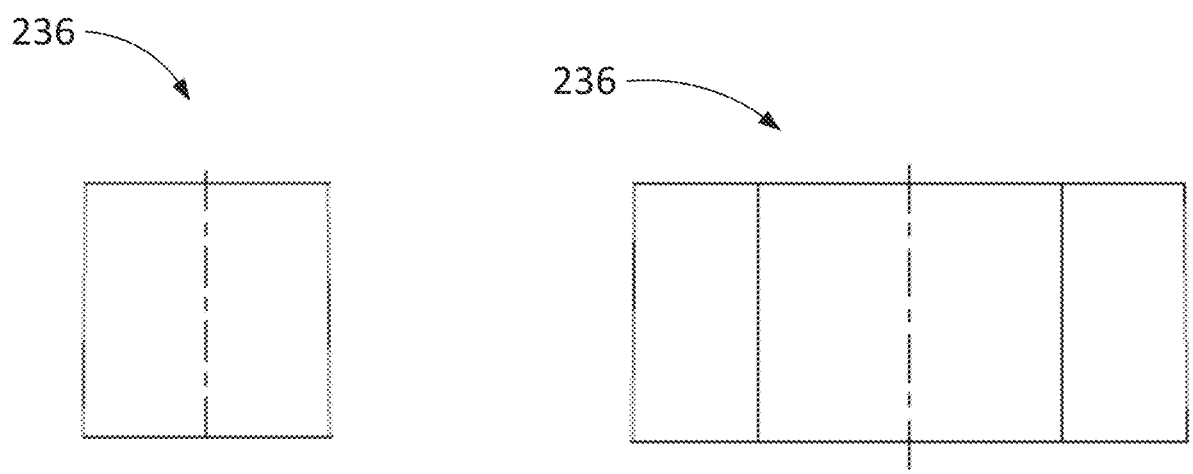
FIG. 11D  FIG. 11E

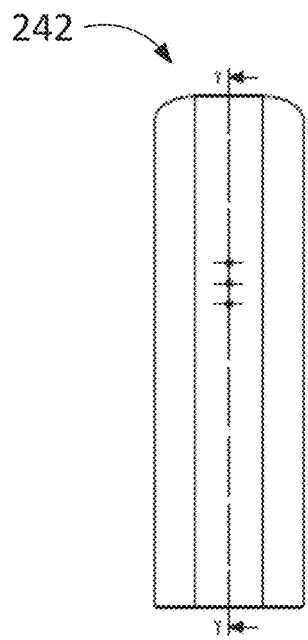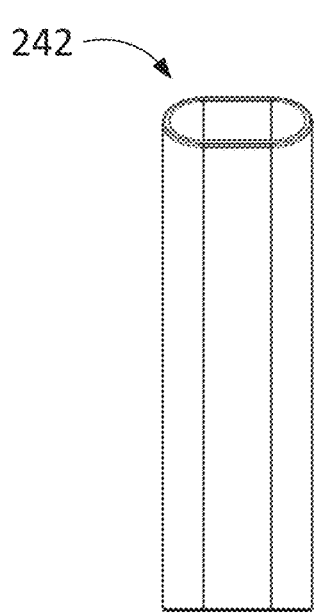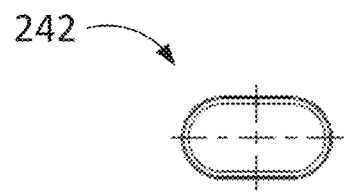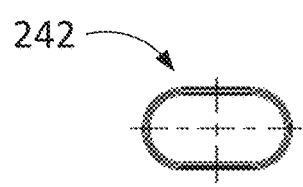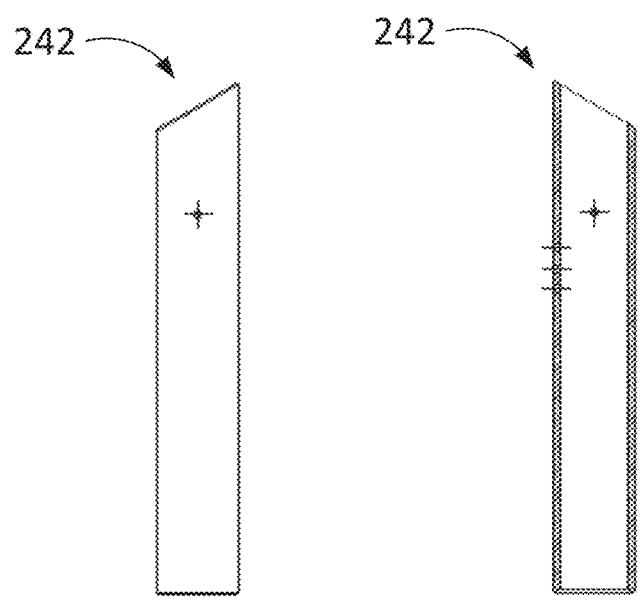
FIG. 12B    FIG. 12C    FIG. 12D    FIG. 12E    FIG. 12F    FIG. 12G

280

280

280

241

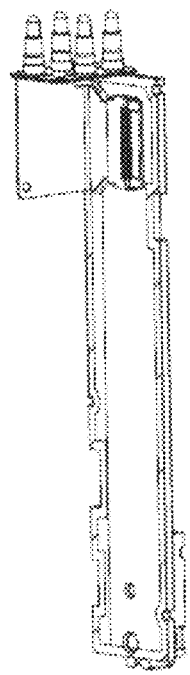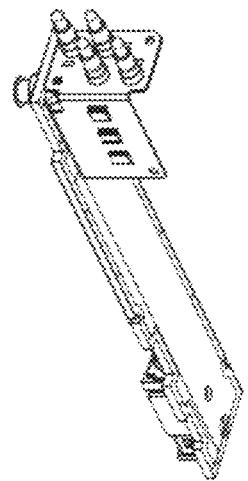
FIG. 34A    FIG. 34B
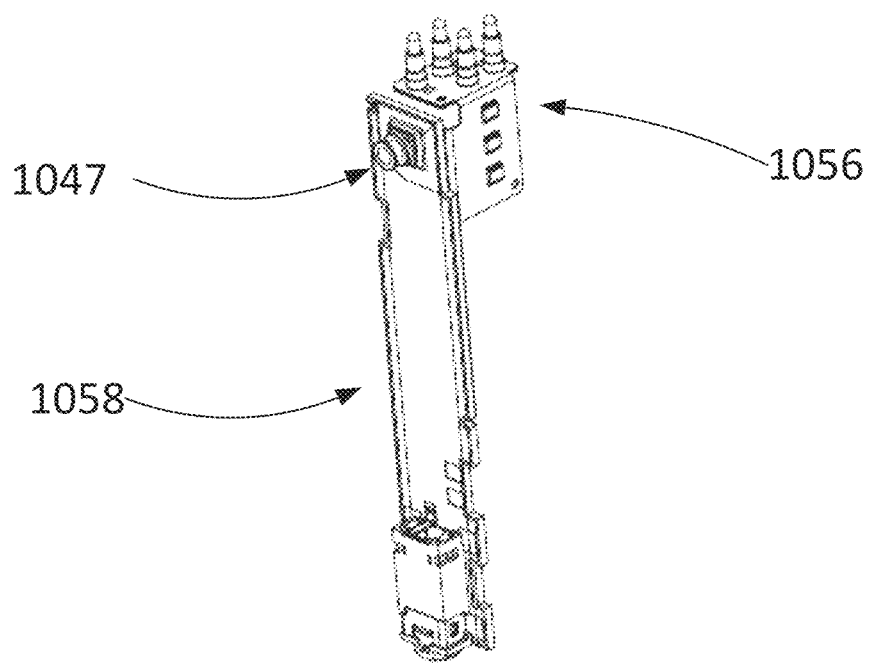
FIG. 34C

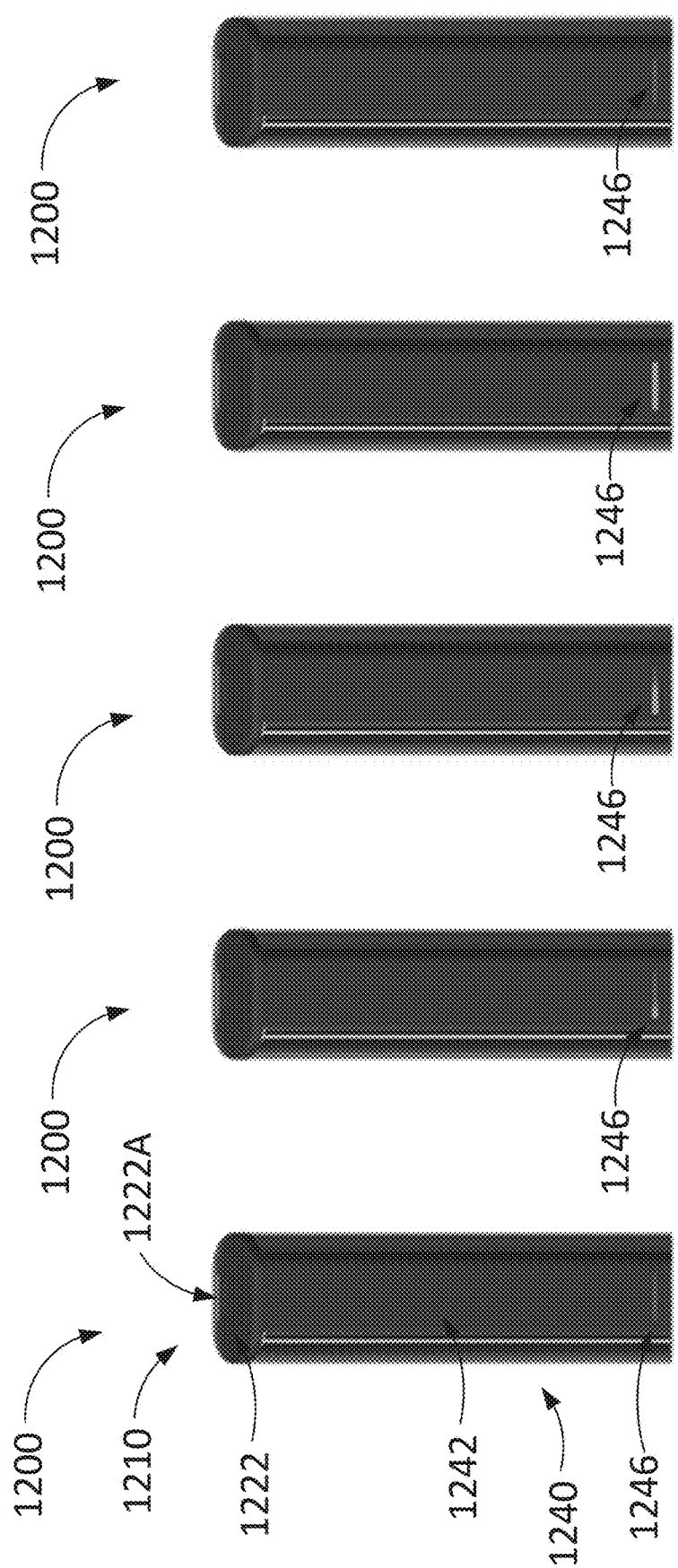

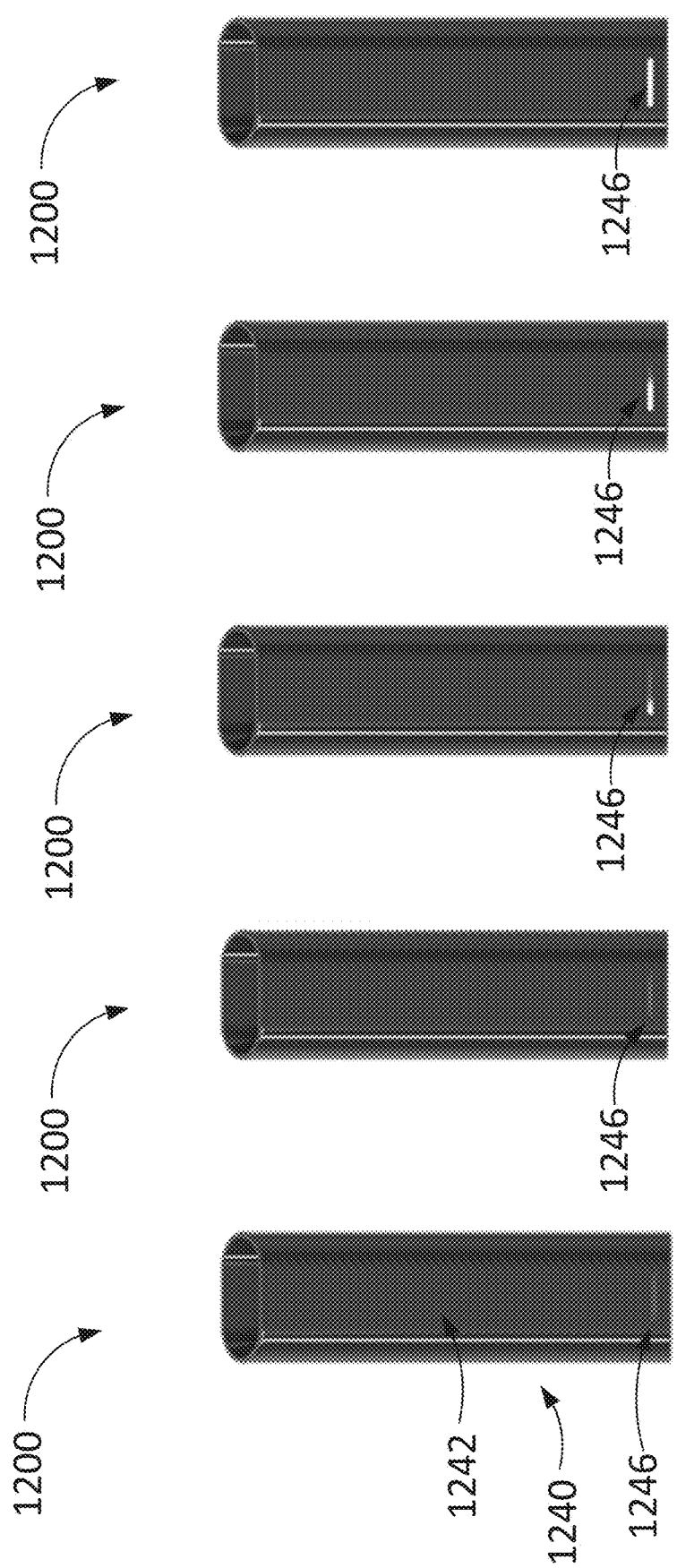

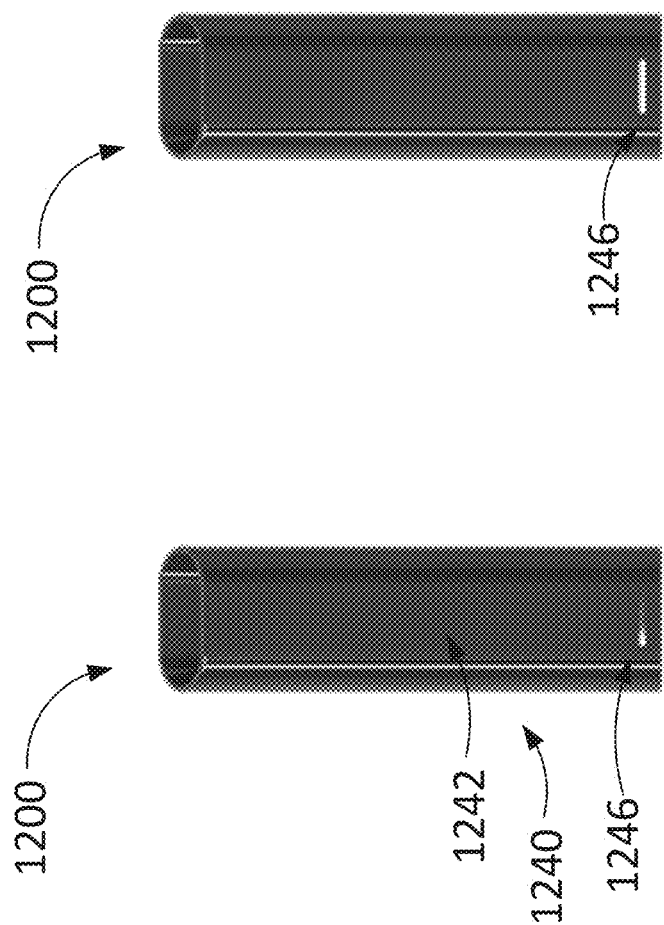

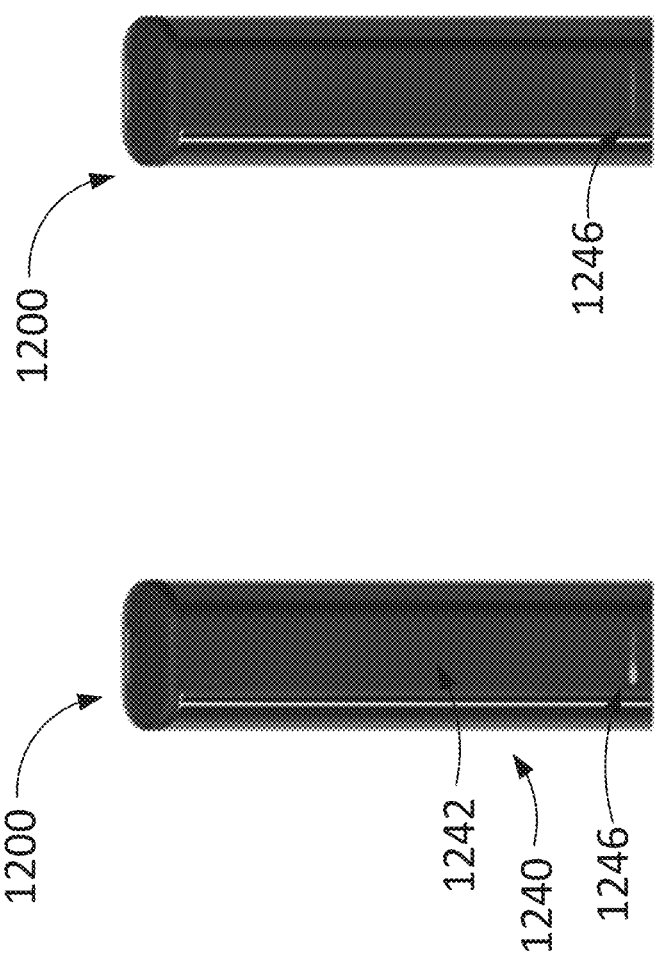

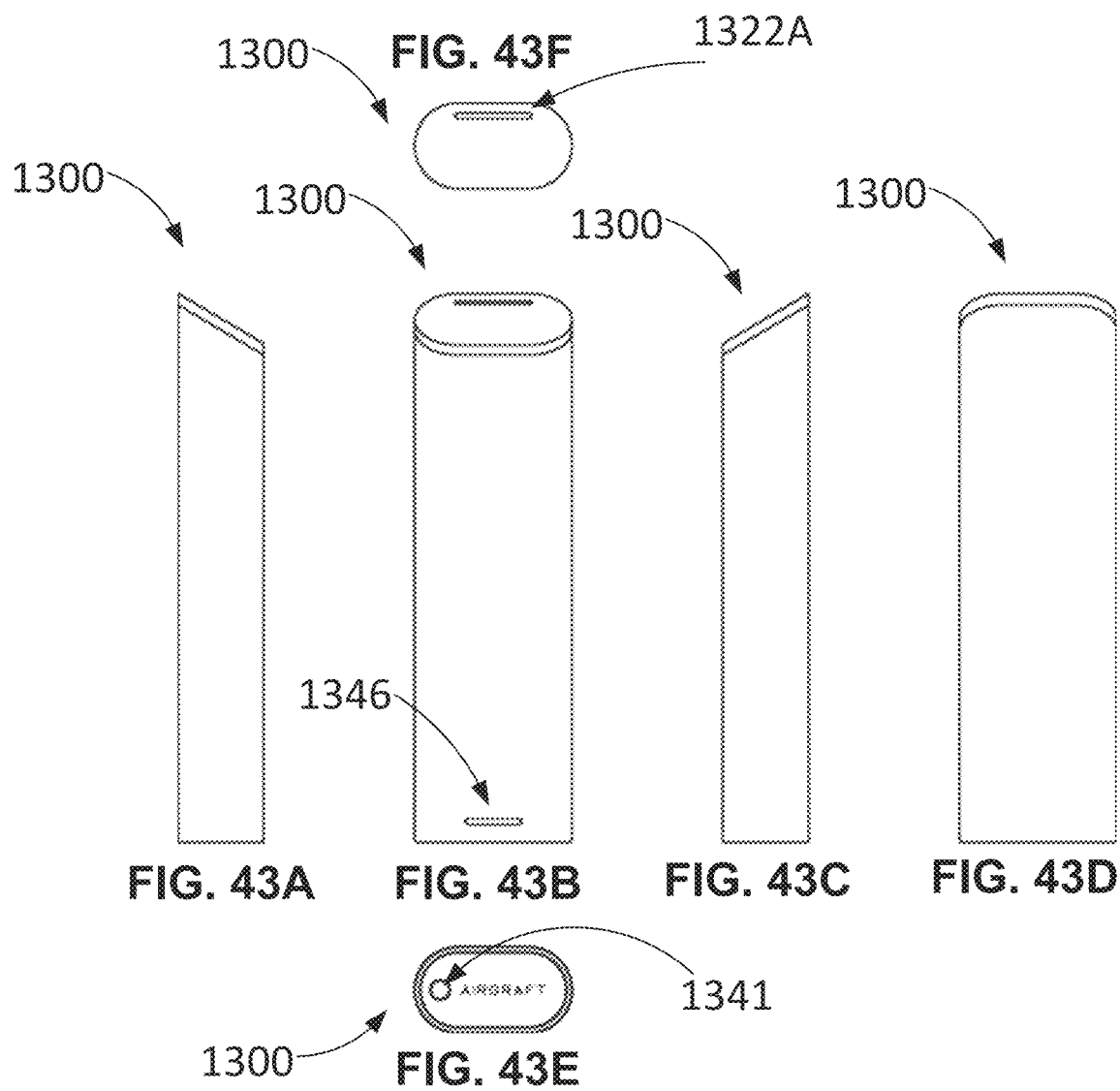

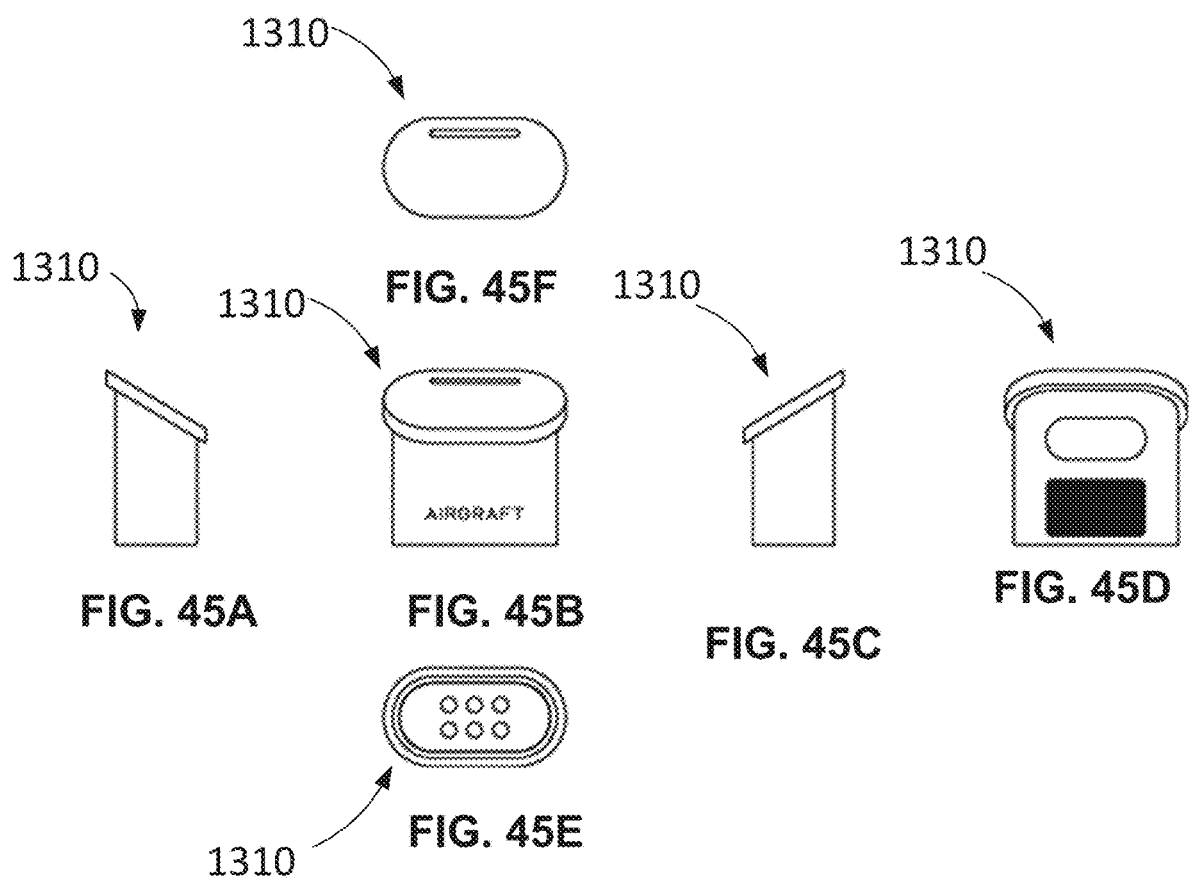

| V ref [V] | Temperature of the heating element [°C] |
|---|---|
| 0.2916057636 | 20 |
| 0.2904464889 | 25 |
| 0.2892963915 | 30 |
| 0.2881553734 | 35 |
| 0.2870233171 | 40 |
| 0.2859001208 | 45 |
| 0.284785681 | 50 |
| 0.2836798956 | 55 |
| 0.2825826643 | 60 |
| 0.2814938881 | 65 |
| 0.2804134697 | 70 |
| 0.2793413132 | 75 |
| 0.2782773242 | 80 |
| 0.2772214098 | 85 |
| 0.2761734784 | 90 |
| 0.2751334397 | 95 |
| 0.274101205 | 100 |

VARIABLE-VISCOSITY CARRIER VAPORIZERS WITH ENHANCED THERMAL AND HYDRODYNAMIC PROPERTIES

CROSS-REFERENCE TO RELATED APPLICATIONS

This application claims priority to and the benefit of U.S. Provisional Application No. 62/746,258, filed Oct. 16, 2018, entitled "High-Viscosity Carrier Vaporizers With Enhanced Thermal and Hydrodynamic Properties," and U.S. Provisional Application No. 62/886,240, filed Aug. 13, 2019, entitled "Variable-Viscosity Carrier Vaporizers With Enhanced Thermal and Hydrodynamic Properties," the entire contents of each of which are hereby expressly incorporated by reference for all purposes.

BACKGROUND

Electronic vapor delivery systems are increasingly popular. Such systems have been developed for inhalation-based delivery of *cannabis* components and nicotine.

SUMMARY

In some embodiments, a system includes a cartridge assembly and a pen assembly. The cartridge assembly includes a mouthpiece assembly and a bracket cartridge assembly. The mouthpiece assembly includes a mouthpiece component defining a mouthpiece opening and an outer housing defining a vapor outlet and including a recessed sidewall portion. The pen assembly includes a pen housing and a bracket assembly configured to engage with the bracket cartridge assembly of the cartridge assembly such that a temperature of a coil of a wick assembly of the cartridge assembly may be increased and a carrier material within a reservoir defined by the cartridge assembly may be vaporized by the coil of the wick assembly. When the cartridge assembly is engaged with the pen housing, the recessed sidewall portion of the outer housing and an inner surface of the pen housing may form a fluid path from the vapor outlet to the mouthpiece opening. The fluid path has a first portion and a second portion closer to the mouthpiece opening than the first portion. The fluid path has an increased cross-sectional area in the second portion than the first portion.

BRIEF DESCRIPTION OF THE DRAWINGS

FIGS. 6A-6G are various views of an outer housing of the cartridge assembly of FIG. 3. Specifically, FIG. 6A is a back view of the outer housing, FIG. 6B is a top view of the outer housing, FIG. 6C is a bottom view of the outer housing, FIG. 6D is a side view of the outer housing, and FIG. 6E is a front view of the outer housing. FIG. 6F is a cross-sectional view of the outer housing taken along line A-A in FIG. 6A. FIG. 6G is an enlarged view of the region indicated as Detail B in FIG. 6F.

FIG. 8A is a back view, FIG. 8B is a top view, FIG. 8C is a bottom view, and FIG. 8D is a front view of the upper portion shown in FIG. 7. FIG. 8E is a side view of the upper portion, and FIG. 8F is a cross-sectional view taken along line A-A in FIG. 8A.

FIGS. 11A-11G are various views of a lower portion shown in FIG. 7. Specifically, FIG. 11A is a back view of the lower portion, FIG. 11B is a top view of the lower portion, FIG. 11C is a bottom view of the lower portion, FIG. 11D is a side view of the lower portion, and FIG. 11E is a front view of the lower portion. FIG. 11F is a cross-sectional view taken along line A-A in FIG. 11A. FIG. 11G is an enlarged view of the portion of FIG. 11F identified as Detail C.

FIG. 12B is a back view, FIG. 12C is a front view, FIG. 12D is a top view, and FIG. 12E is a bottom view of a pen housing of a pen assembly of FIG. 3. FIG. 12F is a right side view and FIG. 12G is a cross-sectional illustration taken along line Y-Y in FIG. 12B of the pen housing.

FIG. 13A is a top view of the cap, FIG. 13B is a bottom view of the cap, FIG. 13C is a back view of the cap, and FIG. 13D is a front view of the cap. FIG. 13E is a right side view and FIG. 13F is a left side view, respectively, of the cap. FIG. 13G is a cross-sectional illustration of the cap taken along line A-A in FIG. 13A. FIG. 13H is an enlarged view of the portion of FIG. 13G identified as Detail A.

FIG. 14A is a back view of the cap bracket and FIG. 14B is a top view of the cap bracket. FIG. 14C is a cross-sectional view of the cap bracket taken alone line A-A in FIG. 14A. FIG. 14D is a front view of the cap bracket.

FIG. 15A is a back view of the bracket, FIG. 15B is a top view of the bracket, and FIG. 15C is a bottom view of the bracket. FIG. 15D is a right side view of the bracket, FIG. 15E is a front view of the bracket, and FIG. 15F is a left side view of the bracket.

FIG. 16A is a front view of the system, FIG. 16B is a back view of the system, FIG. 16C is a side view of the system, FIG. 16D is a top view of the system, and FIG. 16E is a bottom view of the system.

FIG. 26A is a back view, FIG. 26B is a top view, FIG. 26C is a bottom view, and FIG. 26D is a front view of the upper portion. FIG. 26E is a side view of the upper portion, and FIG. 26F is a cross-sectional view of the upper portion taken along line A-A in FIG. 26A.

FIG. 30A is a back view of the lower portion, FIG. 30B is a top view of the lower portion, FIG. 30C is a bottom view of the lower portion, FIG. 30D is a side view of the lower portion, and FIG. 30E is a front view of the lower portion. FIG. 30F is a cross-sectional view taken along line A-A in FIG. 30A. FIG. 30G is an enlarged view of the portion of FIG. 30F identified as Detail C.

FIG. 33A is a back view of the indicator bracket and FIG. 33B is a front view of the indicator bracket. FIG. 33C is a top view of the indicator bracket. FIG. 33D is a side view of the indicator bracket.

FIGS. 34A, 34B, and 34C are various perspective views of a portion of the bracket assembly of FIG. 32.

FIG. 37A is a perspective view of the cap. FIG. 37B is a top view of the cap, FIG. 37C is a bottom view of the cap, FIG. 37D is a back view of the cap, and FIG. 37E is a front view of the cap. FIG. 37F is a right side view and FIG. 37G is a left side view, respectively, of the cap.

FIGS. 38A-41B show front views of a system in various stages of operation, according to an embodiment.

FIGS. 42A-48 are perspective views of an electronic vapor delivery system and components of the system various configurations, according to an embodiment.

DETAILED DESCRIPTION

As the popularity of, and commercial interest in, electronic vapor delivery systems (also referred to as "vapor devices" or "vaporizers") such as electronic cigarettes ("e-cigs") continues to grow, their manufacture and distribution is becoming more globally widespread. Not every substance, however, has the same viscosity and optimal vaporization temperature. Additionally, as vaporizers become more popular, they may be more likely to be obtained and actuated by unintended users, raising security concerns. Furthermore, drawing vapor through a mouthpiece of a vaporizer often requires significant effort (e.g., the production of significant negative pressure via sucking) by a user. Systems and methods for improved electronic vapor delivery, including smoother vapor drawing, improved security, and temperature optimization, for example, are set forth herein.

Figure 1A:
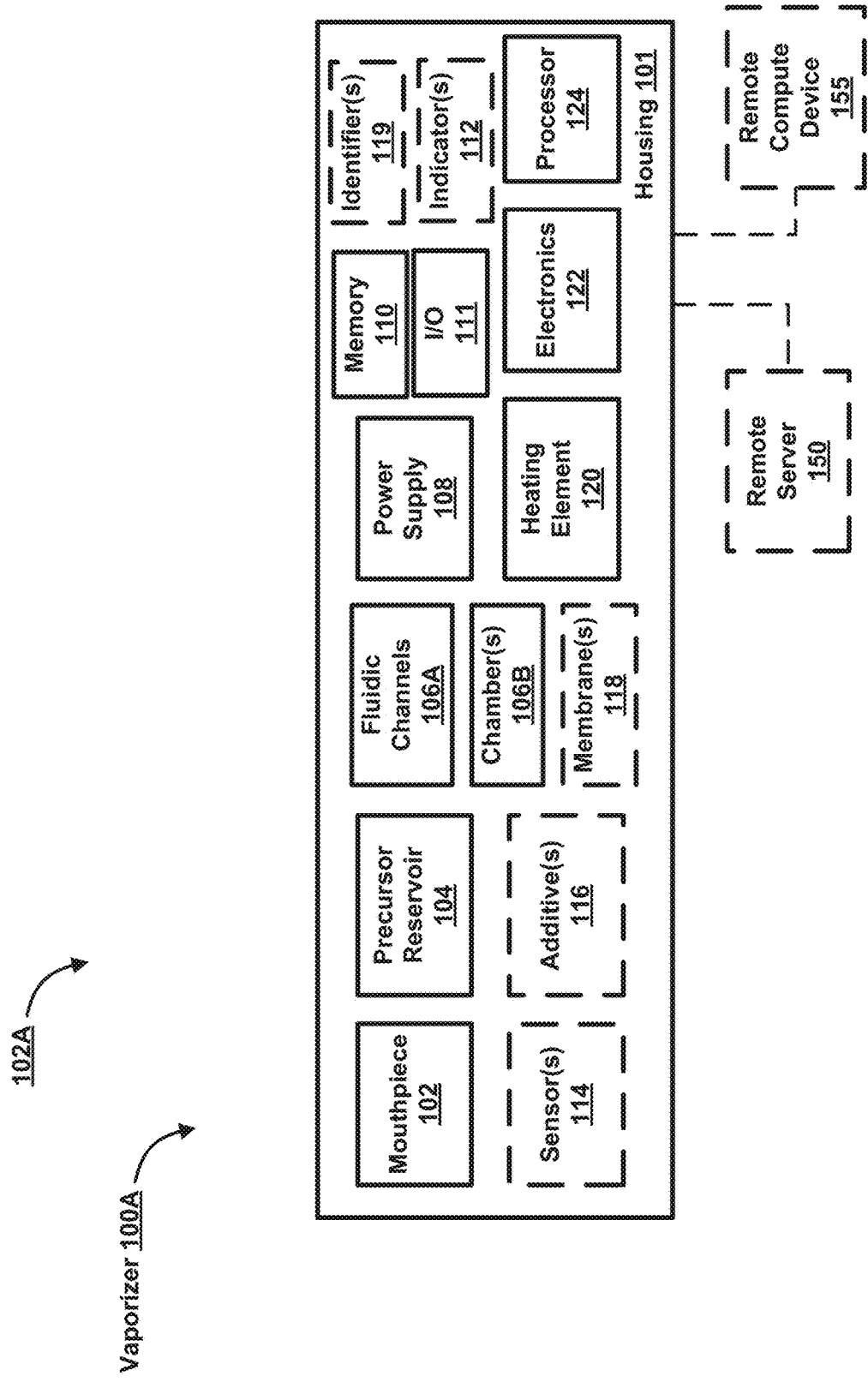
FIG. 1A is a schematic block diagram of a system including a disposable vaporizer, according to an embodiment.

FIG. 1A is a schematic block diagram of a system 102A including a disposable (or "single-use") vaporizer, according to an embodiment. As shown in FIG. 1A, a disposable vaporizer 100A includes a mouthpiece 102, a precursor reservoir 104, fluidic channels 106A (e.g., microfluidics or other passageways), one or more chambers 106B, a power supply 108, a memory 110, an input/output module 111, a heating element 120, electronics 122, and a processor 124, all disposed within a common (e.g., monolithic) housing 101. The memory 110, the electronics 112, and the processor 124 can be included, for example, in a control assembly.

Optionally, the disposable vaporizer 100A also includes one or more of: identifier(s) 119, sensor(s) 114, additive(s) 116, membrane(s) 118, and indicator(s) 112, also disposed within the common housing 101.

The mouthpiece 102 can comprise one or more of: ceramic, heat-resistant plastic, anodized aluminum, or any other suitable material. The power supply 108 can include any suitable battery or fuel cell, for example having high-drain characteristics. The precursor reservoir 104 can be in fluid communication with at least one of the mouthpiece 102, the one or more chambers 106B (e.g., vapor expansion chambers), and the fluidic channels 106A, such that carrier material can travel from the precursor reservoir 104 into a fluid path defined by the mouthpiece 102, the fluidic channels 106A, and the one or more chambers 106B as a result of triggering heating and vaporization of the carrier material. In some embodiments, heating of the carrier material can be initiated by the control assembly 130 in response to a user's sucking/drawing on the mouthpiece 102 during use (e.g., via activation of a pressure sensor of the sensor(s) 114). In some embodiments, the vaporizer 100A can include a mechanical interface (e.g., a button) (e.g., included in the input/output module 111) that the user can manually actuate to trigger the heating and vaporization of the carrier material.

The memory 110 can be operatively coupled (e.g., in electronic communication with) the processor 124. The memory 110 can include any electronic component capable of storing electronic information. The term memory may refer to various types of processor-readable media such as random access memory (RAM), read-only memory (ROM), non-volatile random access memory (NVRAM), programmable read-only memory (PROM), erasable programmable read only memory (EPROM), electrically erasable PROM (EEPROM), flash memory, magnetic or optical data storage, registers, etc. Memory is said to be in electronic communication with a processor if the processor can read information from and/or write information to the memory. Memory that is integral to a processor is in electronic communication with the processor.

The input/output module 111 can include one or more of: a push-button control for causing vapor generation, a battery indicator, an electromechanical connector for charging and/or data communication, a light source (e.g., one or more light-emitting diodes), etc. The heating element 120 can include a coil heater, rod-shaped heater, pancake heater, chemical heater, or any other heater that is sized, dimensioned, and constituted of material suitable for heating a carrier material. The heating element 120 can be part of a heating assembly that includes the heating element 120 and a wick (e.g., a cotton and/or ceramic wick) coupled to the heating element. In some embodiments, for example, the heating assembly can include a ceramic cylindrical wick portion defining a central passageway, a coil coupled to and/or disposed within the cylindrical wick portion configured to heat the cylindrical wick portion, and a cotton wick portion wrapped around the outer surface of the cylindrical wick portion. In some embodiments, for example, the heating assembly can include a wick (e.g., a cotton wick) and a coil having a portion wrapped around the wick and two ends extending away from the wick. The two ends can be configured to be coupled to the processor 124 (e.g., of a control assembly) such that the temperature of the coil can be controlled, at least in part, by a current applied to the ends of the coil. The wick can be configured to transport carrier material toward a portion of the wick adjacent the coil.

The electronics 122 can include one or more of: a GPS receiver, an antenna, heater control circuitry (e.g., configured to control a temperature of the heating element of the heating assembly 120), or a transceiver for wireless (e.g., Bluetooth) communication with a command center or other remote compute device (such as a mobile device of a user). The sensor(s) 114 can include one or more of: a pressure sensor, a temperature sensor, a position sensor, an orientation sensor, etc. The identifier(s) 119 may include, for example, a bar code, a QR code, and/or a near-field communication (NFC) device such that the vaporizer 100A may be identified and/or recognized by an external device. The identifier(s) 119 can also include a tracking component which may be or include an integrated circuit ((e.g., Application-Specific Integrated Circuits (ASICs)).

The processor 124 can include one or more of: a general purpose processor, a central processing unit (CPU), a microprocessor, a digital signal processor (DSP), a controller, a microcontroller, a state machine and so forth. Under some circumstances, a "processor" may refer to an application specific integrated circuit (ASIC), a programmable logic device (PLD), a field programmable gate array (FPGA), etc. The term "processor" may refer to a combination of processing devices, e.g., a combination of a DSP and a microprocessor, a plurality of microprocessors, one or more microprocessors in conjunction with a DSP core or any other such configuration.

In some embodiments, the vaporizer 100A can include one or more additives 116 combined with carrier material within the reservoir 104. The one or more additives 116 can include one or more flavorants. The membrane(s) 118 can be disposed on an outer surface of the vaporizer 100A (e.g., within an opening defined by the housing 101) and arranged such that carrier material and/or additive 116 can be supplied to the reservoir 104 via the membrane(s) 118. The membrane(s) 118 can include a valved impermeable or semi-permeable material, for example comprising a rubber, polyvinyl chloride (PVC), etc. The indicator(s) 112 can include one or more of: an illumination source (e.g., one or more light-emitting diodes), a speaker, a display screen, etc.

In some embodiments, in use, the disposable vaporizer 100A is configured such that, when a user sucks, or "draws," on an opening defined by the mouthpiece, the resulting change in pressure within the vaporizer 100A is measured by a sensor (e.g., a pressure sensor) of the sensor(s) 114. In response to the sensor 114 sensing a change in pressure (e.g., above a threshold change in pressure or to a threshold pressure level), the processor 124 can actuate the heater control circuitry of the electronics 122 to pass a current through the heating element that is in contact with, or in sufficiently close proximity to, the carrier material or a wick material containing at least a portion of the carrier material, so as to cause the volatilization of a portion of the carrier material. One or more characteristics of the current or affecting the delivery of the current passed through the heating element (e.g., voltage, wattage) can be controlled by the processor 124 based on, for example, an ambient temperature measured by a temperature sensor of the sensor(s) 114, a resistance of the heating element, and/or a heating profile or target temperature range associated with the carrier material (e.g., as determined by the processor 124 and/or provided to the processor 124 prior to use). The volatilized carrier material, or vapor, travels toward the mouthpiece via one or more of the expansion chamber(s) and the fluidic channels and exits the vaporizer via the opening in the mouthpiece for inhalation by the user. In some embodiments, a control assembly of the vaporizer 100A (e.g., the electronics 122 and/or the processor 124) can be coupled via a wired (e.g., Ethernet connection) or a wireless connection (e.g., via a WiFi network connection) to a remote server 150. In some embodiments, the control assembly 130 can be operatively coupled to a remote compute device 155 (e.g., a mobile compute device such as a smartphone) via a wired or wireless connection (e.g. Bluetooth connection). In some implementations, the remote server 150, the memory 110, and/or the remote compute device 155 can include a database and be configured to provide information related to carrier materials, carrier material profiles, information related to components in a carrier material (e.g., known boiling points of a volatilizable component in an oil), standardized volumes associated with usage of a vaporizer, standardized quantities of volatilized components, a quantity of aerosols associated with the volatilization of a standard carrier material, vapor pressure, atmospheric pressure, and/or environmental or ambient temperatures associated with usage of a vaporizer at specific geographic locations, etc. In some implementations, the remote server 150, the memory 110, and/or the remote compute device 155 can include a database of materials providing information related to temperatures or temperature ranges at which the carrier material should be vaporized (e.g., as determined by a manufacturer of the vaporizer 100A, a manufacturer of the carrier material, and/or a user of the vaporizer 100A). The control assembly can be configured to access the database and control the heating element 120 based, at least in part, on information provided in the database. In some instances, the remote compute device 155 can include a user interface including one or more control items and one or more display items configured to perform functions associated with communication with the vaporizer 100B, remote control of the vaporizer 100B, and/or display information associated with functioning or usage of the vaporizer 100B. In some embodiments, the processor 124 can be configured to apply current to the heating element 120 only upon receiving approval from the remote compute device 155 or the remote server 150. The approval may be based, at least in part, on information transmitted to the remote compute device 155 or the remote server 150 which may be based, at least in part, on information read on the tracking component (also referred to as a tracking chip).

Figure 1B:
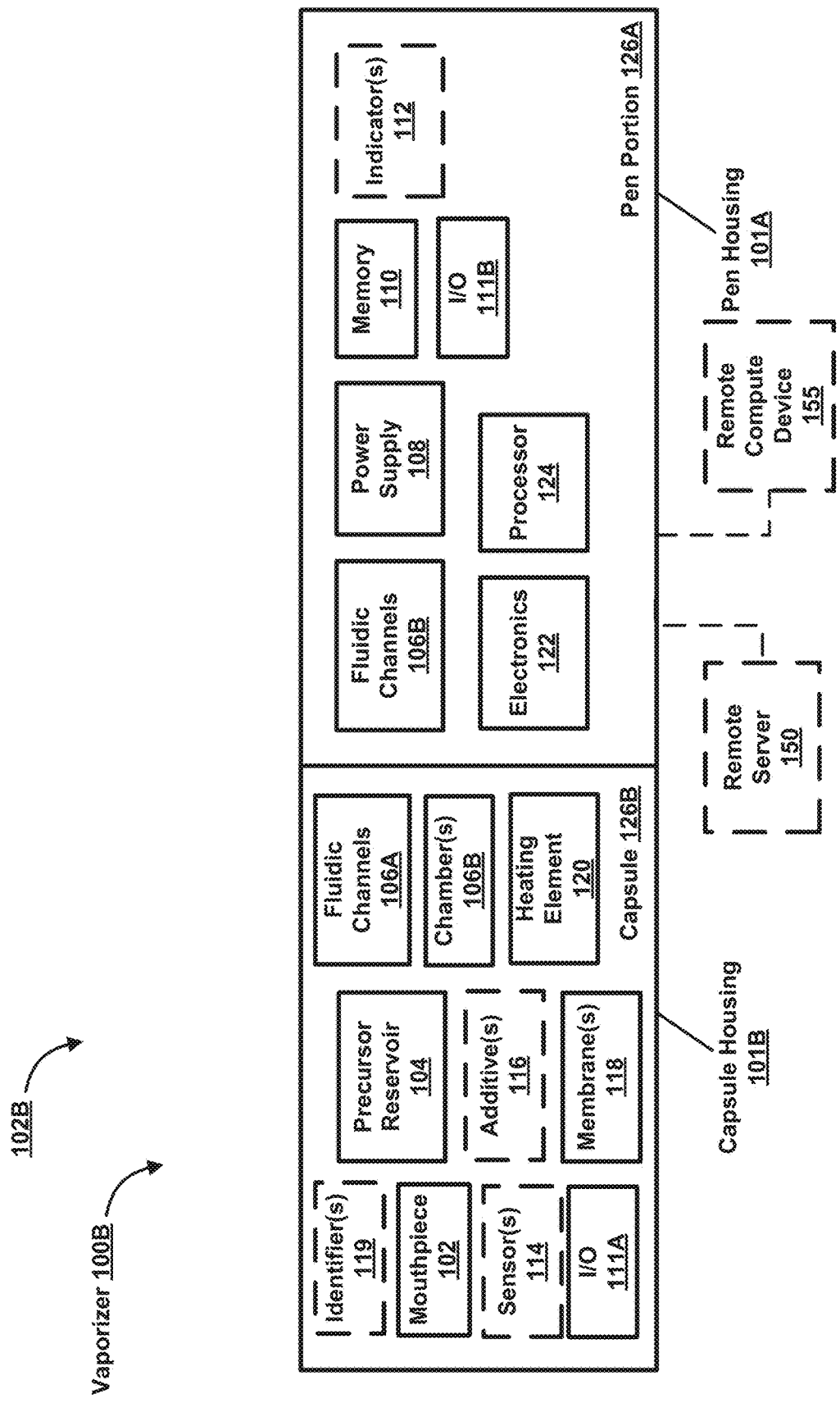
FIG. 1B is a schematic block diagram of a system including a reusable vaporizer, according to an embodiment.

FIG. 1B is a schematic block diagram of a system 102B including a reusable vaporizer, according to an embodiment. As shown in FIG. 1B, a reusable vaporizer 100B includes a pen portion 126A and a capsule portion 126B. The pen portion 126A and the capsule portion 126B of the reusable vaporizer 100B can collectively include components that are the same or similar in structure and/or function to the components of the vaporizer 100A described above. For example, the capsule portion 126B (also referred to as a "capsule," a "capsule assembly," and a "cartridge") includes a mouthpiece 102, a precursor reservoir 104, one or more fluidic channels 106A, one or more chambers 106B, a heating element 120, membrane(s) 118, an optional input/output (I/O) module 111A, optionally one or more identifier(s) 119, optional sensor(s) 114, and optionally additive(s) 116, all disposed within a capsule housing 101B. The one or more identifiers 119 can include a tracking component 128. The pen portion 126A includes fluidic channels 106B, a power supply 108, memory 110, input/output module 111B, electronics 122, a processor 124, an input/output (I/O) module 111B, and optionally indicator(s) 112, all disposed within a pen housing 101A. The memory 110, the electronics 122, and the processor 124 can all be included in a control assembly, and can be optionally configured to communicate with a remote server 150 and/or a remote compute device 155. The pen portion 126A (i.e., the pen housing 101A and its contents) can also be referred to as a "battery portion" of the vaporizer 100B. The capsule 126B can be manufactured, shipped and/or sold separately from the pen portion 126A, and assembled by a user to form the vaporizer 100B.

To assemble the vaporizer 100B, a user may, prior to use (e.g., upon purchase of a new capsule), connect the capsule 126B with the pen portion 126A of the vaporizer 100B. The capsule 101B and the pen portion 126A can be configured to be mechanically and electrically connected, for example by one or more of screw attachment, press-fit attachment, snap-fit attachment, magnetic attachment, or any other suitable connection means. For example, the capsule 101B can include a first engagement mechanism configured to releasably coupled to a corresponding second engagement mechanism of the pen portion 126A such that an interface assembly of the capsule 101B (which can include the tracking component 128 and/or one or more portions of the heating element 120 such as the ends of a coil) can be coupled to an electrical interface of the pen portion 126A when the first engagement mechanism is releasably coupled to the corresponding second engagement mechanism. As can be inferred from the foregoing, the pen portion 126A can be considered the reusable portion of the vaporizer 100B, and the capsule 126B can be considered the disposable or "replaceable" portion of the vaporizer 100B. The identifier(s) 119 may include, for example, a bar code, a QR code, and/or a near-field communication (NFC) device such that the vaporizer 100A may be identified and/or recognized by an external device and/or the pen portion 126A. For example, the control assembly 130 can be configured to be coupled to the tracking component 128 when the capsule 126B is coupled to the pen portion 126A such that the control assembly (e.g., the processor 124) can access information contained in the tracking component 128. The tracking component 128 may be, for example, an integrated circuit (e.g., Application-Specific Integrated Circuits (ASICs)). The tracking component 128 can be configured to contain data related to the capsule 126B. In some implementations, the tracking component 128 may contain capsule identification information corresponding to the capsule 126B such that the control assembly 130 may recognize the capsule 126B and such that information about the contents of the capsule 126B can be received from the tracking component 128 by the processor 124.

To assemble the vaporizer 100B, a user may, prior to use (e.g., upon purchase of a new capsule), connect the capsule assembly 126B with the pen assembly 126A of the vaporizer 100B. The control assembly (e.g., the processor 124) of the vaporizer 100B can be coupled using any suitable connection such that the control assembly can receive information from the tracking component 128, the remote server 150', and/or the remote compute device 155'. For example, the control assembly can be coupled to the tracking component 128 via a connection subassembly (not shown) which may be coupled to or included within the control assembly. The connection subassembly can include, for example, electrical connectors (e.g., pogo pins) coupled to or included in a printed circuit board such that the control assembly can access information contained in the tracking component 128.

As another example, the control assembly 130 can be coupled via a wired (e.g., Ethernet connection) or a wireless connection (e.g., via a WiFi network connection) to a remote server 150. The control assembly can also be operatively coupled to a remote compute device 155 (e.g., a mobile compute device such as a smartphone) via a wired or wireless connection (e.g. Bluetooth connection). In some implementations, the remote server 150, the memory 110, and/or the remote compute device 155 can include a database and be configured to provide information related to carrier materials, carrier material profiles, information related to components in a carrier material (e.g., known boiling points of a volatilizable component in an oil), standardized volumes associated with usage of a vaporizer, standardized quantities of volatilized components, a quantity of aerosols associated with the volatilization of a standard carrier material, vapor pressure, atmospheric pressure, and/or environmental or ambient temperatures associated with usage of a vaporizer at specific geographic locations, etc. In some implementations, the remote server 150, the memory 110, and/or the remote compute device 155 can include a database of materials providing information related to temperatures or temperature ranges at which the carrier material should be vaporized (e.g., as determined by a manufacturer of the vaporizer 100A, a manufacturer of the carrier material, and/or a user of the vaporizer 100A). The control assembly 130 can be configured to access the database and control the heating element 120 based, at least in part, on information provided in the database. In some instances, the remote compute device 155 can include a user interface including one or more control items and one or more display items configured to perform functions associated with communication with the vaporizer 100B, remote control of the vaporizer 100B, and/or display information associated with functioning or usage of the vaporizer 100B. In some instances, the remote compute device 155 can include a user interface including one or more control items and one or more display items configured to perform functions associated with communication with the vaporizer 100B, remote control of the vaporizer 100B, and/or display information associated with functioning or usage of the vaporizer 100B. In some embodiments, the processor 124 can be configured to apply current to the heating element 120 only upon receiving approval from the remote compute device 155 or the remote server 150. The approval may be based, at least in part, on information transmitted to the remote compute device 155 or the remote server 150 which may be based, at least in part, on information read on the tracking component (also referred to as a tracking chip).

In use, a user can draw fluid through the mouthpiece opening 102 by applying the user's mouth to the mouthpiece 102 and applying negative pressure to the mouthpiece opening (e.g., by sucking). In implementations including a pressure sensor (e.g., of the sensor(s) 114) in communication with the control assembly, the negative pressure can trigger the pressure sensor. In response to receiving an indication of negative pressure from the pressure sensor (indicated that flow is occurring through the mouthpiece opening), the control assembly (e.g., the processor 124) may actuate heater control circuitry of the control assembly such that a current is passed to a heating element (e.g., a coil) of the heating element 120 (e.g., via a connector subassembly including, for example, pogo pins). Alternatively, in implementations including an activation button in communication with the control assembly, the user can actuate the activation button such that the control assembly, in response to receiving an actuation signal from the activation button, may actuate heater control circuitry of the control assembly such that a current is passed through the heating element and the heating element is heated to a particular temperature. One or more characteristics of the current or affecting the delivery of the current passed through the heating element (e.g., voltage, wattage) can be controlled by the processor 124 based on, for example, an ambient temperature measured by a temperature sensor of the sensor(s) 114, a resistance of the heating element, and/or a heating profile or target temperature range associated with the carrier material (e.g., as determined by the processor 124 and/or provided to the processor 124 prior to use).

In some embodiments, the systems 102A and/or 102B in FIGS. 1A and 1B can be substantially the same or similar in structure and/or function to any of the systems described in the U.S. Provisional Patent Application No. 62/886,244 filed on Aug. 13, 2019, entitled "Methods and Systems for Heating Carrier Material Using a Vaporizer" and in the U.S. Provisional Patent Application No. 62/886,256 filed on Aug. 13, 2019, entitled "Methods and Systems for Delivering a Dose Using a Vaporizer" which are both incorporated by reference herein in their entireties.

Figure 2A:
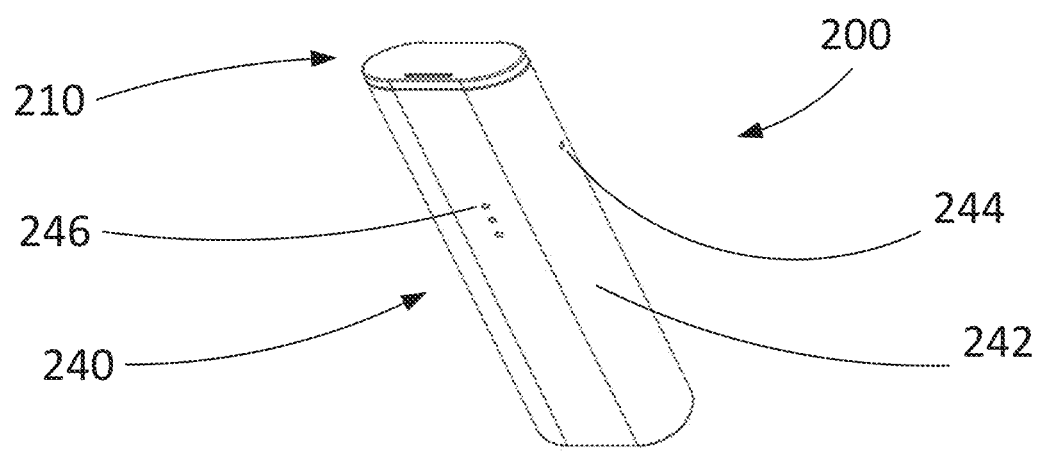
FIGS. 2A and 2B are perspective views of a system in an assembled and an exploded configuration, respectively, according to an embodiment.
Figure 2B:
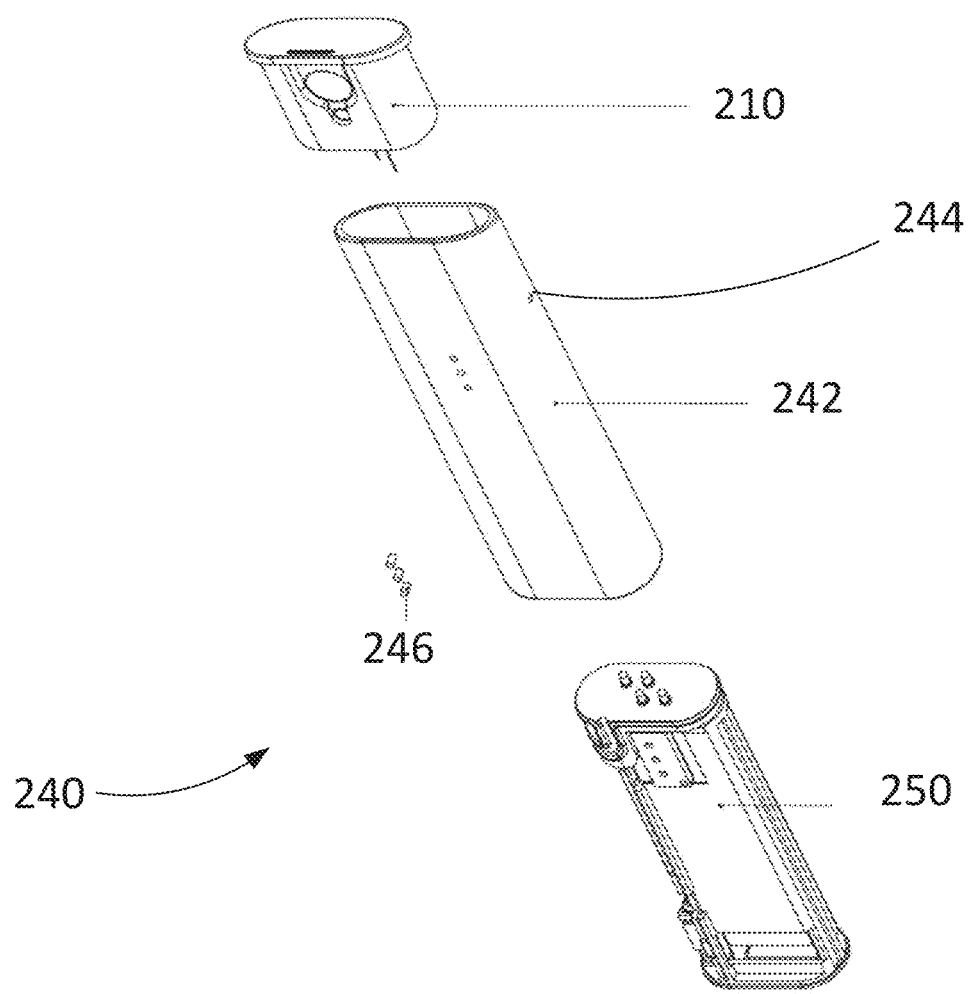

FIGS. 2A and 2B are perspective views of an electronic vapor delivery system 200 in an assembled and an exploded configuration, respectively. The system 200 may be the same or similar in structure and/or function to any of the systems described herein, such as, for example, the reusable vaporizer 100B described above with respect to FIG. 1B. For example, the system 200 includes a cartridge assembly 210 and a pen assembly 240. The cartridge assembly 210 may be the same or similar in structure and/or function to the capsule 126B described above, and the pen assembly 240 may be the same or similar in structure and/or function to the pen portion 126A described above. The pen assembly 240 includes a pen housing 242 and a bracket assembly 250. The pen assembly 240 also includes indicator cover elements 246 (e.g., translucent portions configured such that light transmitted from indicator features 257 described below may be visible through the indicator cover elements 246). Furthermore, in some implementations, the pen housing 242 may define an inlet 244 in the sidewall of the pen housing 242 such that air may be drawn into an interior of the system 200 via the inlet 244. In some implementations, the pen housing 242 may define one or more inlets 244 in any suitable location on the pen housing 242, such as on opposite sides of the pen housing 242. In some implementations, the pen housing 242 may not define an inlet 244 in the sidewall of the pen housing 242.

Figure 2C:
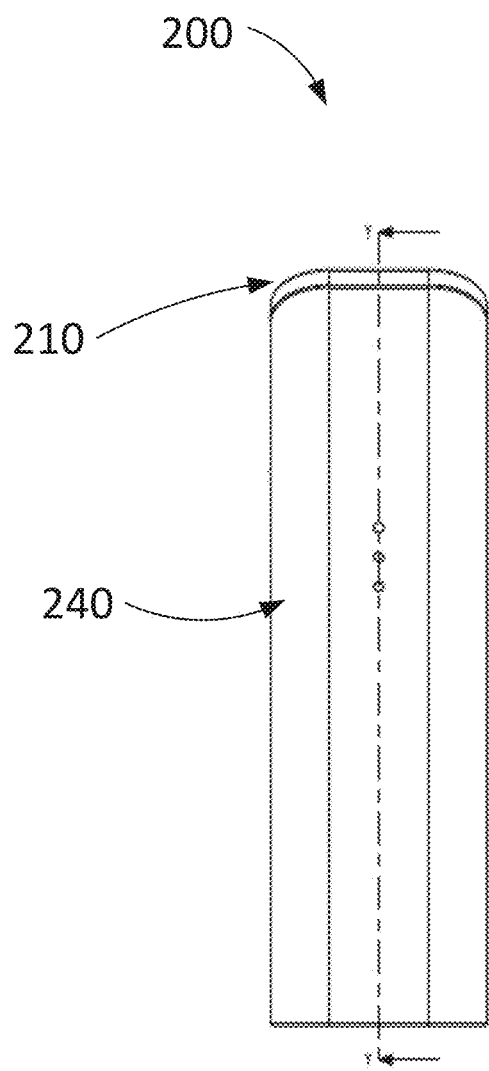
FIGS. 2C and 2D are a back view and a front view, respectively, of the system of FIG. 2A.
Figure 2D:
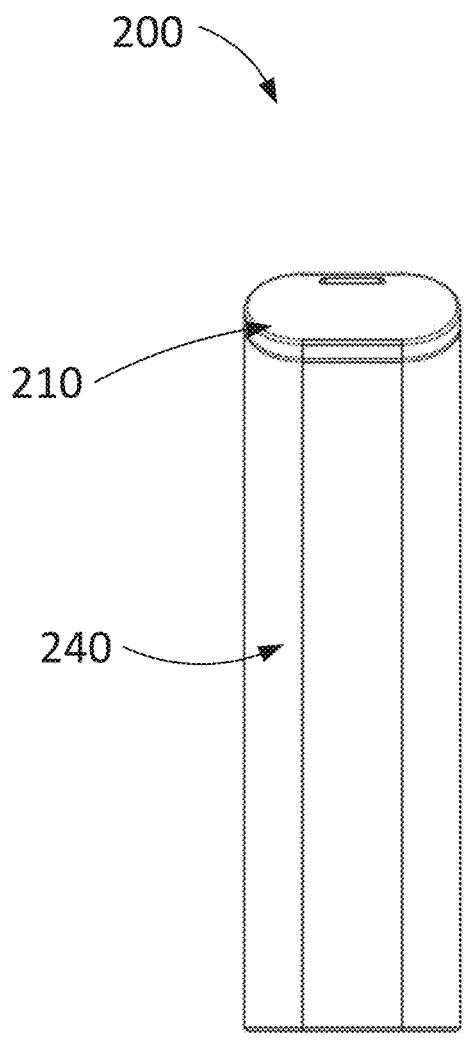
Figure 2E:
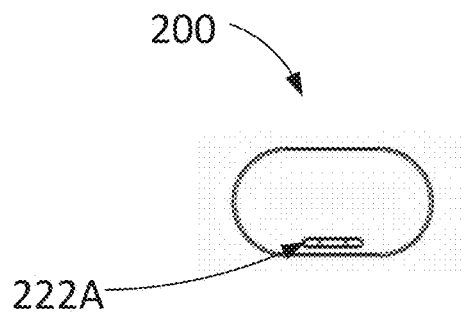
FIGS. 2E and 2F are a top view and a bottom view, respectively, of the system of FIG. 2A.
Figure 2F:
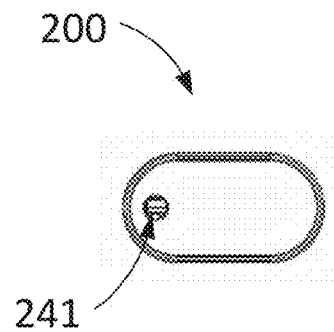
Figure 2G:
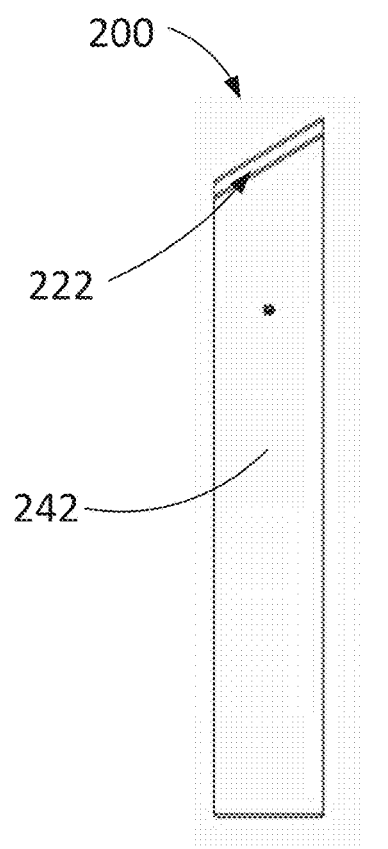
FIGS. 2G and 2H are a right side view and a left side view, respectively, of the system of FIG. 2A.
Figure 2H:

FIGS. 2C and 2D are a back view and a front view, respectively, of the system 200. FIGS. 2E and 2F are a top view and a bottom view, respectively, of the system 200. As shown in FIG. 2F, the bottom of the pen housing 242 may define a bottom opening 241 such that air may be drawn into an interior of the system 200 via the bottom opening 241 and/or such that a charging device may be reversibly engaged with a power supply of the system (e.g., power supply 284 discussed below). FIGS. 2G and 2H are a right side view and a left side view, respectively, of the system 200. The mouthpiece component 222 and the pen housing 242 may be formed such that the outer profile of the system 200 has any suitable angle near the mouthpiece opening 222A for engagement with a user's mouth. For example, the angle may be about 60 degrees or less than 60 degrees.

Figure 3A:
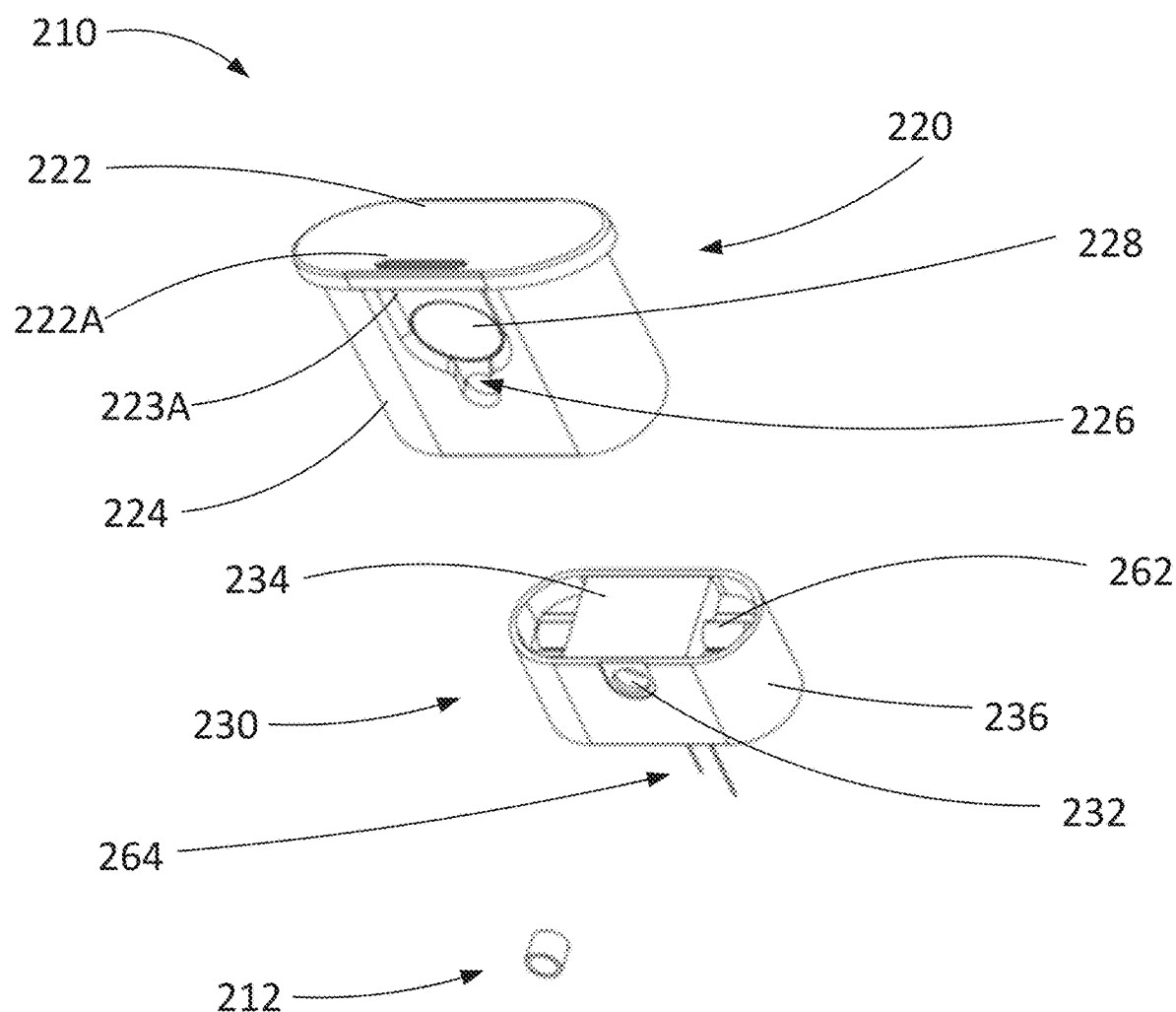
FIG. 3A is an exploded perspective view of a cartridge assembly of FIG. 2B.

FIG. 3A is a perspective view of the cartridge assembly 210 in an exploded configuration. As shown in FIG. 3A, the cartridge assembly 210 includes a mouthpiece assembly 220, a bracket cartridge assembly 230, and a pipe chimney 212 (also referred to as a chimney component). The mouthpiece assembly 220 is configured to receive the bracket cartridge assembly 230 within an interior of the mouthpiece assembly 220 such that a vapor outlet 226 of the mouthpiece assembly 220 aligns with a vapor outlet 232 of the bracket cartridge assembly 230. When the bracket cartridge assembly 230 is disposed within the mouthpiece assembly 220 such that the vapor outlet 226 of the mouthpiece assembly 220 aligns with the vapor outlet 232 of the bracket cartridge assembly 230, the pipe chimney 212 can be disposed within the vapor outlet 226 and the vapor outlet 232 such that gaseous fluid and/or vapor may flow through the pipe chimney 212 from an interior of the bracket cartridge assembly 230 to an exterior of the cartridge assembly 210 (e.g., the first recessed portion 221).

Figure 3B:
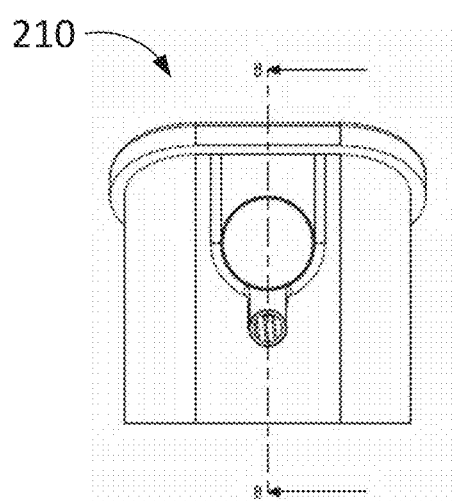
FIGS. 3B and 3C are a back view and a front view, respectively, of the cartridge assembly of FIG. 2B.
Figure 3C:
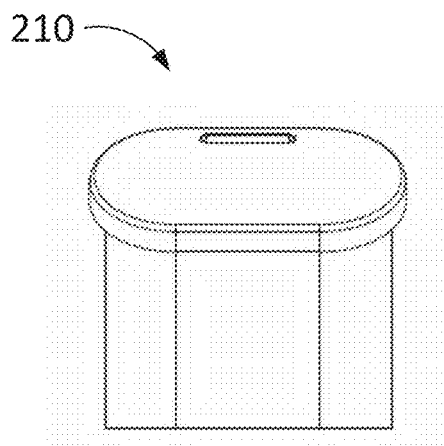
Figure 3D:
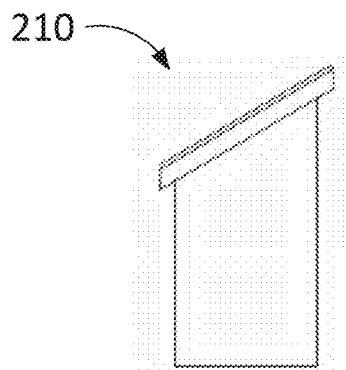
FIGS. 3D and 3E are a right side view and a left side view, respectively, of the cartridge assembly of FIG. 2B in an assembled configuration.
Figure 3E:
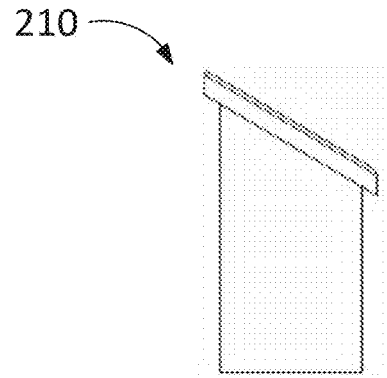
Figure 3F:
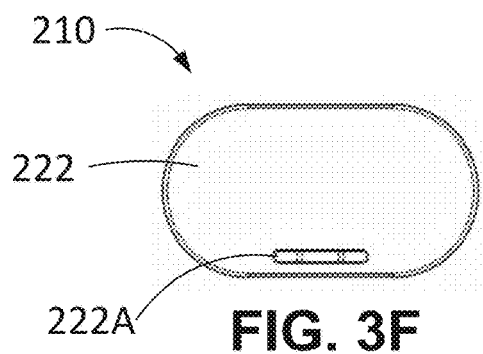
FIGS. 3F and 3G are a top view and a bottom view, respectively, of the cartridge assembly of FIG. 2B in an assembled configuration.
Figure 3G:
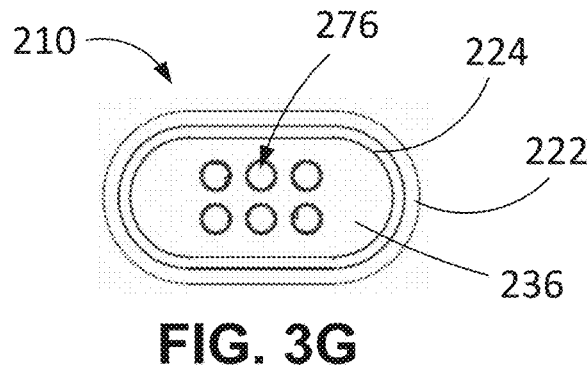

FIGS. 3B and 3C are a back view and a front view, respectively, of the cartridge assembly 210 in an assembled configuration. FIGS. 3D and 3E are a right side view and a left side view, respectively, of the cartridge assembly 210 in an assembled configuration. FIGS. 3F and 3G are a top view and a bottom view, respectively, of the cartridge assembly 210 in an assembled configuration.

Figure 4A:
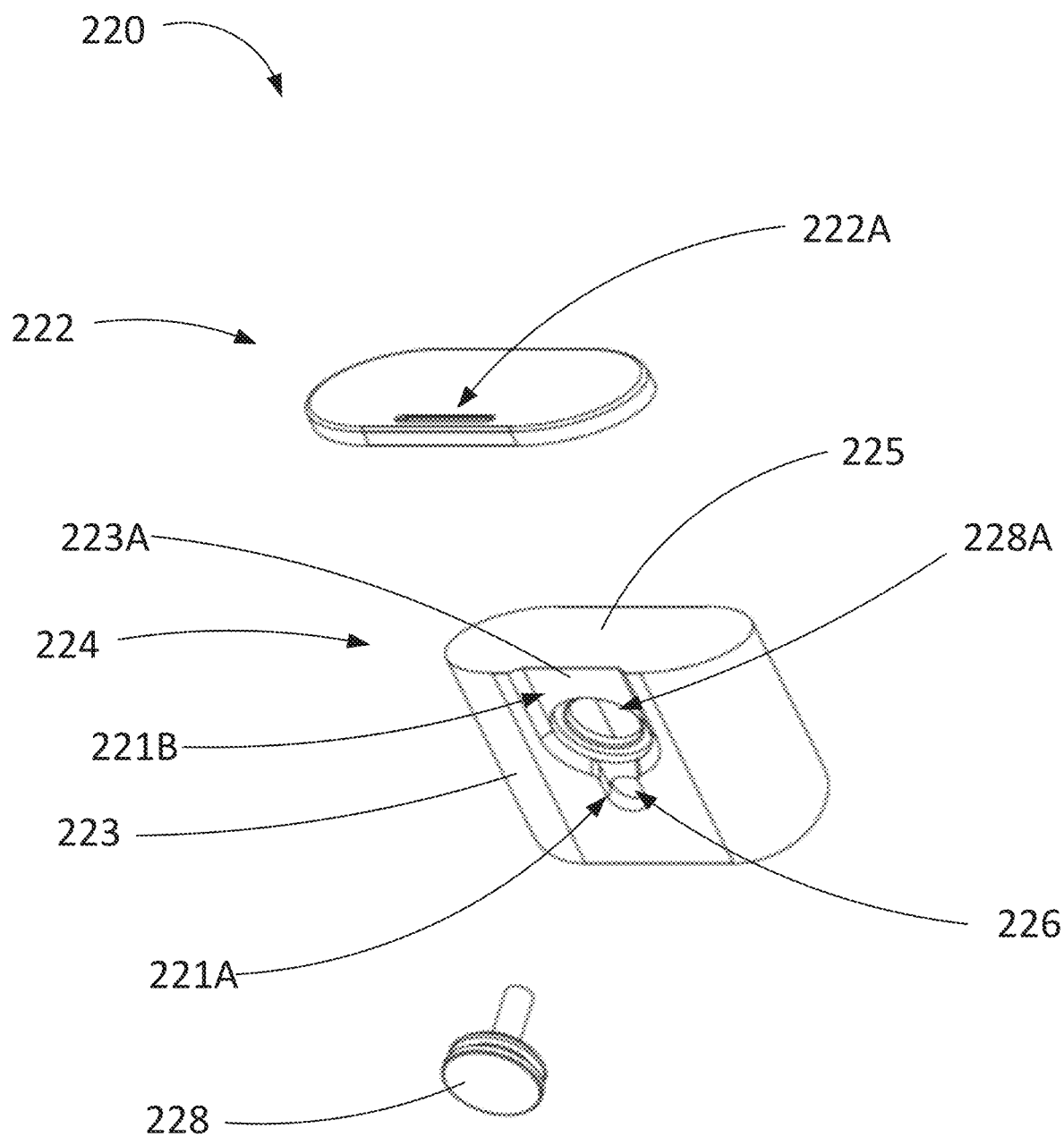
FIG. 4A is an exploded perspective view of a mouthpiece assembly of the cartridge assembly of FIG. 3.

FIG. 4A is an exploded perspective view of the mouthpiece assembly 220. As shown in FIG. 4A, the mouthpiece assembly 220 includes a mouthpiece component 222, an outer housing 224, and a plug 228. The mouthpiece assembly 220 defines a mouthpiece opening 222A. The outer housing 224 includes a sidewall 223, a recessed sidewall portion 223A, and an upper surface 225. The recessed sidewall portion 223A of the outer housing 224 defines a first recessed portion 221A and a second recessed portion 221B. The portion of the recessed sidewall portion 223A defining the first recessed portion 221A may also define the vapor outlet 226. The portion of the recessed sidewall portion 223A defining the second recessed portion 221B may also define a fill inlet 228A. Thus, fluidic carrier material may be introduced into an interior of the outer housing 224 via the fill inlet 228A. In some implementations, the first recessed portion 221A may have a first width and the second recessed portion 221B may have a second width greater than the first width. In some implementations, the first recessed portion 221A may have a first cross-sectional area and the second recessed portion 221B may have a second cross-sectional area greater than the first cross-sectional area, the first cross-sectional area and the second cross-sectional area lying in parallel planes. In some implementations, the first recessed portion 221A may have a first volume and the second recessed portion 221B may have a second volume greater than the first volume. As fluid (e.g., vapor) flows from the vapor outlet 226 through the first recessed portion 221A and through the second recessed portion 221B, the fluid pressure of the fluid may reduce due to the fluid expanding into the larger volume region of the second recessed portion 221B.

Figure 4B:
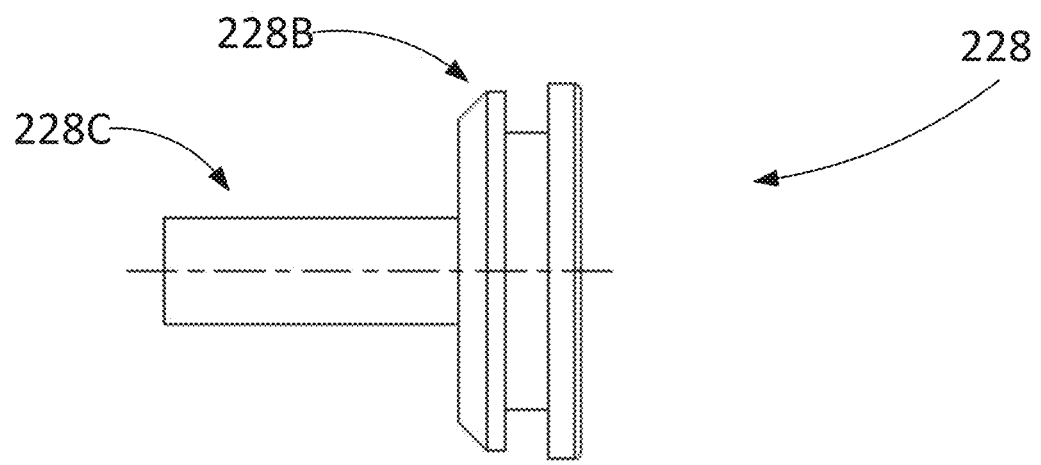
FIGS. 4B and 4C are a side view and an end view, respectively, of a plug of FIG. 4A.
Figure 4C:
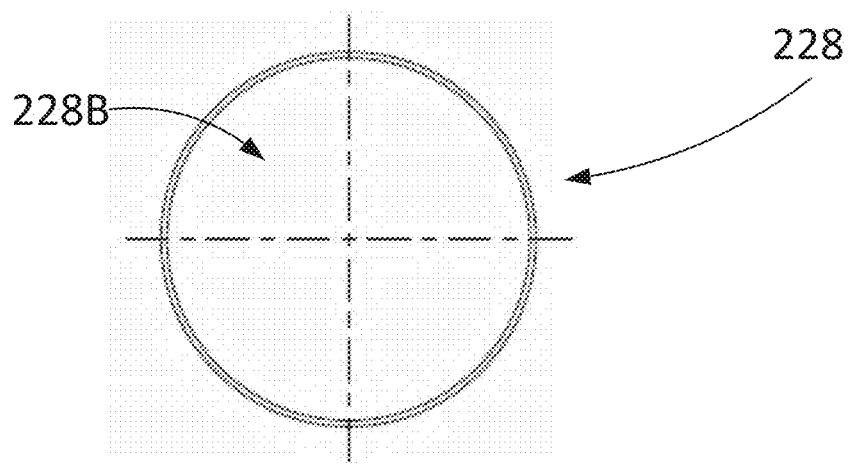

The plug 228 may be configured such that the plug 228 has a complementary shape to the portion of the outer housing 224 defining the fill inlet 228A. The plug 228 may be configured to sealingly engage with the fill inlet 228. For example, FIGS. 4B and 4C are a side view and an end view, respectively, of the plug 228. As shown in FIG. 4B, the plug 228 may include a cover portion 228B and a stem portion 228C. When the plug 228 is sealingly engaged with the fill inlet 228, the surface of the cover portion 228B opposite the stem portion 228C may be configured to be disposed in the same plane as the recessed sidewall portion 223A and form a portion of the outer surface of the cartridge assembly 210. In some implementations, the plug 228 may be configured to be releasably engaged with the portion of the outer housing 224 defining the fill inlet 228 such that the plug 228 may be removed for the introduction of carrier material into the interior of the outer housing 224. In some implementations, the plug 228 may be configured to be pierced by a piercing element (e.g., a hollow needle) such that carrier material may be introduced into the interior of the outer housing 224 through the plug 228. The plug 228 may include a material (e.g., elastomeric) such that the plug 228 reseals after removal of a piercing element from the plug 228.

Figure 5A:
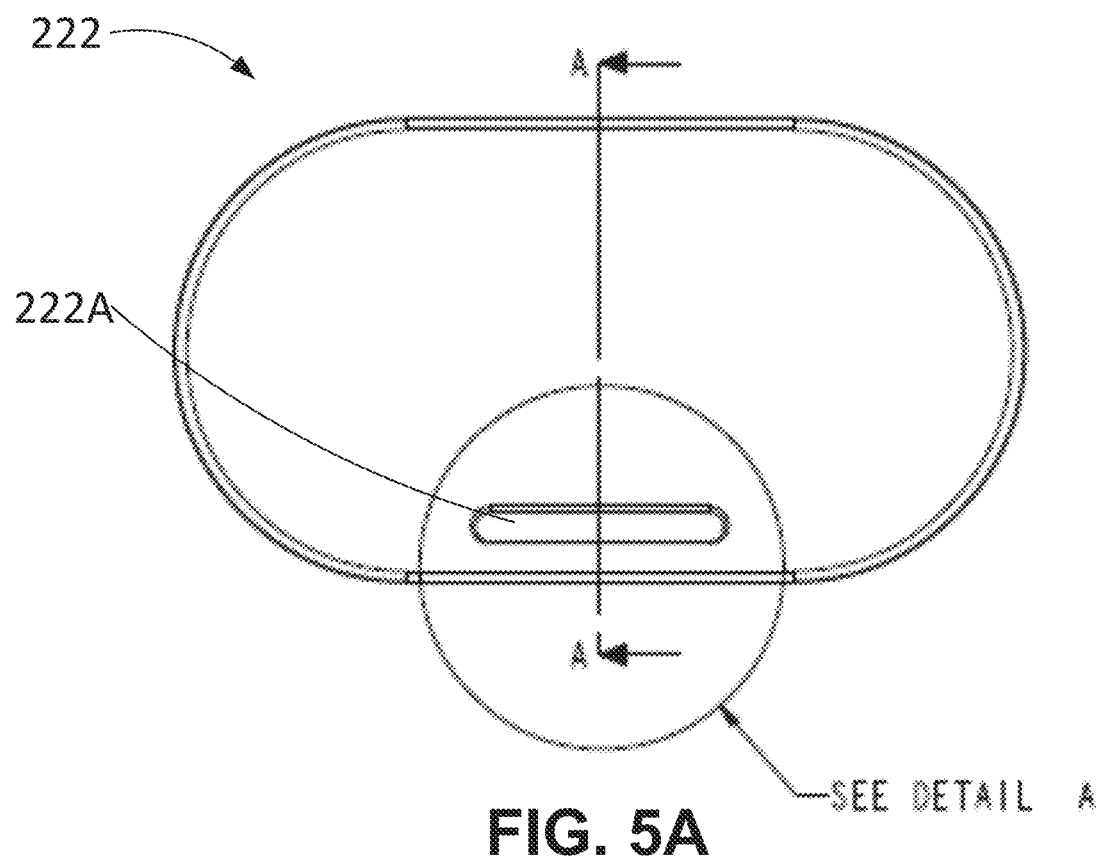
FIG. 5A is a top view of a mouthpiece component of the mouthpiece assembly of FIG. 4.

FIG. 5A is a top view of the mouthpiece component 222 of the mouthpiece assembly 220. As shown in FIG. 5A, the mouthpiece opening 222A may be formed as an elongated opening near an outer edge of the mouthpiece component 222. A portion of the upper surface of the mouthpiece component 222 may be disposed between the mouthpiece opening 222A and the outer edge of the mouthpiece component 222 near which the mouthpiece opening 222A is defined.

Figure 5B:
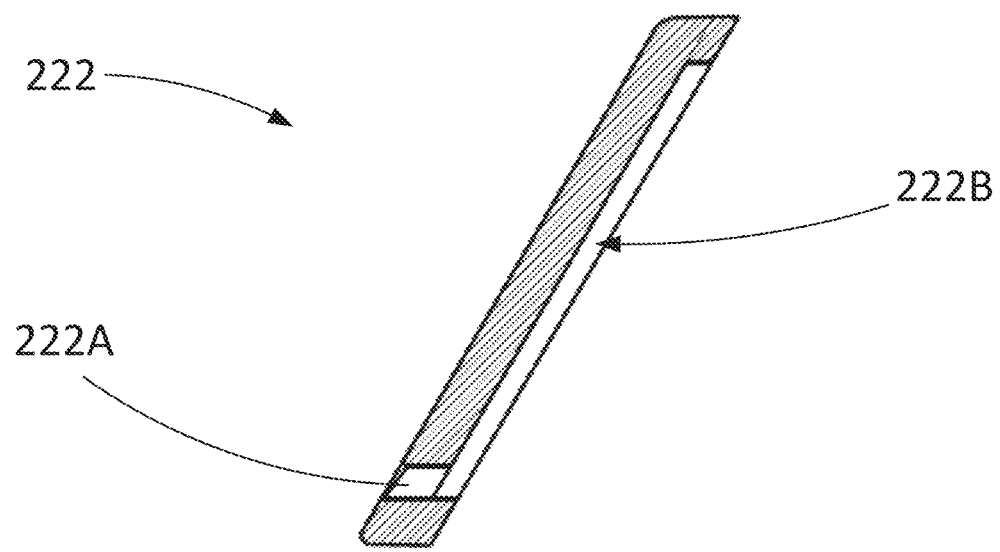
FIG. 5B is a cross-sectional view of the mouthpiece component of FIG. 5A taken along line A-A in FIG. 5A.
Figure 5C:
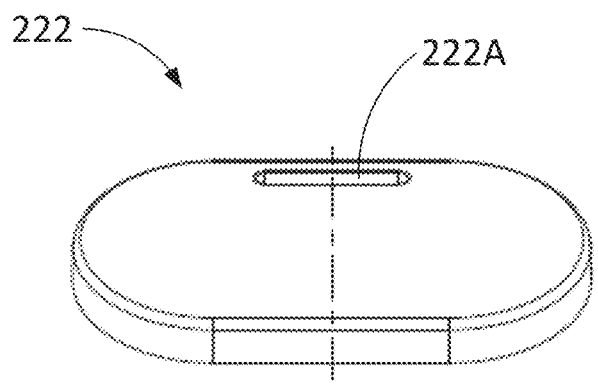
FIG. 5C is a front view of the mouthpiece component of FIG. 5A.
Figure 5D:
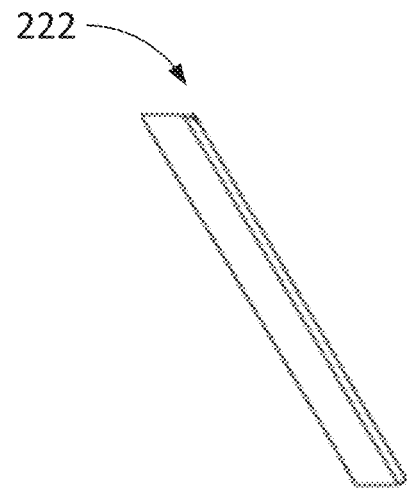
FIG. 5D is a side view of the mouthpiece component of FIG. 5A.
Figure 5E:
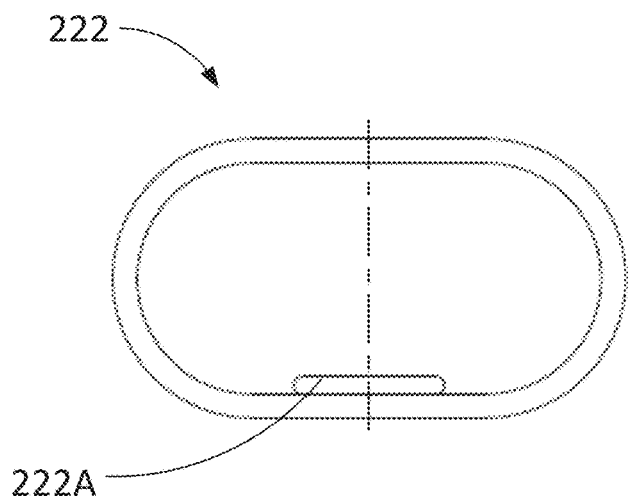
FIG. 5E is a bottom view of the mouthpiece component of FIG. 5A.
Figure 5F:
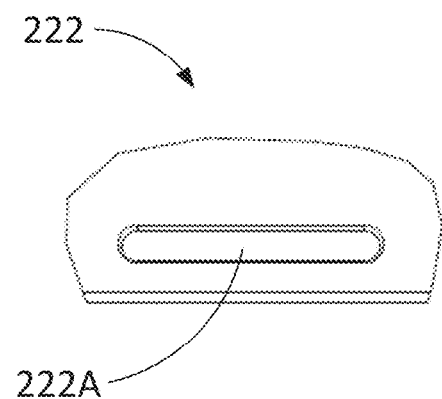
FIG. 5F is an enlarged view of the region identified as Detail A in FIG. 5A.

FIG. 5B is a cross-sectional view of the mouthpiece component 222 taken along line A-A in FIG. 5A. FIG. 5C is a front view of the mouthpiece component 222, FIG. 5D is a side view of the mouthpiece component 222, and FIG. 5E is a bottom view of the mouthpiece component 222. FIG. 5F is an enlarged view of the region identified as Detail A in FIG. 5A. As shown in FIG. 5B, the mouthpiece assembly 220 defines a mouthpiece recess 222B in a bottom surface of the mouthpiece assembly 220. The mouthpiece recess 222B and the mouthpiece opening 222A may be in fluidic communication such that gaseous fluid and/or vapor may flow through the mouthpiece opening 222A via the mouthpiece recess 222B. The mouthpiece opening 222A may be adjacent to an edge of the mouthpiece recess 222B. The mouthpiece assembly 220 is configured to receive a top portion of the outer housing 224 (e.g., the upper surface 225 and an upper portion of the sidewall 223) into the mouthpiece recess 222B. When the outer housing 224 is disposed within the mouthpiece recess 222B, the mouthpiece opening 222A may be aligned with the second recessed portion 221B such that the mouthpiece opening 222A is not obstructed by the upper surface 225 of the outer housing 224. In some embodiments, the width of the mouthpiece opening 221A may be equal to or less than the width of the recessed sidewall portion 223A in the region of the second recessed portion 221B.

The mouthpiece component 222 may be coupled to the outer housing 224 via any suitable manner. For example, the mouthpiece component 222 may be coupled to the outer housing 224 via a friction fit between the mouthpiece component 222 and the outer housing 224. In some embodiments, the mouthpiece component 222 may be coupled to the outer housing 224 via an adhesive.

Figure 6A:
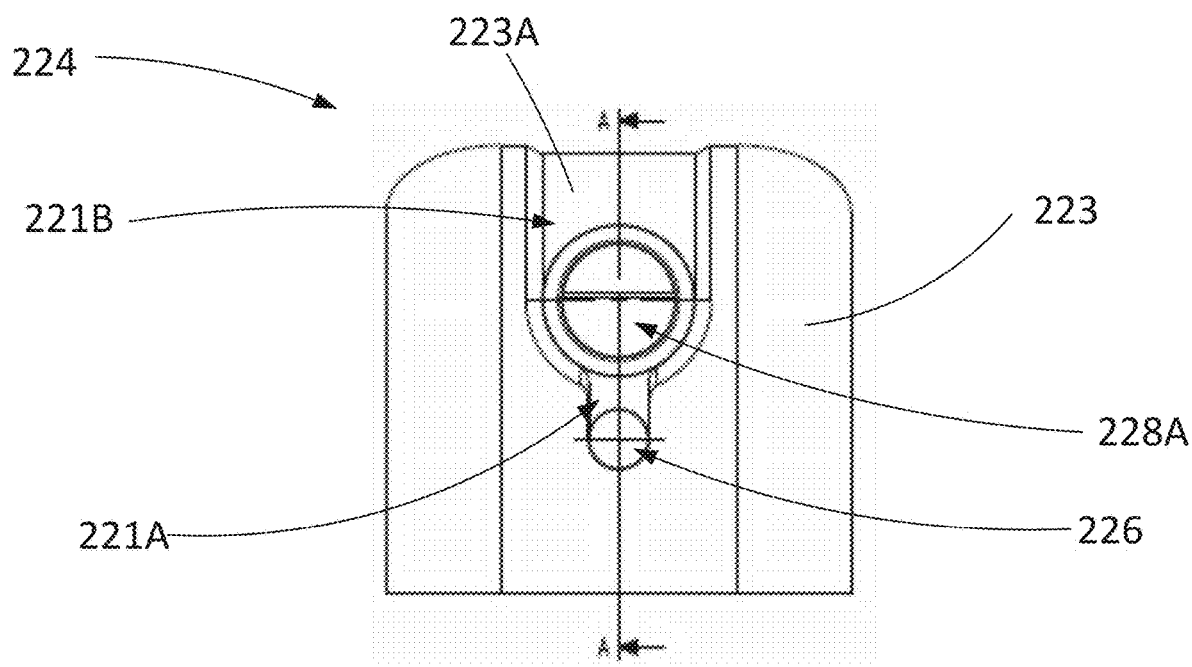
Figure 6B:
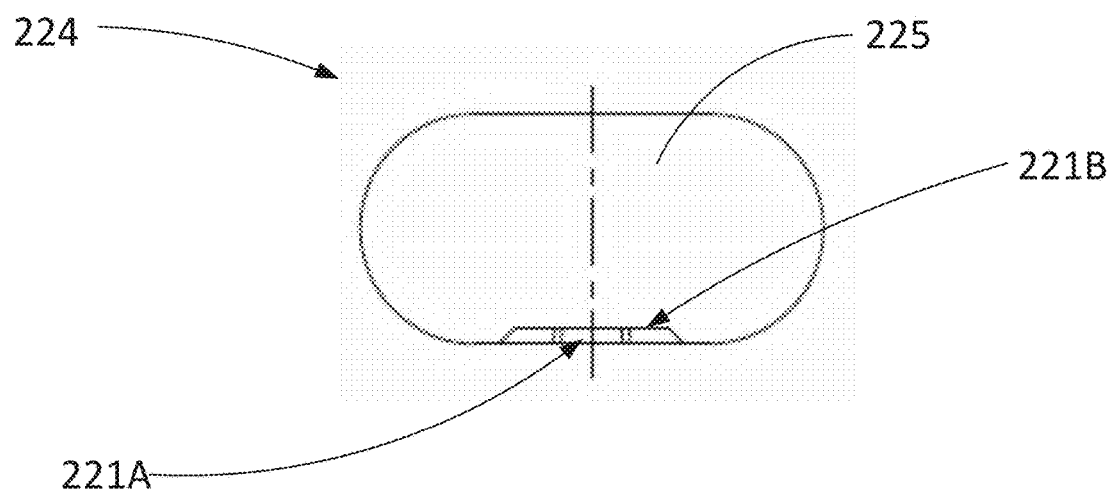
Figure 6F:
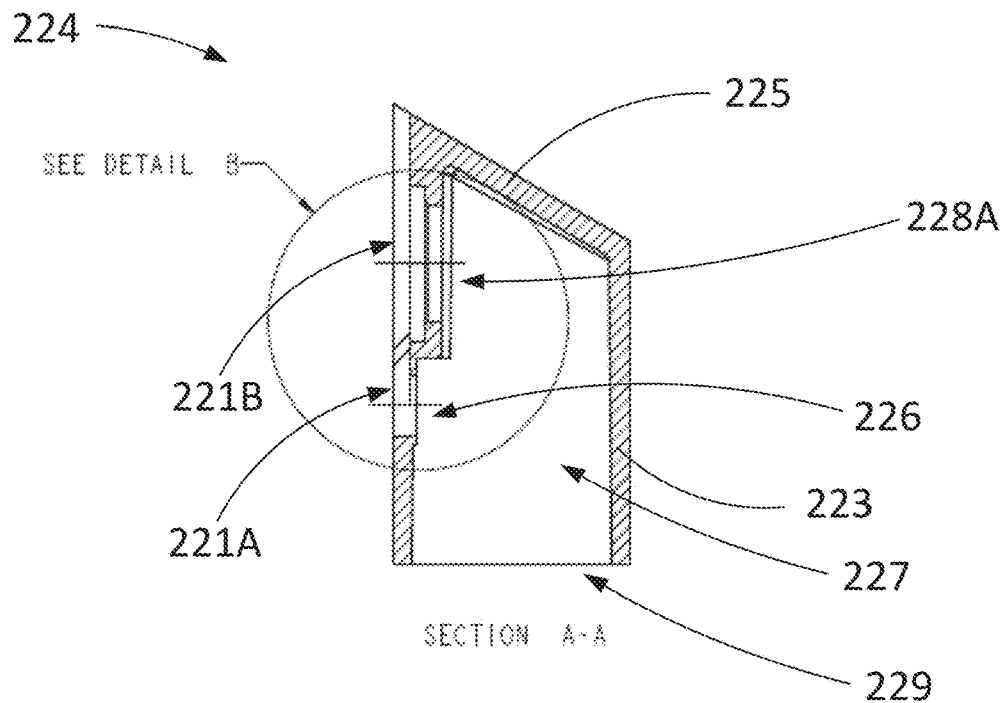
Figure 6G:
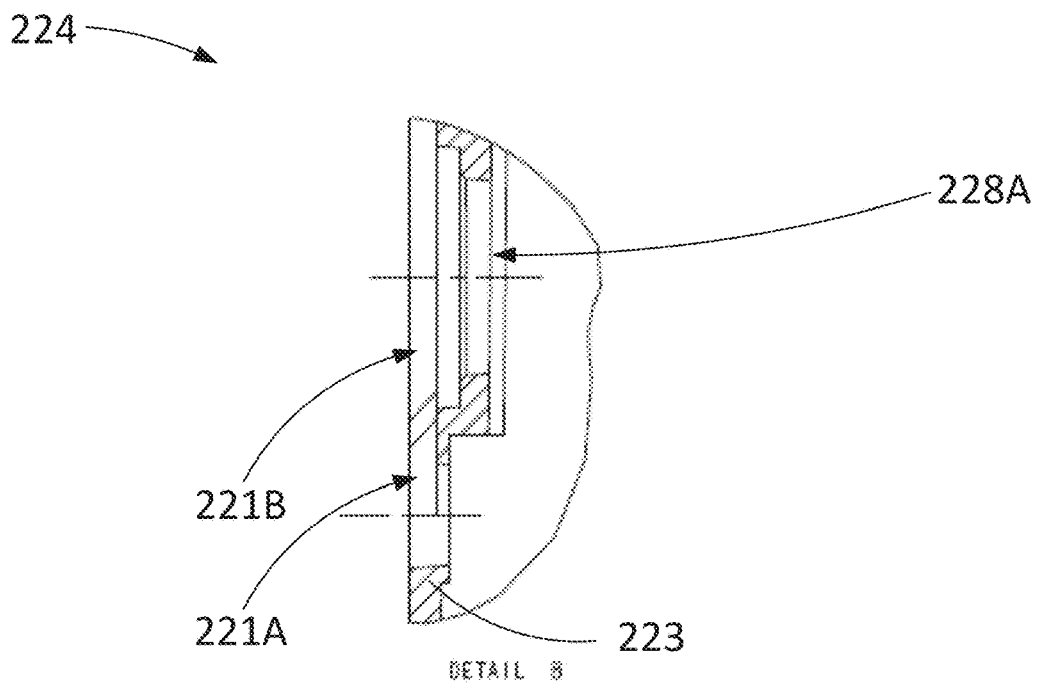

FIGS. 6A-6G are various views of the outer housing 224. Specifically, FIG. 6A is a back view of the outer housing 224, FIG. 6B is a top view of the outer housing 224, FIG. 6C is a bottom view of the outer housing 224, FIG. 6D is a side view of the outer housing 224, and FIG. 6E is a front view of the outer housing 224. FIG. 6F is a cross-sectional view of the outer housing 224 taken along line A-A in FIG. 6A. FIG. 6G is an enlarged view of the region indicated as Detail B in FIG. 6F.

As shown, for example, in FIG. 6F, the outer housing 224 defines an interior 227 accessible via a lower opening 229 defined by the outer housing 224. Thus, the bracket cartridge assembly 230 may be received into the interior 227 via the lower opening 229 such that the vapor outlet 232 of the bracket cartridge assembly 230 is aligned with the vapor outlet 226 of the outer housing 224 and fluid may flow from an interior of the bracket cartridge assembly 230, through the vapor outlet 232, through the vapor outlet 226, and through the first recessed portion 221A and the second recessed portion 221B.

When the mouthpiece component 222 is coupled to the outer housing 224 as shown in, for example, FIG. 3A, the mouthpiece opening 222A may be vertically aligned with the first recessed portion 221A and/or the second recessed portion 221B. Furthermore, as shown in FIG. 6F, the second recessed portion 221A extends to the upper surface 225 of the outer housing 224 such that the upper surface 225 of the outer housing 224 has a recessed edge in the region of the second recessed portion 221A.

Although the recessed sidewall portion 223A is shown as having a first recessed portion 221A having a first width and a second recessed portion 221B having a second width (e.g., see FIG. 6A and FIG. 6F), the recessed sidewall portion 223A may be formed with any suitable shape. Furthermore, although the recessed sidewall portion 223A is shown as having a curved outer profile when transitioning from the sidewall 224 to the recessed sidewall portion 223A and when transitioning from the smaller width portion corresponding to the first recessed portion 221A to the larger width portion corresponding to the second recessed portion 221B, the recessed sidewall portion 223 may have any suitable shape. For example, the recessed sidewall portion 223A may be formed such that an outer edges of the recessed sidewall portion 223A taper away from the vapor outlet 226 from a first width to a second width larger than the first width. In some implementations, the recessed sidewall portion 223A can be formed as a ring-shaped or U-shaped groove. For example, the groove can surround the fill inlet 228A such that vapor may flow from the vapor outlet 226, through the groove via a first or second flow path, and then through the mouthpiece opening 222A of the mouthpiece component 222.

Figure 7:
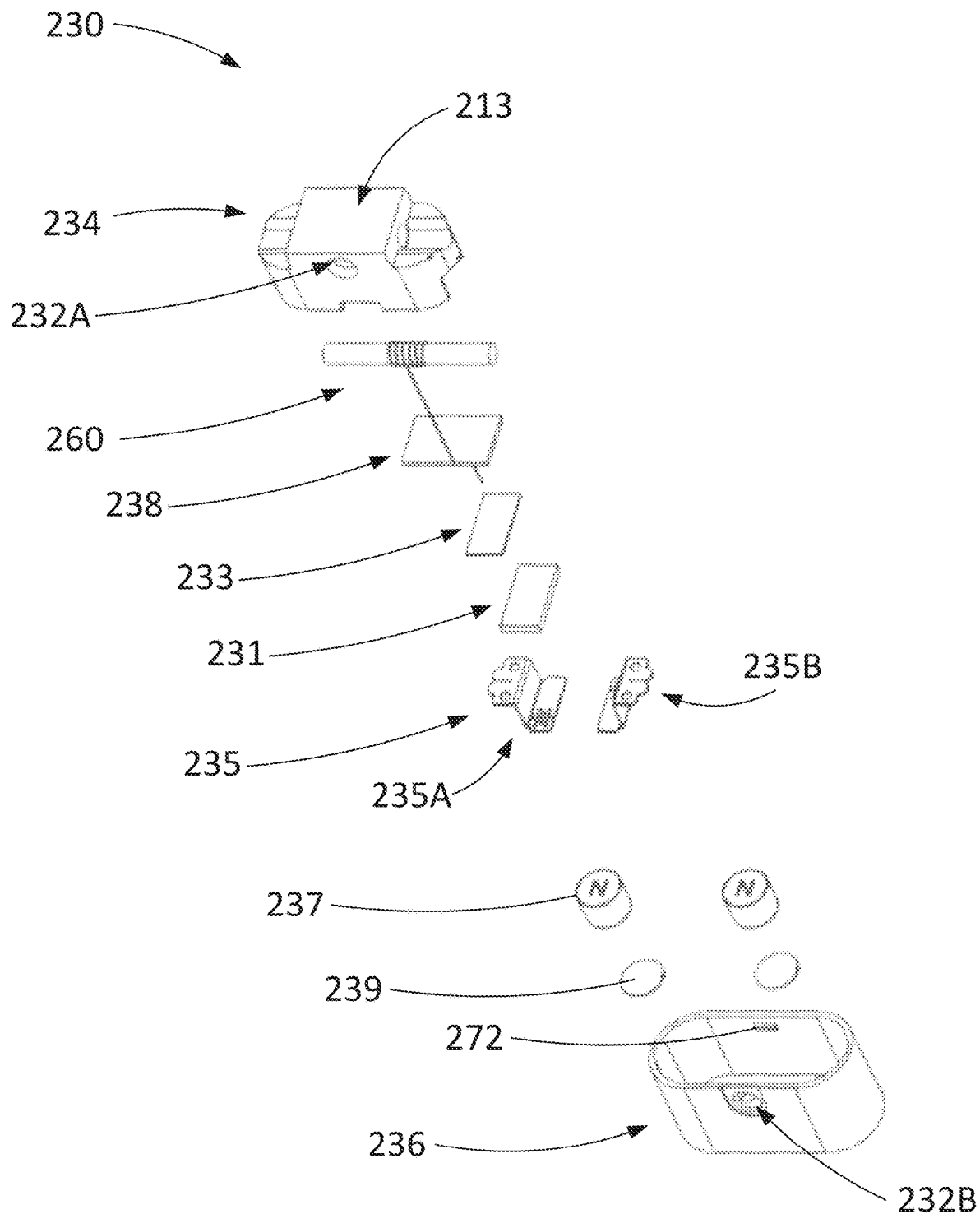
FIG. 7 is an exploded view of a bracket cartridge assembly of FIG. 3.

FIG. 7 is an exploded view of the bracket cartridge assembly 230. As shown in FIG. 7, the bracket cartridge assembly 230 includes an upper portion 234 and a lower portion 236. The lower portion 236 is configured to receive the upper portion 234 within an interior of the lower portion 236 such that a vapor outlet 232A in the upper portion 234 is aligned with a vapor outlet 232B in the lower portion 236, forming the vapor outlet 232. The upper portion 234 includes an upper surface 213 which, when the upper portion 234 is disposed within the interior 227 of the outer housing 224, may, in combination with an interior surface of the outer housing 224, define a reservoir that can be filled with carrier material via the fill inlet 228A in the outer housing 224.

The bracket cartridge assembly 230 may include a wick assembly 260, a filter 238, contact cartridges 235, and magnets 237. Furthermore, the bracket cartridge assembly 230 may include a tracking component 231. The bracket cartridge assembly 230 may also include tracking component tape 233 such that the tracking component 231 may be coupled to the upper portion 234 via the tacking component tape 233. Similarly, the magnets 237 may be attached to the lower portion 236 via magnet tape 239.

The filter 238 may be configured to permit air to be drawn through the filter 238 toward the vapor outlet 232A and to restrict or prevent fluid such as liquid carrier material from leaking out of the bracket cartridge assembly 230 toward the pen assembly 240.

The tracking component 231 may be, for example, an integrated circuit (e.g., Application-Specific Integrated Circuits (ASICs)). The tracking component 231 may be configured to communicate with a control assembly 258 (described below) of the pen assembly 240 when the cartridge assembly 210 is operatively coupled to the pen assembly 240. For example, the tracking component 231 may include contacts configured to be engaged with connectors 259 (described below) (e.g., pogo pins) coupled to or included in a control assembly 258 (described below) (e.g., a printed circuit board) such that the control assembly may access information contained in the tracking component 231. The tracking component 231 may be configured to contain information related to the cartridge assembly 210. In some implementations, the tracking component 231 may contain cartridge identification information corresponding to the cartridge assembly 210 such that the pen assembly 240 may recognize the cartridge identification information. The pen assembly 240 may be configured to wirelessly communicate with a remote server to transmit the cartridge identification information and receive additional information about the cartridge assembly 210 and/or operation instructions with respect to the cartridge assembly 210 based, at least in part, on the cartridge identification information. The pen assembly 240 may be configured to operate or not operate based, at least in part, on the cartridge identification information. For example, the pen assembly 240 may be configured to operate or not operate depending on whether the cartridge identification information matches and/or is within range of an expected value of the pen assembly 240 (e.g., if the cartridge assembly 210 is an appropriate correct cartridge assembly 210, includes a particular carrier material or volume of carrier material, and/or has been engaged with the pen assembly 240 or another pen assembly 240 previously).

In some implementations, the tracking component 231 may contain information related to the specific carrier material disposed in the reservoir defined by the top surface 213 of the upper portion 234 and the inner surface of the outer housing 224. In some implementations, the tracking component 231 may contain information specifying a particular temperature to which the coil 264 (described below) of the wick assembly 260 should be heated via applying a particular current to the coil 264. The particular temperature may be based, at least in part, on the specific carrier material disposed in the reservoir. For example, a first carrier material may achieve optimal vaporization characteristics at a first temperature and a second carrier material may achieve optimal vaporization characteristics at a second temperature. The tracking component 231 may be programmed (e.g., by a seller of the system 200 or the cartridge assembly 210) based on the carrier material in the reservoir such that the tracking component 231 contains information associated with the particular temperature to which the coil 264 is to be heated. In some implementations, the tracking component 231 may contain information specifying a particular heating profile for the coil 264. For example, the heating profile may have a particular ramp-up temperature curve, a particular temperature, duration, and amplitude of modulation, and/or a particular ramp-down temperature curve. The particular temperature and/or heating profile may be based, at least in part, on the particular substance and/or viscosity of the carrier material in the cartridge assembly 210.

Although two magnets 237 are shown in FIG. 7, the bracket cartridge assembly 230 may include any suitable number of magnets. Although FIG. 7 only shows one magnet tape 239, the bracket cartridge assembly 230 may include any suitable amount or number of magnet tape portions such that the magnets 237 can be secured to the lower portion 232B.

Figure 8A:
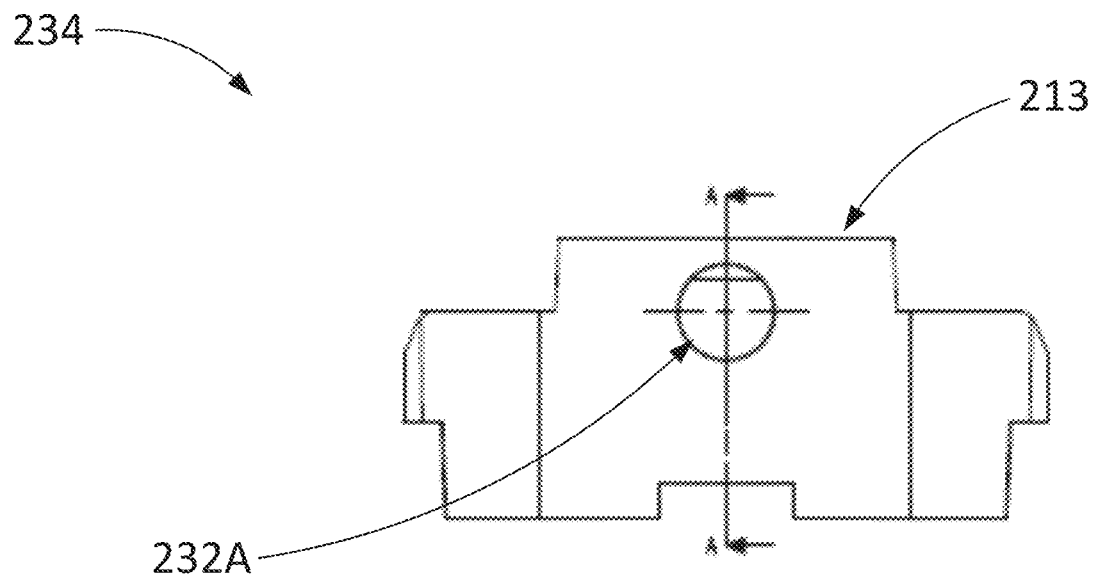
FIGS. 8A-8F are various views of an upper portion shown in FIG. 7. Specifically.
Figure 8B:
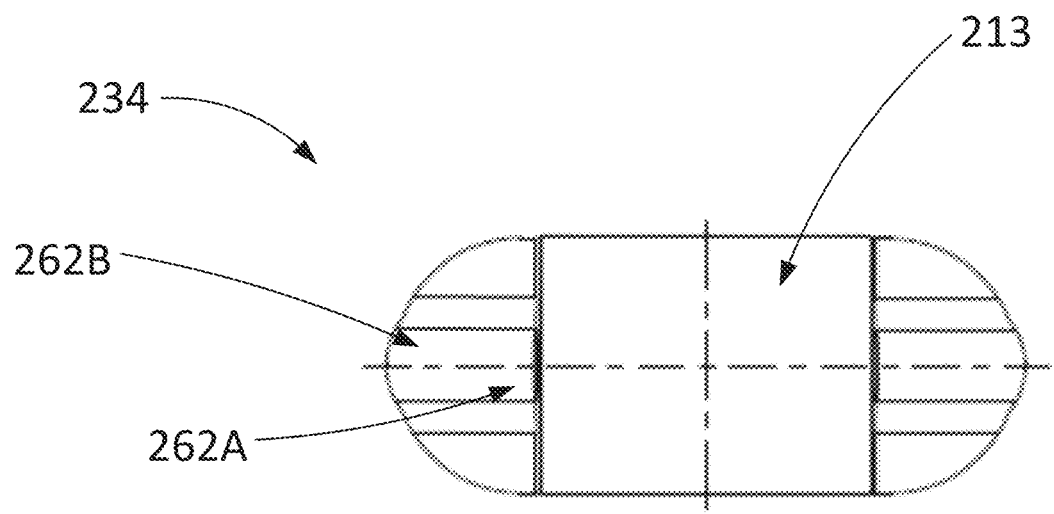
Figure 8C:
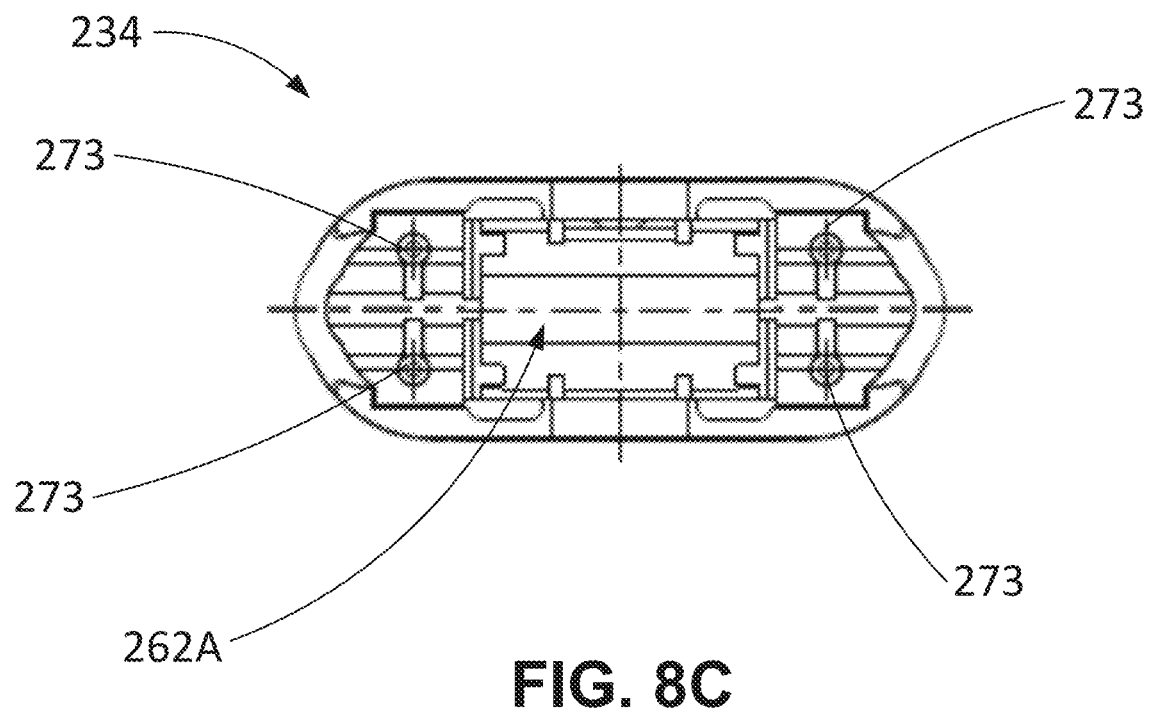
Figure 8D:
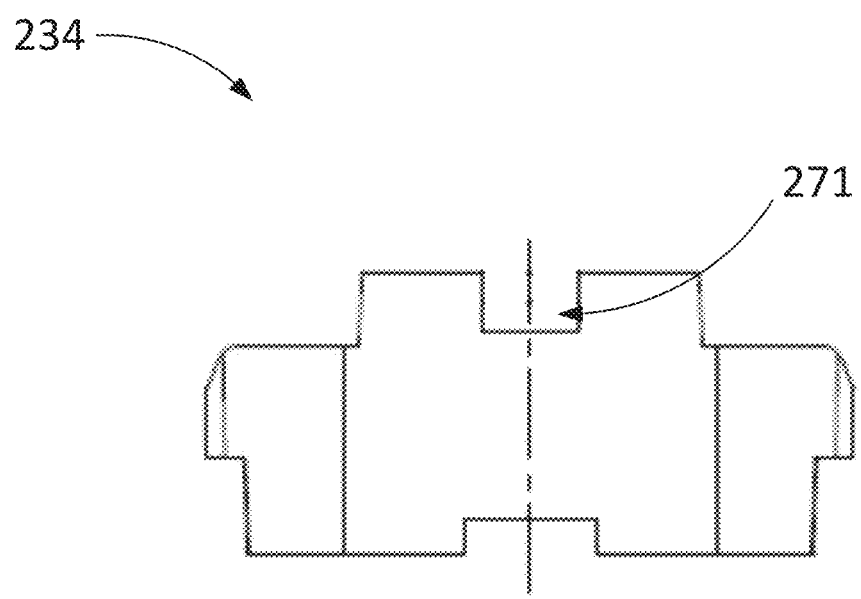
Figure 8E:
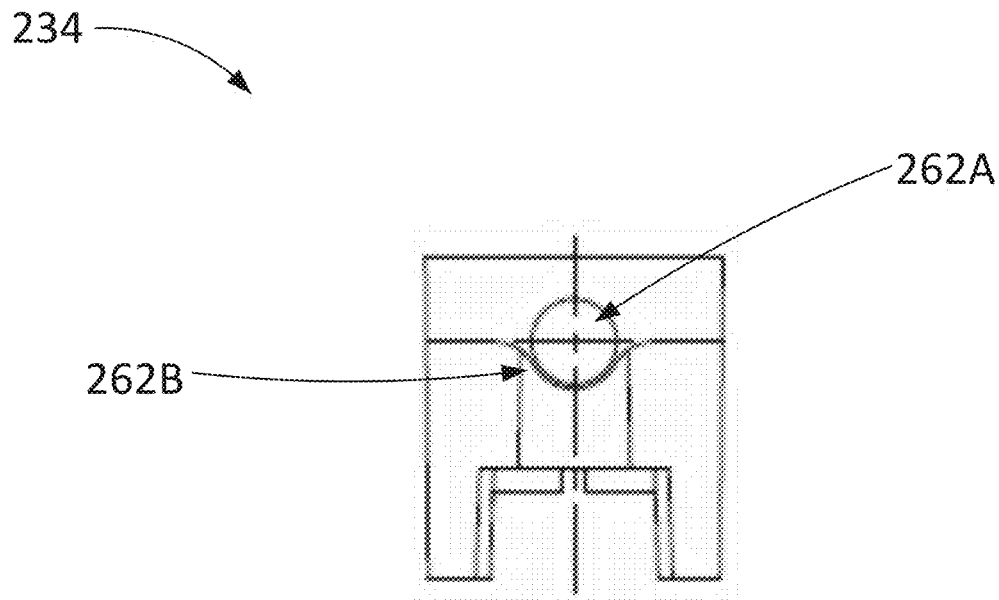
Figure 8F:
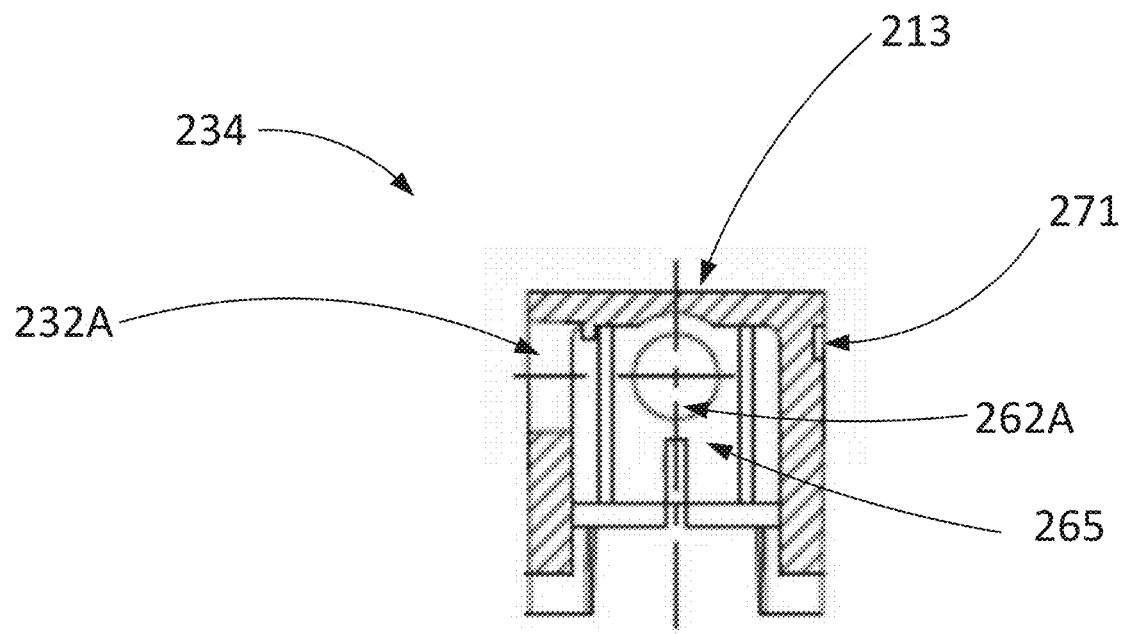

FIGS. 8A-8F are various views of the upper portion 234. Specifically, FIG. 8A is a back view, FIG. 8B is a top view, FIG. 8C is a bottom view, and FIG. 8D is a front view of the upper portion 234. FIG. 8E is a side view of the upper portion 234, and FIG. 8F is a cross-sectional view of the upper portion 234 taken along line A-A in FIG. 8A. As can be seen in various figures, such as FIGS. 8B, 8C and 8E, the upper portion 234 can define wick receiving apertures 262A and wick receiving grooves 262B configured to receive a wick portion of the wick assembly 260. As shown in FIG. 8D, the upper portion 234 defines a recess 271. As shown, the recess 271 may be disposed on an opposite side of the upper portion from the vapor outlet 232A.

As shown in FIG. 8F, for example, the upper portion 234 defines an interior space 265. The interior space 265 is accessible via the wick receiving aperture 262A and the vapor outlet 232A. As shown in FIG. 8C, the upper portion 234 defines a number (e.g., four) of attachment recesses 273 for coupling the upper portion 234 to the contact cartridges 235. For example, the contact cartridges 235 may be coupled to the upper portion 234 via screws disposed in the attachment recesses. In some implementations, any suitable attachment mechanism may be used to couple the contact cartridges 235 to the upper portion 234, such as, for example, adhesive or welding.

Figure 9:
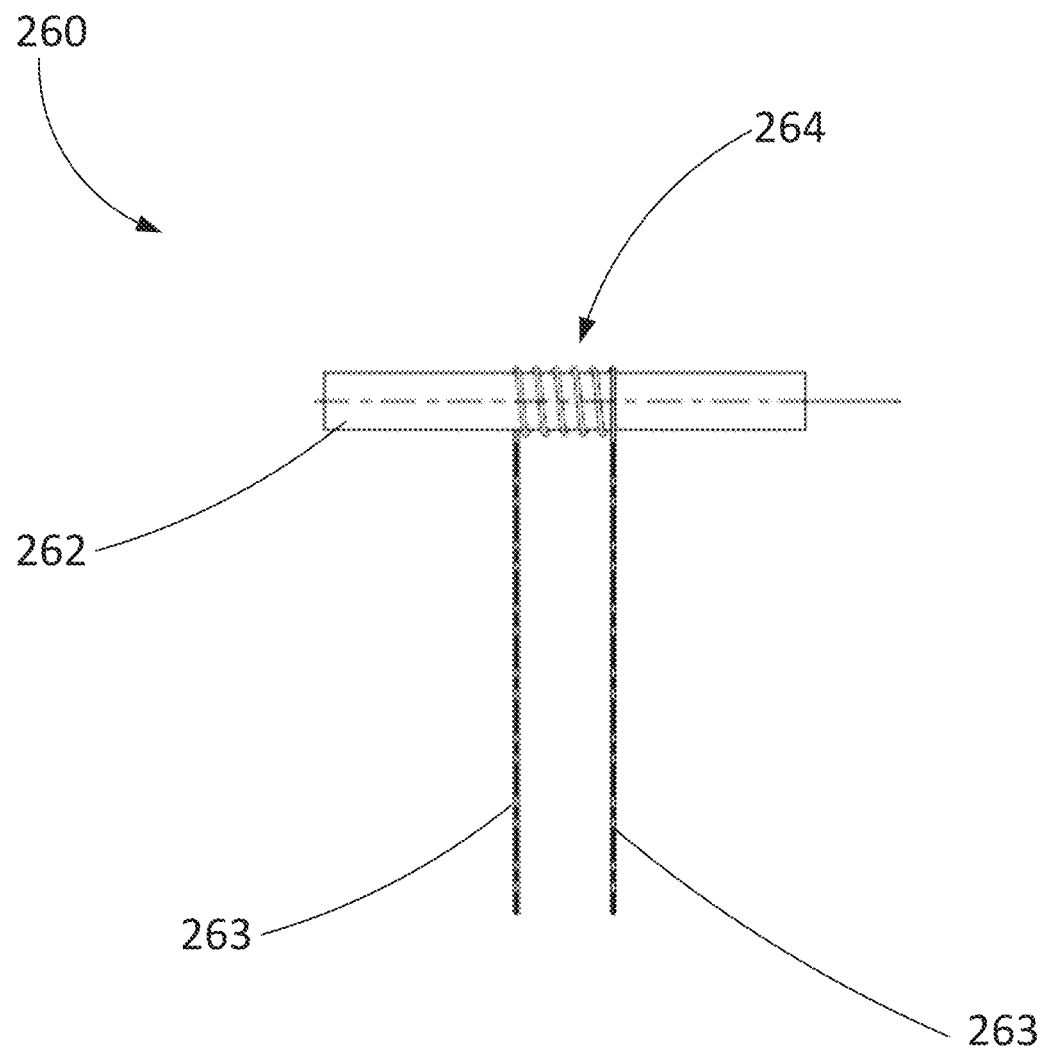
FIG. 9 is a front view of a wick assembly of FIG. 7.

FIG. 9 is a front view of the wick assembly 260. The wick assembly 260 includes a wick 262 and a coil 264. As shown in FIG. 9, the coil includes a portion wrapped around a portion of the wick 262 and two end portions 263 extending away from the wick 262. The wick 262 is configured to transport carrier material toward the portion of the wick 262 adjacent the coil 264.

The coil 264 may be formed of any suitable material such as, for example, titanium. The wick 262 may be formed of any suitable material such as, for example, cotton. For example, the wick 262 may be formed of ekowool cotton. The wick 262 may have any suitable diameter, such as, for example, 1.0 mm. In some embodiments, the wick 262 may have an outer diameter substantially similar to the diameter of the wick receiving apertures 262A of the upper portion 234 such that the wick 262 can be disposed within the wick receiving apertures 262A. In some embodiments, the coil 264 may include six turns around an outer surface of the wick 262 with a pitch of 0.5. In some embodiments, the coil 264 may include any suitable number of turns and having any suitable pitch. In some embodiments, the resistance of the coil may be 1.0Ω.

The wick assembly 260 may be disposed relative to the upper portion 234 such that the portion of the wick 262 adjacent the coil 264 is disposed within the interior portion 265 and the ends of the wick 262 are disposed within the oppositely-disposed wick receiving apertures 262A and are received by the wick receiving grooves 262B of the upper portion 234. Thus, the carrier material in the reservoir defined by the top surface 213 of the upper portion 234 and the interior of the outer housing 224 may be in contact with the ends of the wick 262. The carrier material may then travel through the wick 262 toward the coil 264. In some implementations, the wick 262 may be configured to prevent carrier material within the reservoir from flowing through the wick receiving apertures 262A and into the interior 265 of the upper portion 234 (e.g., leakage of carrier material) except through the wick 264 such that the carrier material is maintained in the reservoir until the carrier material disposed near or adjacent the coil 264 has been vaporized. For example, the wick 262 may have a sufficiently large outer diameter such that the wick 262 is in contact with the edge of the upper portion 234 defining each wick receiving aperture 262A. As the carrier material near or adjacent the coil 264 is vaporized, additional carrier material may travel through the ends of the wick 262 and toward the portion of the wick 262 near the coil 264. The vapor may exit the upper portion 234 through the vapor outlet 232A.

Figure 10A:
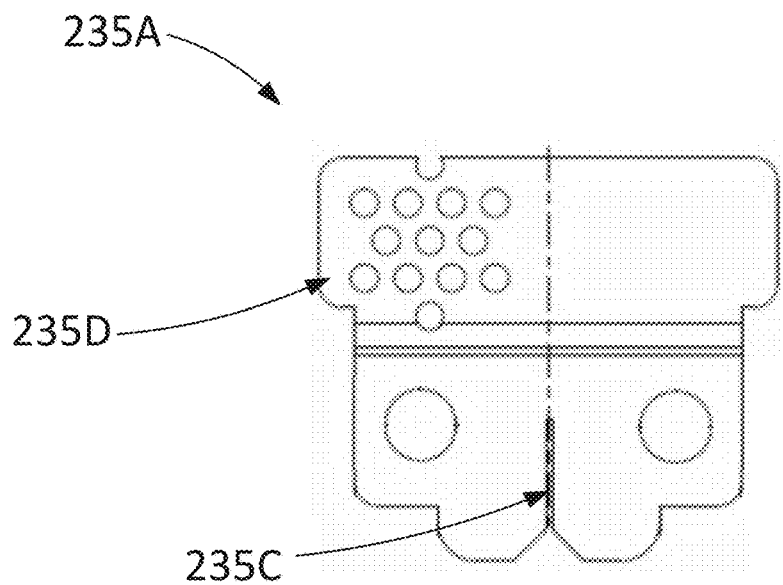
FIGS. 10A and 10B are a bottom view and a side view of a contact cartridge of FIG. 7.
Figure 10B:
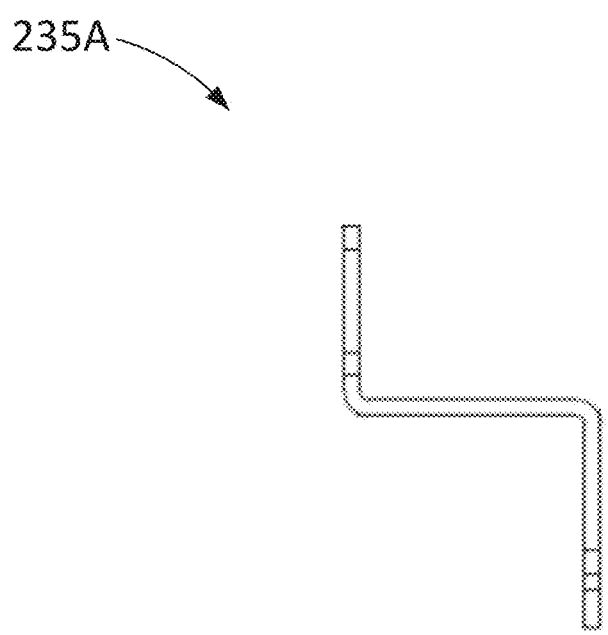

The contact cartridges 235 include a first contact cartridge 235A and a second contact cartridge 235B. FIGS. 10A and 10B are a bottom view and a side view of the first contact cartridge 235A. The first contact cartridge 235A is configured to be engaged with the first end portion 263 of the coil 264 and the second contact cartridge 235B is configured to be engaged with the second end portion 263 of the coil 264. For example, the first contact cartridge 235A may define a slit 235C. The first end portion 263 may be threaded through the slit 235C such that the coil 264 is maintained in contact with the first contact cartridge 235A. Due to the engagement between the first end portion 263 and the first contact cartridge 235A (and the similar engagement between the second end portion 263 and the second contact cartridge 235B), heating the first contact cartridge 235A and/or the second contact cartridge 235B may cause corresponding heating of the coil 264.

The first contact cartridge 235A and/or the second contact cartridge 235B may each define one or more through-holes such that air may be drawn from the pen assembly 240 to the vapor outlet 232B via the one or more through-holes of the first contact cartridge 235A and/or the second contact cartridge 235B. For example, as shown in FIG. 10A, the first contact cartridge 235A may define a plurality of through-holes 235D. Although not shown in FIGS. 7 and 10A, the first contact cartridge 235A and the second contact cartridge 235B may each also include a recess or opening configured to receive a portion of a connector 259 (described below) such that the first contact cartridge 235A and the second contact cartridge 235B may each engage with a connector 259 and such that a temperature of the first contact cartridge 235A and the second contact cartridge 235B (and, thus, the temperature of the coil 264) may be controlled, at least in part, by the temperature of and/or current flowing through the connectors 259 engaged with each of the first contact cartridge 235A and the second contact cartridge 235B.

Figure 11A:
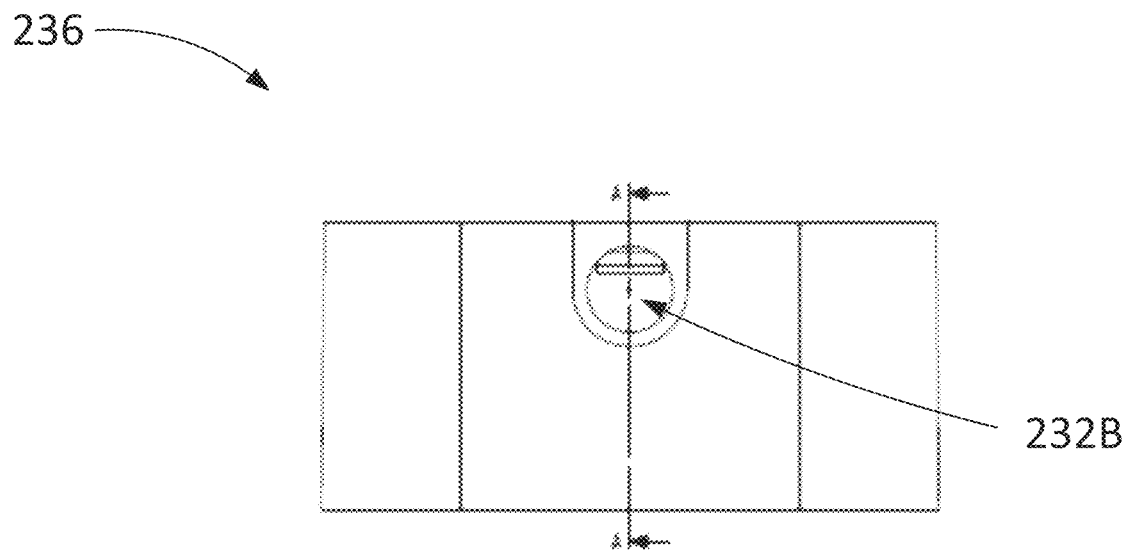
Figure 11B:
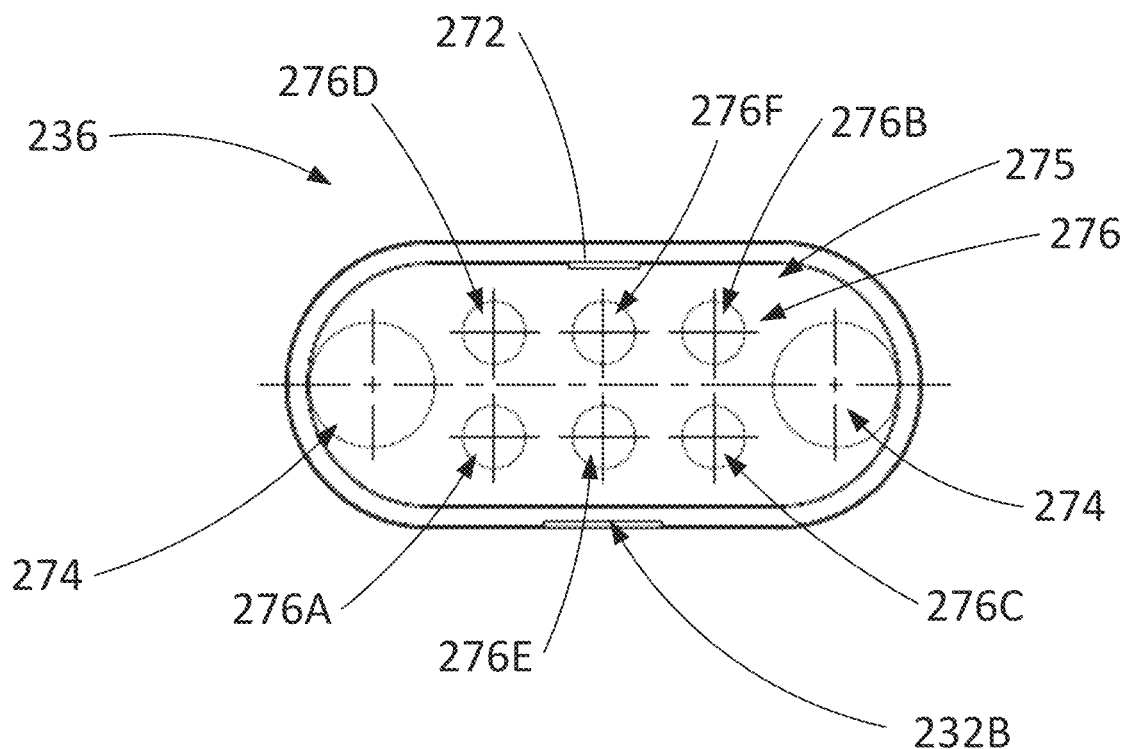
Figure 11F:
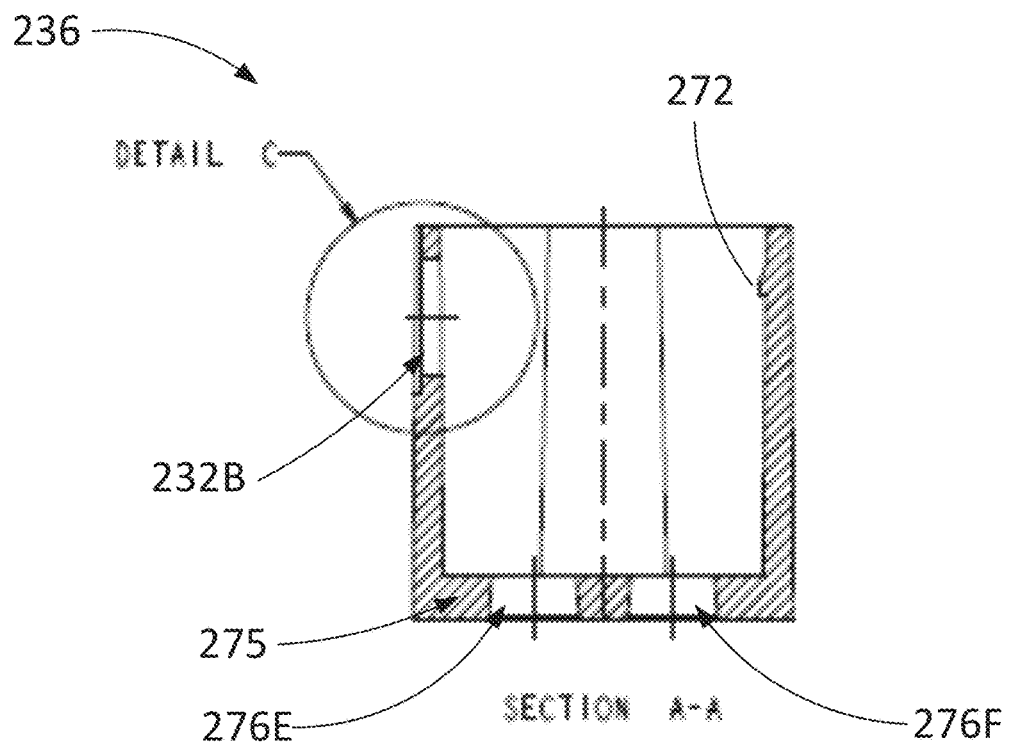
Figure 11G:
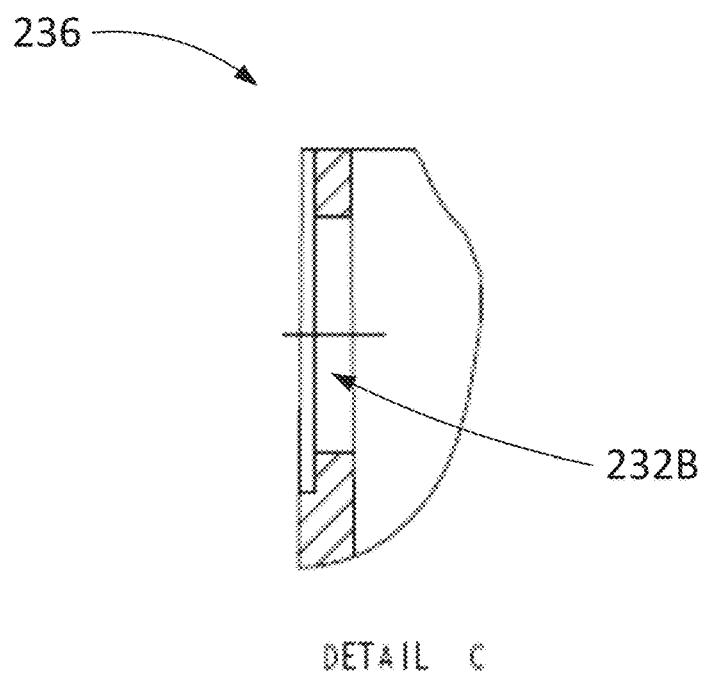

FIGS. 11A-11G are various views of the lower portion 236. Specifically, FIG. 11A is a back view of the lower portion 236, FIG. 11B is a top view of the lower portion 236, FIG. 11C is a bottom view of the lower portion 236, FIG. 11D is a side view of the lower portion 236, and FIG. 11E is a front view of the lower portion 236. FIG. 11F is a cross-sectional view taken along line A-A in FIG. 11A. FIG. 11G is an enlarged view of the portion of FIG. 11F identified as Detail C.

The lower portion 236 includes a bottom surface 275. As shown in FIGS. 11B, 11C, and 11F, the lower portion 236 defines a number of openings 276 in the bottom surface 275 of the lower portion 236. For example, the lower portion 236 may define six openings 276. A number of the openings 276 may be configured such that air may be drawn through the openings 276 to the vapor outlet 232. A number of the openings 276 may be shaped and sized to receive connectors 259 (described below) of a connection assembly 256 (described below) when the cartridge assembly 210 is operatively coupled to the pen assembly 240. For example, as shown in FIGS. 11B and 11C, the openings 276 may include a first opening 276A and a second opening 276B configured such that air may be drawn through the first opening 276A and the second opening 276B. The openings 276 may include a third opening 276C and a fourth opening 276D shaped and sized to receive connectors 259 (described below) such that the connectors may operatively engage the first contact cartridge 235A and the second contact cartridge 235B, respectively. The openings 276 may include a fifth opening 276E and a sixth opening 276F shaped and sized to receive connectors 259 (described below) such that the connectors 259 may operatively engage the tracking component 231.

Additionally, as shown in FIG. 11B, the lower portion 236 defines a number of magnet receiving recesses 274. The number of magnet receiving recesses 274 may correspond to the number of magnets 237 included in the bracket cartridge assembly 230. For example, the lower portion 236 may define two magnet receiving recesses 274 to receive two magnets 237. The magnets 237 may be coupled to the lower portion 236 via magnet tape 239 disposed within the magnet receiving recesses 274.

As shown in, for example, FIGS. 11B and 11F, the lower portion 236 includes a projection 272 extending into the interior of the lower portion 236 from an inner surface of a sidewall of the lower portion 236. The projection 272 is sized and positioned to be disposed within the recess 271 of the upper portion 234 such that the upper portion 234 and the lower portion 236 may be secured to each other (e.g., via a snap fit).

Figure 12A:
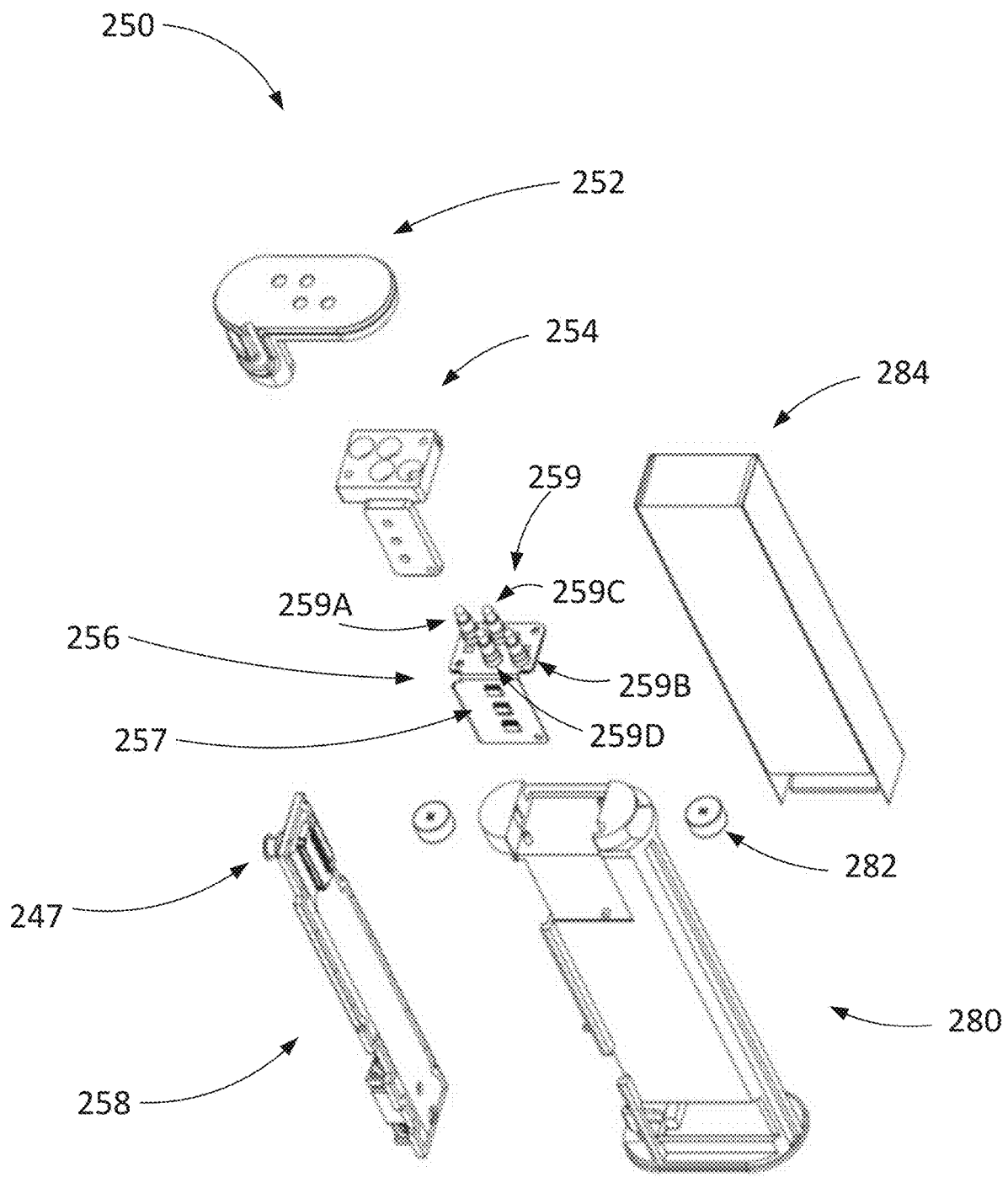
FIG. 12A is an exploded perspective view of the bracket assembly of FIG. 3.

FIG. 12A is an exploded perspective view of the bracket assembly 250 of the pen assembly 240. FIG. 12B is a back view, FIG. 12C is a front view, FIG. 12D is a top view, and FIG. 12E is a bottom view of the pen housing 242 of the pen assembly 240. FIG. 12F is a right side view and FIG. 12G is a cross-sectional illustration taken along line Y-Y in FIG. 12B of the pen housing 242. As shown in FIG. 12A, the bracket assembly 250 includes a cap 252, a cap bracket 254, a connection assembly 256, and a bracket 280. The bracket assembly 250 also includes a power supply 284 and a control assembly 258. The bracket assembly 250 also includes a number of magnets 282.

The power supply 284 can include any suitable battery or fuel cell, for example having high-drain characteristics. The control assembly 258 may include, for example, a printed circuit board. The control assembly 258 may include a memory and a processor.

The memory may include any electronic component capable of storing electronic information. The term memory may refer to various types of processor-readable media such as random access memory (RAM), read-only memory (ROM), non-volatile random access memory (NVRAM), programmable read-only memory (PROM), erasable programmable read only memory (EPROM), electrically erasable PROM (EEPROM), flash memory, magnetic or optical data storage, registers, etc. Memory is said to be in electronic communication with a processor if the processor can read information from and/or write information to the memory. Memory that is integral to a processor is in electronic communication with the processor.

The processor can include one or more of: a general purpose processor, a central processing unit (CPU), a microprocessor, a digital signal processor (DSP), a controller, a microcontroller, a state machine and so forth. Under some circumstances, a "processor" may refer to an application specific integrated circuit (ASIC), a programmable logic device (PLD), a field programmable gate array (FPGA), etc. The term "processor" may refer to a combination of processing devices, e.g., a combination of a DSP and a microprocessor, a plurality of microprocessors, one or more microprocessors in conjunction with a DSP core or any other such configuration.

The control assembly 258 may also include one or more of: a GPS receiver, an antenna, heater control circuitry, and/or a transceiver for wireless (e.g., Bluetooth) communication with a command center or other remote compute device (such as a mobile device of a user). The control assembly 258 may also include one or more of: a pressure sensor 247, a temperature sensor, a position sensor, an orientation sensor, etc.

Figure 13A:
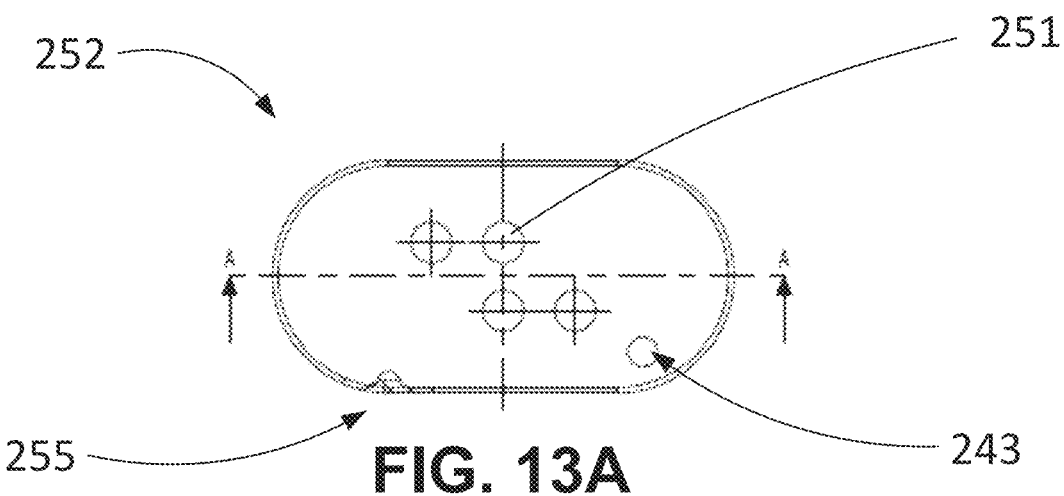
FIGS. 13A-13H are various views of a cap of the bracket assembly of FIG. 12. Specifically.
Figure 13B:
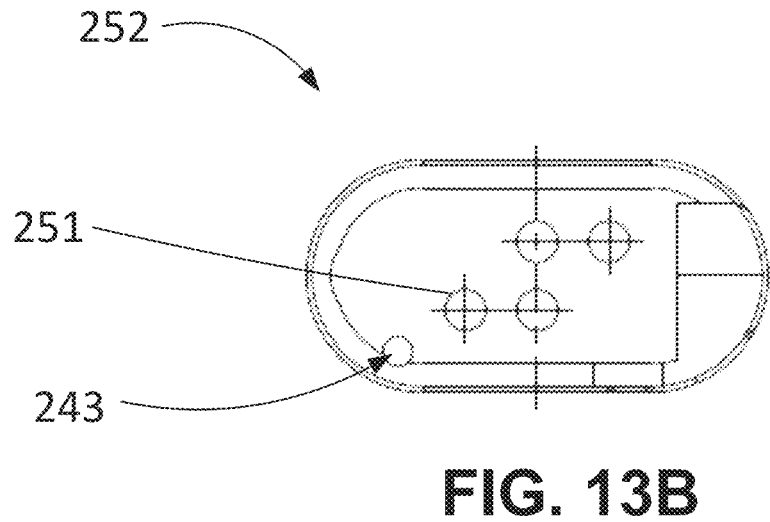
Figure 13C:
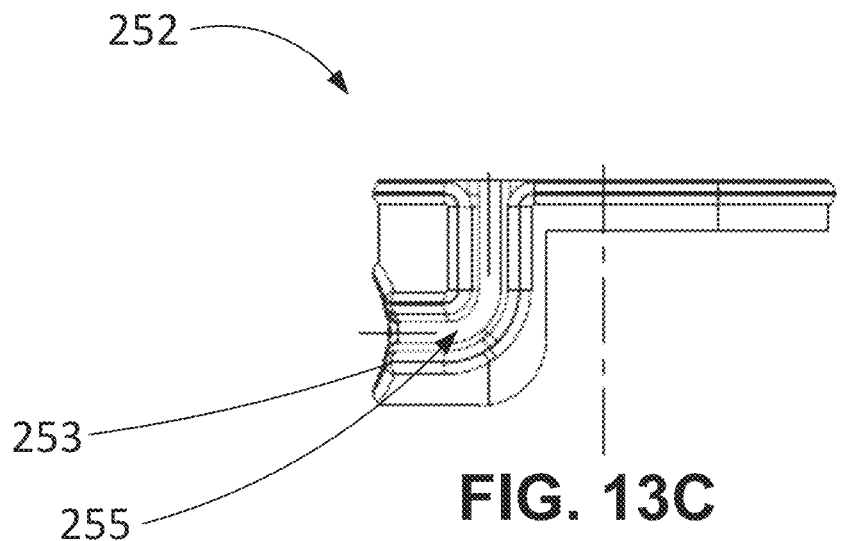
Figure 13D:
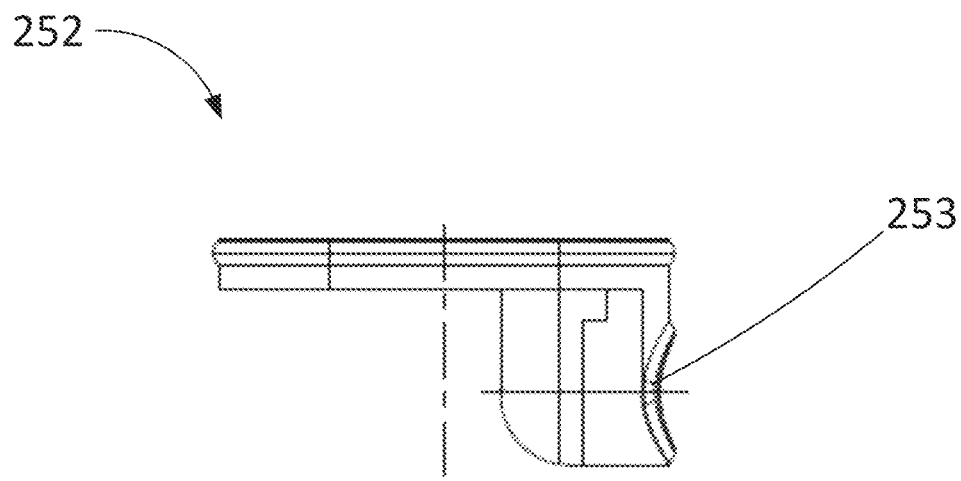
Figure 13E:
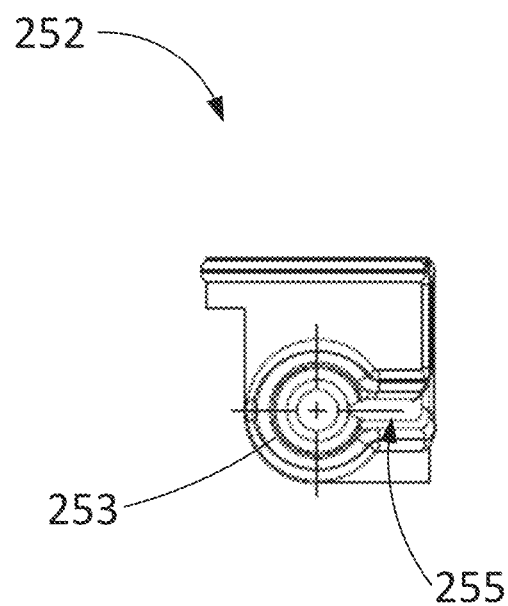
Figure 13F:
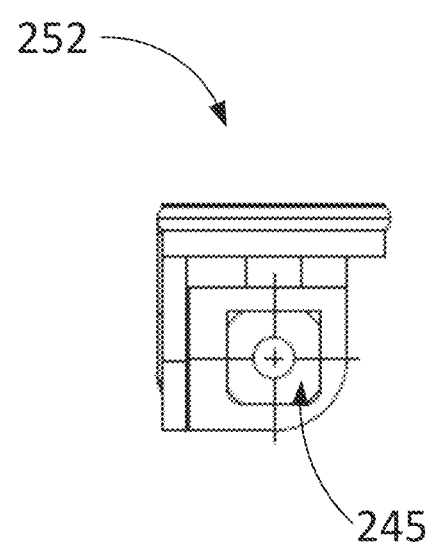
Figure 13G:
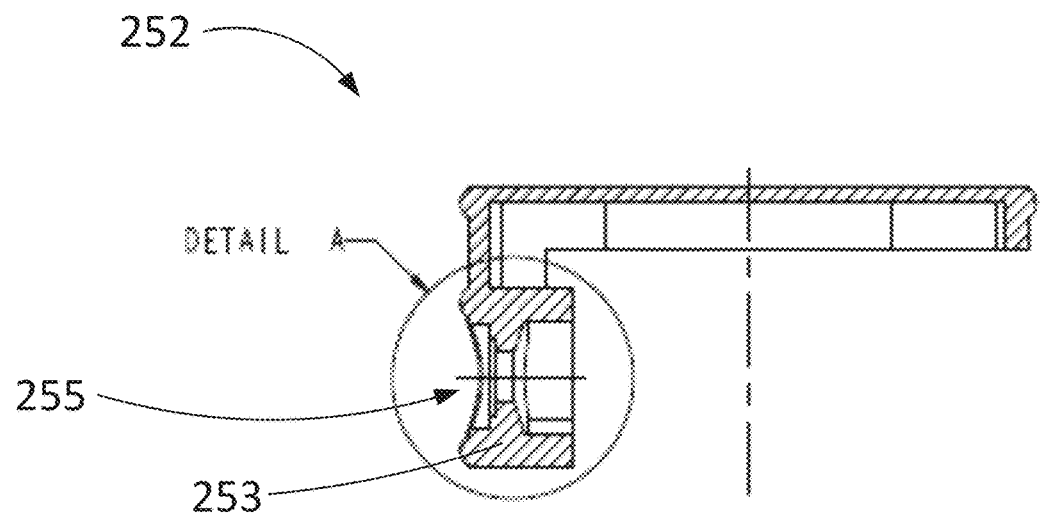
Figure 13H:
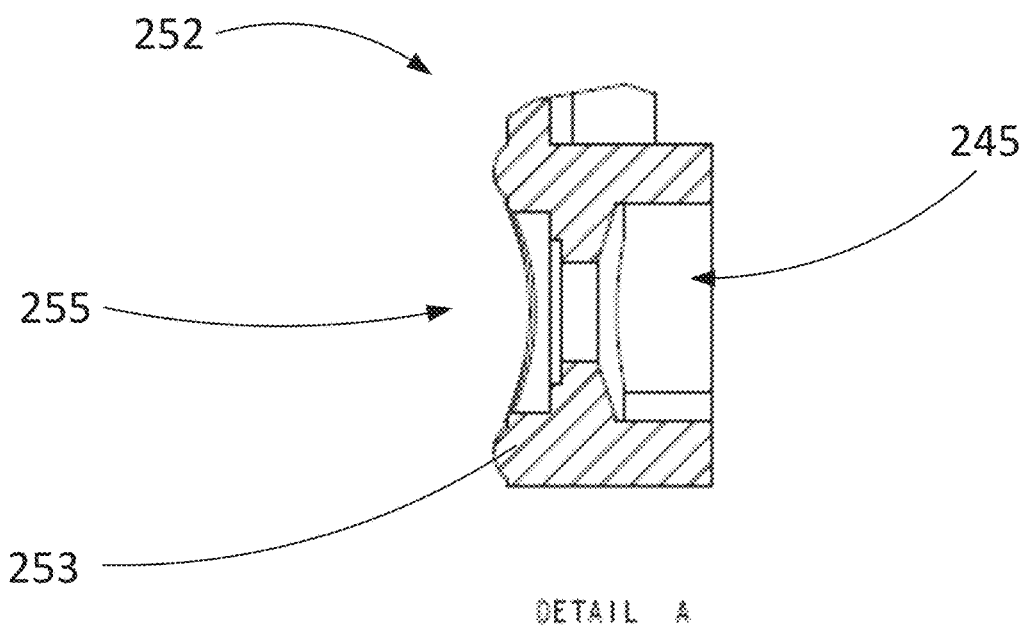

FIGS. 13A-13H are various views of the cap 252 of the bracket assembly 250. Specifically, FIG. 13A is a top view of the cap 252, FIG. 13B is a bottom view of the cap 252, FIG. 13C is a back view of the cap 252, and FIG. 13D is a front view of the cap 252. FIG. 13E is a right side view and FIG. 13F is a left side view, respectively, of the cap 252. FIG. 13G is a cross-sectional illustration of the cap 252 taken along line A-A in FIG. 13A. FIG. 13H is an enlarged view of the portion of FIG. 13G identified as Detail A. As shown in FIGS. 13A and 13B, for example, the cap 252 defines a number (e.g., four) of openings 251. The openings 251 may be configured to receive connectors 259 (described below) of the connection assembly 256.

As shown in FIGS. 13A, 13C, and 13G, for example, the cap 252 includes an extension portion 253 defining an airflow groove 255. In some implementations, the extension portion 253 may be shaped such that, when the bracket assembly 250 is disposed within a pen housing 242 and coupled to the cartridge assembly 210, air may be drawn from an area external to the pen housing 242, through the inlet 244, through the groove 255, and into the interior of the upper portion 234. As shown in FIG. 13H, the extension portion 253 may be configured to form a seal with the inner surface of the pen housing 242. As described above, in some implementations, the pen housing 242 does not define an inlet 244. The cap 252 may define an airflow opening 243 configured such that air can be drawn through the airflow opening 243 toward the vapor outlet 232. As shown in FIGS. 13H and 13F, the cap 252 may also define a sensor recess 245 such that, for example, the pressure sensor 247 may be engaged with the sensor recess 245 of the cap 252. The pressure sensor 247 may be in fluid communication with the interior regions of the system 200 via the airflow groove 255. For example, the airflow groove 255 may be in fluid communication with other interior regions of the system 200 such that the pressure sensor 247 may sense a change in air pressure within the system 200 (e.g., due to a drawing action by a user on the mouthpiece opening 222A) by sensing a change in air pressure within the airflow groove 255.

Figure 14A:
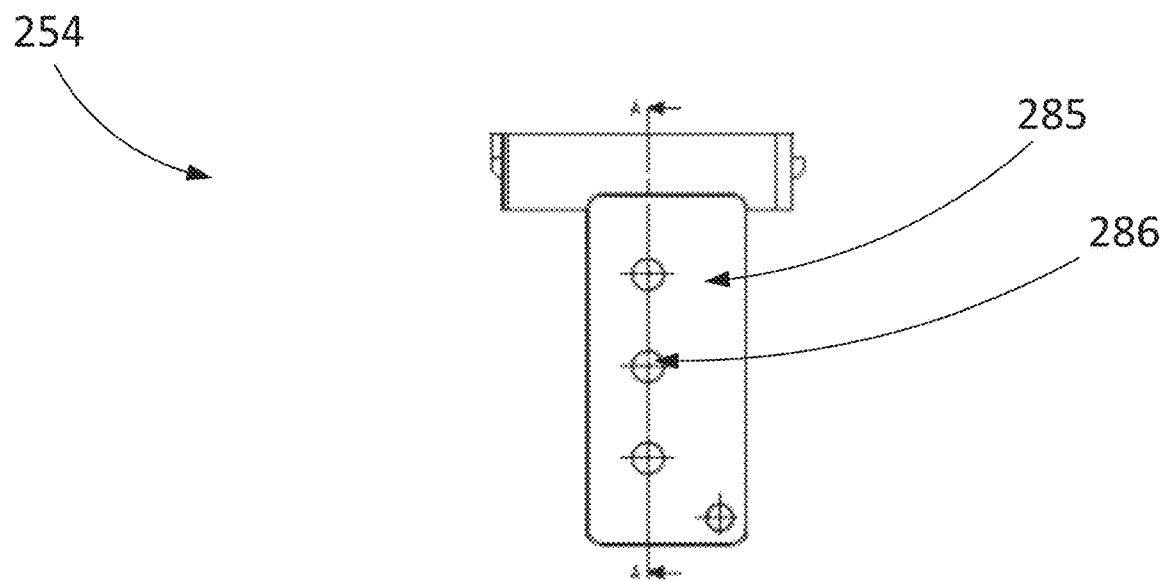
FIGS. 14A-14D are various views of a cap bracket of the bracket assembly of FIG. 12. Specifically.
Figure 14B:
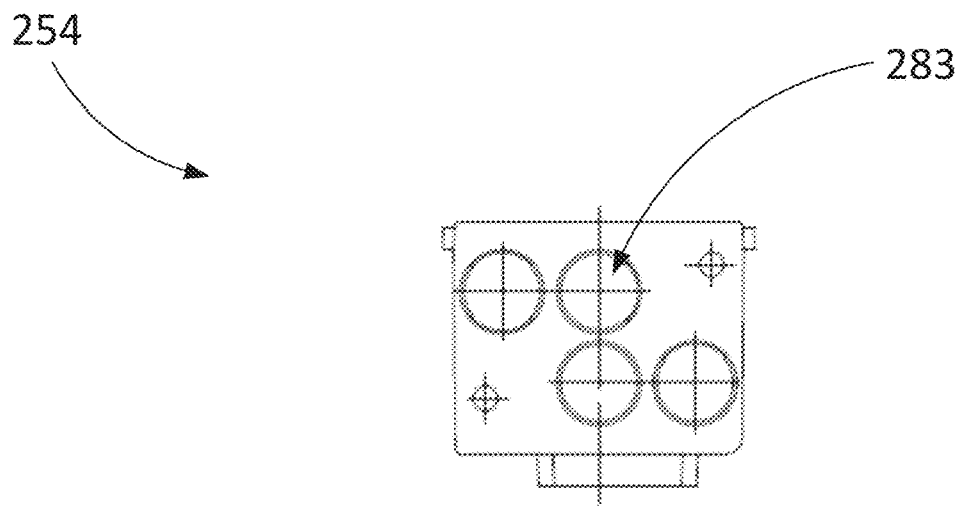
Figure 14C:
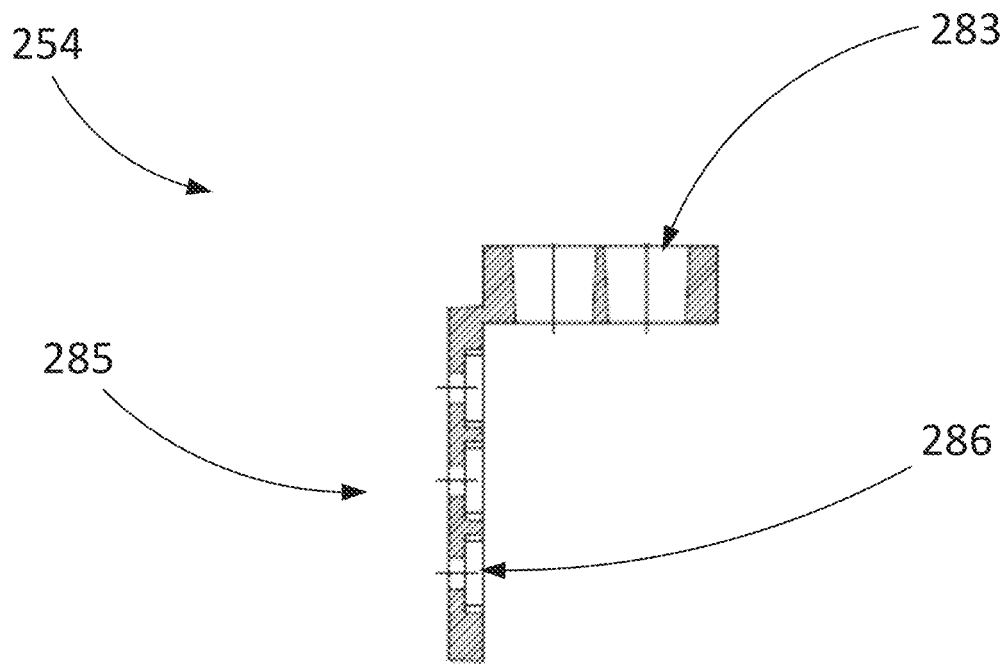
Figure 14D:
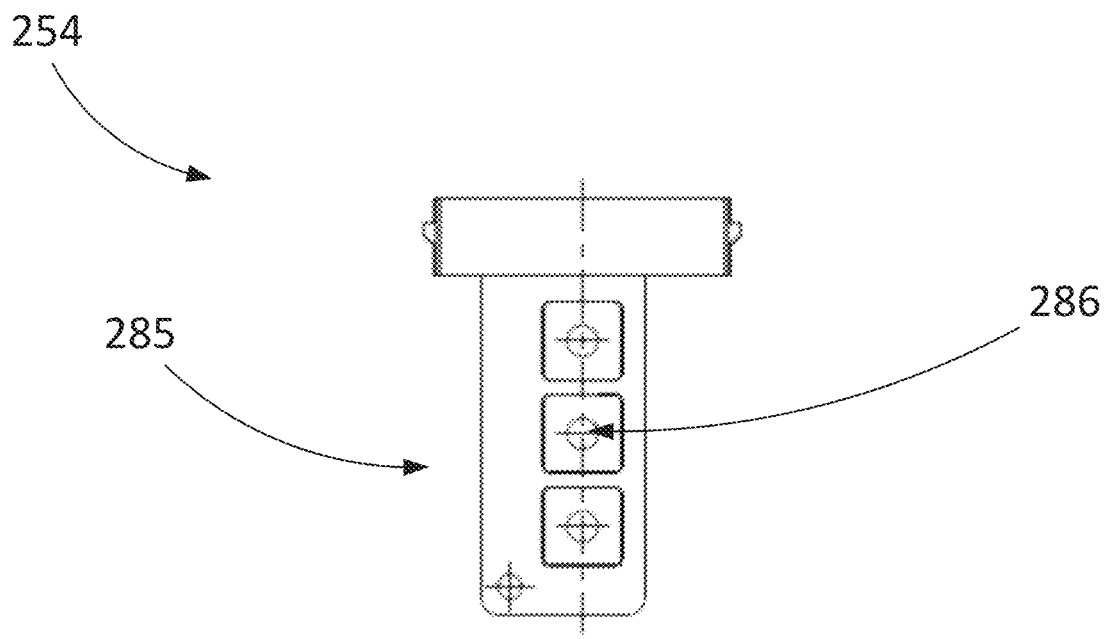

FIGS. 14A-14D are various views of the cap bracket 254 of the bracket assembly 250. Specifically, FIG. 14A is a back view of the cap bracket 254 and FIG. 14B is a top view of the cap bracket 254. FIG. 14C is a cross-sectional view of the cap bracket 254 taken alone line A-A in FIG. 14A. FIG. 14D is a front view of the cap bracket 254.

As shown in FIG. 14A, for example, the cap bracket 254 includes an indicator extension 285. The indicator extension 285 defines a number (e.g., three) of apertures 286. The apertures 286 are configured to be disposed in alignment with the indicator cover elements 246 of the pen housing 242 when the bracket assembly 250 is disposed within the pen housing 242. As shown in FIG. 14C, the apertures 286 may each be shaped to receive an indicator feature 257 (described below) of the connection assembly 256.

As can be seen FIG. 14B, for example, the cap bracket 254 also defines a number (e.g., four) of openings 283 in an upper surface of the cap bracket 254. The openings 283 are configured to be aligned with the openings 251 in the cap 252 when the cap 252 and the cap bracket 254 are coupled to each other and the bracket 280 and are disposed within the pen housing 242. The openings 283 are configured to receive the connectors 259 of the connection assembly 256 (described below).

As shown in FIG. 12A, the connection assembly 256 may include a number of connectors 259. For example, as shown, the connection assembly 256 may include four connectors 259. The connectors 259 may be, for example, pogo pins. The connectors 259 may be configured to operatively couple the control assembly 258 to components of the cartridge assembly 210. For example, a first connector 259A and a second connector 259B may be configured to operatively couple the control assembly 258 to the first contact cartridge 235A and the second contact cartridge 235B, respectively, such that the control assembly 258 may control the temperature of the first contact cartridge 235A and the second contact cartridge 235B when the first connector 259A and the second connector 259B contact the first contact cartridge 235A and the second contact cartridge 235B, respectively, thereby controlling the temperature of the coil 264. A third connector 259C and a fourth connector 245D may be configured to couple the control assembly 258 to the tracking component 231 of the cartridge assembly 210 such that the control assembly 258 may obtain information from the tracking component 231 when the third connector 259C and/or the fourth connector 245D are engaged with the tracking component 231.

The connection assembly 256 may include indicator features 257. The indicator features 257 may include, for example, light emitting diodes (LEDs). The indicator features 257 may be configured to transmit light through the apertures 286 defined by the cap bracket 254 and through the indicator cover elements 246 coupled to the pen housing 242. The indicator features 257 may be configured to indicate, for example, a fill level of the reservoir of the cartridge assembly 210. The connection assembly 256 may include any suitable number of indicator features 257, such as, for example, three. In some implementations, the connection assembly 256 may be operatively coupled to the control assembly 258 such that one or more of the indicator features 257 illuminates such that a user can determine whether the fill level of the reservoir of the cartridge assembly 210 is full or mostly full (e.g., 100% or between 75% and 100%), empty or near empty (e.g., 0% or between 25% and 0%), or at a medium amount or within a medium range between full and empty (e.g., 50% or between 75% and 25%). For example, all three of the indicator features 257 may be illuminated when the reservoir of the cartridge assembly 210 is full or almost full. Two of the three indicator features 257 may be illuminated when the reservoir of the cartridge assembly 210 is within a medium range. One of the three indicator features 257 may be illuminated when the reservoir of the cartridge assembly 210 is low or empty.

Figure 15A:
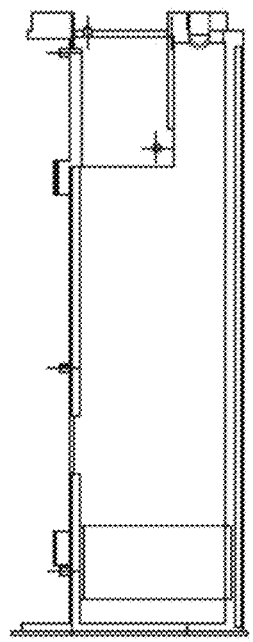
FIGS. 15A-15F are various views of a bracket of the bracket assembly of FIG. 12. Specifically.
Figure 15B:
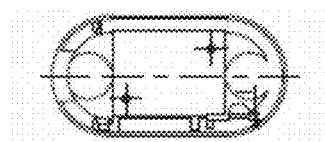
Figure 15C:
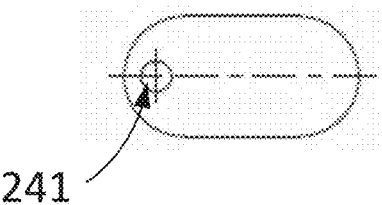
Figure 15D:
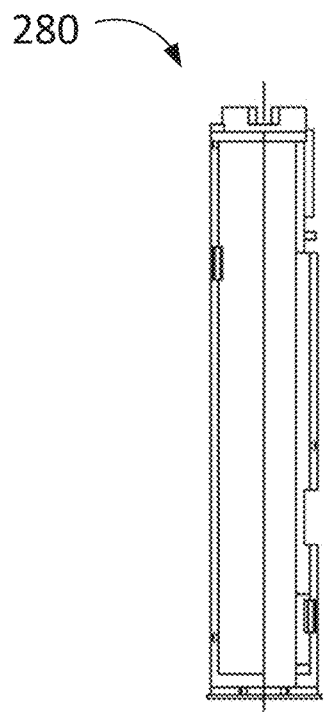
Figure 15E:
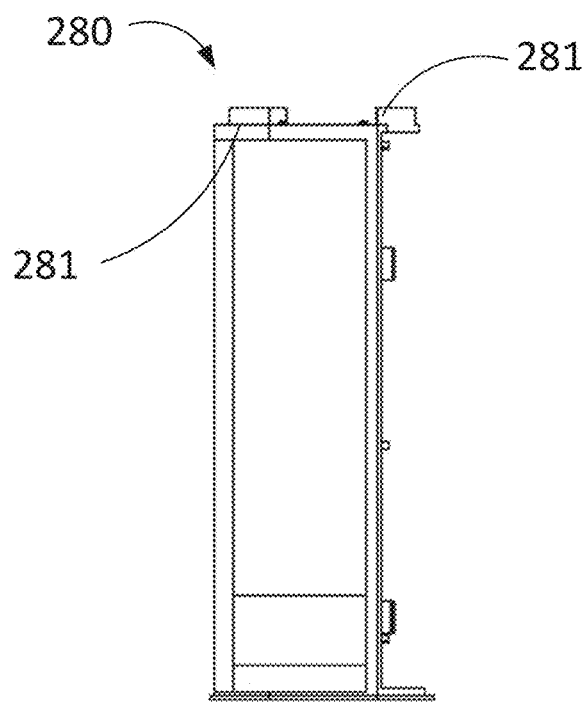
Figure 15F:
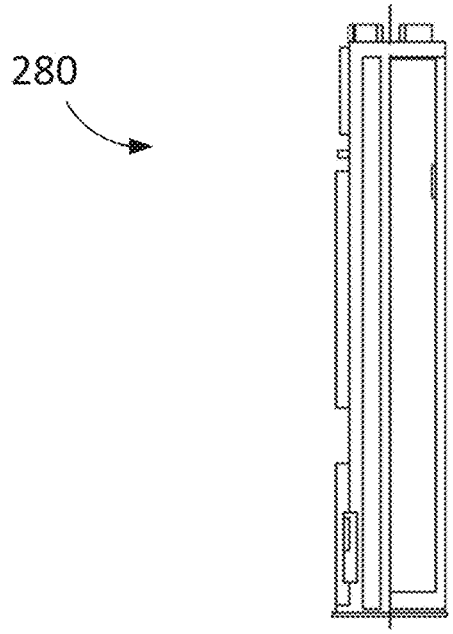

FIGS. 15A-15F are various views of the bracket 280. Specifically, FIG. 15A is a back view of the bracket 280, FIG. 15B is a top view of the bracket 280, and FIG. 15C is a bottom view of the bracket 280. FIG. 15D is a right side view of the bracket 280, FIG. 15E is a front view of the bracket 280, and FIG. 15F is a left side view of the bracket 280. As shown in FIG. 15E, for example, the bracket 280 may define a number of magnet receiving apertures 281 shaped and sized to receive the magnets 282. Furthermore, the bracket 280 is configured to be coupled to the battery 284 and the control assembly 258. As shown in FIG. 15C, a bottom portion of the bracket 280, which may form at least a bottom portion of the system 200 as shown in FIG. 2F, defines the bottom opening 241 (described above) such that air may be drawn into an interior of the system 200 via the bottom opening 241 and/or such that a charging device may be reversibly engaged with a power supply of the system (e.g., power supply 284 discussed below)

In use, the cartridge assembly 210 can be operatively coupled to the pen assembly 240 by inserting the outer housing 224 into the pen housing 242 and translating the cartridge assembly 210 toward the cap 252 of the pen assembly 240 such that the connectors 259 of the pen assembly 259 are received by the openings 276 in the bottom surface 275 of the lower portion 236. When received within the opening 276D and the opening 276C in the bottom surface 275 of the lower portion 236, the first connector 259A and the second connector 259B are in contact with the coil 264 of the wick assembly 260. Furthermore, the third connector 259C and the fourth connector 259D may be received by the openings 276F and 276E such that the third connector 259C and the fourth connector 259D are in operative contact with the tracking component 231. Furthermore, when the cartridge assembly 210 is fully received within the pen housing 242, the mouthpiece assembly 220 may be in contact with the pen housing 242 and an interior surface of the pen housing 242, in combination with the recessed sidewall portion 223A, may collectively form an expansion chamber having a first expansion portion corresponding to the first recessed portion 221A of the outer housing 224 and a second expansion portion corresponding to the second recessed portion 221B of the outer housing 224.

The user may draw fluid through the mouthpiece opening 222A by applying the user's mouth to the mouthpiece assembly and applying negative pressure to the mouthpiece opening 222A (e.g., via by sucking). In implementations including a pressure sensor 247 in communication with the control assembly 258, the negative pressure may trigger the pressure sensor 247. In response to receiving indication of negative pressure from the pressure sensor 247, the control assembly 258 may actuate heater control circuitry of the control assembly 258 such that a current is passed through the connector 259A and the connector 259B, through the contact cartridges 235, and through the coil 264 and the coil 264 is heated to a particular temperature. The pressure sensor 247, in combination with the control assembly 258, may be configured to determine that flow is occurring through the mouthpiece opening 222A and the flow rate of the flow. In some embodiments, the current provided to the coil 264 may be based, at least in part, on the flow rate and/or duration of flow as determined based on the change in pressure sensed by the pressure sensor 247. Alternatively, in implementations including an activation button (not shown) in communication with the control assembly 258, the user may actuate the activation button such that the control assembly 258, in response to receiving an actuation signal from the activation button, may actuate heater control circuitry of the control assembly 258 such that a current is passed through the coil 264 and the coil 264 is heated to a particular temperature.

With the coil 264 heated to the particular temperature and in contact with the wick containing at least a portion of the carrier material, the coil 264 may vaporize a portion of the carrier material. The vaporized carrier material, or vapor, travels from the interior 265 of the lower portion 236, through the pipe chimney 212, through the first expansion portion, through the second expansion portion, and out of the mouthpiece opening 222A. As the vapor exits the mouthpiece opening 222A, the user may inhale the vapor.

As the carrier material is converted to vapor by the coil 264, the amount of carrier material remaining in the reservoir will decrease. When the amount of carrier material remaining in the reservoir decreases below a threshold level (e.g., between 0 and 10% of the original amount), the user may remove the cartridge assembly 210. The user may then insert a second cartridge assembly 210 having carrier material in a reservoir of the cartridge assembly 210 above a threshold level such that carrier material from the second cartridge assembly 210 may be vaporized and inhaled. The user may repeatedly remove cartridge assemblies and install new cartridge assemblies to the same pen assembly 240, disposing of each cartridge assembly when the carrier material within a reservoir of each respective cartridge assembly drops below a threshold level.

The pen housing 242 and the mouthpiece component 222 may be formed of any suitable material. For example, the pen housing 242 and the mouthpiece component 222 may include ceramic, heat-resistant plastic, and/or anodized aluminum. In some embodiments, the mouthpiece component 222 and/or the pen housing 242 may be formed of ceramic to improve the user experience (e.g., improved feel on a user's mouth). In some implementations, due to being formed of ceramic having sufficiently insulative properties, the interior of the system 200 (e.g., the interior of the upper portion 234 near the coil 264 and/or the portion of the pen assembly 240 near the heater control circuitry of the control assembly 258) may not need to include any insulation to prevent an outer surface of the system 200 from rising above a threshold temperature. For example, in some implementations, the coil 264 may be configured to be heated to a temperature ranging between about 250 degrees Celsius and about 500 degrees Celsius. The pen housing 242 and the mouthpiece component 222 may be configured such that the outer surface of the pen housing 242 and the mouthpiece component 222 remains below, for example, 44 degrees Celsius or a temperature below 44 degrees Celsius to prevent burns to the user. In some implementations, rather than including the coil 264, the system 200 may include another heating element (e.g., a ceramic heating element) configured to vaporize the carrier material. A ceramic heating element may be configured to be heated to a temperature ranging between about 200 degrees Celsius and about 450 degrees Celsius, and the pen housing 242 and the mouthpiece component 222 may be configured such that the outer surface of the pen housing 242 and the mouthpiece component 222 remains below, for example, 44 degrees Celsius or a temperature below 44 degrees Celsius to prevent burns to the user. Furthermore, forming the mouthpiece component 222 and/or the pen housing 242 of ceramic may insulate the internal components of the system 200 from the external environment such that the internal components are protected from extreme temperatures (e.g., heat and cold). In some implementations, the mouthpiece component 222 and/or the pen housing 242 may be sufficiently insulative such that additional insulation is not needed within the pen housing 242 to protect the internal components of the system 200 from heat or cold.

The pen housing 242 and the mouthpiece component 222 may be formed as any suitable color. For example, the pen housing 242 and/or the mouthpiece component 222 may be, white, grey, black, or multi-colored. In some embodiments, the pen housing 242, the outer housing 224, and/or the mouthpiece component 222 may be translucent such that the interior contents of the system 200 may be viewed by a user. In some embodiments, the pen housing 242, the outer housing 224, and/or the mouthpiece component 222 may be opaque such that a user cannot see through the pen housing 242, the outer housing 224, and/or the mouthpiece component 222.

In some implementations, the system 200 may include a flow rate sensor (not shown) in communication with the control assembly 258. The control assembly 258 may be configured to determine a fill level of carrier material in the reservoir based, at least in part, on the flow rate of air through a portion of the system 200 caused by a user drawing air through the system 200. In some implementations, the control assembly 258 may be configured to determine the fill level of carrier material in the reservoir based, at least in part, on calculated flow rates of air based on pressure changes and durations of pressure change sensed by the pressure sensor 247. In some implementations, the system 200 may be configured to meter a dose from the cartridge assembly 210 (e.g., via heating the coil 264 for particular duration of time) based on the intensity and/or duration of an inhalation of a user through the mouthpiece opening 222A. For example, the system 200 may be configured to meter a dose from the cartridge assembly 210 based on data collected by a flow rate sensor and/or based on data collected by a pressure sensor. Metering a dose from the cartridge assembly 210 may be based on the intensity and/or duration of an inhalation as well as the specific heating profile associated with the particular cartridge assembly 210.

In some implementations, the system may be configured to communicate a fill level of carrier material in the reservoir to a command center of other remote compute device (e.g., a mobile device of a user). For example, the transceiver of the control assembly 258 may be configured to send fill level data to a mobile device such that a user may be able to view a fill level (e.g., a percentage remaining) of carrier material in the reservoir periodically and/or in real time.

In some implementations, a user may be able to use a remote compute device (e.g., a mobile device) to set a temperature of the coil 264 of the wick assembly 260 prior to or during use. Thus, if the user desires a particular coil temperature or a higher or lower coil temperature, the user may set the temperature or request a temperature change via the remote compute device. The remote compute device may then send the instructions remotely (e.g., via Bluetooth) to the transceiver of the control assembly 258. The control assembly 258 may then adjust the current sent to the coil 264 via the heater control circuitry according to the instructions sent from the remote compute device.

In some implementations, the pen assembly 240 may be configured to disable the cartridge assembly 210. For example, the pen assembly 240 may communicate with the tracking component 231 of the cartridge assembly 210 and program the tracking component 231 such that neither the pen assembly 240 nor any other pen assembly 240 will operate to heat the coil 264 of the cartridge assembly 210 after reading the tracking component 231 of the cartridge assembly 210.

In some implementations, the pen assembly 240 may disable the cartridge assembly 210 upon identifying the user of the system 200 as being below an age threshold corresponding to the carrier material in the cartridge assembly 210. For example, in some implementations, the system 200 may only operate when a user's user profile on a remote compute device (e.g., a smartphone) reflects that the age of the user is at or above the age threshold. After the cartridge assembly 210 is coupled to the pen assembly 240 and the pen assembly 240 identifies the contents of the cartridge assembly 210 (e.g., via reading the information on the tracking component 231), the pen assembly 240 may wirelessly communicate with the remote compute device to verify the age of the user based on a user profile associated with the pen assembly 240. If the age of the user, as reflected by the user profile, is below the age threshold associated with the carrier material of the cartridge assembly 210, the pen assembly 240 may not operate and/or may disable the cartridge assembly 210 such that the cartridge assembly 210 cannot be used with any pen assembly 240.

In some implementations, the pen assembly 240 may disable the cartridge assembly 210 upon the fill level of the cartridge assembly 210 being reduced by a particular percentage or amount. For example, the pen assembly 240 may disable the cartridge assembly 210 when the fill level drops below a threshold percentage of the initial fill level such that the cartridge assembly 210 will continue to be operable in conjunction with the pen assembly 240 only until the cartridge assembly 210 is removed from the pen assembly 240. The threshold percentage may be, for example, between about 10% and about 20% of the initial fill level. In some implementations, the threshold percentage may be between about 10% and about 20% of the cartridge assembly 210 being empty of carrier material. Disablement upon reaching a threshold may prevent tampering with the cartridge assembly 210 after use or partial use of the cartridge assembly 210. In some implementations, the pen assembly 240 may disable the cartridge assembly 210 and cease operating when the fill level drops below a threshold percentage of the initial fill level or of an empty level or below a threshold fill level. In some implementations, engagement of the cartridge assembly 210 with the pen assembly 240 may trigger a notification to initiate on a user's remote compute device (e.g., smartphone). For example, the pen assembly 240 may extract identification information corresponding to the cartridge assembly 210 via the tracking component 231 and transmit that identification information to the user's remote compute device. The user may access a platform on the remote compute device (e.g., via clicking on the notification) via which the user may review information corresponding to the cartridge assembly 210. For example, the information may include origin, a taste profile, an effect profile, an intensity profile, background information related to a grower, extractor, formulator, or cultivator of the substance, vintage of the carrier material, ratings, recommended alternative carrier materials, the fill level of the cartridge assembly 210, a location for re-purchasing a cartridge assembly 210 with the particular carrier material, and/or any other suitable information.

In some implementations, a user may be able to set a threshold distance between the system 200 and a mobile device of the user such that the system 200 will not operate if the system 200 is disposed a distance greater than the threshold distance from the mobile device. For example, the system 200 may include a proximity sensor. The control assembly 258 may be programmed not to activate the heater control circuitry to send a current to the coil 264 if the proximity sensor senses that the system 200 is more than a threshold distance from the user's mobile device. In some implementations, the user may set the threshold distance via an interface of the mobile device. For example, the user may set the distance as five feet, fifty feet, or one hundred feet. The mobile device may then transmit the instruction including the threshold distance to the control assembly 258 of the system 200 (e.g., via Bluetooth).

In some implementations, the system 200 may be configured to only operate within particular geographic regions. For example, the system 200 may include a GPS receiver and may only operate in regions with particular regulations allowing for use of the device. In some implementations, the particular geographic regions within which the system 200 may be able to operate may be adjusted remotely (e.g., via communication with a server) such that the geographic regions within which the system 200 may operate may be expanded or narrowed. In some implementations, the system 200 may be configured to not operate in particular geographic regions based on the particular carrier material disposed within the cartridge assembly 210. For example, a system 200 including a cartridge with a particular carrier material may be operable in a first location but not in a second location based on the particular regulations of each of the first location and the second location with respect to the carrier material. The pen assembly 240 can identify the contents of the cartridge assembly 210 (e.g., the particular carrier material) when engaged with the cartridge assembly 210 (e.g., via accessing identification information corresponding to the cartridge assembly 210 stored in the tracking component 231) and can determine whether to activate or not activate the heater control circuitry based on location information gathered by a GPS receiver of the system 200 or received from a remote compute device associated with the system 200. For example, a processor of the system 200 can be figured to apply current to the heating element only upon receiving approval or information from the GPS or a remote compute device that the system 200 and/or the remote compute device is disposed in a particular geographic region or not disposed in a particular geographic region.

In some implementations, the system 200 may be configured to be remotely disabled (e.g., via communication with a server). For example, in the event of a recall of the carrier material within the cartridge assembly 210, after the cartridge assembly 210 has been coupled to the pen assembly 240 and the pen assembly 240 has identified the contents of the cartridge assembly 210 (e.g., via accessing identification information corresponding to the cartridge assembly 210 stored in the tracking component 231), the pen assembly 240 may disable the cartridge assembly 210 and/or not operate to heat the coil 264 upon receiving an indication (e.g., via a transceiver of the control assembly 258) that the contents of the cartridge assembly 210 have been recalled.

In some embodiments, the system 200 may be configured to not operate (e.g., stay in an inactive or disabled state) if an application associated with the system 200 on a remote compute device (e.g., a smartphone or other mobile device) is not open and/or running. For example, the pen assembly 240 can be configured to wireless communicate with a user's remote compute device to determine if an application associated with the system is open. If the application is open, the control assembly 258 can activate the heater control circuitry to send a current to the coil 264 such that the system 200 can be used by the user. If the application is not open on the user's remote compute device, the control assembly 258 may be programmed not to activate the heater control circuitry to send a current to the coil 264 such that the system 200 is disabled or inactive. Such a feature may be integrated into the system 200 separately or in combination with the threshold distance-based safety feature described above or another proximity sensor-based safety feature. Such a feature may prevent, for example, the usage of the system 200 by someone who is not in control of the status of the application on the remote compute device (e.g., a child who may have access to the system 200 but not the remote compute device).

In some embodiments, an identification number or password (e.g., a personal identification number (PIN)) may be required to enable operation of the system 200. For example, an application of a remote compute device (e.g., a smartphone or other mobile device) associated with the system 200 may require correct entry of an identification number to transition the system 200 between a disabled status and an enabled status. After the identification number is correctly entered into the remote compute device via a user interface of the remote compute device, the application can communicate with the control assembly 258 of the system 200 to enable operation of the system 200 (e.g., activation of the heater control circuitry). The identification number may be alphanumeric, numeric, or any other suitable sequence. In some embodiments, the user may set the identification number prior to using the system 200. In some embodiments, the application may have a threshold number of incorrect entries (e.g., three or five incorrect entries) before initiating a lockout period (e.g., one hour) such that the system 200 may not be enabled for use as a vaporizer until the lockout period has expired.

In some embodiments, the system 200 may be prevented from operating if an application of a remote compute device (e.g., a mobile device such as a smartphone) associated with the system 200 determines that the system 200 is in a moving vehicle. For example, the application of the remote compute device may determine that the remote compute device is in a moving vehicle based on data collected by an accelerometer and/or GPS of the remote compute device. The application may, for example, have a threshold velocity (e.g., 10 miles per hour) that the application may use to determine if the remote compute device is likely located within a moving vehicle. If the remote compute device determines that the remote compute device is moving at a velocity above the velocity threshold, the remote compute device can determine that the remote compute device is likely in a moving vehicle and disable the system 200 and/or prevent the system 200 from operating. Such a feature may prevent a user from using the system 200 while driving or riding in a vehicle. For example, a processor of the system 200 can be figured to apply current to the heating element only upon receiving approval or information from the remote compute device that the remote compute device is moving at a velocity under the velocity threshold. The processor of the system 200 can query the remote compute device (e.g., via an antenna of the control assembly 258) to determine if the remote compute device is moving at a speed above a threshold speed. In some embodiments, the system 200 can include an accelerometer that the processor can directly receive information from and process.

In some embodiments, the system 200 may be prevented from operating based on the contents of the cartridge assembly 210 (also referred to as including a "substance lock" feature). For example, the pen assembly 240 may be configured to wirelessly communicate with a remote compute device running an application associated with the system 200. The application can be configured to allow a user to identify particular contents (e.g., particular carrier materials or ingredients such as THC or nicotine) via a user interface of the remote control device that will not be able to be vaporized by the system 200 (e.g., for a period of time or until the user changes the status of the carrier material to active or allowed). The pen assembly 240 can identify the contents of the cartridge assembly 210 (e.g., the particular carrier material or ingredients) when engaged with the cartridge assembly 210 (e.g., via accessing identification information corresponding to the cartridge assembly 210 stored in the tracking component 231) and can determine whether to activate or not activate the heater control circuitry based on the user-set status of the particular carrier material or ingredients in the application. Thus, a user can prevent accidental inhalation of a particular carrier material or ingredients at an unwanted time by setting the carrier material or an ingredient included in the carrier material to a first status (e.g., a disabled status), and then can allow inhalation of the particular carrier material at a later time by transitioning the status of the carrier material in the application to a second status (e.g., an enabled status). When the carrier material or the ingredient is set to a disabled status, other cartridge assemblies 210 including different carrier materials and/or ingredients may be engaged with the pen assembly 240 and the system can operate normally with respect to the other cartridge assemblies 210.

The carrier material may be and/or include any suitable material configured to be vaporized and inhaled by a user. For example, the carrier material may include *cannabis*, nicotine, plant-based oils, and/or pharmaceuticals configured to be vaporized for inhalation.

In some embodiments, the system 200 may include a biometric sensor (not shown). The biometric sensor may be accessible via, for example, an opening in the pen housing 242. The biometric sensor may be operatively coupled to the control assembly 258 such that the control assembly 258 will only activate the heater control circuitry to send current to the coil 264 if the biometric sensor is activated. In some implementations, the biometric sensor may activate upon recognition of a characteristic of a user. The characteristic of the user may be, for example, a fingerprint of a user or an electrical capacity of a user.

Figure 16A:
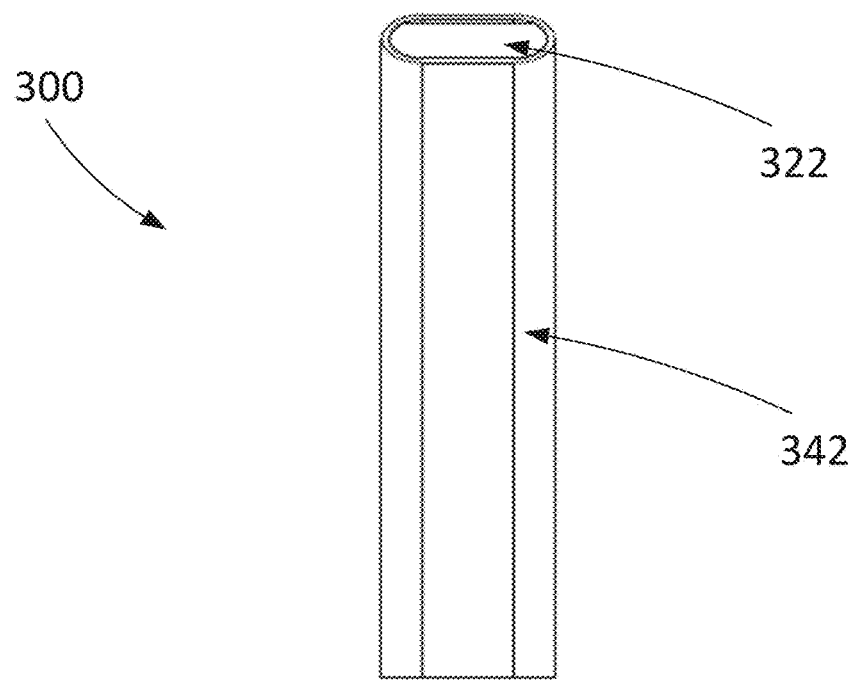
FIGS. 16A-16E are various views of a system, according to an embodiment. Specifically.
Figure 16B:
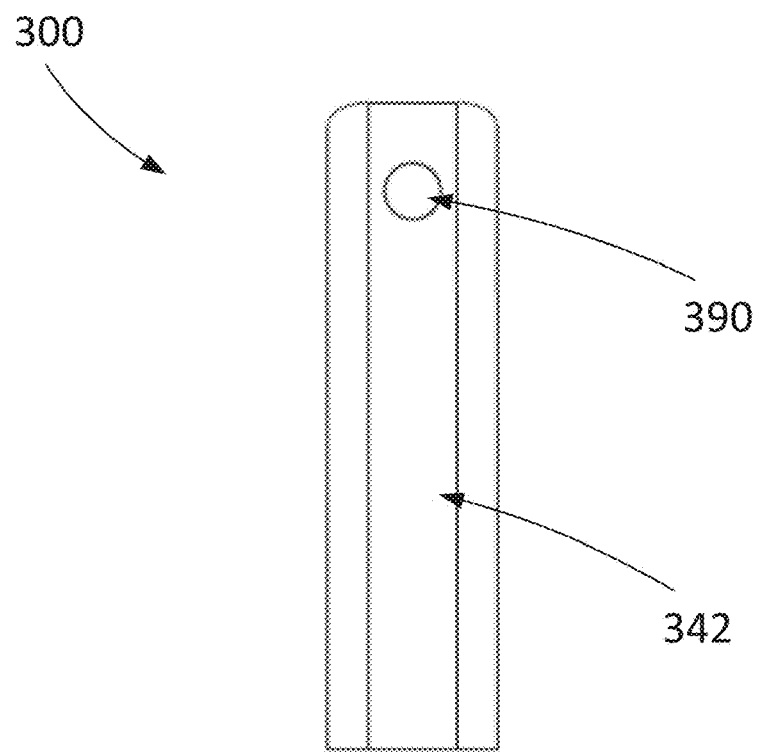
Figure 16C:
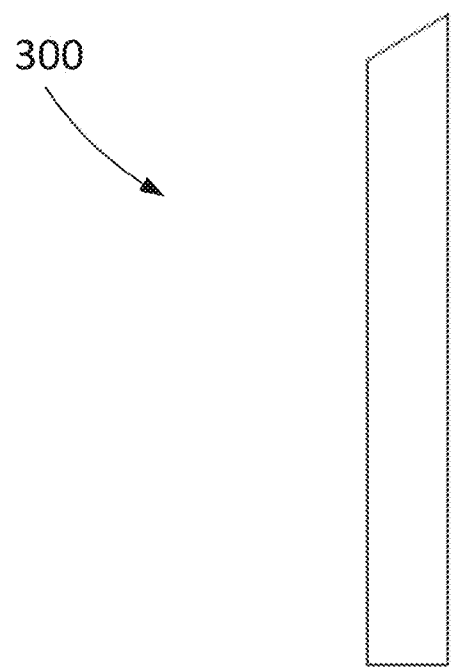
Figure 16D:
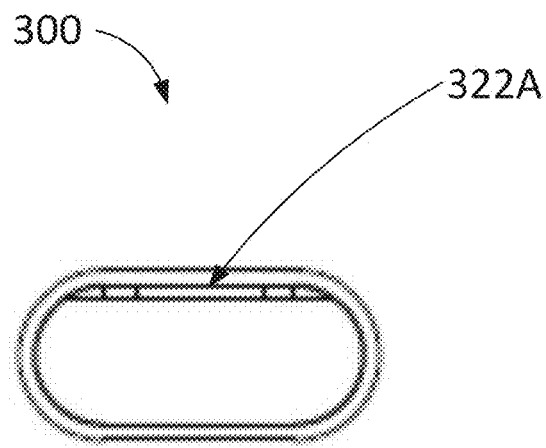
Figure 16E:
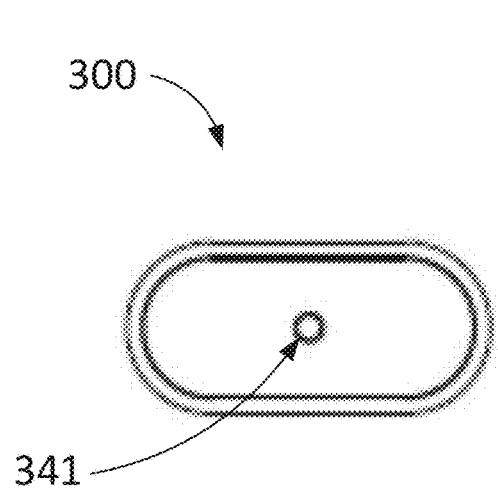

In some embodiments, rather than a system including a pen assembly configured to receive any number of cartridge assemblies such that the pen assembly may be used repeatedly with various cartridge assemblies, a system may be disposable after a reservoir containing the carrier material is depleted. For example, FIGS. 16A-16E are various views of a system 300. Specifically, FIG. 16A is a front view of the system 300, FIG. 16B is a back view of the system 300, FIG. 16C is a side view of the system 300, FIG. 16D is a top view of the system 300, and FIG. 16E is a bottom view of the system 300.

The system 300 may include a pen housing 342 and a mouthpiece component 322. In some embodiments, the pen housing 342 and the mouthpiece component 322 may be formed as a monolithic structure. In some embodiments, the pen housing 342 and the mouthpiece component 322 may be formed separately and coupled together via, for example, a mechanical attachment mechanism and/or adhesive.

As shown in FIG. 16B, the system 300 may include a fill port 390. For example, the fill port 390 may include an opening defined by the pen housing 342 and filled by a plug member. Thus, a reservoir of the system 300 may be able to be filled with the carrier material via the fill port 390 such that the carrier material may be converted into vapor and drawn through a mouthpiece opening 322A (shown in FIG. 16D).

In some embodiments, the system 300 may be similar to any of the systems described herein, such as the system 200 described above. For example, the system 300 may be the same as the system 200 with the exception of the mouthpiece component 322 not being removable from the pen housing 242 and the pen housing 342 defining a fill port 390.

In some embodiments, the system 300 may have a detachable bottom portion such that components such as a bracket cartridge assembly and/or a bracket assembly may be loaded in the pen housing 342 prior to use. The bracket cartridge assembly may be the same or similar in structure and/or function to the bracket cartridge assembly 210 described above, except that the bracket cartridge assembly does not include the mouthpiece assembly 220. For example, as shown in FIG. 16E, the system 300 may define a bottom opening 341 such that air may be drawn into an interior of the system 300 via the bottom opening 341 and/or such that a charging device may be reversibly engaged with a power supply of the system via the bottom opening 341. The bracket assembly 250 may be the same or similar in structure and/or function to the bracket assembly 250 described 250 described above.

Figure 17A:
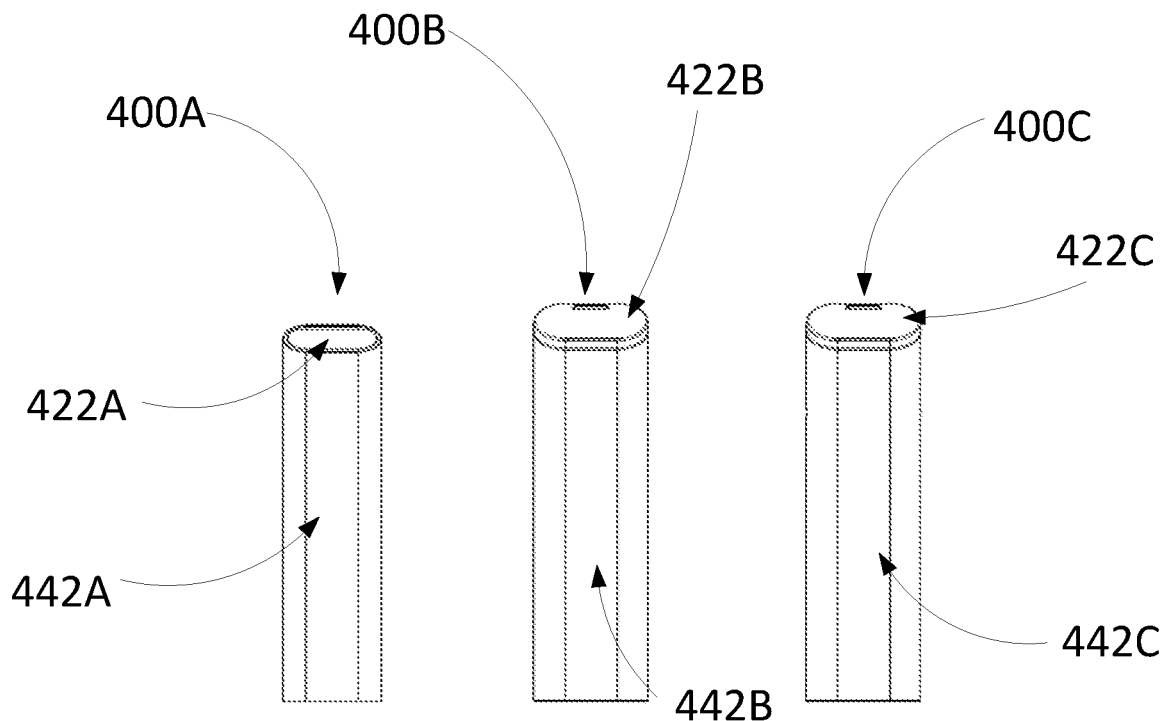
FIGS. 17A and 17B show a front view and a back view, respectively, of a disposable system, a first reusable system, and a second reusable system, according to various embodiments.
Figure 17B:
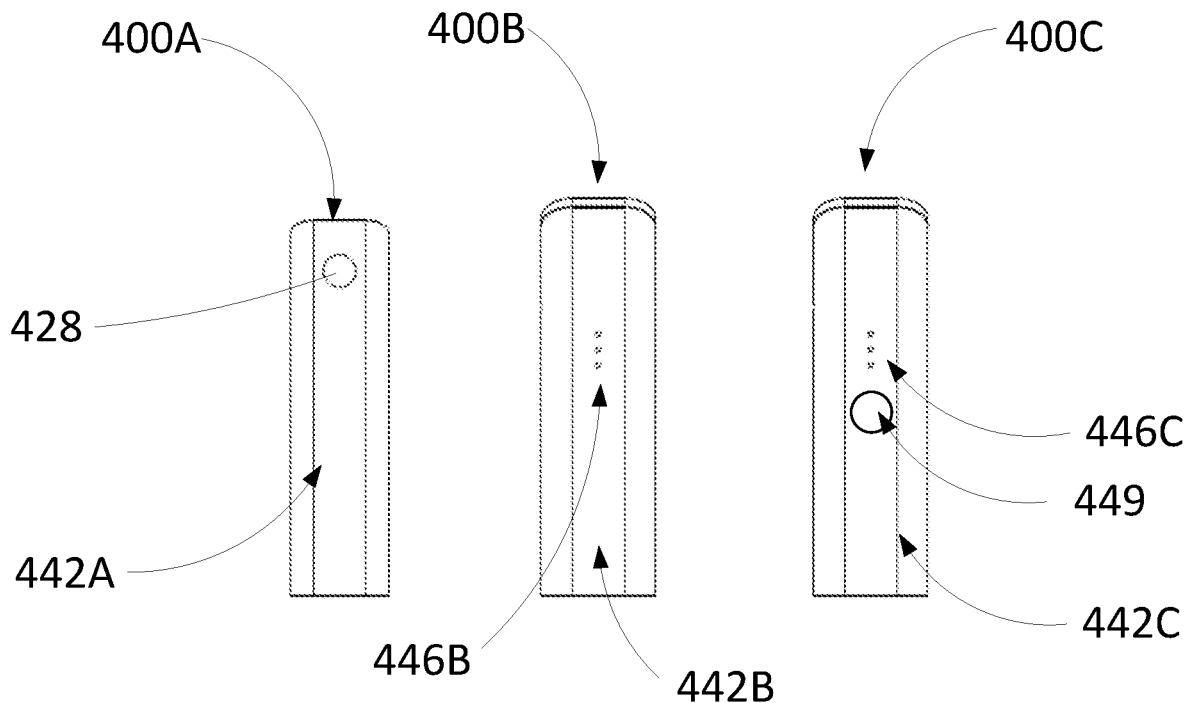

FIGS. 17A and 17B show a front view and a back view, respectively, of a disposable system 400A, a first reusable system 400B, and a second reusable system 400C, respectively. The disposable system 400A may be the same or similar in structure and/or function to the system 300 described above. As shown, the disposable system 400A includes a pen housing 442A defining a fill port and a plug 428 sealing the fill port. The pen housing 442A includes a top surface and sidewalls. The pen housing 442A defines a mouthpiece opening 422A in a top surface of the pen housing 442A. The top surface and the sidewalls of the pen housing 442A may be monolithically formed.

The first reusable system 400B may be the same or similar in structure and/or function to any of the systems described herein, such as, for example, the system 200. The first reusable system 400B includes a pen housing 442B and a mouthpiece component 422B reversibly coupleable to the pen housing 442B. The mouthpiece component 422B may be a portion of a cartridge assembly similar to cartridge assembly 210 described above. The mouthpiece component 422B defines a mouthpiece opening. As shown in FIG. 17B, the pen housing 442B includes indicator cover elements 446B.

The second reusable system 400C may be the same or similar in structure and/or function to any of the systems described herein, such as, for example, the system 200. The first reusable system 400C includes a pen housing 442C and a mouthpiece component 422C reversibly coupleable to the pen housing 442C. The mouthpiece component 422C may be a portion of a cartridge assembly similar to cartridge assembly 210 described above. The mouthpiece component 422C defines a mouthpiece opening. As shown in FIG. 17B, the pen housing 442C includes indicator cover elements 446C and a biosensor 449. The biosensor 449 may be in communication with a control assembly of the second usable system 400C.

Figure 18:
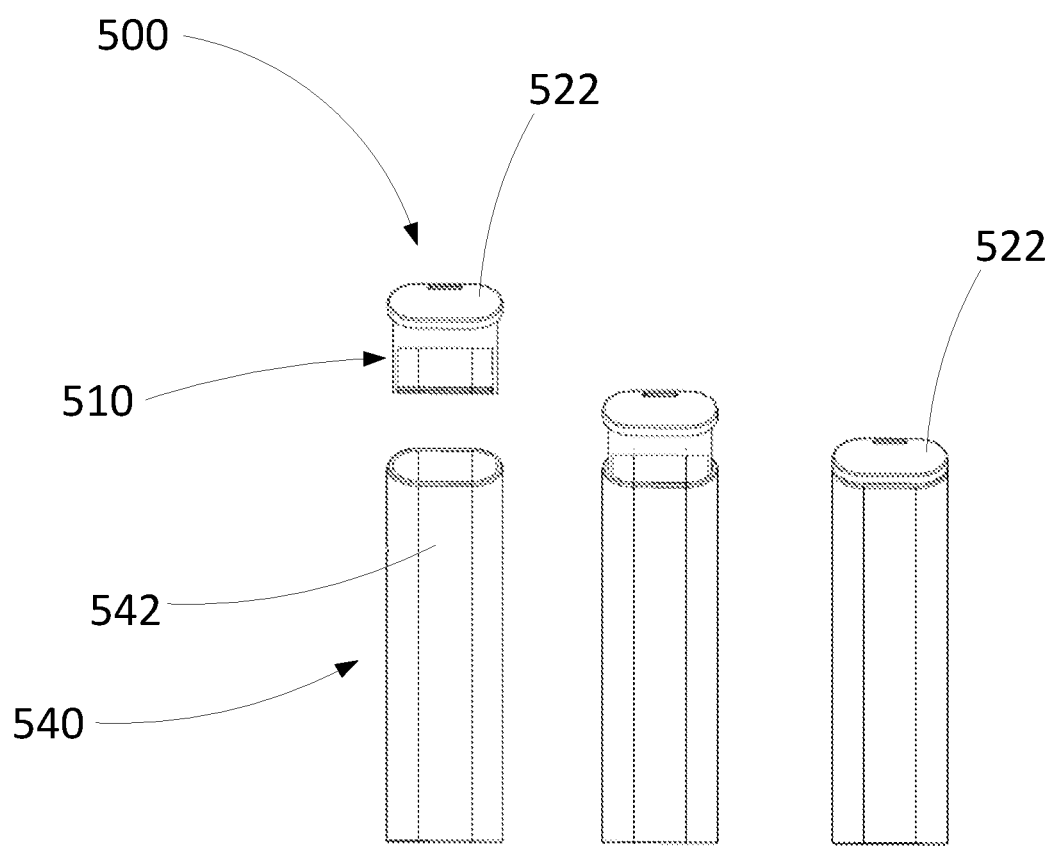
FIG. 18 is a front view of a system in various stages of operation, according to an embodiment.

FIG. 18 is a front view of a system 500 in three stages of an operation coupling a pen assembly 540 to a cartridge assembly 510. The system 500 may be the same or similar in structure and/or function to the system 200 described above. As shown, the cartridge assembly 510 may first be separate and disengaged from the pen assembly 540. The cartridge assembly 510 may then be partially inserted into an interior of the pen housing 542. The cartridge assembly 510 may then be translated relative to the pen housing 542 until a mouthpiece component 522 of the cartridge assembly 510 is engaged with the pen housing 542 of the pen assembly 542.

Figure 19:
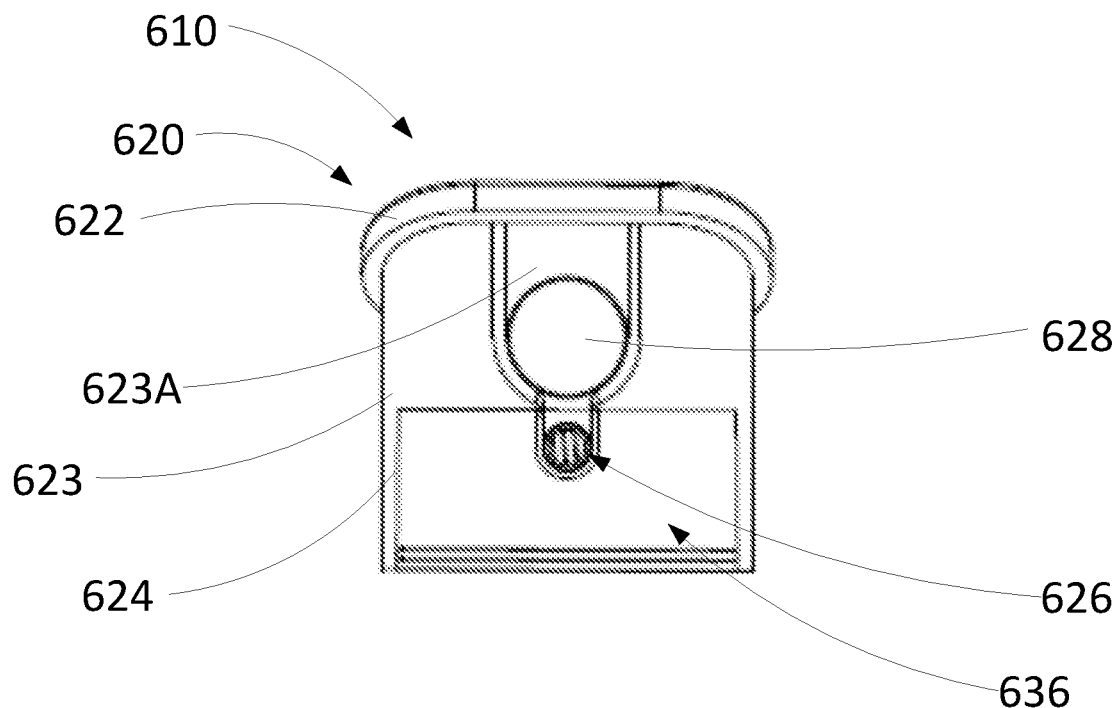
FIG. 19 is a front view of a cartridge assembly, according to an embodiment.

FIG. 19 is a back view of a cartridge assembly 610. The cartridge assembly 610 may be the same or similar in structure and/or function to any of the cartridge assemblies described herein, such as the cartridge assembly 210. The cartridge assembly 610 includes a mouthpiece assembly 620 including a mouthpiece component 622 and an outer housing 624. The outer housing 624 has a sidewall 623, defines a vapor outlet 626, and includes a recessed sidewall portion 623A. The outer housing 624 may form at least a portion of a reservoir accessible view a fill inlet defined by the sidewall and/or the recessed sidewall portion 623A. The cartridge assembly 610 also includes a plug 628 configured to seal with the fill inlet defined by the outer housing 624. As shown, the sidewall 623 may be transparent such that the contents of the cartridge assembly 610 (e.g., the carrier material within the reservoir) may be viewed through the sidewall 623 of the outer housing 624.

The cartridge assembly 610 also includes a bracket cartridge assembly which may be the same or similar in structure and/or function to any of the bracket cartridge assemblies described herein, such as the bracket cartridge assembly 230. The bracket cartridge assembly of the cartridge assembly 610 includes a lower portion 636 which may be the same or similar in structure and/or function to any of the lower portions described herein, such as the lower portion 636.

Figure 20:
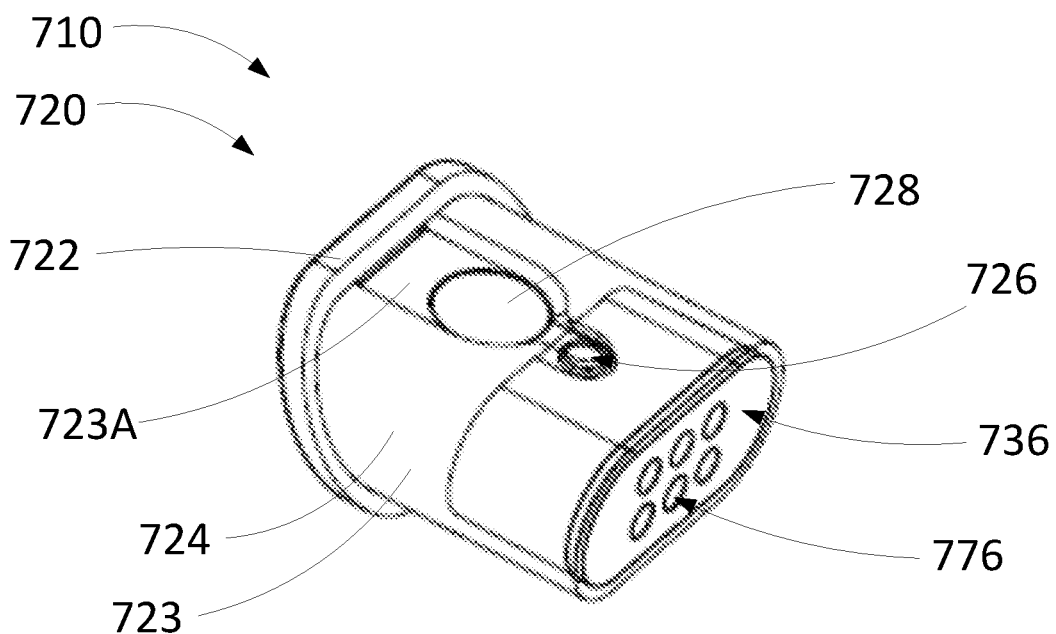
FIG. 20 is a perspective view of a cartridge assembly, according to an embodiment.

FIG. 20 is a perspective view of a cartridge assembly 710. The cartridge assembly 710 may be the same or similar in structure and/or function to any of the cartridge assemblies described herein, such as the cartridge assembly 210. The cartridge assembly 710 includes a mouthpiece assembly 720 including a mouthpiece component 722 and an outer housing 724. The outer housing 724 has a sidewall 723, defines a vapor outlet 726, and includes a recessed sidewall portion 723A. The outer housing 724 may form at least a portion of a reservoir accessible view a fill inlet defined by the sidewall and/or the recessed sidewall portion 723A. The cartridge assembly 710 also includes a plug 728 configured to seal with the fill inlet defined by the outer housing 724. As shown, the sidewall 723 may be opaque such that the contents of the cartridge assembly 710 (e.g., the carrier material within the reservoir) may not be viewed through the sidewall 723 of the outer housing 724.

The cartridge assembly 710 also includes a bracket cartridge assembly which may be the same or similar in structure and/or function to any of the bracket cartridge assemblies described herein, such as the bracket cartridge assembly 230. The bracket cartridge assembly of the cartridge assembly 710 includes a lower portion 736 which may be the same or similar in structure and/or function to any of the lower portions described herein, such as the lower portion 236. The lower portion 736 defines openings 776.

Figure 21:
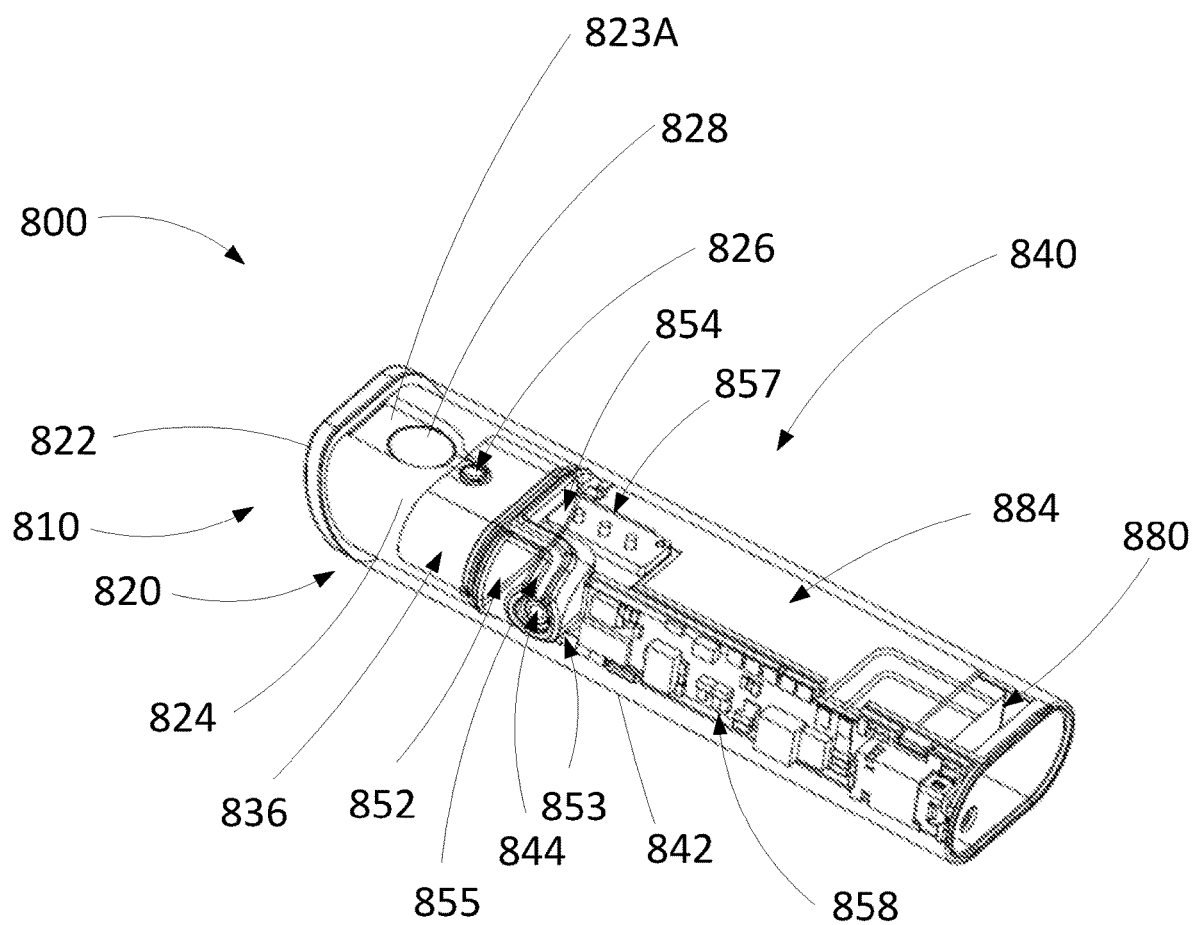
FIG. 21 is a perspective view of a system having a transparent pen housing, according to an embodiment.

FIG. 21 is a perspective view of a system 800 in an assembled configuration. The system 800 may be the same or similar in structure and/or function to any of the systems described herein, such as the system 200 described above. For example, the system 800 includes a cartridge assembly 810 and a pen assembly 840. The cartridge assembly 810 includes a mouthpiece assembly 820 and a bracket cartridge assembly. The mouthpiece assembly 820 includes a mouthpiece component 822, an outer housing 824, and a vapor outlet 826. The bracket cartridge assembly includes a vapor outlet (not shown) aligned with the vapor outlet 826, a wick assembly (not shown) an upper portion (not shown), and a lower portion 836.

The pen assembly includes a pen housing 842 and a bracket assembly. As shown in FIG. 21, the pen housing 842 is transparent such that the interior components of the system 800 may be seen through the pen housing 842. The bracket assembly includes a cap 852 having an extension portion 853, a bracket 880, and a control assembly 858. The extension portion 853 includes an airflow groove 855 which may be in fluidic communication with an environment external to the system 800 via an inlet 844 in the pen housing 842 and which may be in fluidic communication with a pressure sensor of the control assembly 858. The bracket assembly also includes a cap bracket 854 and a connection assembly including indicator features 857. The bracket assembly also includes a power source 884.

Figure 22A:
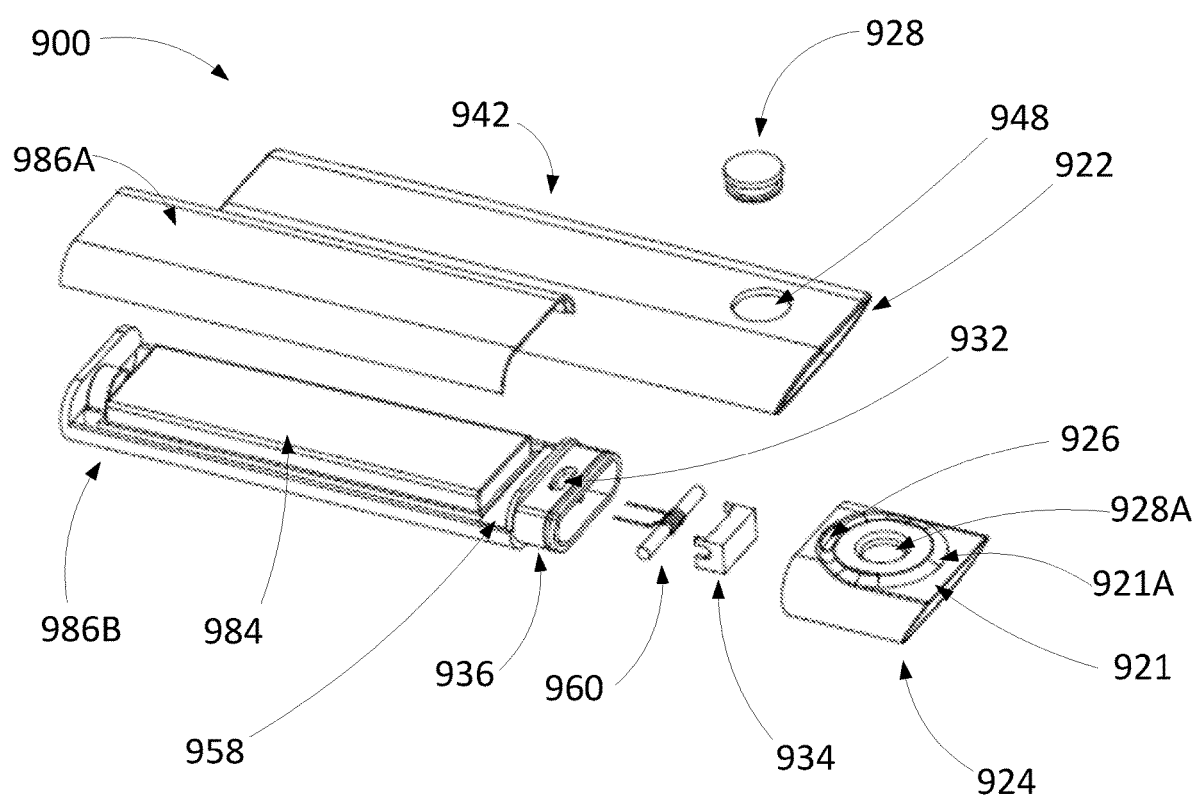
FIG. 22A is an exploded view of a system in an exploded configuration, according to an embodiment.

In some embodiments, rather than having a widening flow path from the vapor outlet of the mouthpiece assembly to the mouthpiece opening, a system may include a circular, semicircular, and/or U-shaped flow path from the vapor outlet to the mouthpiece opening. For example, FIG. 22A is an exploded view of a system 900 in an exploded configuration. The system 900 may be the same or similar in structure and/or function to any of the systems described herein. For example, the system 900 includes an outer housing 924, an upper portion 934, a lower portion 936, and a wick assembly 960. When assembled, a vapor outlet 932 of the lower portion 936 is configured to align with a vapor outlet 926 of the outer housing 924 such that an interior of the lower portion 936 is in fluidic communication with the vapor outlet 926 of the outer housing 924 and vapor may flow from the interior of the lower portion 936, through the vapor outlet 932, and through the vapor outlet 926. The system 900 also includes a control assembly 958 and a power source 984 enclosed within a first inner housing portion 986A and a second inner housing portion 986B.

Figure 22B:
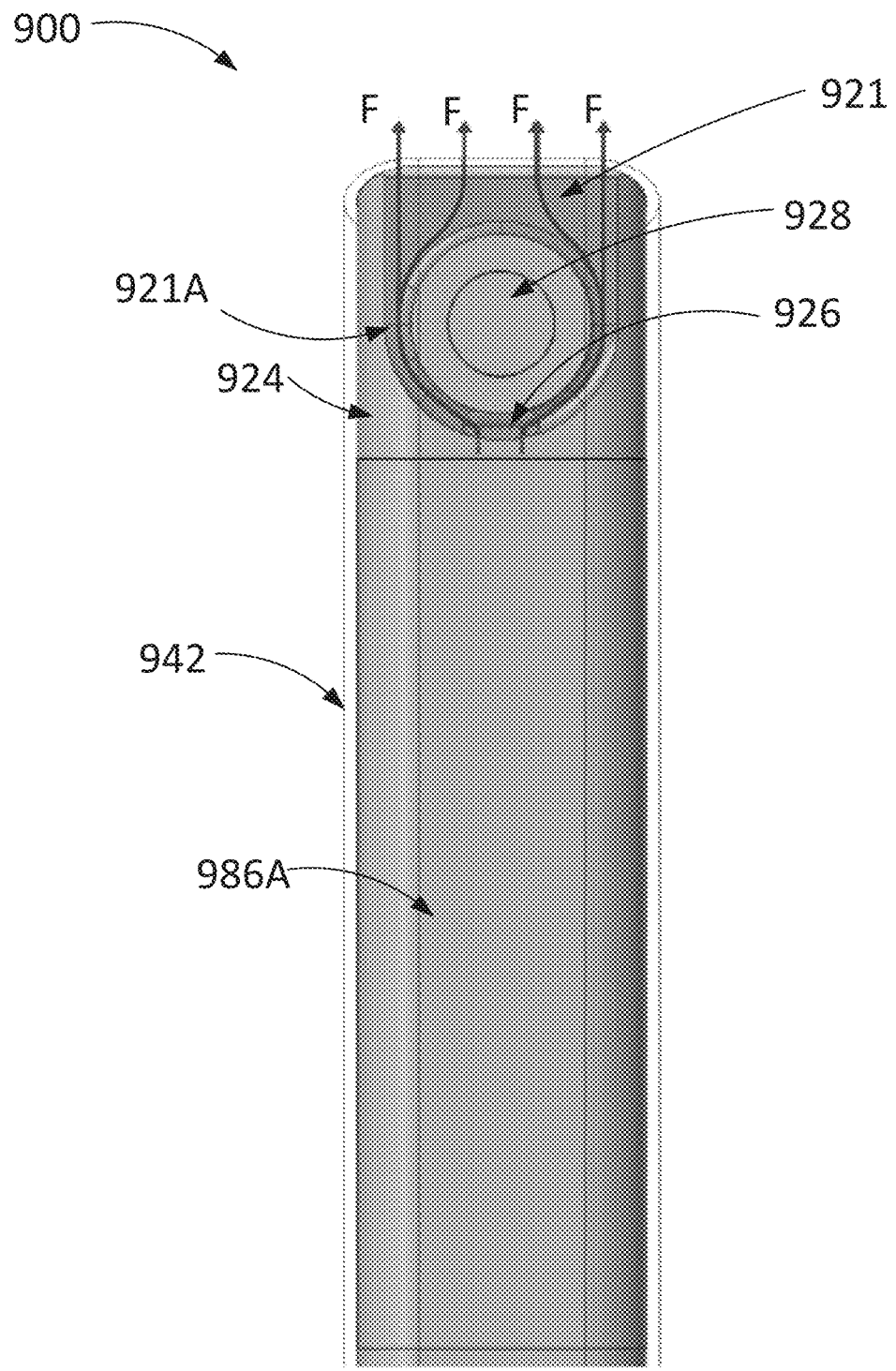
FIG. 22B is a back view of the system of FIG. 22 in an assembled configuration.

FIG. 22B is a back view of the system 900 in an assembled configuration. As shown in FIGS. 22A and 22B, the outer housing 924 may define a fill inlet 928A and a recessed portion 921 including a circular recessed portion 921A that is farther recessed than a remained of the recessed portion 921. The recessed portion 921 may be substantially U-shaped. The recessed portion 921 extends from the vapor outlet 926 to the upper surface of the outer housing 924. The recessed portion 921 may surround the fill inlet 928A. The vapor outlet 926 may be defined within a portion of the recessed portion 921.

The system 900 also includes a pen housing 942. The pen housing 942 includes a mouthpiece 922 defining a mouthpiece opening (not shown). The mouthpiece 922 may be monolithically formed with the pen housing 942. The pen housing 942 also defines a fill opening 948 configured to be releasably sealed by a plug 928. When the system 900 is assembled, the outer housing 924 may be coupled to the inner housing portions 986A, 986B such that the upper portion 934, the wick assembly 960, and the lower portion 936 are enclosed within the outer housing 924 and the inner housing portions 986A, 986B. The pen housing 942 may then be translated over the outer housing 924 and the inner housing portions 986A, 986B such that the fill opening 928A is aligned with the fill opening 948. The fill opening 928A and the fill opening 948 may then be sealed via coupling the plug 928 to the fill opening 928A via the fill opening 948.

When assembled, the recessed portion 921, including the circular recessed portion 921A, and the inner surface of the pen housing 942 may form a chamber via which vapor exiting the vapor outlet 926 may travel to reach the mouthpiece opening of the mouthpiece 922. Thus, a user may draw vapor from the interior of the lower portion 936, through the vapor outlet, through either of two routes through the circular recessed portion 921A, through the portion of the recessed portion 921 defined between the circular recessed portion 921A and the top edge of the outer housing 924, and out of the mouthpiece opening of the mouthpiece 922 (e.g., along the fluid flow paths identified by arrows F in FIG. 22B) such that the vapor may be inhaled by the user.

Figure 23:
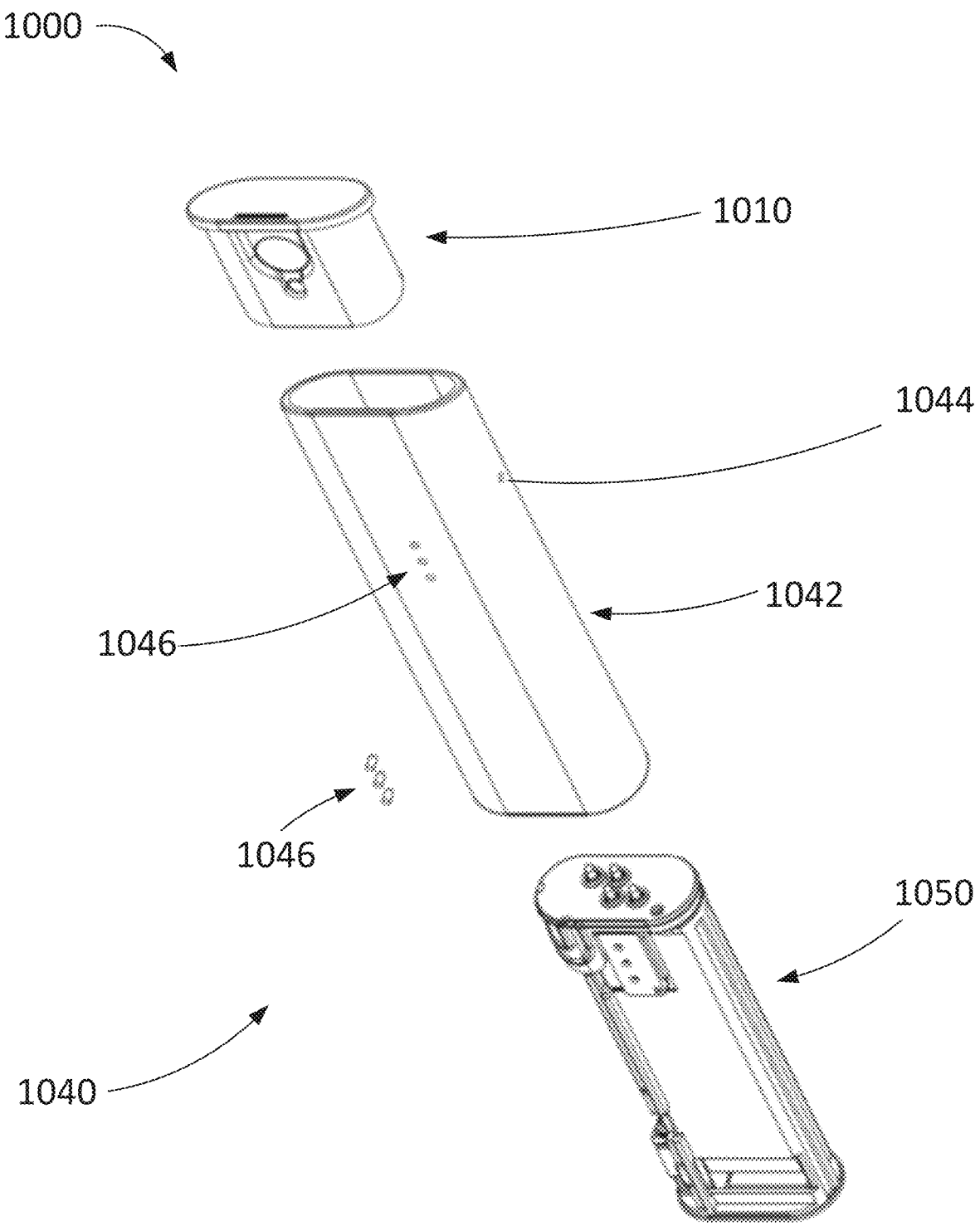
FIG. 23 is perspective view of an electronic vapor delivery system in an exploded configuration, according to an embodiment.

FIG. 23 is perspective view of an electronic vapor delivery system 1000 in an exploded configuration. The system 1000 may be the same or similar in structure and/or function to any of the systems described herein, such as, for example, the reusable vaporizer 100B described above with respect to FIG. 1B and/or the electronic vapor delivery system 200 described above. For example, the system 1000 includes a cartridge assembly 1010 and a pen assembly 1040. The cartridge assembly 1010 may be similar in structure and/or function to the cartridge assembly 210 described above, and the pen assembly 1040 may be similar in structure and/or function to the pen assembly 240 described above. The pen assembly 1040 includes a pen housing 1042 and a bracket assembly 1050. The pen assembly 1040 also includes indicator cover elements 1046 (e.g., translucent portions configured such that light transmitted from indicator features similar to indicator features 257 described above may be visible through the indicator cover elements 1046). Furthermore, in some implementations, the pen housing 1042 may define an inlet 1044 in the sidewall of the pen housing 1042 such that air may be drawn into an interior of the system 1000 via the inlet 1044. In some implementations, the pen housing 1042 may define one or more inlets 1044 in any suitable location on the pen housing 1042, such as on opposite sides of the pen housing 1042. In some implementations, the pen housing 1042 may not define an inlet 1044 in the sidewall of the pen housing 1042.

Figure 24:
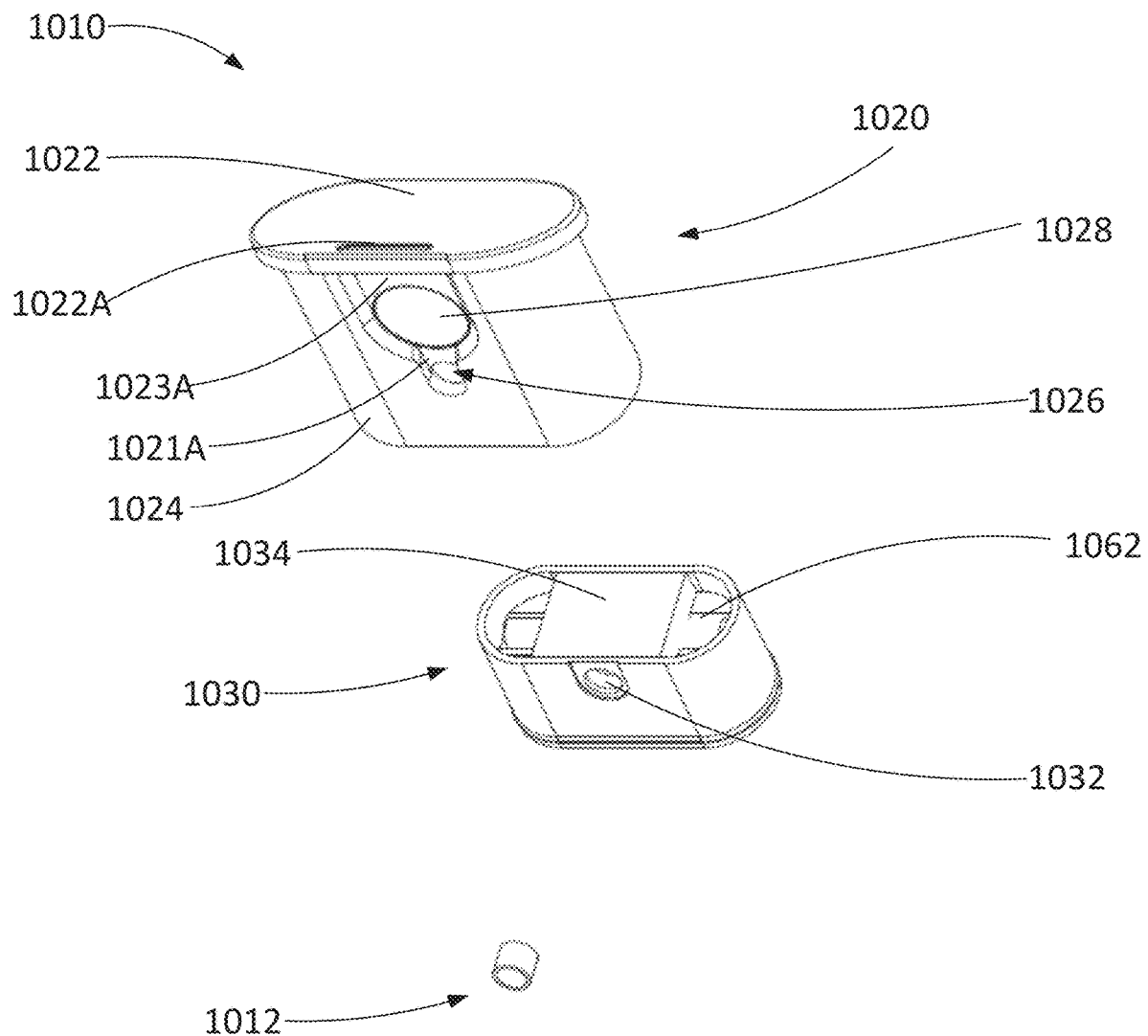
FIG. 24 is a perspective view of a cartridge assembly of the system of FIG. 23 in an exploded configuration.

FIG. 24 is a perspective view of the cartridge assembly 1010 in an exploded configuration. As shown in FIG. 24, the cartridge assembly 1010 includes a mouthpiece assembly 1020, a bracket cartridge assembly 1030, and a pipe chimney 1012. The mouthpiece assembly 1020 is configured to receive the bracket cartridge assembly 1030 within an interior of the mouthpiece assembly 1020 such that a vapor outlet 1026 of the mouthpiece assembly 1020 aligns with a vapor outlet 1032 of the bracket cartridge assembly 1030. When the bracket cartridge assembly 1030 is disposed within the mouthpiece assembly 1020 such that the vapor outlet 1026 of the mouthpiece assembly 1020 aligns with the vapor outlet 1032 of the bracket cartridge assembly 1030, the pipe chimney 1012 can be disposed within the vapor outlet 1026 and the vapor outlet 1032 such that gaseous fluid and/or vapor may flow through the pipe chimney 1012 from an interior of the bracket cartridge assembly 1030 to an exterior of the cartridge assembly 1010 (e.g., into the first recessed portion 1021A).

Figure 25:
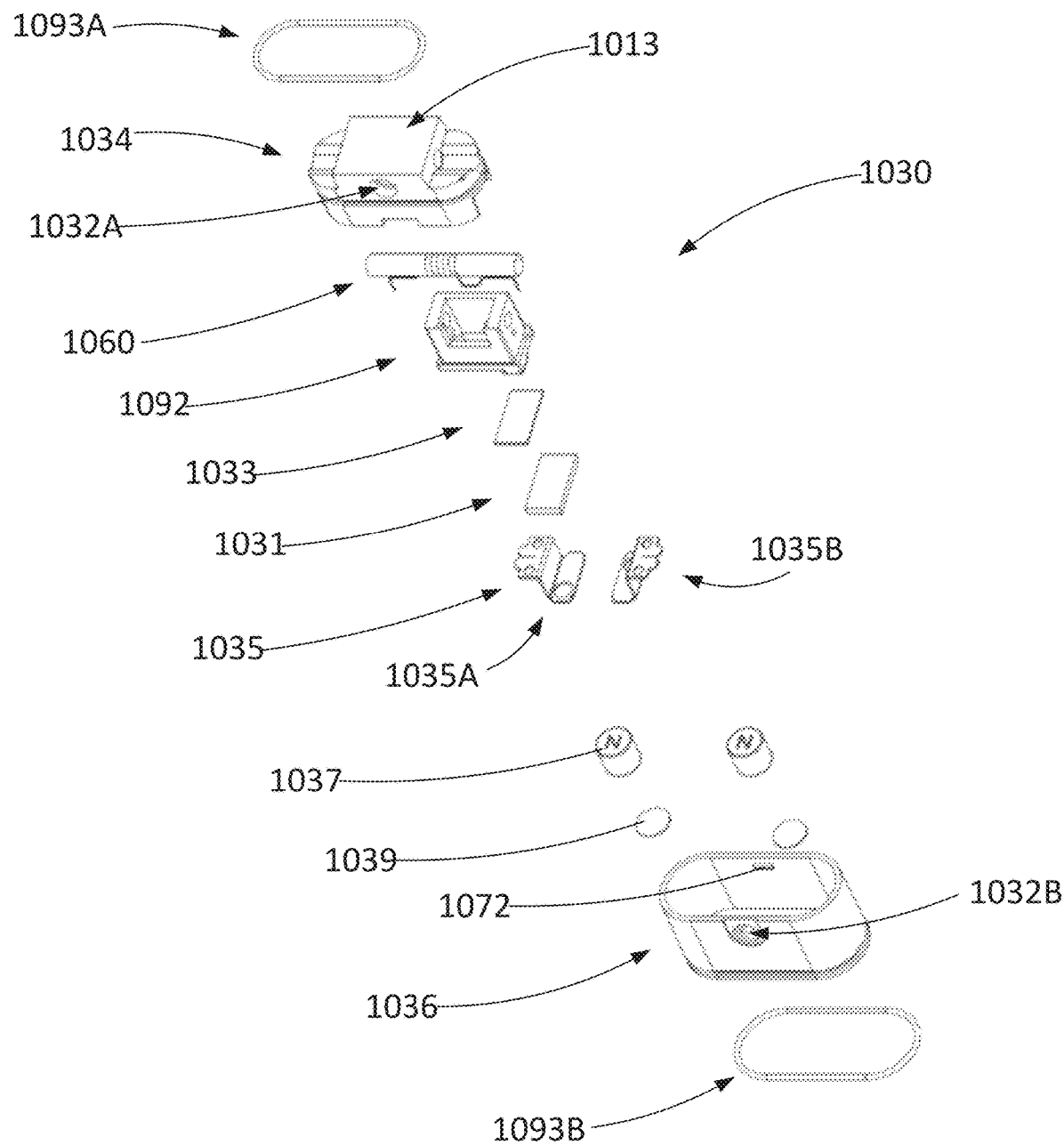
FIG. 25 is an exploded view of a bracket cartridge assembly of the system of FIG. 23.

FIG. 25 is an exploded view of the bracket cartridge assembly 1030. As shown in FIG. 25, the bracket cartridge assembly 1030 includes an upper portion 1034 and a lower portion 1036. The lower portion 1036 is configured to receive the upper portion 1034 within an interior of the lower portion 1036 such that a vapor outlet 1032A in the upper portion 1034 is aligned with a vapor outlet 1032B in the lower portion 1036, forming the vapor outlet 1032. The upper portion 1034 includes an upper surface 1013 which, when the upper portion 1034 is disposed within the interior 1027 of the outer housing 1024, may, in combination with an interior surface of the outer housing 1024, define a reservoir that can be filled with carrier material via the fill inlet 1028A in the outer housing 1024.

The bracket cartridge assembly 1030 may include a wick assembly 1060, a cap 1092, contact cartridges 1035, and magnets 1037. Furthermore, the bracket cartridge assembly 1030 may include a tracking component 1031. The bracket cartridge assembly 1030 may also include tracking component tape 1033 such that the tracking component 1031 may be coupled to the upper portion 1034 via the tacking component tape 1033. Similarly, the magnets 1037 may be attached to the lower portion 1036 via magnet tape 1039. Although two magnets 237 are shown in FIG. 25, the bracket cartridge assembly 230 may include any suitable number of magnets. Although FIG. 25 only shows one magnet tape 239, the bracket cartridge assembly 230 may include any suitable amount or number of magnet tape portions such that the magnets 237 can be secured to the lower portion 232B.

The tracking component 1031 may be the same or similar in structure and/or function to the tracking component 231 described above and will not be further described herein.

As shown in FIG. 25, the bracket cartridge assembly 1030 may include a first sealing member (e.g., O-ring) 1093A and a second sealing member (e.g., O-ring) 1093B. The first O-ring 1093A and the second O-ring 1093B may be configured to engage with the upper portion 1034 and the lower portion 1036, respectively. The first O-ring 1093A is configured to provide a seal between an outer surface of the upper portion 1034 and an inner surface of the lower portion 1036 such that carrier material is prevented from leaking from the region above the upper portion 1034, into the interior of the lower portion 1036, and toward the pen assembly 1040. The second O-ring 1093B is configured to provide a seal between an outer surface of the lower portion 1036 and an inner surface of the outer housing 224 such the carrier material is prevented from flowing from the region defined between the outer housing 1024 and the lower portion 1036 toward the pen assembly 1040.

Figure 26A:
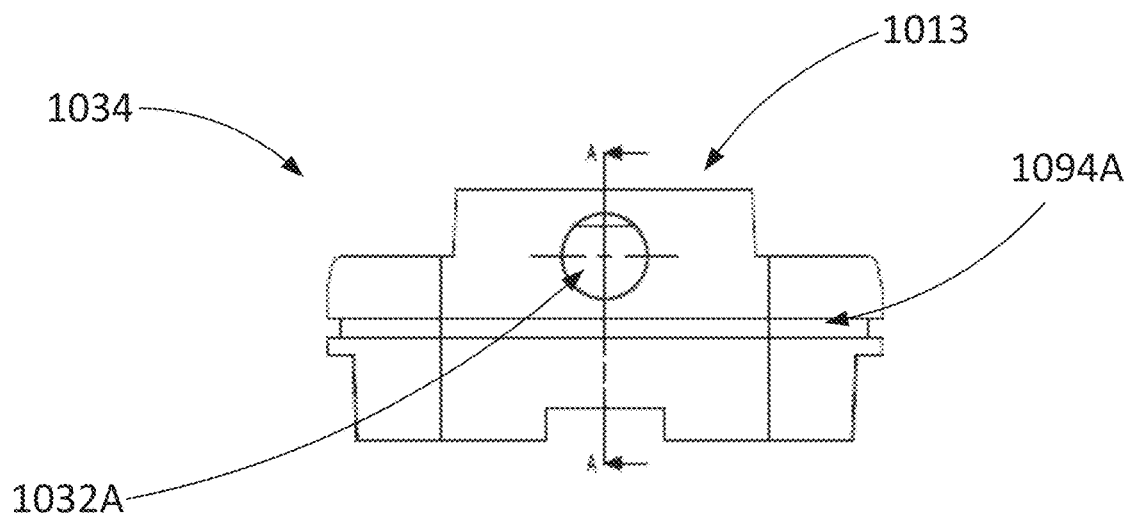
FIGS. 26A-26F are various views of an upper portion of the bracket cartridge assembly shown in FIG. 25. Specifically.
Figure 26B:
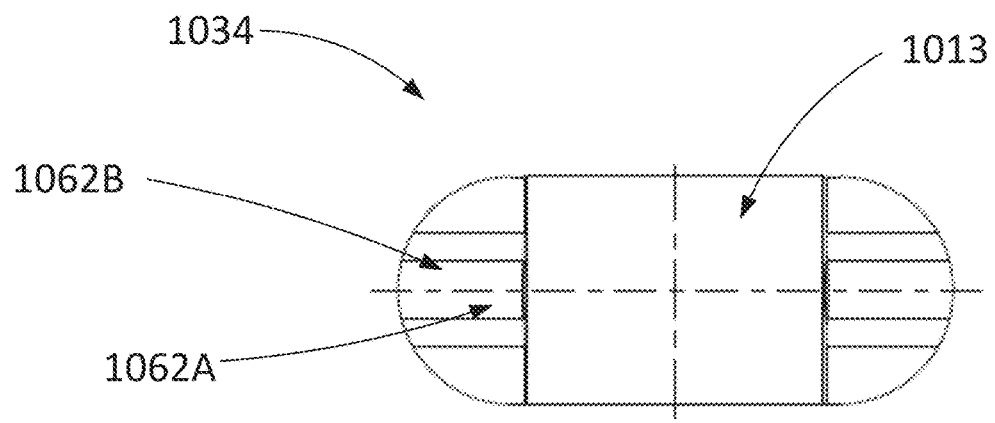
Figure 26C:
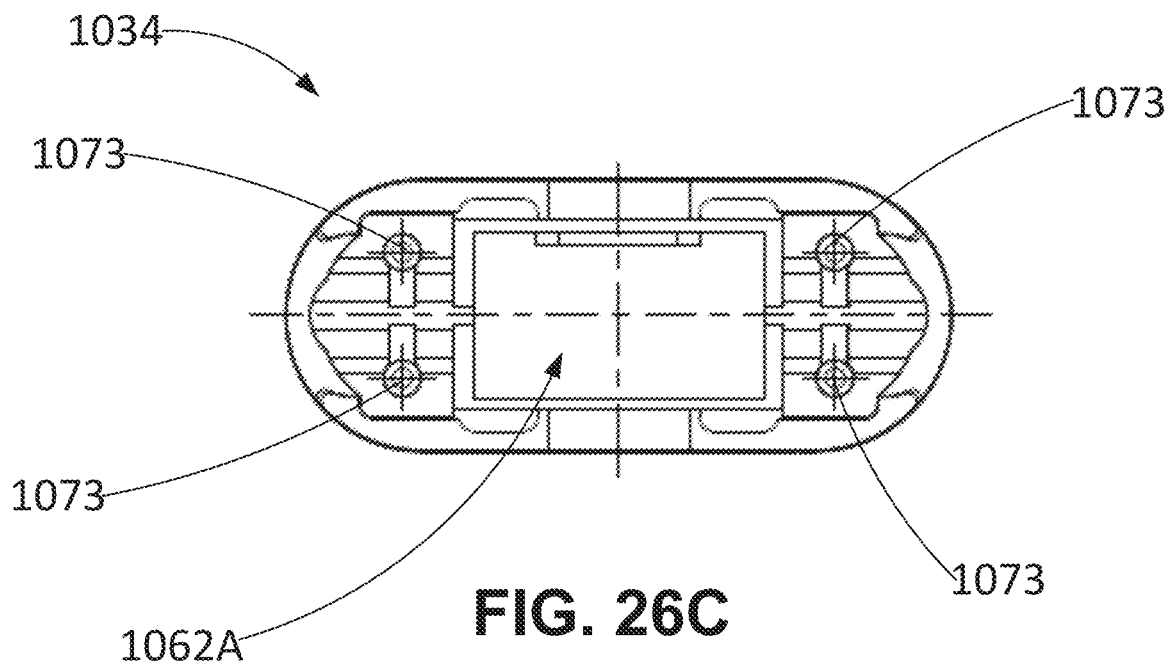
Figure 26D:
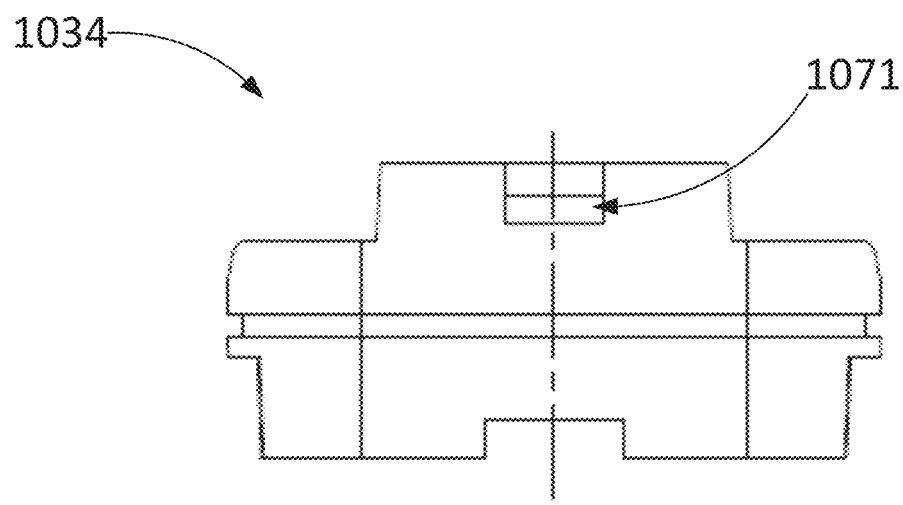
Figure 26E:
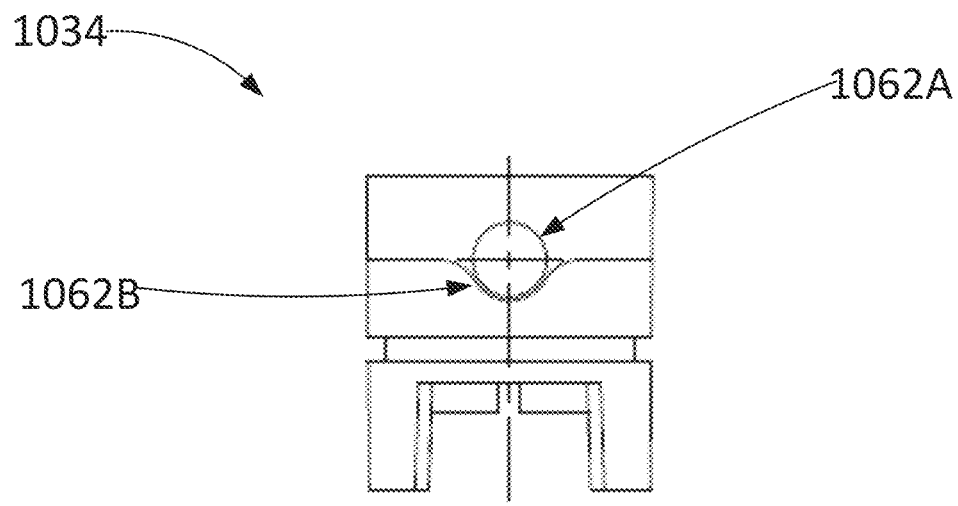
Figure 26F:
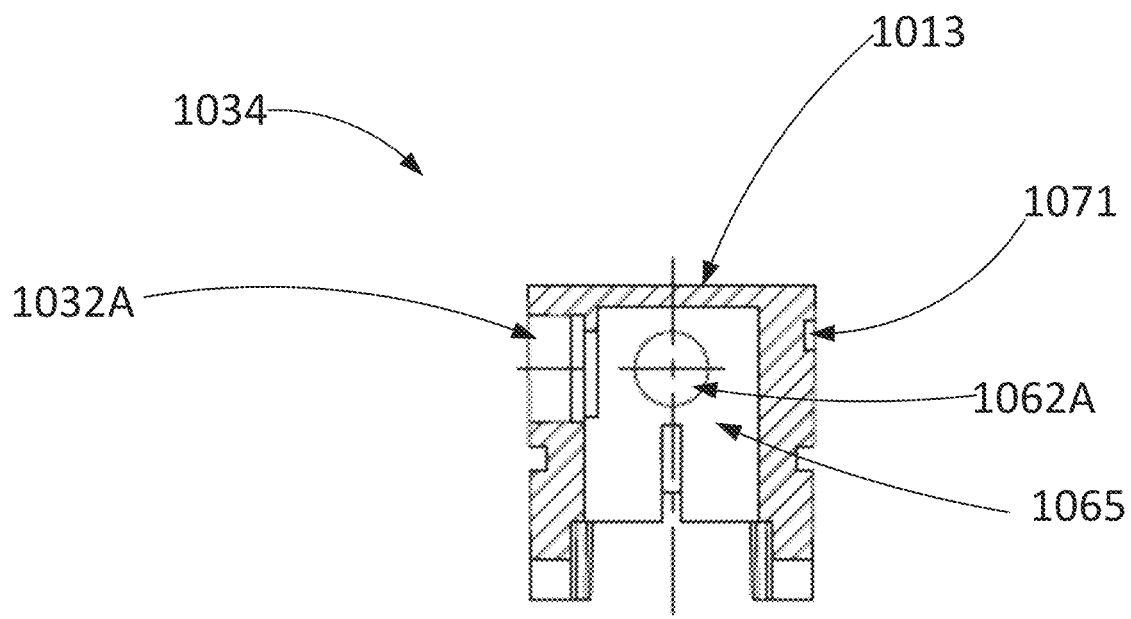

FIGS. 26A-26F are various views of the upper portion 1034. Specifically, FIG. 26A is a back view, FIG. 26B is a top view, FIG. 26C is a bottom view, and FIG. 26D is a front view of the upper portion 234. FIG. 26E is a side view of the upper portion 1034, and FIG. 26F is a cross-sectional view of the upper portion 1034 taken along line A-A in FIG. 26A. As can be seen in various figures, such as FIGS. 26B, 26C and 26E, the upper portion 1034 can define wick receiving apertures 1062A and wick receiving grooves 1062B configured to receive a wick portion of the wick assembly 1060. As shown in FIG. 26D, the upper portion 1034 defines a recess 1071. As shown, the recess 1071 may be disposed on an opposite side of the upper portion from the vapor outlet 1032A. As shown in, for example, FIG. 26A, the upper portion 1034 defines a groove 1094A in the outer surface of the upper portion 1034 configured to receive the first O-ring 1093A shown in FIG. 25.

As shown in FIG. 26F, for example, the upper portion 1034 defines an interior space 1065. The interior space 1065 is accessible via the wick receiving aperture 1062A and the vapor outlet 1032A. As shown in FIG. 26C, the upper portion 1034 defines a number (e.g., four) of attachment recesses 1073 for coupling the upper portion 1034 to the contact cartridges 1035. For example, the contact cartridges 1035 may be coupled to the upper portion 1034 via screws disposed in the attachment recesses. In some implementations, any suitable attachment mechanism may be used to couple the contact cartridges 1035 to the upper portion 1034, such as, for example, adhesive or welding.

Figure 27A:
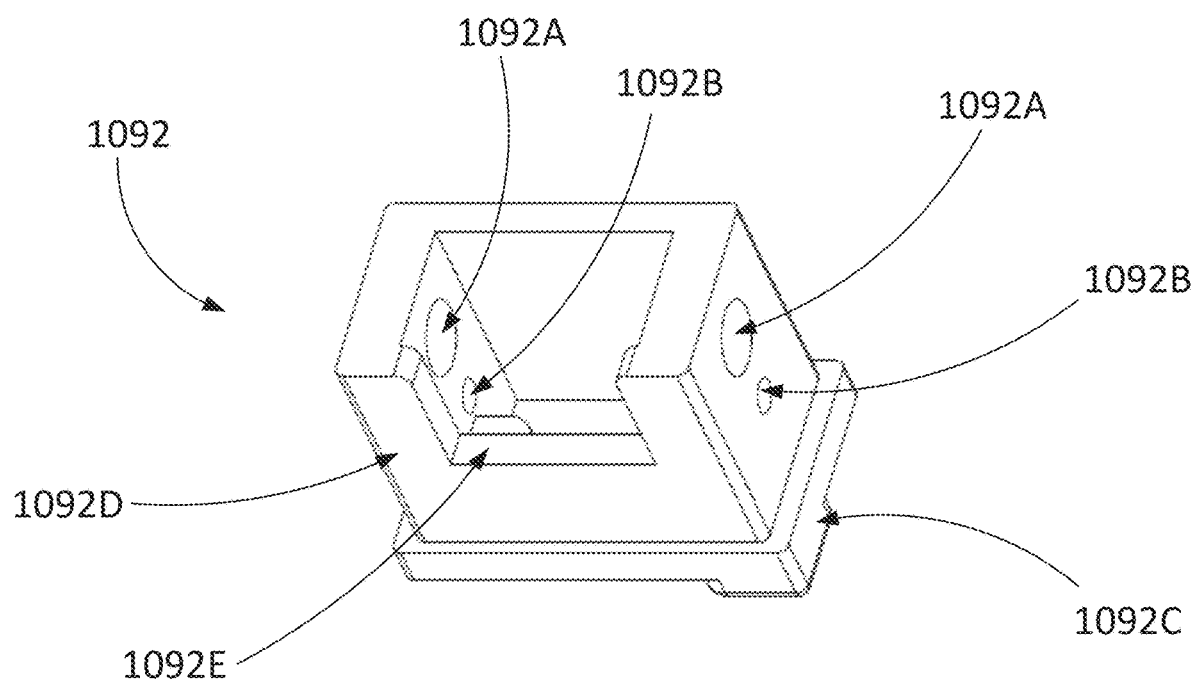
FIGS. 27A and 27B are a back view and a top view, respectively, of a cap of the cartridge assembly of FIG. 23.
Figure 27B:
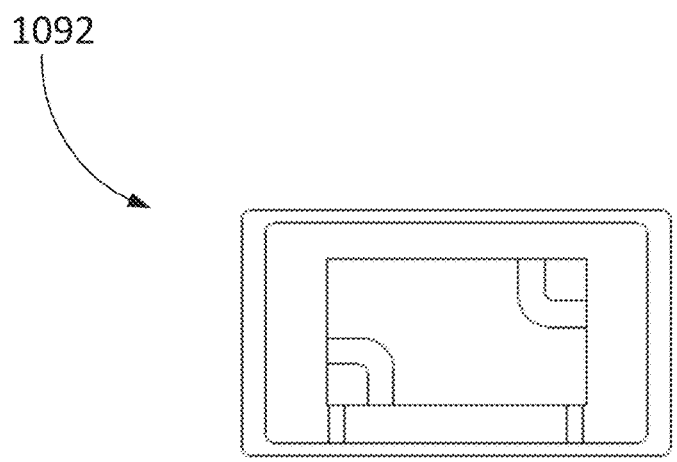
Figure 27C:
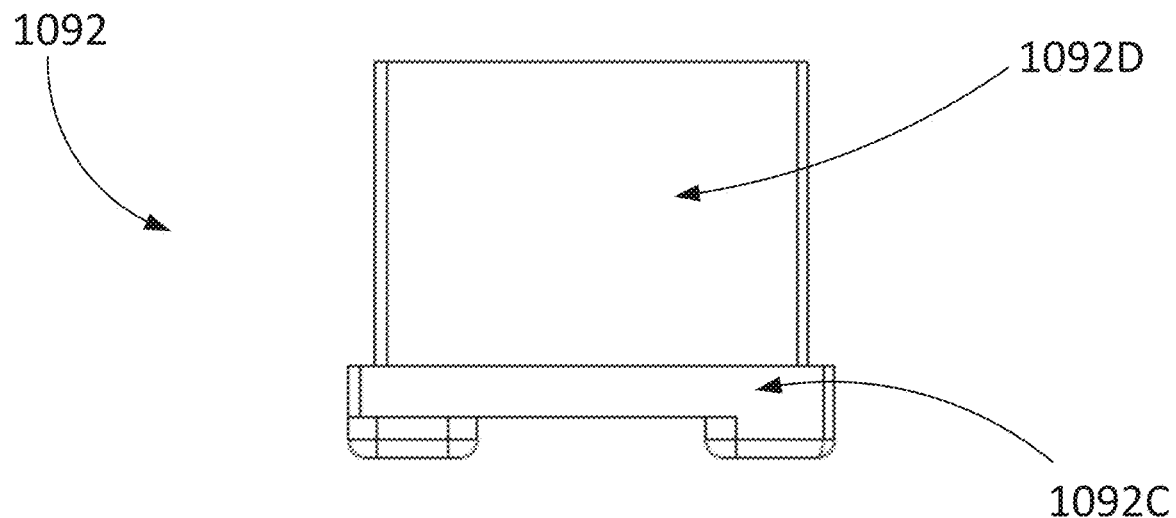
FIGS. 27C and 27D are a front view and a side view, respectively, of the cap of the cartridge assembly of the system of FIG. 23.
Figure 27D:
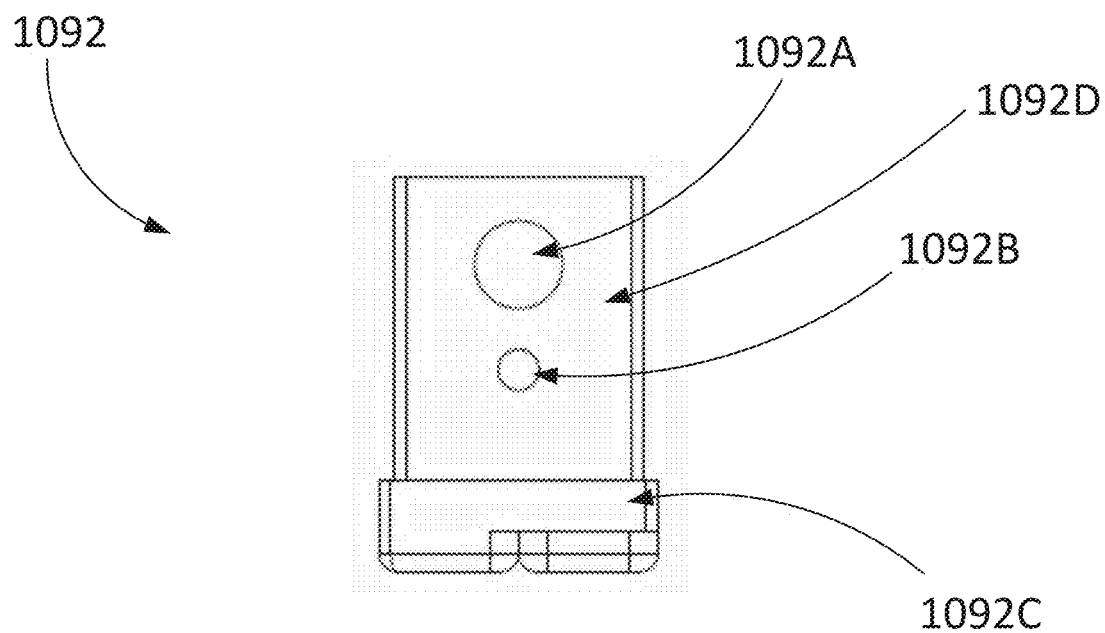

FIGS. 27A and 27B are a back view and a top view, respectively, of the cap 1092. FIGS. 27C and 27D are a front view and a side view, respectively, of the cap 1092. The cap 1092 may be formed of any suitable material configured to prevent carrier material from passing through the cap 1092, such as, for example, silicone. The cap 1092 may include a base 1092C and a sidewall 1092D extending upward from the base 1092C. The sidewall 1092C may define wick receiving apertures 1092A in oppositely-disposed portions of the sidewall 1092C configured to receive the wick 262. The sidewall 1092C may also define a number of inlet openings 1092B such that air may flow into an interior of the cap 1092. The coil 1064 may also be disposed within the inlet openings 1092B such that the coil 1064 is coupled to the contact cartridges 1035 via passing through the inlet openings 1092B. Additionally, the sidewall 1092C may define an opening 1092E such that vapor may flow from an interior of the cap 1092 and through the pipe chimney 1012 via the opening 1092E. As shown in FIG. 27A, the opening 1092E may extend to an upper edge of the sidewall 1092C. The cap 1092 and the base 1092C may be configured to define an interior with sufficient depth and volume to retain any carrier material that may leak from the portion of the wick 1062 disposed within or above the cap 1092 when the wick 1062 is disposed within the wick receiving apertures 1092A.

Figure 28A:
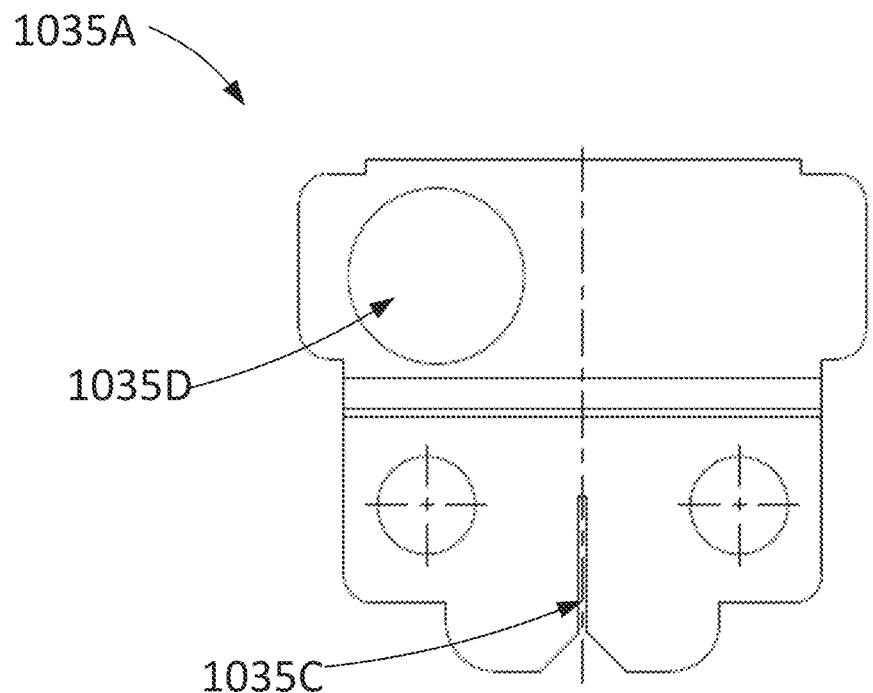
FIGS. 28A and 28B are a bottom view and a side view of a contact cartridge of the cartridge assembly of FIG. 23.
Figure 28B:
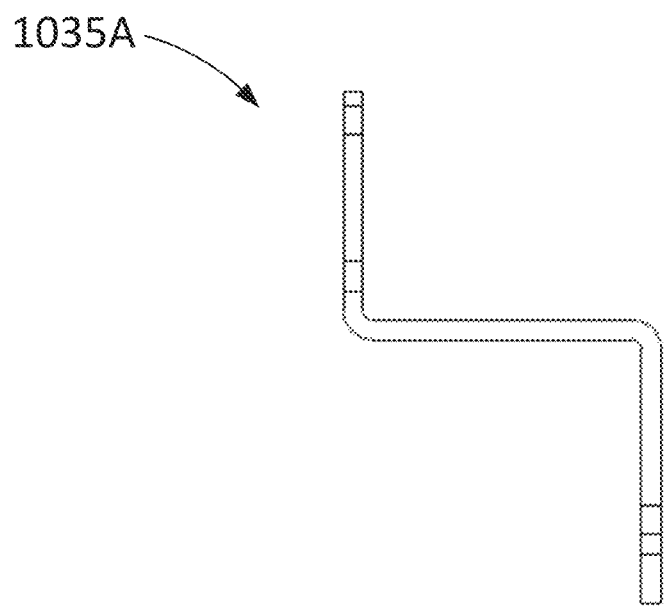

The contact cartridges 1035 include a first contact cartridge 1035A and a second contact cartridge 1035B. FIGS. 28A and 28B are a bottom view and a side view of the first contact cartridge 1035A. The first contact cartridge 1035A is configured to be engaged with a first end portion 1063 of a coil 1064 (described below and as shown in FIG. 29B) and the second contact cartridge 1035B is configured to be engaged with a second end portion 1063 of the coil 1064 (described below and as shown in FIG. 29B). For example, the first contact cartridge 1035A may define a slit 1035C. The first end portion 1063 may be threaded through the slit 1035C such that the coil 1064 is maintained in contact with the first contact cartridge 1035A. Due to the engagement between the first end portion 1063 and the first contact cartridge 1035A (and the similar engagement between the second end portion 1063 and the second contact cartridge 1035B), heating the first contact cartridge 1035A and/or the second contact cartridge 1035B may cause corresponding heating of the coil 1064.

The first contact cartridge 1035A and/or the second contact cartridge 1035B may each define one or more through-holes such that air may be drawn from the pen assembly 1040 to the vapor outlet 1032B via the one or more through-holes of the first contact cartridge 1035A and/or the second contact cartridge 1035B. For example, as shown in FIG. 28A, the first contact cartridge 1035A may define a through-hole 1035D. Although not shown in FIG. 28A, the first contact cartridge 1035A and the second contact cartridge 1035B may each also include a recess or opening configured to receive a portion of a connector 1059 (described below) such that the first contact cartridge 1035A and the second contact cartridge 1035B may each engage with a connector 1059 and such that a temperature of the first contact cartridge 1035A and the second contact cartridge 1035B (and, thus, the temperature of the coil 1064) may be controlled, at least in part, by the temperature of and/or current flowing through the connectors 1059 engaged with each of the first contact cartridge 1035A and the second contact cartridge 1035B.

Figure 29A:
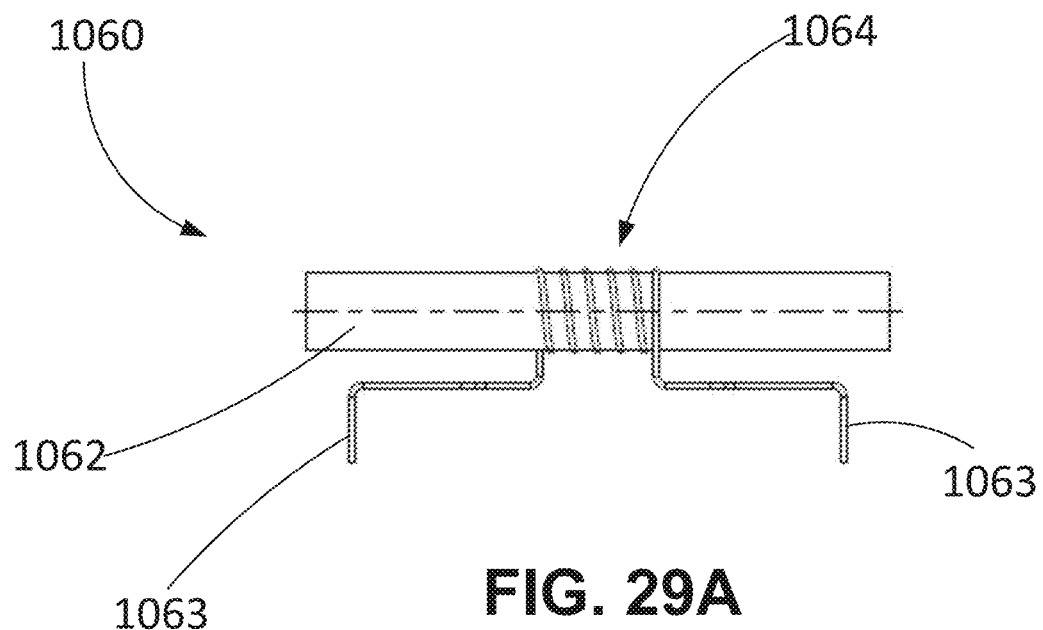
FIG. 29A is a front view of a wick assembly of the cartridge assembly of FIG. 23.
Figure 29B:
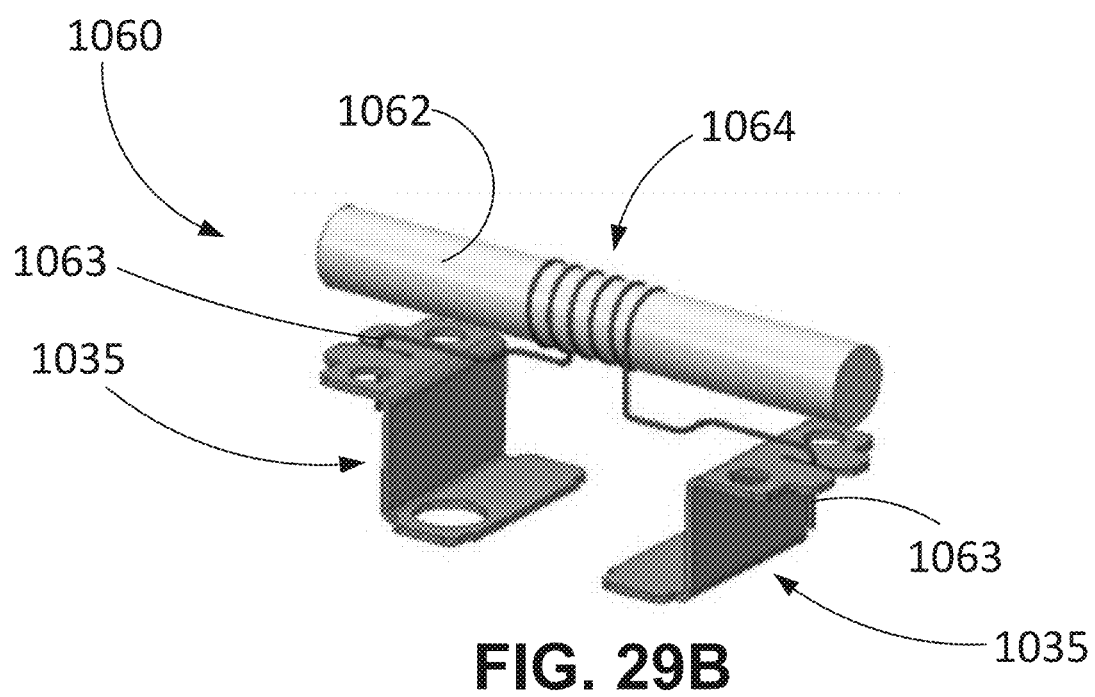
FIG. 29B is a perspective view of the wick assembly of FIG. 29A engaged with the contact cartridges of the cartridge assembly of FIG. 23.

FIG. 29A is a front view of the wick assembly 1060. The wick assembly 1060 includes a wick 1062 and a coil 1064. As shown in FIG. 29A, the coil includes a portion wrapped around a portion of the wick 1062 and two end portions 1063 extending away from the wick 1062. As shown in FIG. 29B, which is a perspective view of the wick assembly 1060 engaged with the contact cartridges 1035, the end portions 1063 can be secured in the slits 1035C of the contact cartridges. The wick 1062 is configured to transport carrier material toward the portion of the wick 1062 adjacent the coil 1064.

The coil 1064 may be formed of any suitable material such as, for example, titanium. The wick 1062 may be formed of any suitable material such as, for example, cotton. For example, the wick 1062 may be formed of ekowool cotton. The wick 1062 may have any suitable diameter, such as, for example, 1.0 mm. In some embodiments, the wick 1062 may have an outer diameter substantially similar to the diameter of the wick receiving apertures 1062A of the upper portion 1034 such that the wick 1062 can be disposed within the wick receiving apertures 1062A. In some embodiments, the coil 1064 may include six turns around an outer surface of the wick 1062 with a pitch of 0.5. In some embodiments, the coil 1064 may include any suitable number of turns and having any suitable pitch. In some embodiments, the resistance of the coil may be 1.0Ω.

The wick assembly 1060 may be disposed relative to the upper portion 1034 such that the portion of the wick 1062 adjacent the coil 1064 is disposed within the interior portion 1065 and the ends of the wick 1062 are disposed within the oppositely-disposed wick receiving apertures 1062A and are received by the wick receiving grooves 1062B of the upper portion 1034. Thus, the carrier material in the reservoir defined by the top surface 1013 of the upper portion 1034 and the interior of the outer housing 1024 may be in contact with the ends of the wick 1062. The carrier material may then travel through the wick 1062 toward the coil 1064. In some implementations, the wick 1062 may be configured to prevent carrier material within the reservoir from flowing through the wick receiving apertures 1062A and into the interior 1065 of the upper portion 1034 (e.g., leakage of carrier material) except through the wick 1064 such that the carrier material is maintained in the reservoir until the carrier material disposed near or adjacent the coil 1064 has been vaporized. For example, the wick 1062 may have a sufficiently large outer diameter such that the wick 1062 is in contact with the edge of the upper portion 1034 defining each wick receiving aperture 1062A. As the carrier material near or adjacent the coil 1064 is vaporized, additional carrier material may travel through the ends of the wick 1062 and toward the portion of the wick 1062 near the coil 1064. The vapor may exit the upper portion 1034 through the vapor outlet 1032A.

Figure 30A:
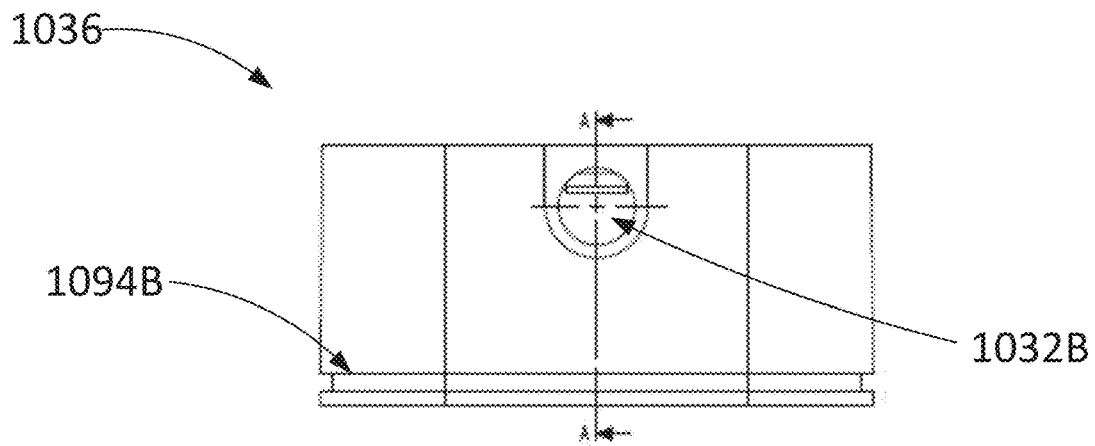
FIGS. 30A-30G are various views of a lower portion of the bracket cartridge assembly shown in FIG. 25. Specifically.
Figure 30B:
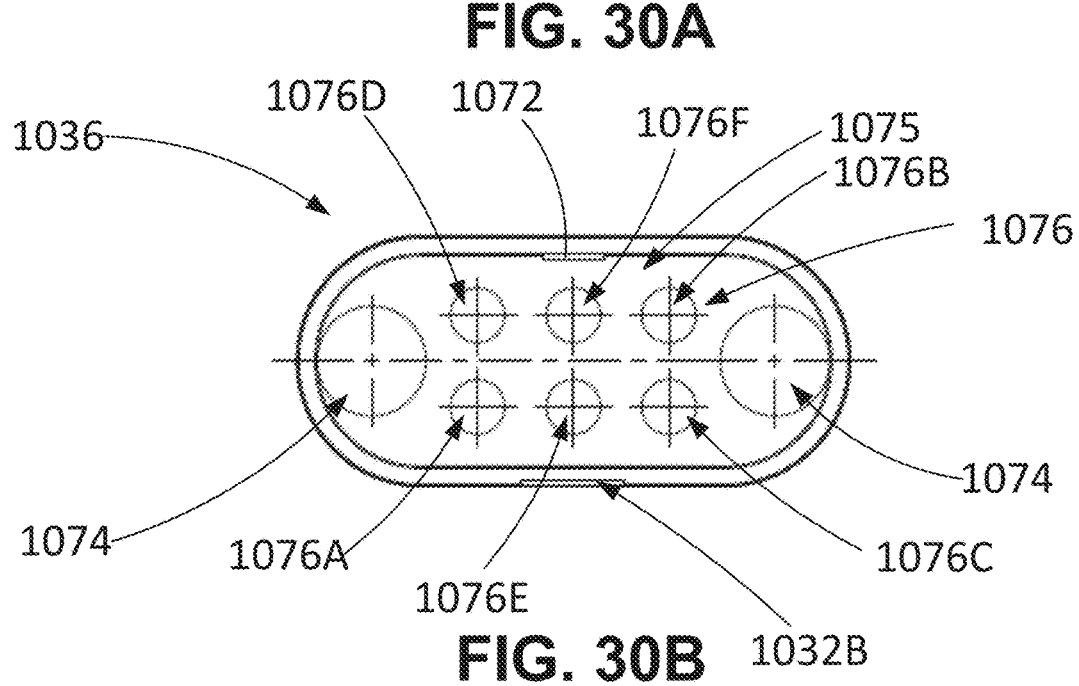
Figure 30C:
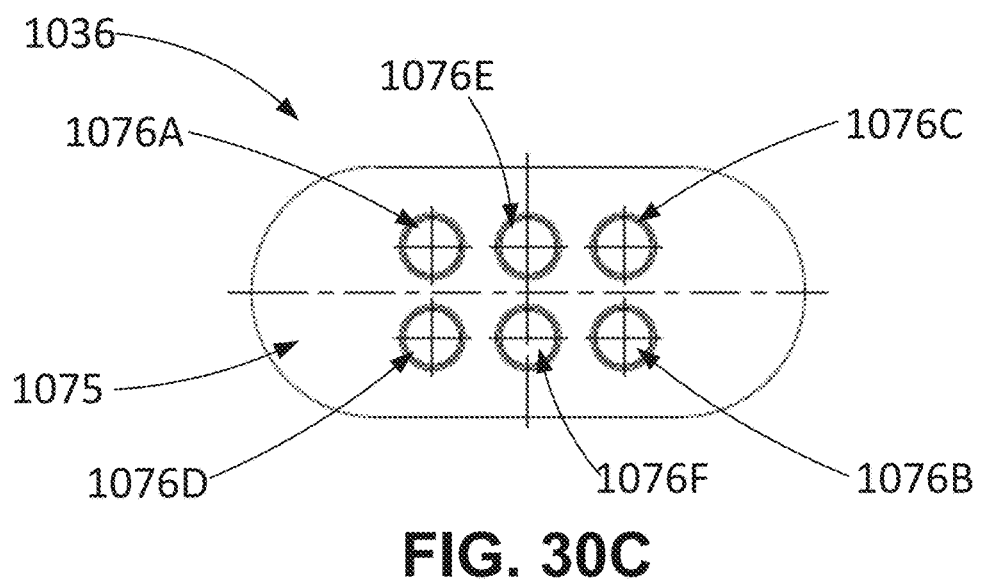
Figure 30D:
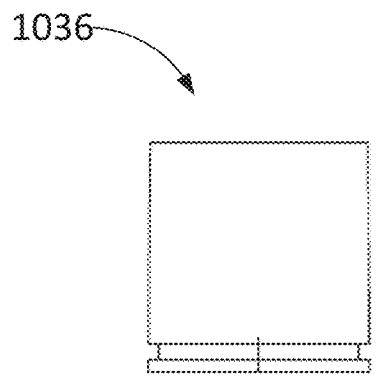
Figure 30E:
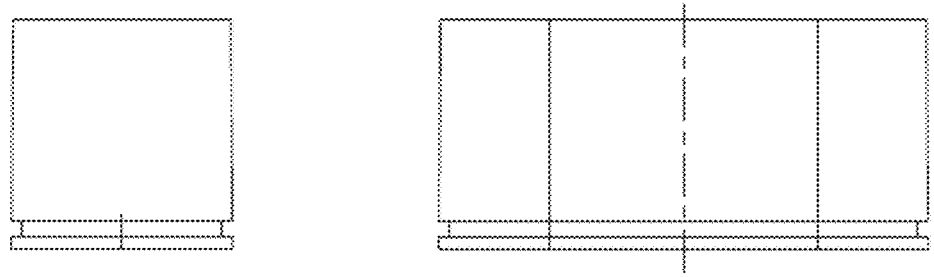
Figure 30F:
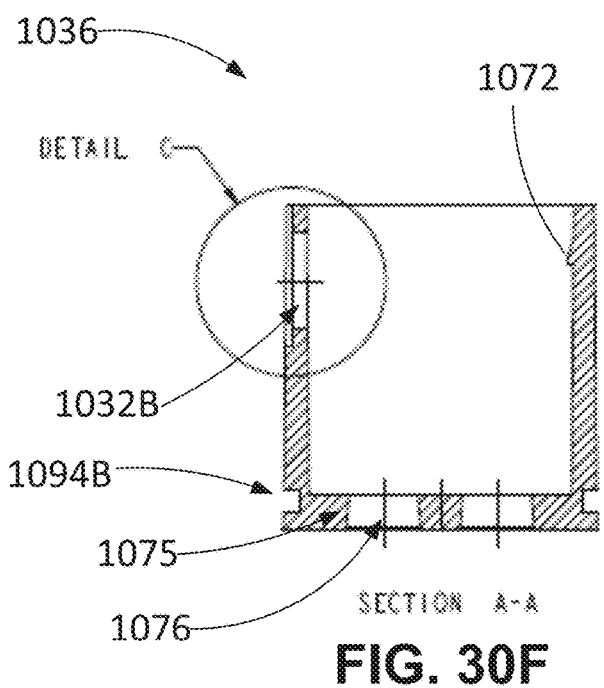
Figure 30G:
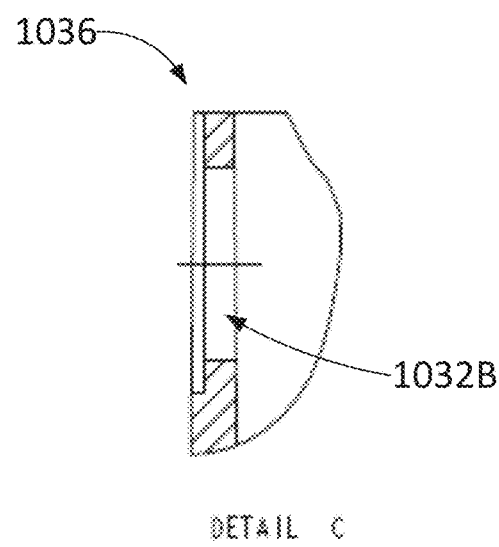

FIGS. 30A-30G are various views of the lower portion 1036. Specifically, FIG. 30A is a back view of the lower portion 1036, FIG. 30B is a top view of the lower portion 1036, FIG. 30C is a bottom view of the lower portion 1036, FIG. 30D is a side view of the lower portion 1036, and FIG. 30E is a front view of the lower portion 1036. FIG. 30F is a cross-sectional view taken along line A-A in FIG. 30A. FIG. 30G is an enlarged view of the portion of FIG. 30F identified as Detail C. As shown in, for example, FIG. 30A, the lower portion 1036 defines a groove 1094B in the outer surface of the lower portion 1036 configured to receive the second o-ring 1093B shown in FIG. 30.

The lower portion 1036 includes a bottom surface 1075. As shown in FIGS. 30B, 30C, and 30F, the lower portion 1036 defines a number of openings 1076 in the bottom surface 1075 of the lower portion 1036. For example, the lower portion 1036 may define six openings 1076. A number of the openings 1076 may be configured such that air may be drawn through the openings 1076 to the vapor outlet 1032. A number of the openings 1076 may be shaped and sized to receive connectors 1059 (described below) of a connection assembly 1056 (described below) when the cartridge assembly 1010 is operatively coupled to the pen assembly 1040. For example, as shown in FIGS. 30B and 30C, the openings 1076 may include a first opening 1076A and a second opening 1076B configured such that air may be drawn through the first opening 1076A and the second opening 1076B. The openings 1076 may include a third opening 1076C and a fourth opening 1076D shaped and sized to receive connectors 1059 (described below) such that the connectors may operatively engage the first contact cartridge 1035A and the second contact cartridge 1035B, respectively. The openings 1076 may include a fifth opening 1076E and a sixth opening 1076F shaped and sized to receive connectors 1059 (described below) such that the connectors 1059 may operatively engage the tracking component 1031.

Additionally, as shown in FIG. 30B, the lower portion 1036 defines a number of magnet receiving recesses 1074. The number of magnet receiving recesses 1074 may correspond to the number of magnets 1037 included in the bracket cartridge assembly 1030. For example, the lower portion 1036 may define two magnet receiving recesses 1074 to receive two magnets 1037. The magnets 1037 may be coupled to the lower portion 1036 via magnet tape 1039 disposed within the magnet receiving recesses 1074.

As shown in, for example, FIGS. 30B and 30F, the lower portion 1036 includes a projection 1072 extending into the interior of the lower portion 1036 from an inner surface of a sidewall of the lower portion 1036. The projection 1072 is sized and positioned to be disposed within the recess 1071 of the upper portion 1034 such that the upper portion 1034 and the lower portion 1036 may be secured to each other (e.g., via a snap fit).

Figure 31A:
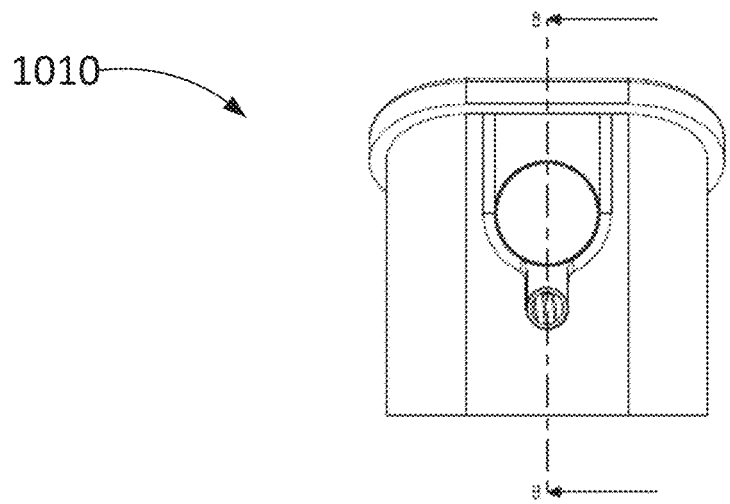
FIG. 31A is a back view of the cartridge assembly of FIG. 23 in an assembled configuration.
Figure 31B:
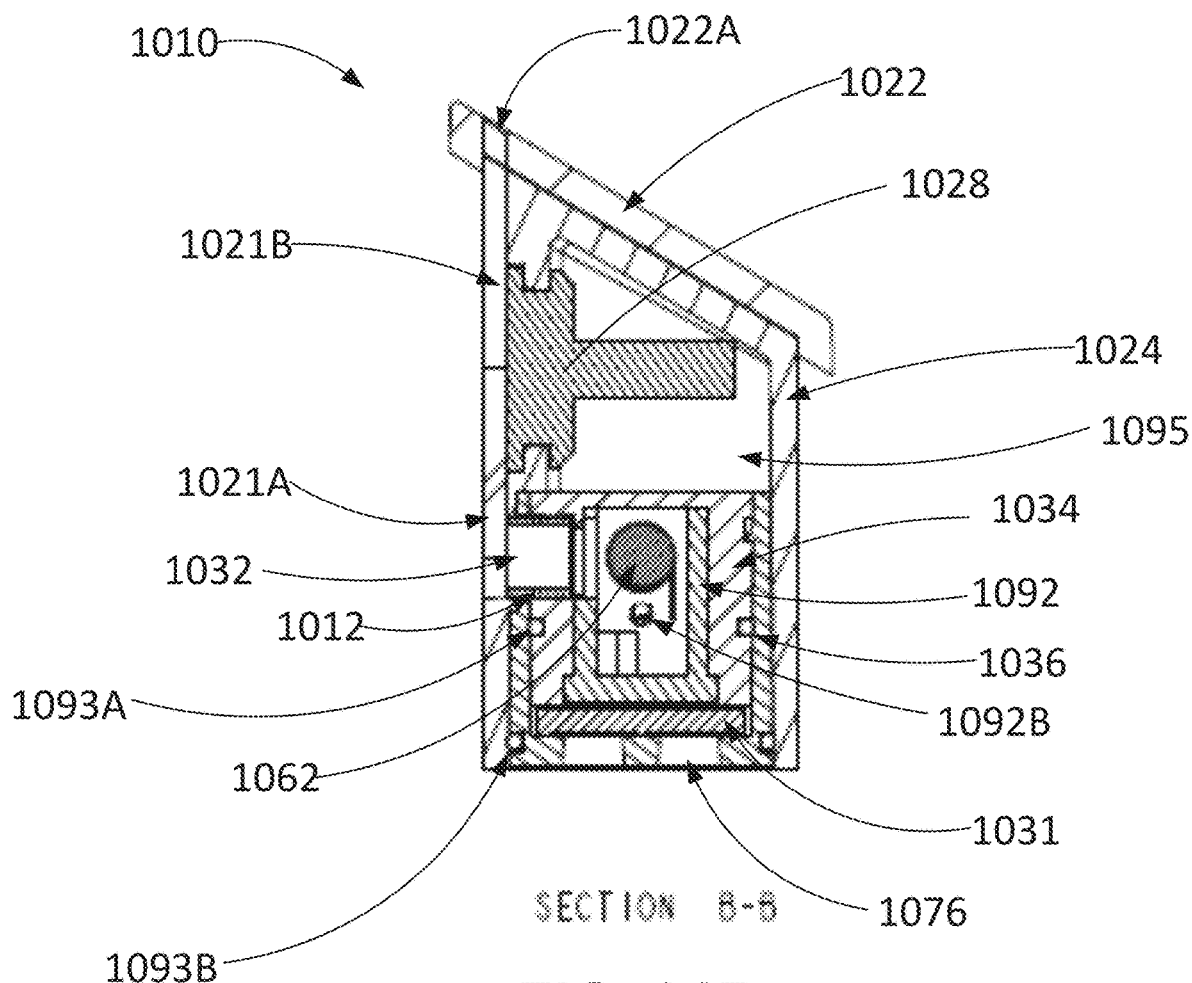
FIG. 31B is a cross-sectional illustration of the cartridge assembly taken along line B-B in FIG. 31A.

FIG. 31A is a back view of the cartridge assembly 1010 in an assembled configuration. FIG. 31B is a cross-sectional illustration of the cartridge assembly 1010 taken along line B-B in FIG. 31A. As shown, the air inlet 1092B of the cap 1092 is in fluid communication with the mouthpiece outlet 1022A via the pipe chimney 1032, the first recessed portion 1021A, and the second recessed portion 1021B. Additionally, as shown in FIG. 31B, the cap 1092 is disposed such that any leakage of carrier material from the wick 1062 that is not converted into vapor may be collected in the interior of the cap 1092.

Figure 32:
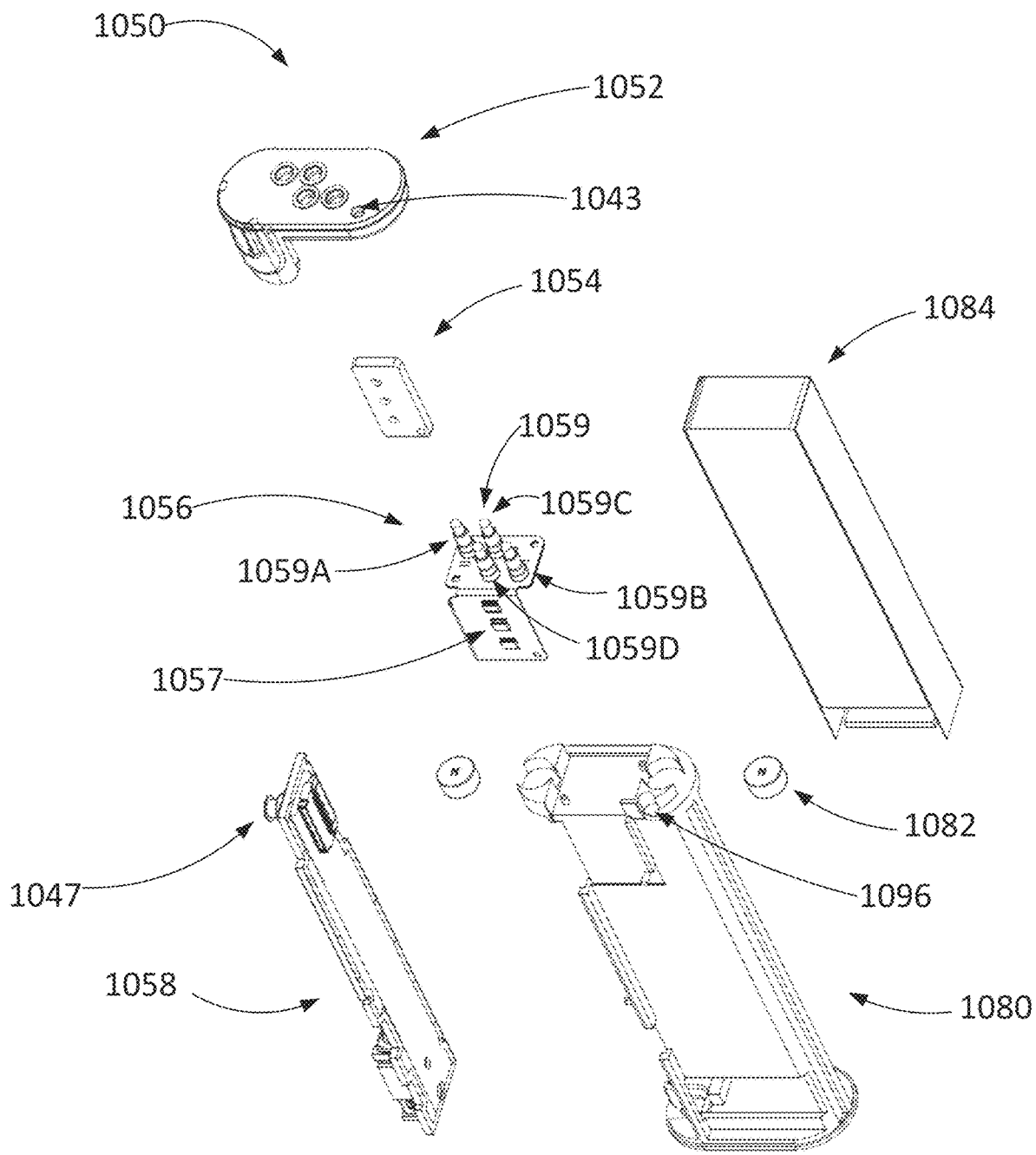
FIG. 32 is an exploded perspective view of a bracket assembly of a pen assembly of FIG. 23.

FIG. 32 is an exploded perspective view of the bracket assembly 1050 of the pen assembly 1040. As shown in FIG. 32, the bracket assembly 1050 includes a cap 1052, an indicator bracket 1054, a connection assembly 1056, and a bracket 1080. The bracket assembly 1050 also includes a power supply 1084 and a control assembly 1058. The power supply 1084 and the control assembly 1058 may be the same or similar in structure and/or function to any of the power supplies and control assemblies described herein, respectively. For example, the power supply 1084 may be the same or similar in structure and/or function to the power supply 284 described above and the control assembly 1058 may be the same or similar in structure and/or function to the control assembly 258 described above. For example, the power supply 1084 may include a pressure sensor 1047. The bracket assembly 1050 also includes a number of magnets 1082. As shown in FIG. 32, the bracket 1080 defines a through-hole 1096 configured to align with the airflow opening 243 of the cap 1052 (described below) such that air may be drawn through open spaces between the bracket 1080 and an inner surface of the pen housing 1042, through the through-hole 1096, and through the airflow opening 1043.

Figures 33A, 33B:
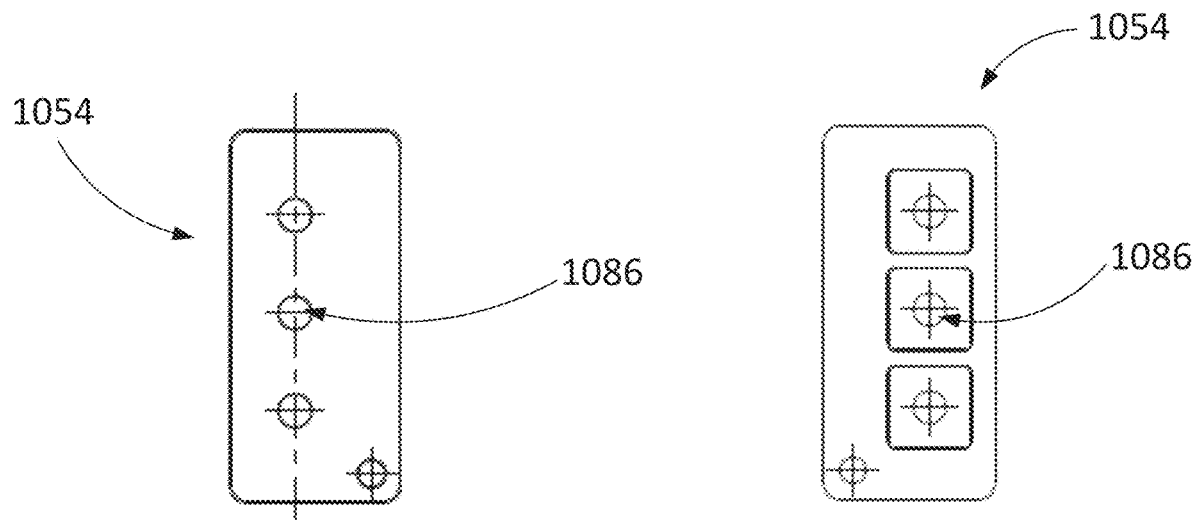
FIGS. 33A-33D are various views of an indicator bracket of the bracket assembly of FIG. 32. Specifically.
Figures 33C, 33D:
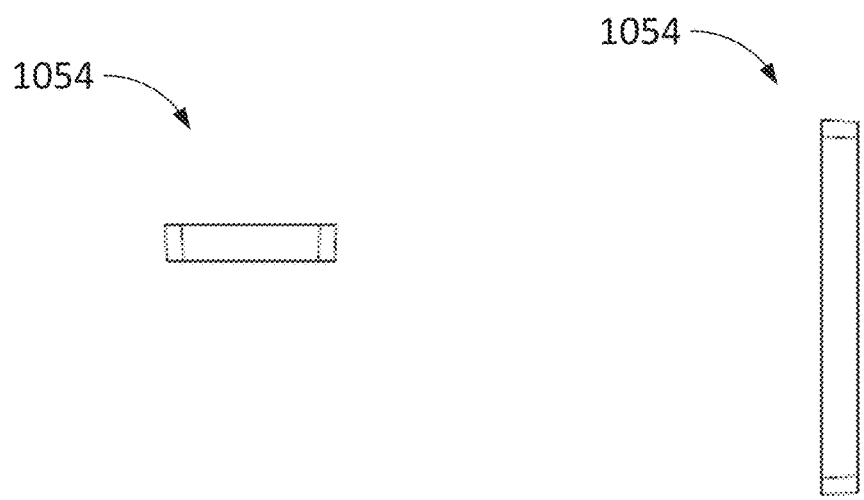

FIGS. 33A-33D are various views of the indicator bracket 1054 of the bracket assembly 1050. Specifically, FIG. 33A is a back view of the indicator bracket 1054 and FIG. 33B is a front view of the indicator bracket 1054. FIG. 33C is a top view of the indicator bracket 1054. FIG. 33D is a side view of the indicator bracket 1054.

As shown in FIG. 33A, for example, the indicator bracket 1054 defines a number (e.g., three) of apertures 1086. The apertures 1086 are configured to be disposed in alignment with the indicator cover elements 1046 of the pen housing 1042 when the bracket assembly 1050 is disposed within the pen housing 1042. As shown in FIG. 33B, the apertures 1086 may each be shaped to receive an indicator feature 1057 of the connection assembly 1056. The connection assembly 1056 may include indicator features 1057. The indicator features 1057 may be the same or similar in structure and/or function to any of the indicator features described herein, such as, for example, the indicator features 257 described above.

As shown in FIG. 32, the connection assembly 1056 may include a number of connectors 1059. For example, as shown, the connection assembly 1056 may include four connectors 1059. The connectors 1059 may be, for example, pogo pins. The connectors 1059 may be configured to operatively couple the control assembly 1058 to components of the cartridge assembly 1010. For example, a first connector 1059A and a second connector 1059B may be configured to operatively couple the control assembly 1058 to the first contact cartridge 1035A and the second contact cartridge 1035B, respectively, such that the control assembly 1058 may control the temperature of the first contact cartridge 1035A and the second contact cartridge 1035B when the first connector 1059A and the second connector 1059B contact the first contact cartridge 1035A and the second contact cartridge 1035B, respectively, thereby controlling the temperature of the coil 1064. A third connector 1059C and a fourth connector 1045D may be configured to couple the control assembly 1058 to the tracking component 1031 of the cartridge assembly 1010 such that the control assembly 1058 may obtain information from the tracking component 1031 when the third connector 1059C and/or the fourth connector 1045D are engaged with the tracking component 1031.

FIGS. 34A, 34B, and 34C are various perspective views of a portion of the bracket assembly 1050. Specifically, FIGS. 34A, 34B, and 34C are various perspective views of the control assembly 1058 and the connection assembly 1056 in an assembled configuration.

Figure 35:
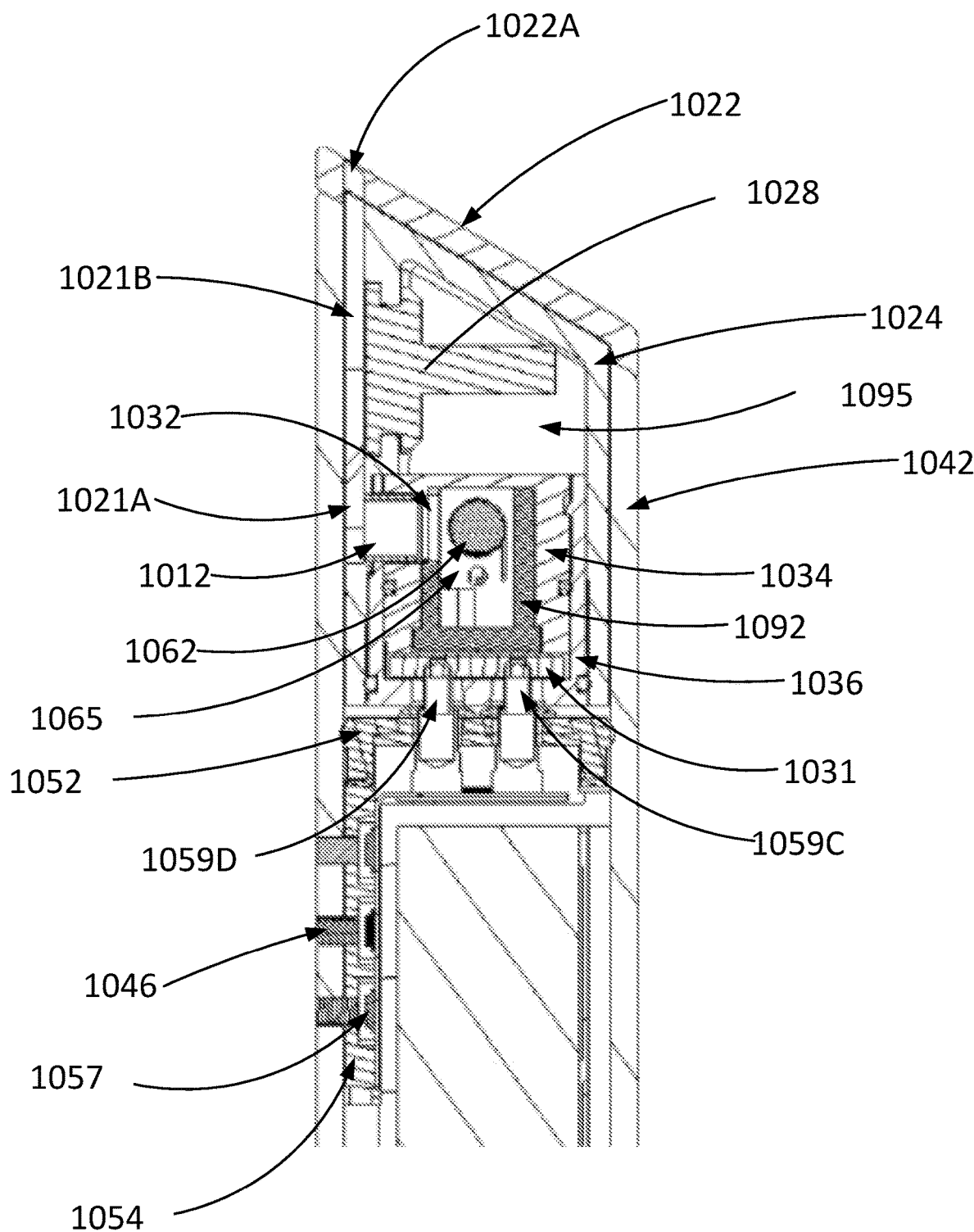
FIG. 35 is a cross-sectional view of a portion of the system of FIG. 23 in an assembled configuration in which the cartridge assembly is engaged with the pen assembly.

FIG. 35 is a cross-sectional view of a portion of the system 1000 in an assembled configuration in which the cartridge assembly 1010 is engaged with the pen assembly 1040. As shown, the connectors 1059C and 1059D are in contact with the tracking component 1031 such that the control assembly may 1058 may communicate with and/or receive information from the tracking component 1031. Also as shown in FIG. 35, the interior surface of the pen housing 1042 and the recessed sidewall portion 1023A collectively form an expansion chamber having a first expansion portion corresponding to the first recessed portion 1021A and a second expansion portion corresponding to the second recessed portion 1021B. The second expansion portion has a larger cross-sectional horizontal area (e.g., the second expansion portion is wider) than the first expansion portion, and thus, as fluid (e.g., vapor) flows from the vapor outlet 1026 through the first recessed portion 1021A and through the second recessed portion 1021B, the fluid pressure of the fluid may reduce due to the fluid expanding into the larger volume region of the second recessed portion 1021B.

The system 1000 may function in use similarly to the system 200 described above. For example, carrier material may be introduced into the reservoir 1095 defined by the outer housing 1024, the plug 1028, and the upper housing 1034 by removing or piercing the plug 1028 and adding carrier material to the reservoir 1095. If the plug 1028 has been removed, the plug 1028 may be engaged with the outer housing 1024 to seal the reservoir 1095. The carrier material may flow into the wick 1062, including the portion of the wick 1062 disposed in the interior of the cap 1092 and in contact or adjacent to the coil 264. The user may draw fluid through the mouthpiece opening 1022A by applying the user's mouth to the mouthpiece assembly and applying negative pressure to the mouthpiece opening 1022A (e.g., via by sucking). In implementations including a pressure sensor 1047 in communication with the control assembly 1058, the negative pressure may trigger the pressure sensor 1047. In response to receiving indication of negative pressure from the pressure sensor 1047, the control assembly 1058 may actuate heater control circuitry of the control assembly 1058 such that a current is passed through the connector 1059A and the connector 1059B, through the contact cartridges 1035, and through the coil 1064 and the coil 1064 is heated to a particular temperature. Alternatively, in implementations including an activation button (not shown) in communication with the control assembly 1058, the user may actuate the activation button such that the control assembly 1058, in response to receiving an actuation signal from the activation button, may actuate heater control circuitry of the control assembly 1058 such that a current is passed through the coil 1064 and the coil 1064 is heated to a particular temperature.

With the coil 1064 heated to the particular temperature and in contact with the wick containing at least a portion of the carrier material, the coil 1064 may vaporize a portion of the carrier material. The vaporized carrier material, or vapor, travels from the interior of the cap 1092, through the pipe chimney 1012, through the first expansion portion, through the second expansion portion, and out of the mouthpiece opening 1022A. As the vapor exits the mouthpiece opening 1022A, the user may inhale the vapor.

As the carrier material is converted to vapor by the coil 1064, the amount of carrier material remaining in the reservoir will decrease. When the amount of carrier material remaining in the reservoir decreases below a threshold level (e.g., between 0 and 10% of the original amount), the user may remove the cartridge assembly 1010. The user may then insert a second cartridge assembly 1010 having carrier material in a reservoir of the cartridge assembly 1010 above a threshold level such that carrier material from the second cartridge assembly 1010 may be vaporized and inhaled. The user may repeatedly remove cartridge assemblies and install new cartridge assemblies to the same pen assembly 1040, disposing of each cartridge assembly when the carrier material within a reservoir of each respective cartridge assembly drops below a threshold level.

Figure 36A:
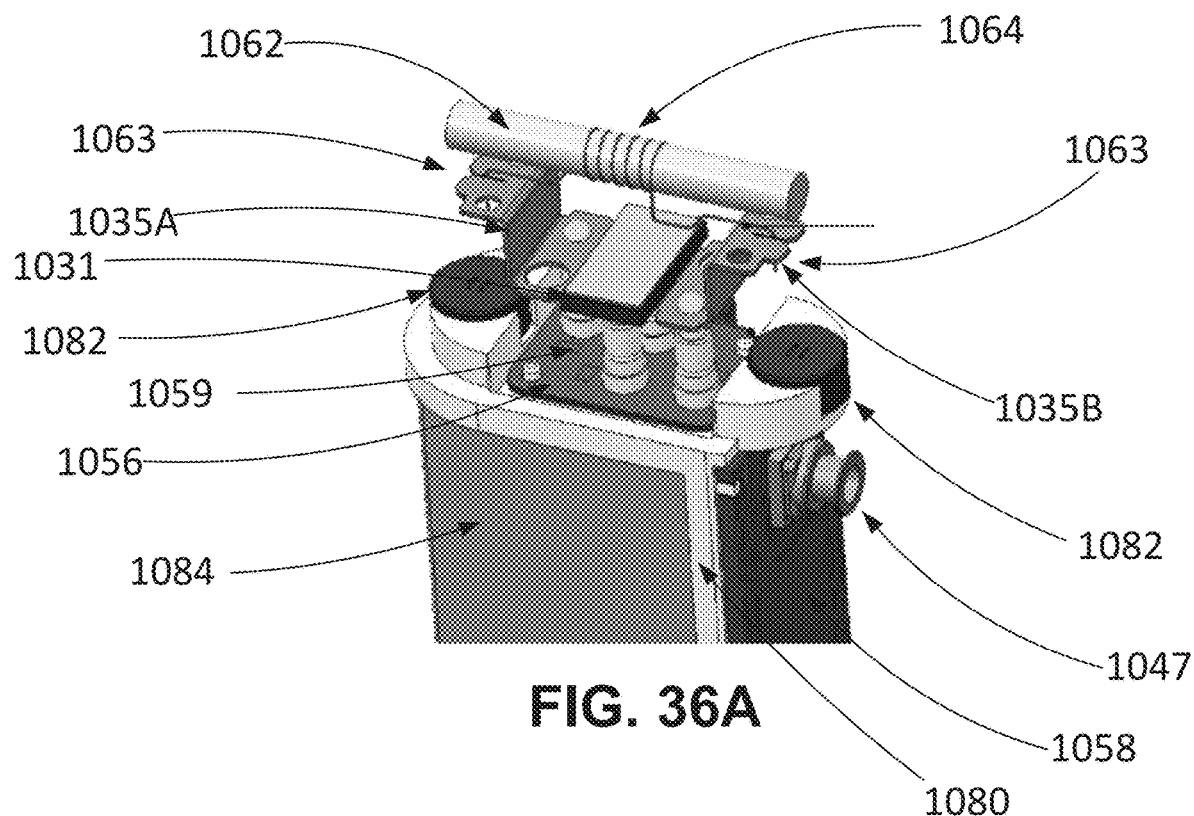
FIGS. 36A-36D are various perspective views of portions of the system of FIG. 23.

FIGS. 36A-36D are various perspective views of portions of the system 1000. Specifically, FIG. 36A illustrates, for example, the relationship between the wick 162, the coil 1064, the contact cartridges 1035A and 1035B, and the connectors 1059. As shown, the connectors 1059 may engage the contact cartridges 1035A and 1035B such that the control assembly 258 may control the temperature of the coil 1064 coupled to the contact cartridges 1035A and 1035B via the connectors 1059 and the contact cartridges 1035A and 1035B.

Figure 36B:
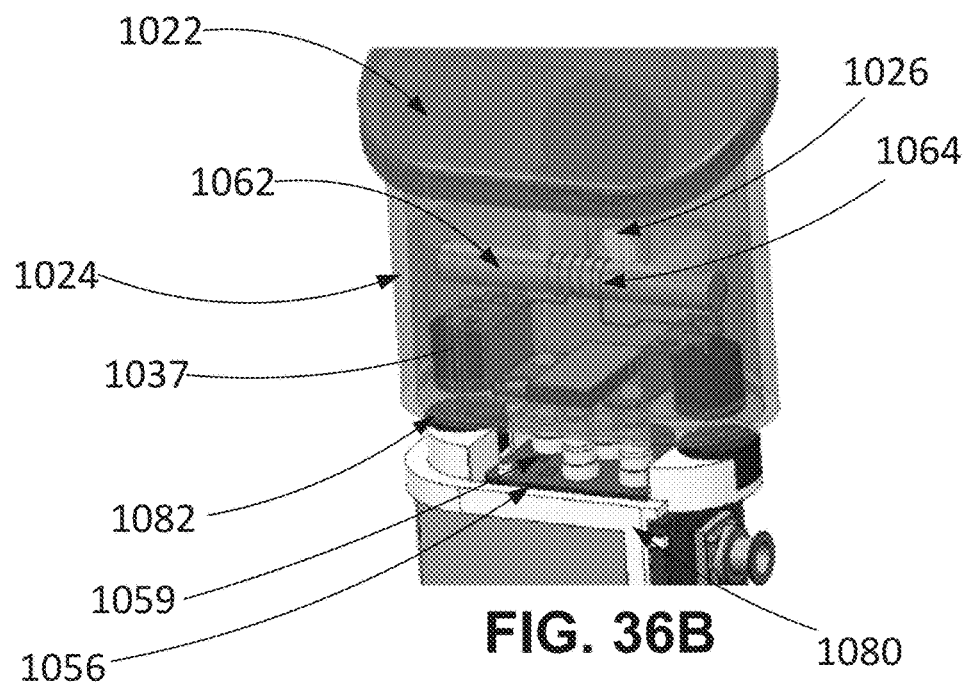

FIG. 36B illustrates the mouthpiece 1022 and the outer housing 1024, both shown as being transparent, disposed in a coupled relationship with some of the components of the pen assembly 240. Specifically, magnets 1037 and magnets 1082 are attracted to each other such that the outer housing 1024 is maintained in engagement with the components of the pen assembly 240. As shown, when the outer housing 1024 is in the configuration relative to the pen assembly 240 as shown in FIG. 36B, the connectors 1059 are in contact with the contact cartridges 1035A and 1035B.

Figure 36C:
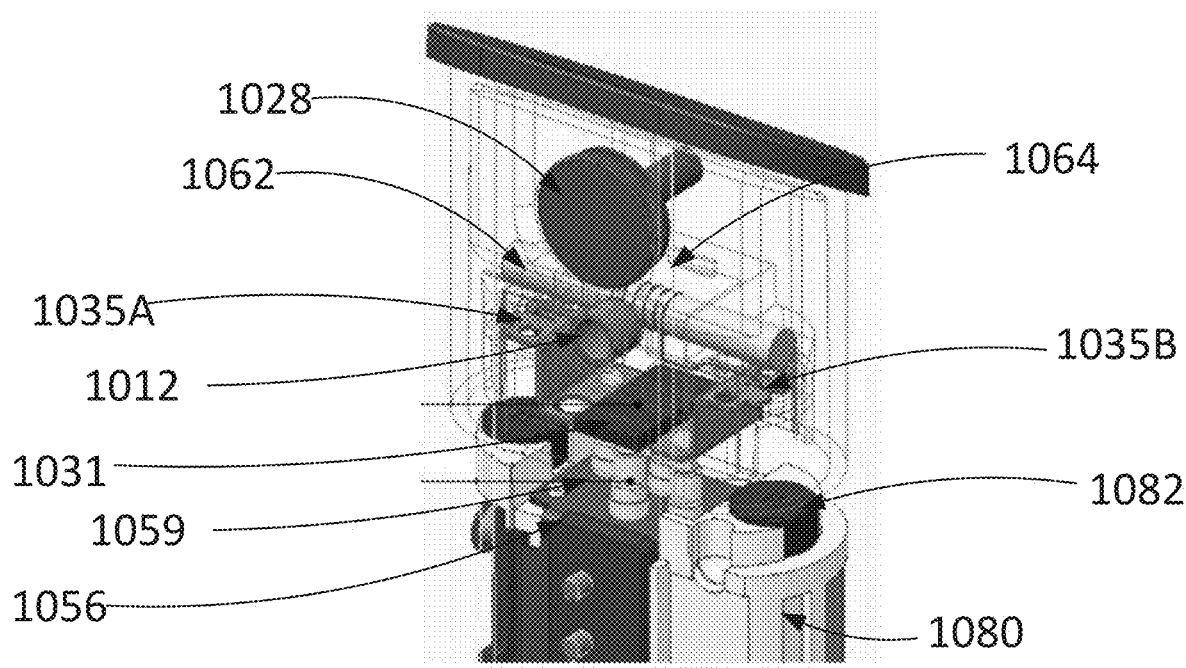

FIG. 36C illustrates the alignment of the chimney pipe 1012 with the portion of the coil 1064 wrapped around the wick 1062. As shown, a central axis of the chimney pipe 1012 may be configured to be perpendicular to a central axis of the wick 1062.

Figure 36D:
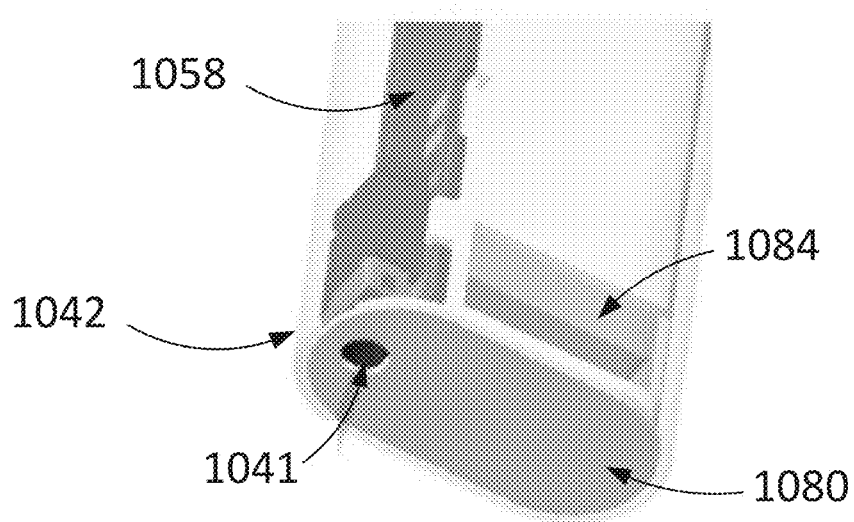

FIG. 36D is a perspective view of the bottom of the system 1000. As shown, the pen housing 1042 and the bracket 1080 may collectively define a bottom opening 1041 such that air may be drawn into an interior of the system 1000 via the bottom opening 1041 and/or such that a charging device may be reversibly engaged with and/or coupled to the power supply of the system (e.g., power supply 1084).

Figure 37A:
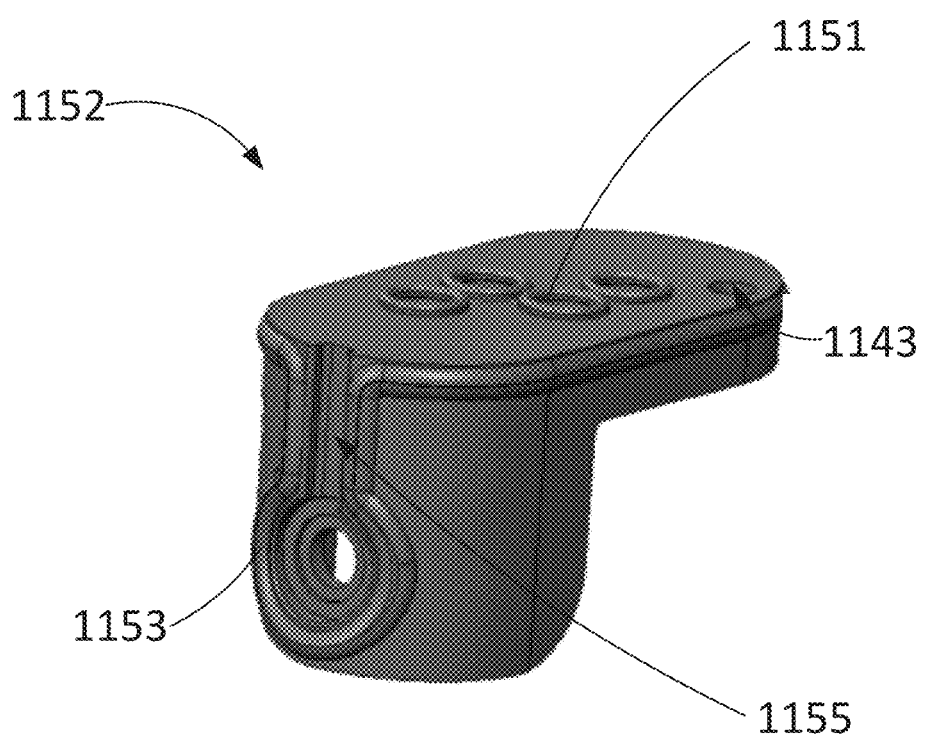
FIGS. 37A-37G are various views of a cap, according to an embodiment. Specifically.
Figure 37B:
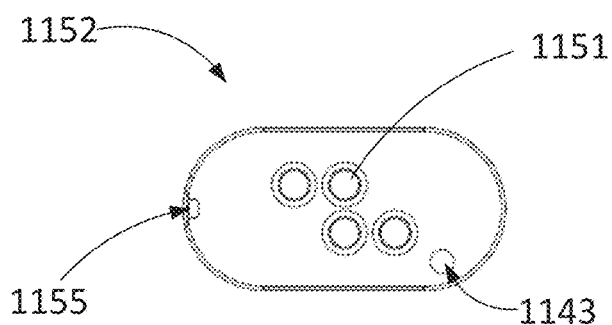
Figure 37C:
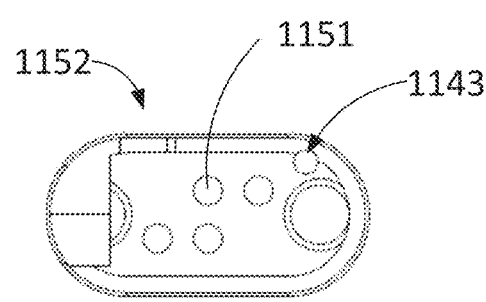
Figure 37D:
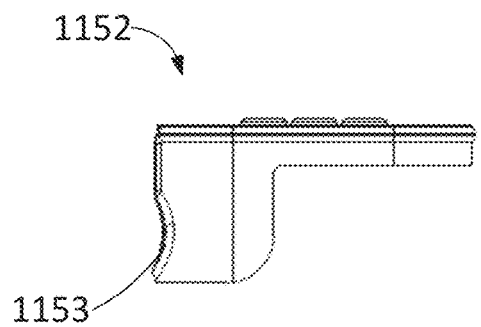
Figure 37E:
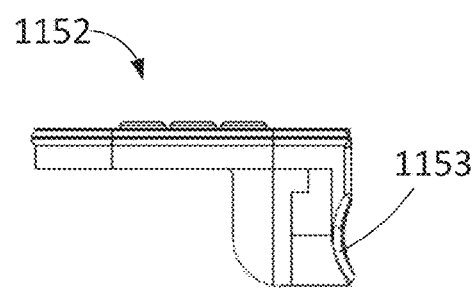
Figure 37F:
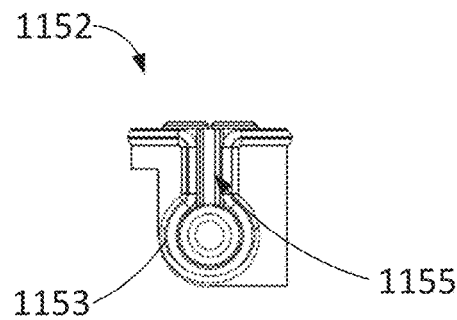
Figure 37G:
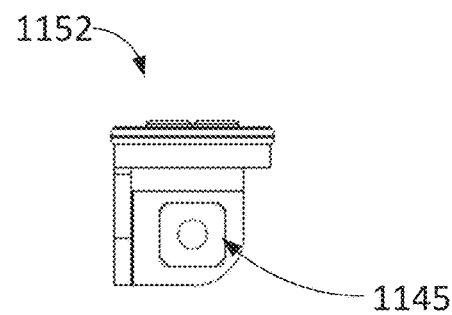

Although the airflow groove of the caps described herein are shown as being non-linear, in some embodiments a cap may include a linear airflow groove. For example, FIGS. 37A-37G are various views of a cap 1152 that may be used in any of the systems described herein, such as the systems 200 or 1000. Specifically, FIG. 37A is a perspective view of the cap 1152. FIG. 37B is a top view of the cap 1152, FIG. 37C is a bottom view of the cap 1152, FIG. 37D is a back view of the cap 1152, and FIG. 37E is a front view of the cap 1152. FIG. 37F is a right side view and FIG. 37G is a left side view, respectively, of the cap 1152. As shown in FIGS. 37A and 37B, for example, the cap 1152 defines a number (e.g., four) of openings 1151. The openings 1151 may be configured to receive connectors, such as any of the connectors described herein (e.g., connectors 259 and/or connectors 1059).

As shown in FIGS. 37B, 37D, and 37F, for example, the cap 1152 includes an extension portion 1153 defining an airflow groove 1155. In some implementations, the extension portion 1153 may be shaped such that the airflow groove 1155 has a linear flow path. As shown in FIG. 37G, the cap 1152 may also define a sensor recess 1145 such that, for example, a pressure sensor (e.g., pressure sensor 247) may be engaged with the sensor recess 1145 of the cap 1152. The extension portion 1153 may be configured to form a seal with the inner surface of a pen housing (e.g., pen housing 242) such that the pressure sensor 1147 may be in fluid communication with a region above the cap 1152 via only the airflow groove 1155. Furthermore, the cap 1152 may define an airflow opening 1143 configured such that air can be drawn through the airflow opening 1143.

FIGS. 38A-41B show front views of a system 1200 in various stages of operation. The system 1200 may be the same or similar in structure and/or function to any of the systems described herein. For example, the system 1200 includes a pen assembly 1240 including a pen housing 1242 and a cartridge assembly 1210 including a mouthpiece component 1222 defining a mouthpiece opening 1222A. As shown, the pen assembly 1240 includes an indicator component 1246 that is configured to indicate at least one characteristic of the system 1200 (e.g., a characteristic of the cartridge assembly 1210 or the contents of the cartridge assembly 1210). The indicator component 1246 can be or include, for example, an LED and/or an LED cover. Various characteristics of the system 1200 can be represented by the indicator component 1246 via displaying different patterns and/or colors corresponding to each characteristic or characteristic type.

As shown in FIGS. 38A-38E, the indicator component 1246 can be configured to indicate a fill level of carrier material (e.g., oil) within the cartridge assembly 1210. The indicator component 1246 can display a first color, such as amber, to represent the oil level. When the cartridge assembly 1210 is engaged with the pen assembly 1240, the indicator component 1246 can display an indication of the fill level of the cartridge assembly 1210 for a duration of time (e.g., three seconds). If the fill level is below a threshold operability level (e.g., below 5%), the indicator component 1246 can show no indication of any color or can show a patterned response, as shown in FIG. 38A. If the fill level is between 5% and 30%, the indicator component 1246 can show an indication representing a range between 5% and 30%, as shown in FIG. 38B. If the fill level is between 30% and 90%, the indicator component 1246 can show an indication representing a range between 30% and 90%, as shown in FIG. 38C. If the fill level is between 90% and 100%, the indicator component 1246 can show an indication representing a range between 90% and 100%, as shown in FIG. 38D. If the cartridge assembly 1210 is rejected by the pen assembly 1240 (e.g., the pen assembly 1240 determines that the system 1200 should be disabled due to, for example, the fill level and/or contents of the cartridge assembly 1210), the indicator component 1246 can show no indication, as shown in FIG. 38E.

As shown in FIGS. 39A-39E, the indicator component 1246 can be configured to indicate a battery status of the pen assembly 1240. The indicator component 1246 can display a second color, such as white, to represent the battery level or status. When the cartridge assembly 1210 is removed from engagement with the pen assembly 1240, the indicator assembly 1246 can display an indication of the battery status for a duration (e.g., three seconds). If the battery level is below a threshold operability level, the indicator assembly 1246 can show nothing to indicate that the battery is in battery conservation mode, as shown in FIG. 39A. If the battery level is above the threshold operability level but below 5%, the indicator component 1246 can show an indication representing a low battery warning, as shown in FIG. 39B. If the battery level is between 5% and 30%, the indicator component 1246 can show an indication representing a range between 5% and 30%, as shown in FIG. 39C. If the battery level is between 30% and 90%, the indicator component 1246 can show an indication representing a range between 30% and 90%, as shown in FIG. 39D. If the battery level is between 90% and 100%, the indicator component 1246 can show an indication representing a range between 90% and 100%, as shown in FIG. 39E.

As shown in FIGS. 40A-40B, the indicator component 1246 can be configured to indicate a charging status of the battery of the pen assembly 1240. As shown in FIG. 40A, when the pen assembly 1240 is engaged with a charging source, the indicator component 1246 can display a pattern to represent that the battery is charging. The pattern can be, for example, a cycling pattern that cycles through the various indications of the ranges of battery level shown in FIGS. 39B-39E. As shown in FIG. 40B, when the charging operation is complete (e.g., the battery level is between 90% and 100%), the indication component 1246 can indicate that the charging operation is complete by displaying the indication shown in FIG. 40B.

As shown in FIGS. 41A-41B, the indicator component 1246 can be configured to indicate a Bluetooth® pairing status of the system 1200. The indicator component 1246 can display a third color, such as blue, to represent the pairing status. Periodically, if the pen assembly 1240 is not registered to an application of a remote compute device, the pen assembly 1240 may be configured to look for a remote compute device with which to pair. When the pen assembly 1240 is searching for a remote compute device with which to pair, the indicator component 1246 can display an indication that the pen assembly 1240 is searching for a device, as shown in FIG. 41A, for a duration of time (e.g., three seconds). If the pen assembly 1240 successfully pairs with a remote compute device, the indicator component 1246 can display an indication that the pen assembly 1240 is paired, as shown in FIG. 41B.

In some embodiments, the indicator component 1246 can be configured to provide a particular indication to alert the user if the user attempts to inhale through the mouthpiece opening 1222A when the system 1200 has been disabled. For example, the indicator component 1246 can display a particular color or pattern if the battery is in conservation mode, if the cartridge assembly 1210 is empty, and/or if the cartridge assembly 1210 is invalid or not recognized by the pen assembly 1240. Furthermore, the indicator component 1246 can be configured to provide a particular indication to the user to reflect the firmware status of the system 1200. For example, the indicator component 1246 can display a fourth color, such as violet, to reflect a firmware status. During a firmware update, the indicator component 1246 can display a cyclical pattern to communicate that the firmware is updating. When the firmware update is complete, the indicator component 1246 can display a different pattern or indication to communicate that the update is complete to the user. For example, the indicator component 1246 can include a steady violet indication.

Figure 42A:
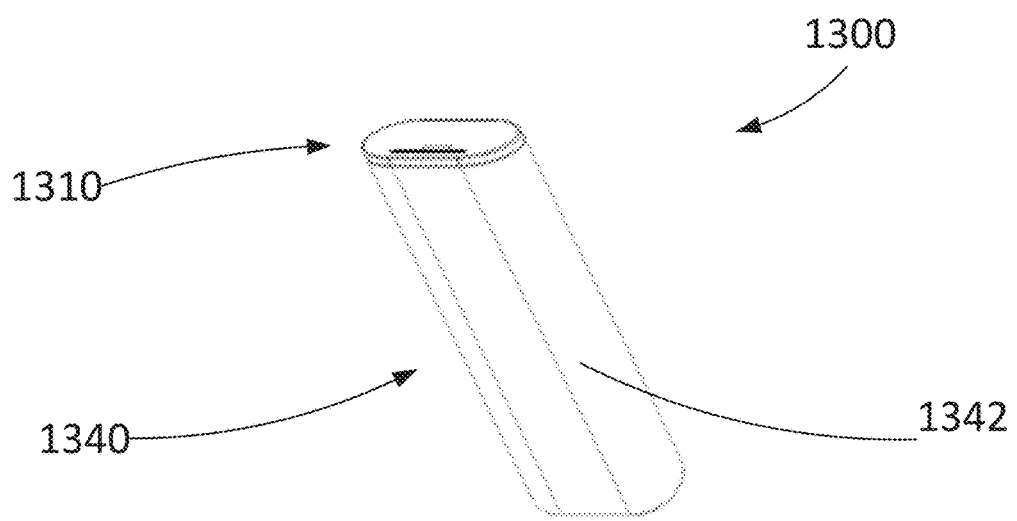
Figure 42B:
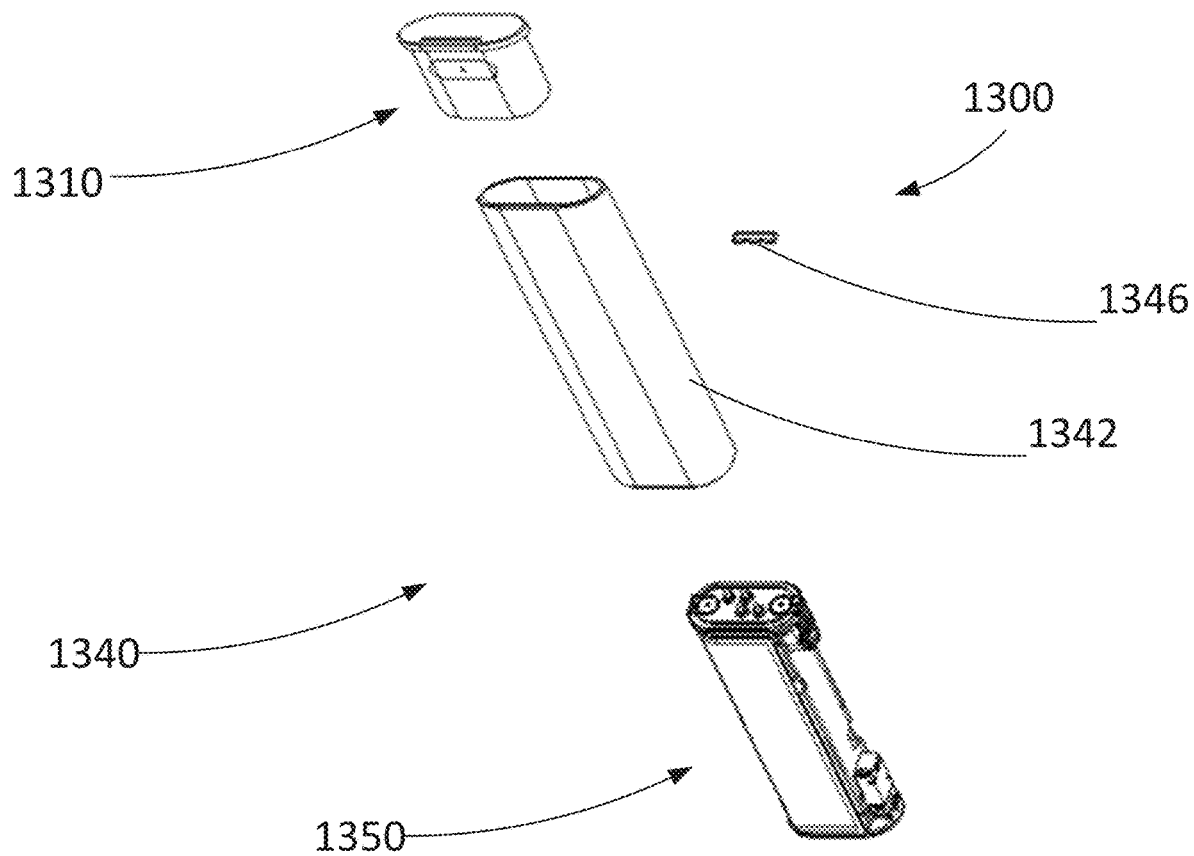

FIGS. 42A and 42B are perspective view of an electronic vapor delivery system 1300 in an assembled and an exploded configuration, respectively. The system 1300 may be the same or similar in structure and/or function to any of the systems described herein. For example, the system 1300 includes a cartridge assembly 1310 (also referred to as a capsule, capsule assembly cartridge, or pod) and a pen assembly 1340 (also referred to as a pen device or vaporizer pen). The pen assembly 1340 includes a pen housing 1342 and a bracket assembly 1350. The pen assembly 1340 also includes indicator components 1346 (e.g., translucent portions configured such that light transmitted from indicator features described below may be visible through the indicator components 1346). Furthermore, in some implementations, the pen housing 1342 may define one or more inlets in any suitable location on the pen housing 1342, such as on opposite sides of the pen housing 1342 and/or in a bottom surface of the pen housing 1342.

FIGS. 43A-43F are various views of the system 1300. Specifically, FIG. 43A is a left side view, FIG. 43B is a front view, FIG. 43C is a right side view, and FIG. 43D is a back view. FIG. 43E is a bottom view and FIG. 43F is a top view, respectively, of the system 1300. As shown in FIG. 43E, the bottom of the pen housing 1342 may define a bottom opening 1341 such that air may be drawn into an interior of the system 1300 via the bottom opening 1341 and/or such that a charging device may be reversibly engaged with a power supply of the system (e.g., power supply 1384 discussed below).

Figure 44A:
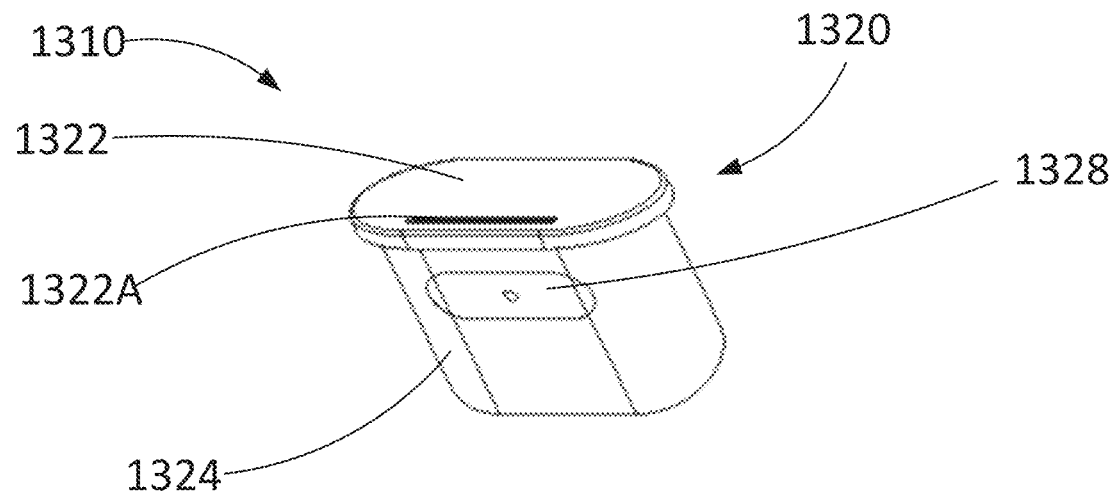
Figure 44B:
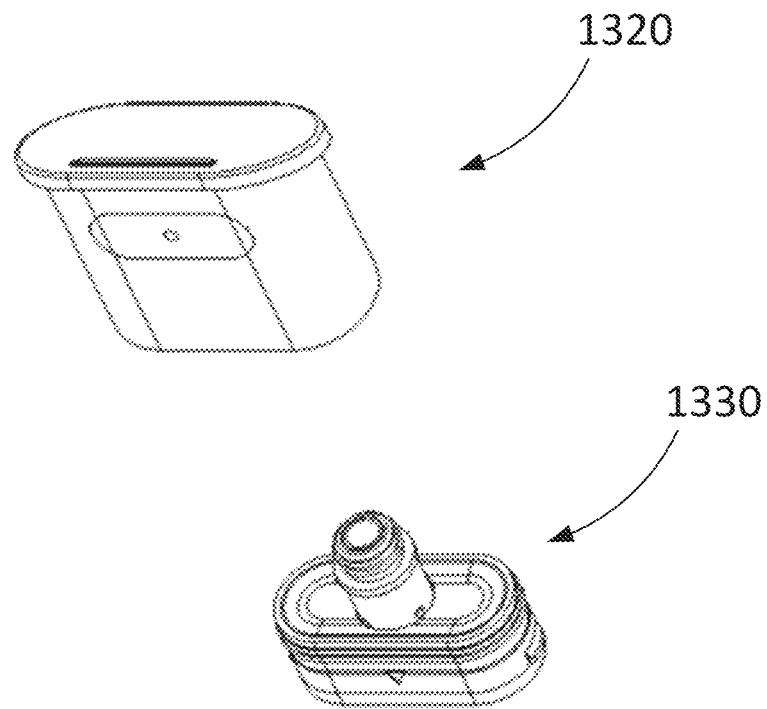

FIGS. 44A and 44B are perspective views of the cartridge assembly 1310 in an assembled and an exploded configuration, respectively. As shown in FIGS. 44A and 44B, the cartridge assembly 1310 includes a mouthpiece assembly 1320 and a lower subassembly 1330. The mouthpiece assembly 1320 includes a mouthpiece component 1322, an outer housing 1324, and an elastomeric plug 1328. The mouthpiece component 1322 defines an elongated mouthpiece opening 1322A. The mouthpiece assembly 1320 is configured to receive the lower subassembly 1330 within an interior of the mouthpiece assembly 1320. The lower subassembly 1330 is configured to seal with an interior surface of the outer housing 1324 such that a reservoir is defined inside the outer housing 1324. Fluid such as a carrier material can be added to the reservoir via the elastomeric plug 1328.

FIGS. 45A-45F are various views of the cartridge assembly 1310. Specifically, FIG. 45A is a left side view, FIG. 45B is a front view, FIG. 45C is a right side view, and FIG. 45D is a back view. FIG. 45E is a bottom view and FIG. 45F is a top view, respectively, of the cartridge assembly 1310.

Figure 46:
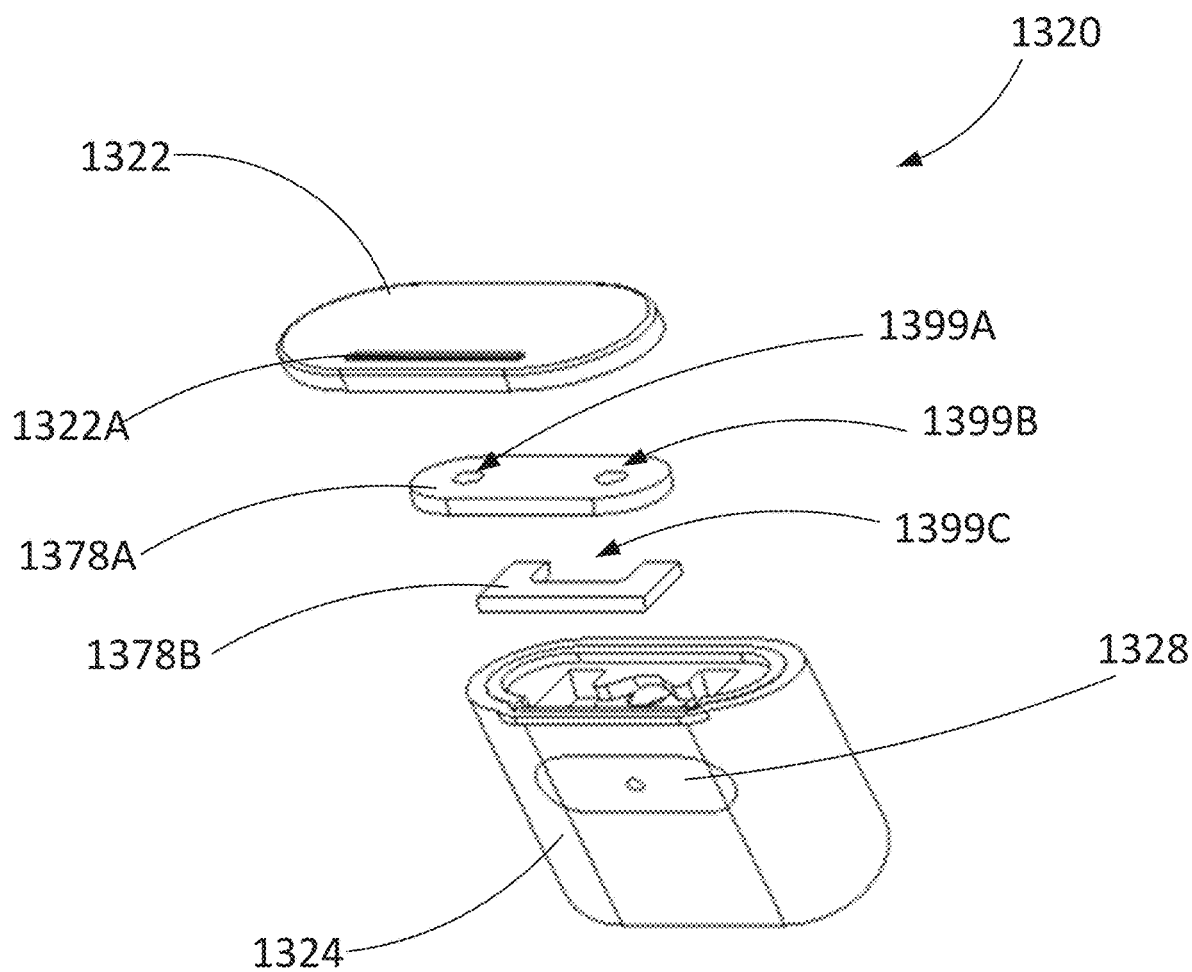

FIG. 46 is a perspective view of the mouthpiece assembly 1320 in an exploded configuration. As shown, the mouthpiece assembly 1320 includes a first filter 1378A and a second filter 1378B. Each of the first filter 1378A and the second filter 1378B can be formed of, for example, cotton. The first filter 1378A and the second filter 1378B are configured to be engaged with the outer housing 1324 (e.g., with upper surfaces of the outer housing 1324) such that the first filter 1378A is spaced from the second filter 1378B and an interior space is defined between the first filter 1378A and the second filter 1378B through which air can flow. As shown in FIG. 46, the first filter 1378A can define a first opening 1399A and a second opening 1399B. The second filter 1378B can define an opening 1399C. The opening 1399C can be, for example, a recess extending from an edge of the second filter 1378B. Although not shown, in some embodiments, the opening 1399C can be fully enclosed by portions of the second filter 1378B. Additionally, although not shown, the first opening 1399A and the second opening 1399B can be formed as recesses extending from an edge of the first filter 1378A. As shown in FIG. 46, a central axis of the opening 1399C can be offset from central axes of each of the first opening 1399A and the second opening 1399B. Fluid can flow through the opening 1399C, through the space between the second filter 1378B and the first filter 1378A, through the first opening 1399A and the second opening 1399B, and through the mouthpiece opening 1322A (e.g., via a recess defined in a bottom surface of the mouthpiece opening 1322A).

Figure 47:
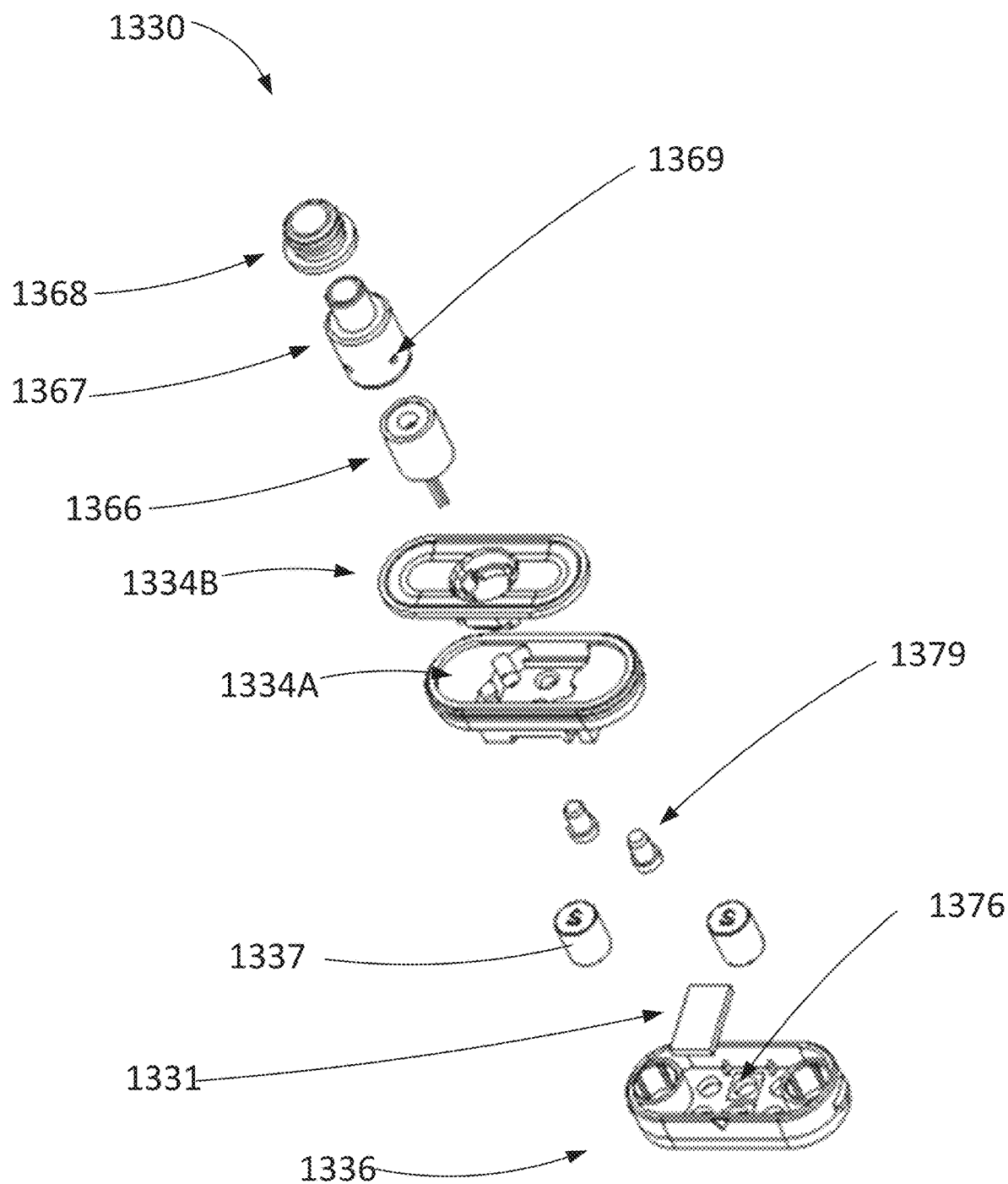

FIG. 47 is a perspective view of the lower subassembly 1330 in an exploded configuration. As shown in FIG. 47, the lower subassembly 1330 (also referred to as an interface assembly) includes a lower portion 1336, an intermediate portion 1334A, and an upper portion 1334B. The lower portion 1336 is configured to receive and engage with an underside of the intermediate portion 1334A, and the intermediate portion 1334A is configured to receive and engage with an underside of the upper portion 1334B. The intermediate portion 1334A may be formed of, for example, silicone. The lower subassembly 1330 includes a tracking component 1331, magnets 1337 (e.g., two magnets), contact pins 1379, a wick assembly 1366, a chimney component 1367, and a silicone cap 1368. The chimney component 1367 may be formed of a metal such as, for example, brass. The wick assembly 1366 can include a wick component and a heating element (e.g., a coil) coupled to and/or disposed within (e.g., partially or fully embedded within) the wick component and configured to heat the cylindrical portion. In some embodiments, the wick component can include a flexible wick portion and a cylindrical portion defining a central passageway. The flexible wick portion can be wrapped around the outer surface of the cylindrical portion such that the flexible wick portion forms an outer surface of the wick assembly 1366. In some embodiments, The wick assembly 1366 may be formed of ceramic, stainless steel (e.g., 303F stainless steel), and cotton. For example, the cylindrical portion can be formed of ceramic, the flexible wick portion can be formed of cotton, and the heating element (e.g., the coil) can be formed of stainless steel. The chimney component 1367 can define a number of openings 1369 (e.g., two, three, or four openings) such that the reservoir defined by the mouthpiece assembly 1320, the housing 1324, and the lower subassembly 1330 is in fluid communication with an outer surface of the wick assembly 1366 via the openings 1369 when the wick assembly 1366 is disposed within an interior of the chimney component 1367. Thus, carrier material can travel from the reservoir, through the openings 1369, through the flexible wick portion, and into the ceramic portion of the wick assembly 1366. When the heating element is heated (e.g., via the contact pins 1379), the temperature of the ceramic portion rises and the carrier material within the ceramic portion can heat and transition to vapor. Air can be drawn through the central passageway of the wick assembly 1366, combine with heated vapor inside the wick assembly 1366, and travel to the mouthpiece opening 1322A via the chimney component 1367.

As shown, the lower portion 1336 can include recesses configured to receive the magnets 1337. Similar to the lower portion 236 described above with respect to the system 200, the lower portion 1336 can define a number of openings 1376 in the bottom surface of the lower portion 1336 (e.g., six openings). The intermediate portion 1334A can define a number of openings 1376 corresponding to the number of openings 1376 in the lower portion 1336 or fewer than the number of openings 1376 in the lower portion 1336. As shown, two of the openings 1376 in the lower portion 1336 can provide access to the tracking component 1331 from the pen assembly 1340. Two of the openings 1376 can provide airflow pathways to corresponding openings of the intermediate portion 1334A and the upper portion 1334B and further to the interior of the wick assembly 1366. Two of the openings 1376 can provide access to the wick assembly 1366 from the pen assembly 1340 via the contact pins 1379 such that the wick assembly 1366 can be controlled be the pen assembly 1340 (e.g., via a heater control circuitry).

Although FIG. 47 shows a particular shaped and arrangement of each of the lower portion 1336, the intermediate portion 1334A, and the upper portion 1334B, in some embodiments, the lower subassembly 1330 can be configured in any suitable way (e.g., to provide a seal for the reservoir defined by the housing 1324 such that the contents of the reservoir do not leak out of the bottom of the cartridge assembly 1310, to provide electrical access from the pen assembly 1340 to the wick assembly 1366, to provide electrical access from the pen assembly 1340 to the tracking component 1331 (e.g., the tracking chip), to provide an airflow path for air to be drawn through the lower subassembly 1330 into the chimney component 1367 via the wick assembly 1366, and/or to mechanically couple the cartridge assembly 1310 to the pen assembly 1340). For example, the lower subassembly 1330 can include any suitable components configured to enclose and seal the components of the cartridge assembly 1310 while providing access to the tracking component 1331 and the wick assembly 1366. These may include o-rings, additional filters, valves, and/or absorption pads. The lower assembly 1330 can include any suitable components in any suitable arrangement to provide a bottom surface of the cartridge assembly 1310 in conjunction with the sidewalls of the housing 1324, maintaining the position of contact elements (contact pins 1379) and the magnets 1337 relative to the housing 1324, control airflow into the mouthpiece assembly 1320 during a draw on the mouthpiece opening 1344A, and prevent leaks from the reservoir of cartridge assembly 1310 during temperature and pressure changes (e.g., while the mouthpiece assembly 1320 is on an airplane or in other high altitude or low altitude conditions).

Figure 48:
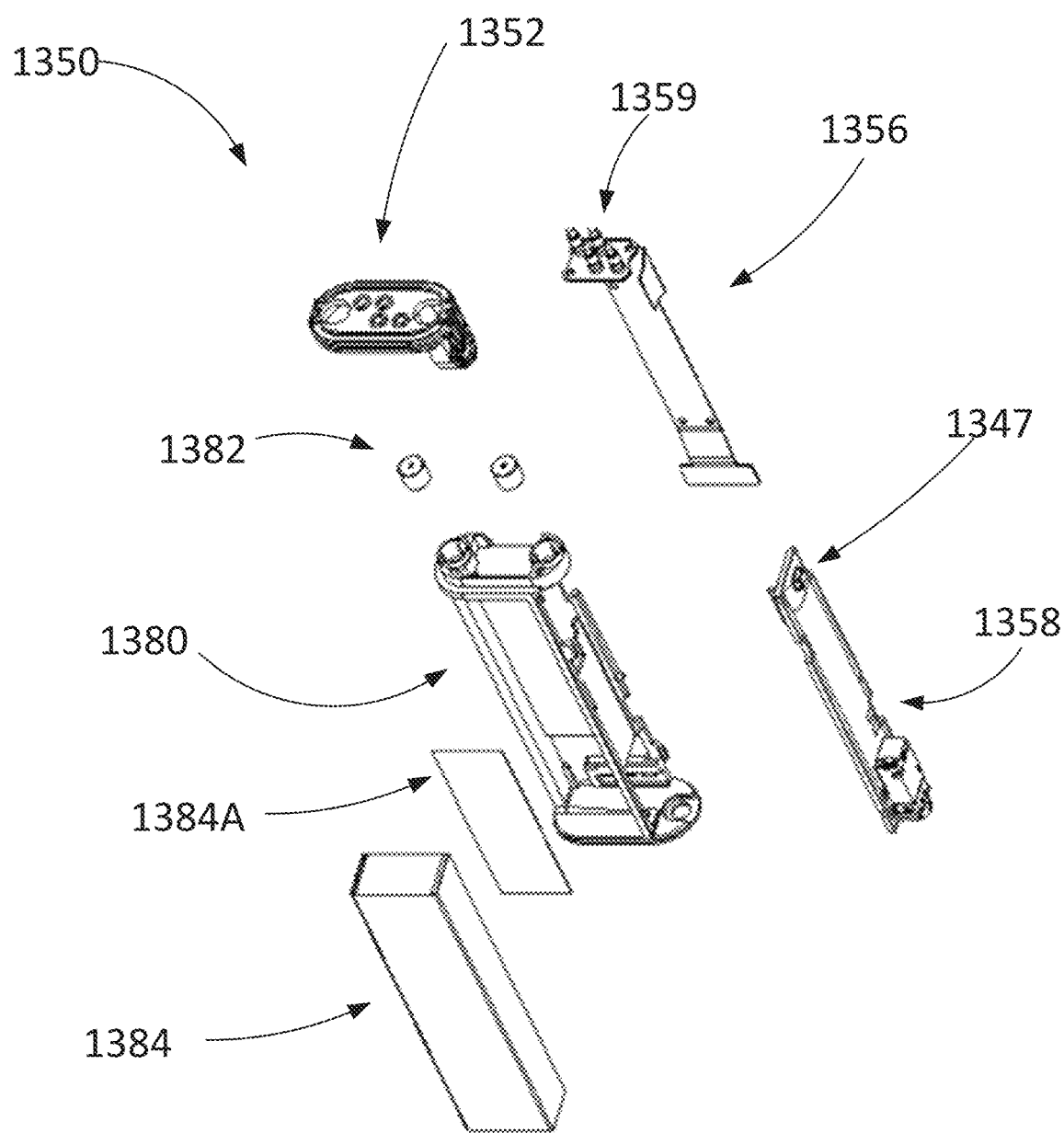

FIG. 48 is a perspective view of the bracket assembly 1350 in an exploded configuration. The bracket assembly 1350 includes a cap 1352, a connection assembly 1356, and a bracket 1380. The bracket assembly 1350 also includes a power supply 1384 and a control assembly 1358. The power supply 1384 can be coupled to the bracket 1380 via tape 1384A. The bracket assembly 1350 also includes a number of magnets 1382 (e.g., two magnets).

The power supply 1384 can include any suitable battery or fuel cell, for example having high-drain characteristics. The control assembly 1358 may include, for example, a printed circuit board such as a flexible printed circuit board. The control assembly 1358 may include a memory and a processor. The memory and the processor can have the same or similar characteristics to any other memory or processor, respectively, described herein. The control assembly 1358 may also include one or more of: a GPS receiver, an antenna, heater control circuitry, and/or a transceiver for wireless (e.g., Bluetooth) communication with a command center or other remote compute device (such as a mobile device of a user). The control assembly 1358 may also include one or more of: a pressure sensor 1347, a temperature sensor, a position sensor, an orientation sensor, etc.

As described above and similarly to the control assembly 258 of the system 200, the control assembly 1358 can include connectors 1359 (e.g., pogo pins) coupled to or included in the control assembly 1358. The connectors 1359 are configured to project through openings in the cap 1352 such that, when the cartridge assembly 1310 is engaged with the pen assembly 1340, two of the connectors 1359 project through openings in the lower portion 1336 and into operative contact with the tracking component 1331 and two of the connectors 1359 project through openings in the lower portion 1336 and into operative contact with the contact pins 1379. Thus, the control assembly 1358 can communicate with the tracking component 1331 and control operation of the wick assembly 1366 via the connectors 1359.

Figure 49A:
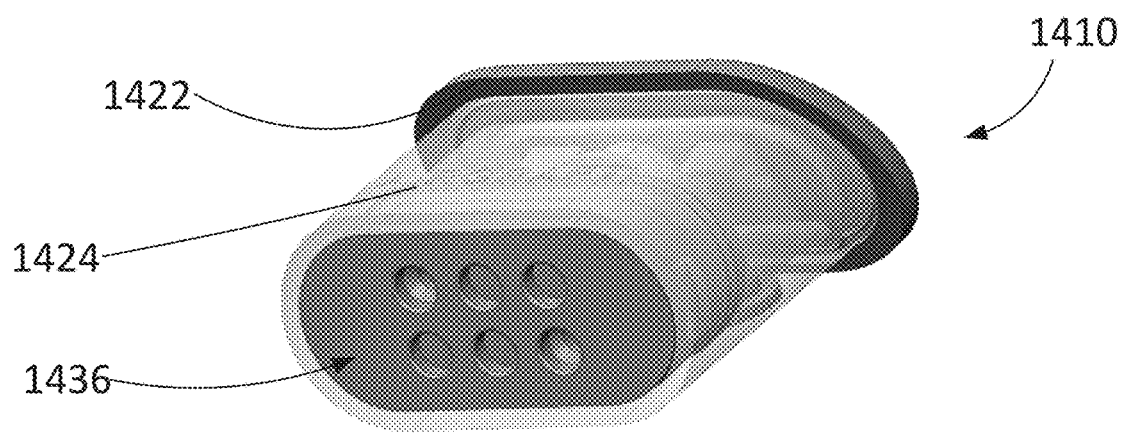
FIGS. 49A-50 are various views of a cartridge assembly, according to an embodiment.
Figure 49B:
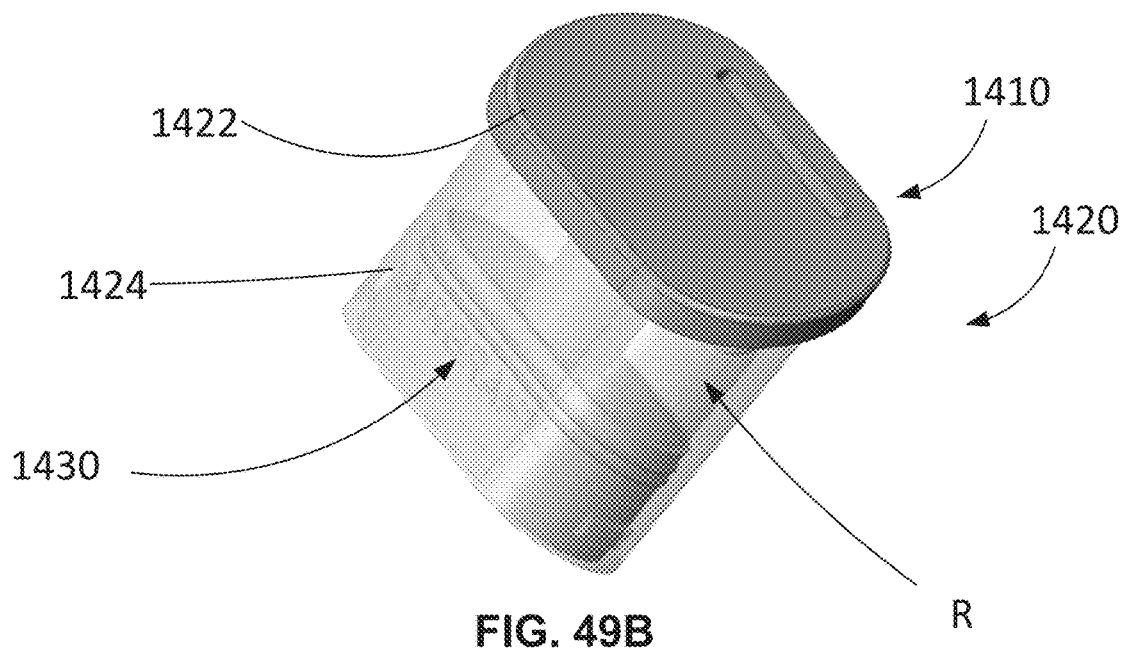
Figure 49C:
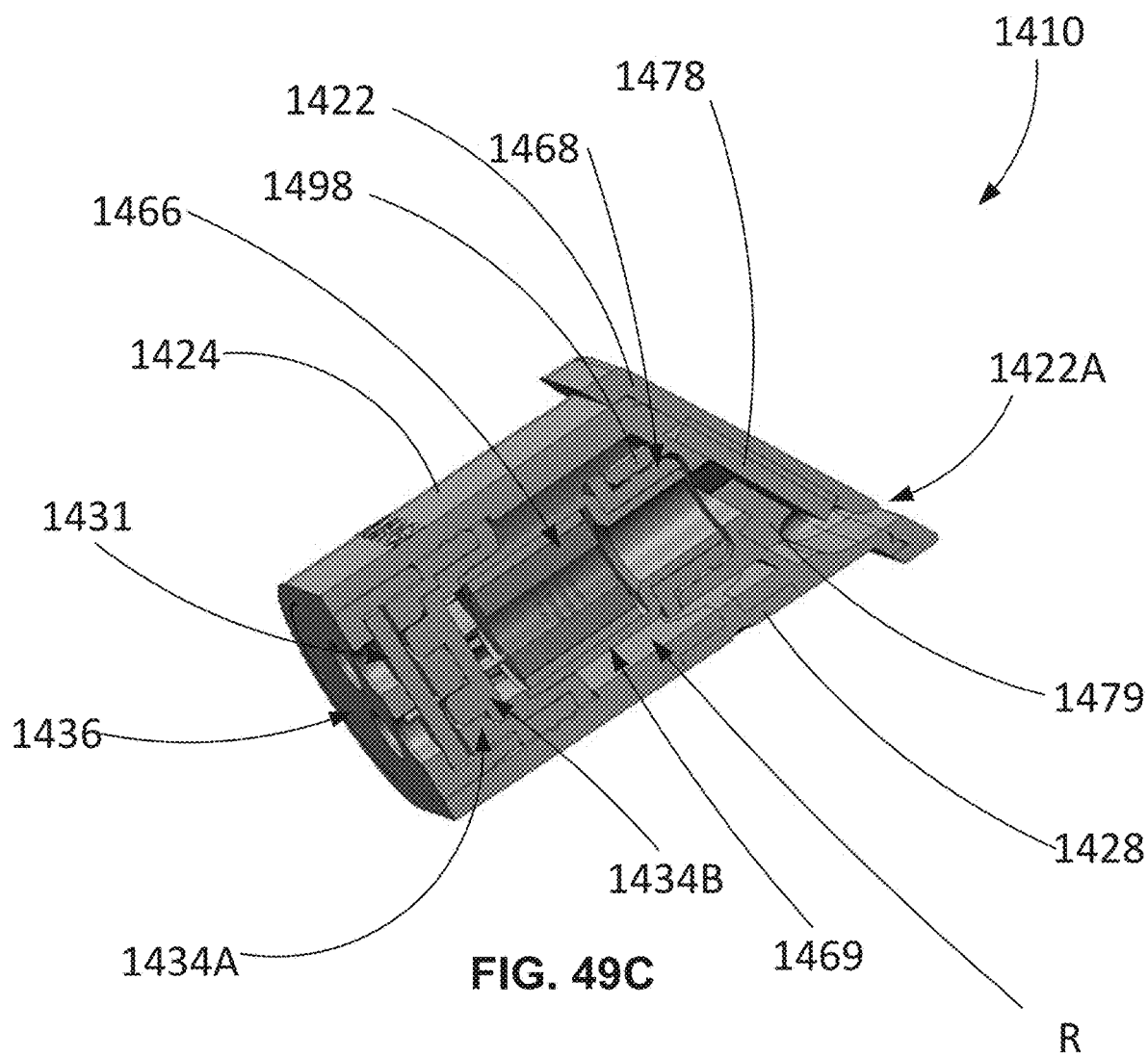

FIGS. 49A-49C are various perspective views of a cartridge assembly 1410, with FIG. 49C being a cross-sectional perspective view. The cartridge assembly 1410 can be the same or similar in structure and/or function to the cartridge assembly 1310 described above with respect to the system 1300. As shown, the cartridge assembly 1410 includes a mouthpiece assembly 1420 and a lower subassembly 1430 (also referred to as an interface assembly). The mouthpiece assembly 1420 includes a mouthpiece component 1422, an outer housing 1424, and an elastomeric plug 1428. The mouthpiece component 1422 defines a mouthpiece opening 1422A. The mouthpiece assembly 1420 is configured to receive the lower subassembly 1430 within an interior of the mouthpiece assembly 1420. The lower subassembly 1430 is configured to seal with an interior surface of the outer housing 1424 such that a reservoir R is defined inside the outer housing 1424. Fluid such as a carrier material can be added to the reservoir via the elastomeric plug 1428. The elastomeric plug 1428 can be a resealable membrane that is configured to reseal after being pierced with a filling needle (e.g., to fill the reservoir R).

As shown in FIG. 49C, the lower subassembly 1430 includes a lower portion 1436, an intermediate portion 1434A, and an upper portion 1434B. The lower portion 1436 is configured to receive and engage with an underside of the intermediate portion 1434A, and the intermediate portion 1434A is configured to receive and engage with an underside of the upper portion 1434B. The intermediate portion 1434A may be formed of, for example, silicone. The lower subassembly 1430 can include a tracking component 1431, magnets 1437 (shown in FIG. 51), and contact pins (not shown). The lower subassembly 1430 can be coupled to a wick assembly 1466, a chimney component 1467, and a silicone cap 1468. The chimney component 1467 may be formed of a metal such as, for example, brass. The silicone cap 1468 can form a seal between an upper portion of the chimney component 1467 and an internal tubular projection 1498 (also referred to as an inner tubular portion) of the housing 1424. The upper portion 1434B can form a seal between the chimney component 1467 and the housing 1424. Thus, as shown in FIG. 49C, the reservoir R can be defined by the housing 1424, the silicone cap 1468, the chimney 1469, and the upper portion 1434B.

The wick assembly 1466 can include a wick component and a heating element (e.g., a coil) coupled to and/or disposed within (e.g., partially or fully embedded within) the wick component and configured to heat the cylindrical portion. In some embodiments, the wick component can include a flexible wick portion and a cylindrical portion defining a central passageway. The flexible wick component can be wrapped around the outer surface of the cylindrical portion such that the flexible wick component forms an outer surface of the wick assembly 1466. In some embodiments, the wick assembly 1466 may be formed of ceramic, stainless steel (e.g., 303F stainless steel), and cotton. For example, the cylindrical portion can be formed of ceramic, the flexible wick portion can be formed of cotton, and the heating element (e.g., the coil) can be formed of stainless steel. The chimney component 1467 can define a number of openings 1469 (e.g., two, three, or four openings) such that the reservoir defined by the mouthpiece assembly 1420, the housing 1324, and the lower subassembly 1430 is in fluid communication with an outer surface of the wick assembly 1466 via the openings 1469 when the wick assembly 1466 is disposed within an interior of the chimney component 1467. Thus, carrier material can travel through from the reservoir, through the openings 1469, through the flexible wick portion, and into the ceramic portion of the wick assembly 1466. When the heating element is heated (e.g., via the contact pins (not shown)), the temperature of the ceramic portion rises and the carrier material within the ceramic portion can heat and transition to vapor. Air can be drawn through the central passageway of the wick assembly 1466, combine with heated vapor inside the wick assembly 1466, and travel to the mouthpiece opening 1422A via the chimney component 1467.

Figure 50:
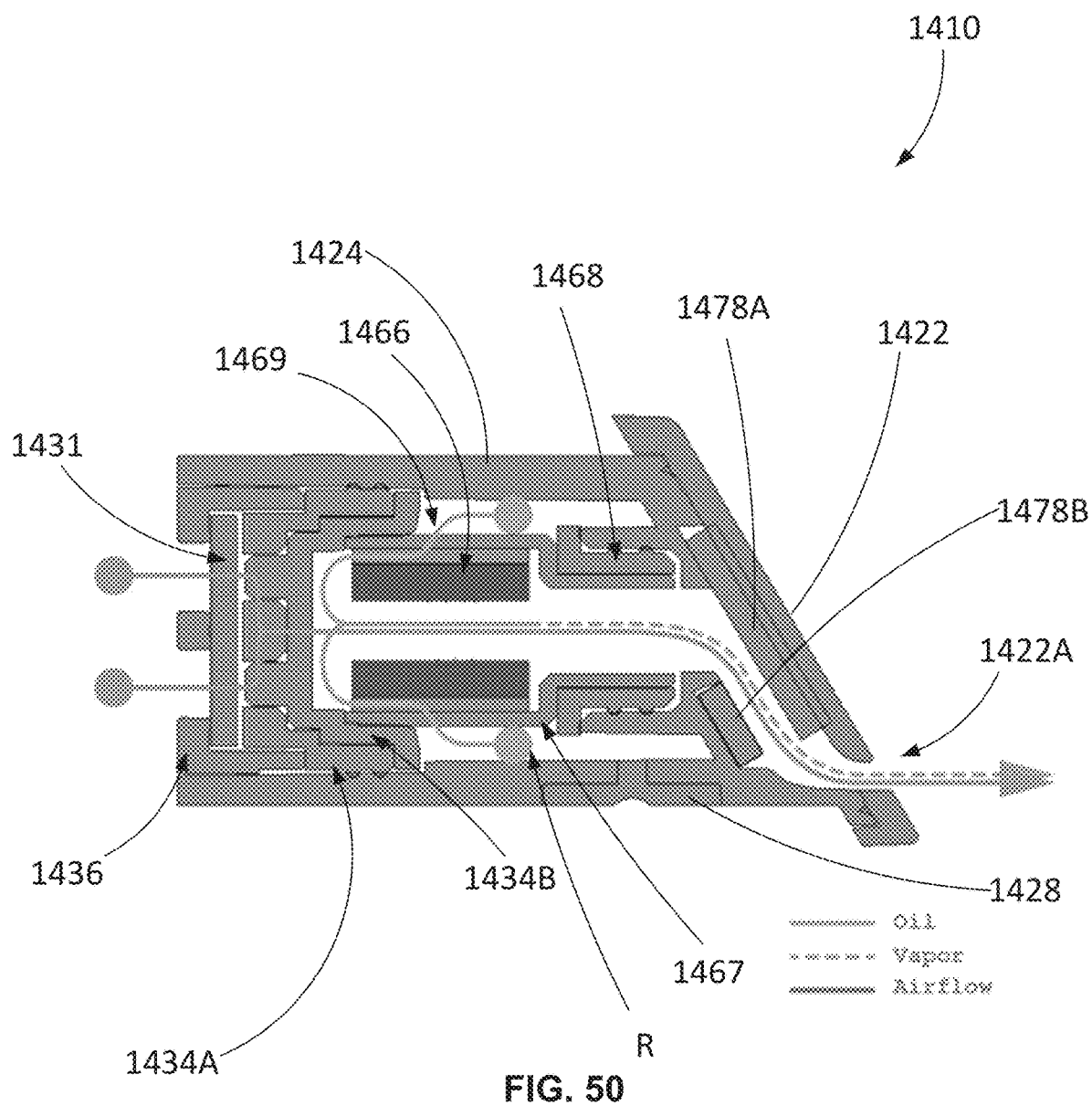

FIG. 50 is a schematic illustration of a cross-section of the cartridge assembly 1410. In use, when the cartridge assembly 1410 is operably engaged with a pen assembly (such as, for example, pen assembly 1340) and heater control circuitry of the pen assembly is activated such that the wick assembly 1466 is operable, fluid (e.g., oil) can flow from the reservoir R, through holes in the coil member 1469, and through the cotton and ceramic portions of the wick assembly 1466. Due to the coil of the wick assembly 1466 being heated by the heater control circuitry, the fluid can be converted into vapor within the central passageway of the wick assembly 1466. As a user draws air through the mouthpiece opening 1422A, air can be drawn through openings in the lower portion 1436, openings in the intermediate portion 1434A, into the central passageway of the wick assembly 1466, and through the mouthpiece opening 1422A. As a result of passing through the interior space defined by the first filter 1478A and the second filter 1478B, any large fluid drops and/or particles that would reduce a user's inhalation experience can be filtered from the vapor and air traveling along the flow path to the user's mouth.

Figure 51:
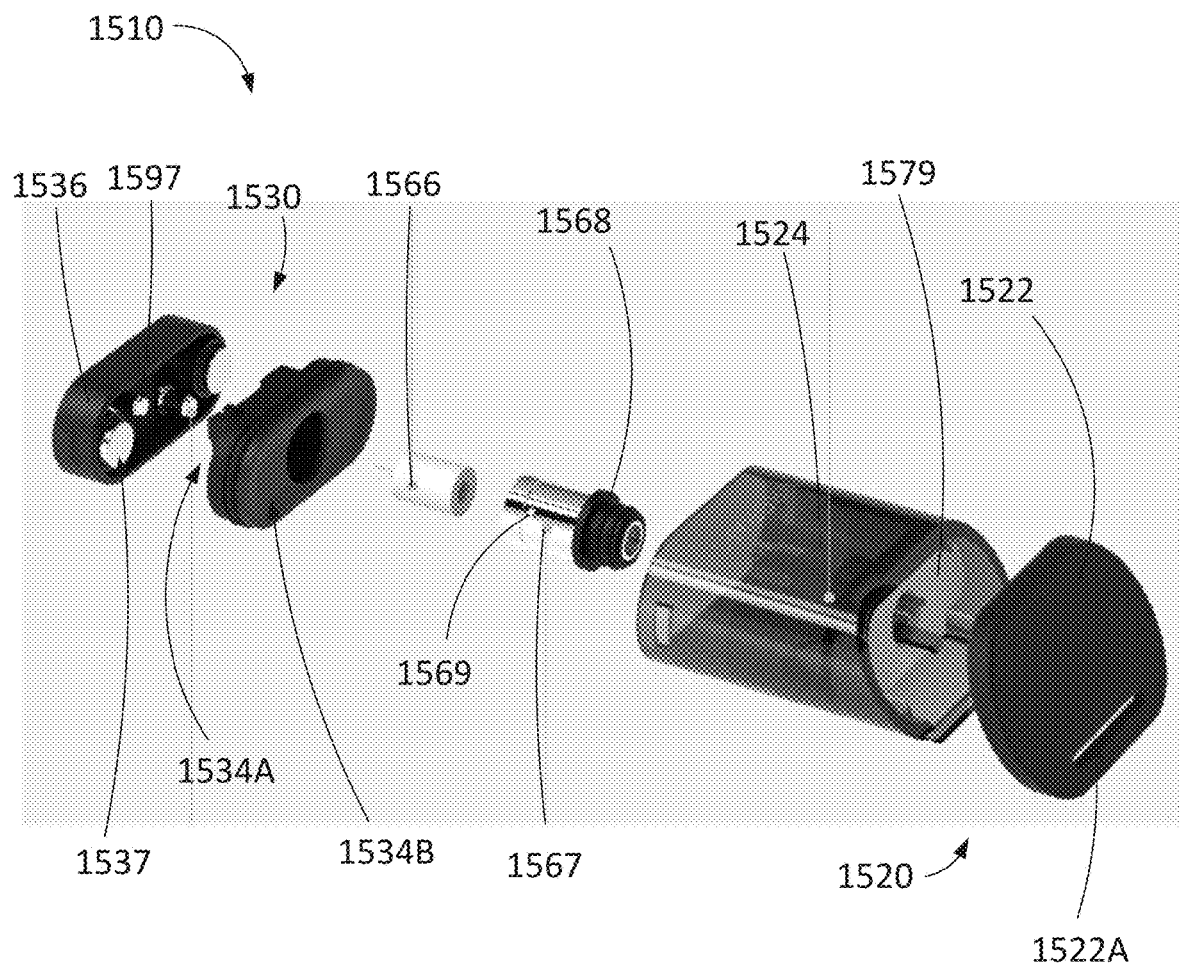
FIGS. 51 and 52 are an exploded view and a cross-sectional view, respectively, of a cartridge assembly, according to an embodiment.

As shown in FIGS. 50 and 51, a first surface of the first filter 1478A can face and be spaced from a second surface of the second filter 1478B, the first surface and the second surface each forming a boundary of a passageway (e.g., an expansion chamber) via which the vapor can travel from the passageway of the chimney component 1467 to the mouthpiece opening 1422A. In some embodiments, the upper surface of the housing 1424 can define a recess configured to receive the second filter 1478B. In some embodiments, the upper surface of the housing can define a recess configured to receive a portion of the first filter 1478A. In some embodiments, the lower surface of the mouthpiece 1422 defines a recess configured to receive at least a portion of the first filter 1478A. In some embodiments, the portion of the passageway defined by the first filter 1478A and the second filter 1478B via which the vapor can travel from the passageway of the chimney component to the mouthpiece opening is wider than the passageway of the chimney component 1467. In some embodiments, the second filter 1478B defines an opening through which the vapor can pass. In some embodiments, the first filter 1478A defines one or more openings through which the vapor can pass.

Figure 52:
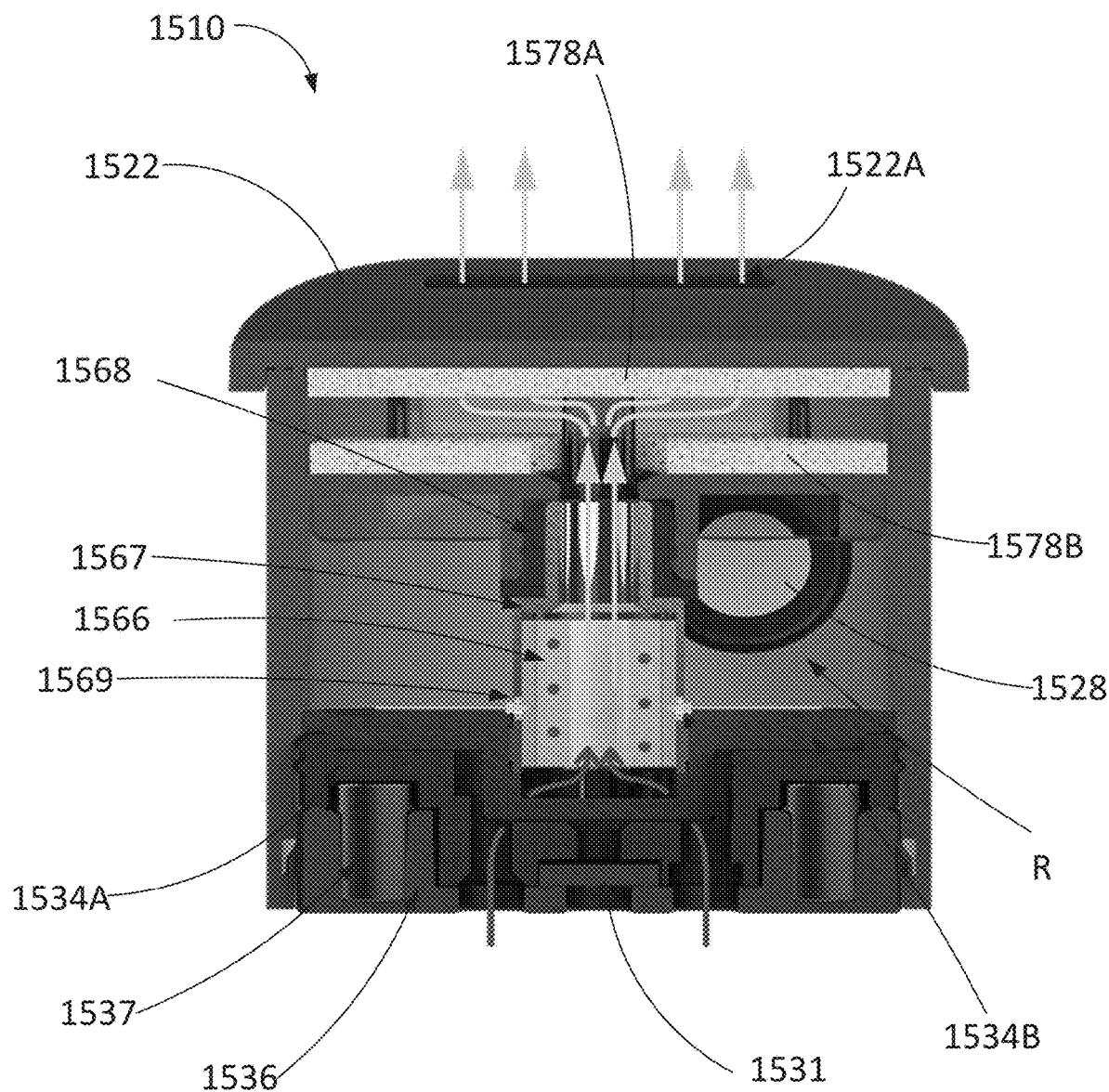

FIGS. 51 and 52 are an exploded view and a cross-sectional illustration, respectively, of a cartridge assembly 1510. The cartridge assembly 1510 can be the same or similar in structure and/or function to any of the cartridge assemblies described herein, such as the cartridge assembly 1410. As shown, the cartridge assembly 1510 includes a mouthpiece assembly 1520 and a lower subassembly 1530 (also referred to as an interface assembly). The mouthpiece assembly 1520 includes a mouthpiece component 1522, an outer housing 1524, and an elastomeric plug 1528. The mouthpiece component 1522 defines a mouthpiece opening 1522A. The mouthpiece assembly 1520 is configured to receive the lower subassembly 1530 within an interior of the mouthpiece assembly 1520. The lower subassembly 1530 is configured to seal with an interior surface of the outer housing 1524 such that a reservoir R is defined inside the outer housing 1524. Fluid such as a carrier material can be added to the reservoir via the elastomeric plug 1528. The elastomeric plug 1528 can be a resealable membrane that is configured to reseal after being pierced with a filling needle (e.g., to fill the reservoir R).

The lower subassembly 1530 includes a lower portion 1536, an intermediate portion 1534A, and an upper portion 1534B. The lower portion 1536 is configured to receive and engage with an underside of the intermediate portion 1534A, and the intermediate portion 1534A is configured to receive and engage with an underside of the upper portion 1534B. The intermediate portion 1534A may be formed of, for example, silicone. The lower subassembly 1530 can include a tracking component 1531, magnets 1537, and contact pins 1597. The lower subassembly 1530 can be coupled to a wick assembly 1566, a chimney component 1567, and a silicone cap 1568. The chimney component 1567 may be formed of a metal such as, for example, brass. The silicone cap 1568 can form a seal between an upper portion of the chimney component 1567 and an internal tubular projection 1598 of the housing 1524. The upper portion 1534B can form a seal between the chimney component 1567 and the housing 1524. Thus, as shown in FIG. 52, the reservoir R can be defined by the housing 1524, the silicone cap 1568, the chimney 1569, and the upper portion 1534B.

The wick assembly 1566 can include a wick component and a heating element (e.g., a coil) coupled to and/or disposed within (e.g., partially or fully embedded within) the wick component and configured to heat the cylindrical portion. In some embodiments, the wick component can include a flexible wick portion and a cylindrical portion defining a central passageway. The flexible wick component can be wrapped around the outer surface of the cylindrical portion such that the flexible wick component forms an outer surface of the wick assembly 1566. In some embodiments, the wick assembly 1566 may be formed of ceramic, stainless steel (e.g., 303F stainless steel), and cotton. For example, the cylindrical portion can be formed of ceramic, the flexible wick portion can be formed of cotton, and the heating element (e.g., the coil) can be formed of stainless steel. The chimney component 1567 can define a number of openings 1569 (e.g., two, three, or four openings) such that the reservoir defined by the mouthpiece assembly 1520, the housing 1524, and the lower subassembly 1530 is in fluid communication with an outer surface of the wick assembly 1566 via the openings 1569 when the wick assembly 1566 is disposed within an interior of the chimney component 1567. Thus, carrier material can travel through from the reservoir, through the openings 1569, through the flexible wick portion, and into the ceramic portion of the wick assembly 1566. When the heating element is heated (e.g., via the contact pins (not shown)), the temperature of the ceramic portion rises and the carrier material within the ceramic portion can heat and transition to vapor. Air can be drawn through the central passageway of the wick assembly 1566, combine with heated vapor inside the wick assembly 1566, and travel to the mouthpiece opening 1522A via the chimney component 1567.

In use, when the cartridge assembly 1510 is operably engaged with a pen assembly (such as, for example, pen assembly 1340) and heater control circuitry of the pen assembly is activated such that the wick assembly 1566 is operable, fluid (e.g., oil) can flow from the reservoir R, through holes in the coil member 1569, and through the cotton and ceramic portions of the wick assembly 1566. Due to the coil of the wick assembly 1566 being heated by the heater control circuitry, the fluid can be converted into vapor within the central passageway of the wick assembly 1566. As a user draws air through the mouthpiece opening 1522A, air can be drawn through openings in the lower portion 1536, openings in the intermediate portion 1534A, into the central passageway of the wick assembly 1566, and through the mouthpiece opening 1522A. As a result of passing through the interior space defined by the first filter 1578A and the second filter 1578B, any large fluid drops and/or particles that would reduce a user's inhalation experience can be filtered from the vapor and air traveling along the flow path to the user's mouth.

In some embodiments, a processor, such as any of the processors of any of the systems described herein, can determine if an insufficient amount of carrier material is disposed near the heating element (e.g., on the wick). Such a circumstance can be caused, for example, by a low level of carrier substance (e.g., oil) in the reservoir, causing the wick to dry. Use of a cartridge or vaporizer having a dry or insufficiently wet wick can cause poor tasting and/or unhealthy particles to be inhaled by the user. Thus, the processor can be configured to determine when a wick coupled to the heating element is insufficiently wet for operation and alert the user and/or disable operation of the pen portion (e.g., discontinue applying current to the heating element).

Figures 53A, 53B:
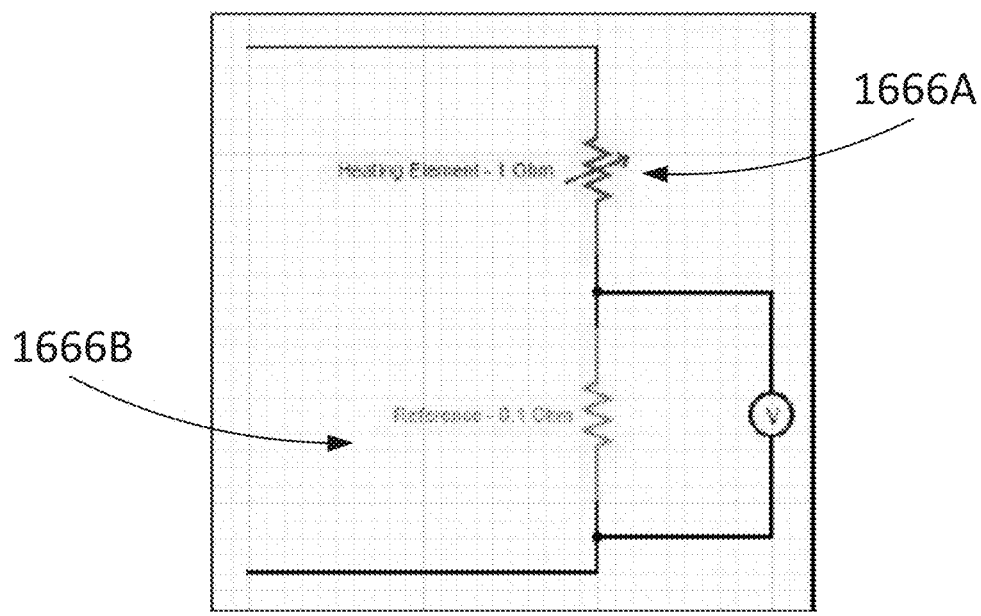
FIG. 53A is a schematic illustration of a heating element in series with a reference resistor used to determine a dry wick condition, according to an embodiment.
FIG. 53B is a table representing the relationship between a number of reference voltages and a temperature of the heating element of FIG. 53A, according to an embodiment.

A heating element, such as any of the heating elements described herein (e.g., a coil-shaped heating element), can function as or include a resistor. Being formed of a metal, the resistance value of the heating element is temperature dependent. The continued use of the cartridge or vaporizer including the heating element will cause the temperature of the heating element to increase. A reference resistor can be coupled to the heating element in series with the heating element. For example, the reference resistor can be disposed in the pen portion and coupled to the heating element via a pogo pin of the pen portion. The processor can be configured to measure a voltage drop on the reference resistor. For example, as shown in FIG. 53A, a heating element 1666A can be disposed in series with a reference resistor 1666B.

In some embodiments, the resistance of the heating element 1666A ($R_{HE}$) is about 1 Ohm at room temperature. Furthermore, $R_{HE}$ follows the law $R(T)=R_0 [1+\alpha(T-T_0)]$, where $R_0$ is the heating element resistance value at room temperature, T is the temperature of the heating element (e.g., a stainless steel coil), $T_0$ is room temperature, and $\alpha$ is a known temperature coefficient. The resistance of the reference resistor ($R_{REF}$) can be constant with a value of about 0.1 Ohm. The total (TOT) voltage drop across the series of the heating element and the reference resistor is equal to the battery voltage, so $V_{TOT}=V_{HE}+V_{REF}$. Additionally, $V_{HE}=V_{TOT}*[R_{HE}(R_{HE} R_{REF})]$, $V_{TOT}$ being known and $V_{REF}$ being measured during operation periodically (e.g., every 125 ms). Therefore, $V_{HE}=V_{TOT}-V_{REF}$. Thus, a table, such as the table shown in FIG. 53B, can be generated (knowing the value of a) displaying the relationship between the temperature of the heating element 1666A and the voltage read on the reference resistor 1666B at a variety of temperatures.

When the wick is sufficiently wet, the carrier material disposed within the wick acts as a heat sink to absorb the heat generated by the heating element. Thus, a heating element coupled to a sufficiently wet wick would reach a lower maximum temperature than a heating element coupled to an insufficiently wet (e.g., a dry) wick. For example, the heating element may reach a maximum temperature of 600° C. when the wick is sufficiently wet, but may reach 700° C. when the wick is insufficiently wet. In some embodiments, the processor can be configured to initiate an alarm and/or cease operation of the pen assembly and/or the cartridge assembly (e.g., discontinue applying current to the heating element 1666A) if the processor identifies the voltage drop on the reference resistor to be below a threshold voltage drop (which would correspond to an increased temperature of the heating element 1666A). For example, the processor can initiate the lighting of an indicator on the pen assembly (e.g., an LED) and/or transmit a message to a wireless device associated with the pen assembly to display an alert on a display of the wireless device such that a user is made aware of a dry wick condition. In some embodiments, the processor can be configured to initiate an alarm and/or cease operation of the pen assembly and/or the cartridge assembly (e.g., discontinue applying current to the heating element 1666A) if the processor determines that the temperature of the heating element is above a threshold temperature based on the measured change in voltage across the reference resistor.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Some embodiments and/or methods described herein can be performed by software (executed on hardware), hardware, or a combination thereof. Hardware modules may include, for example, a general-purpose processor, a field programmable gate array (FPGA), and/or an application specific integrated circuit (ASIC). Software modules (executed on hardware) can be expressed in a variety of software languages (e.g., computer code), including C, C++, Java™, Ruby, Visual Basic™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

Various concepts may be embodied as one or more methods, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments. Put differently, it is to be understood that such features may not necessarily be limited to a particular order of execution, but rather, any number of threads, processes, services, servers, and/or the like that may execute serially, asynchronously, concurrently, in parallel, simultaneously, synchronously, and/or the like in a manner consistent with the disclosure. As such, some of these features may be mutually contradictory, in that they cannot be simultaneously present in a single embodiment. Similarly, some features are applicable to one aspect of the innovations, and inapplicable to others.

In addition, the disclosure may include other innovations not presently described. Applicant reserves all rights in such innovations, including the right to embodiment such innovations, file additional applications, continuations, continuations-in-part, divisionals, and/or the like thereof. As such, it should be understood that advantages, embodiments, examples, functional, features, logical, operational, organizational, structural, topological, and/or other aspects of the disclosure are not to be considered limitations on the disclosure as defined by the embodiments or limitations on equivalents to the embodiments. Depending on the particular desires and/or characteristics of an individual and/or enterprise user, database configuration and/or relational model, data type, data transmission and/or network framework, syntax structure, and/or the like, various embodiments of the technology disclosed herein may be implemented in a manner that enables a great deal of flexibility and customization as described herein.

All definitions, as defined and used herein, should be understood to control over dictionary definitions, definitions in documents incorporated by reference, and/or ordinary meanings of the defined terms.

As used herein, in particular embodiments, the terms "about" or "approximately" when preceding a numerical value indicates the value plus or minus a range of 10%. Where a range of values is provided, it is understood that each intervening value, to the tenth of the unit of the lower limit unless the context clearly dictates otherwise, between the upper and lower limit of that range and any other stated or intervening value in that stated range is encompassed within the disclosure. That the upper and lower limits of these smaller ranges can independently be included in the smaller ranges is also encompassed within the disclosure, subject to any specifically excluded limit in the stated range. Where the stated range includes one or both of the limits, ranges excluding either or both of those included limits are also included in the disclosure.

The indefinite articles "a" and "an," as used herein in the specification and in the embodiments, unless clearly indicated to the contrary, should be understood to mean "at least one."

The phrase "and/or," as used herein in the specification and in the embodiments, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the embodiments, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" or, when used in the embodiments, "consisting of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of," or "exactly one of" "Consisting essentially of," when used in the embodiments, shall have its ordinary meaning as used in the field of patent law.

As used herein in the specification and in the embodiments, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the embodiments, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

While specific embodiments of the present disclosure have been outlined above, many alternatives, modifications, and variations will be apparent to those skilled in the art. Accordingly, the embodiments set forth herein are intended to be illustrative, not limiting. Various changes may be made without departing from the spirit and scope of the disclosure. Where methods and steps described above indicate certain events occurring in a certain order, those of ordinary skill in the art having the benefit of this disclosure would recognize that the ordering of certain steps may be modified and such modification are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

The invention claimed is:

1. An apparatus, comprising:
    a housing including a sidewall and an upper surface, the housing defining a reservoir and an opening in the sidewall of the housing;
    a resealable membrane disposed within the opening, the resealable membrane configured to be pierced by a needle such that the reservoir can receive fluid via the needle and to seal the opening upon removal of the needle from the resealable membrane;
    a wick assembly including a wick component and a heating element, the wick component configured to transport fluid from the reservoir toward the heating element such that the fluid can be transitioned into vapor by the heating element;
    a mouthpiece defining a mouthpiece opening such that the vapor can be drawn from the wick assembly through the mouthpiece opening, the mouthpiece having an upper surface and a lower surface,
    a first filter portion disposed on the lower surface of the mouthpiece and spaced from the upper surface of the housing; and
    a second filter portion disposed on the upper surface of the housing and spaced from the lower surface of the mouthpiece, the first filter portion and the second filter portion defining a space through which vapor can travel between the wick assembly and the mouthpiece opening.

2. The apparatus of claim 1, further comprising:
    an interface assembly configured to be coupled to a vaporizer pen such that a processor of the vaporizer pen can apply a current to the heating element.

3. The apparatus of claim 2, further comprising:
    a first engagement mechanism configured to releasably couple to a corresponding second engagement mechanism of the vaporizer pen such that the interface assembly can be coupled to an electrical interface of the vaporizer pen when the first engagement mechanism is releasably coupled to the corresponding second engagement mechanism.

4. The apparatus of claim 2, wherein each of the first engagement mechanism and the second engagement mechanism include at least one magnet.

5. The apparatus of claim 1, wherein the resealable membrane includes an elastomeric material.

6. The apparatus of claim 1, further comprising:
    a chimney component defining a passageway via which the vapor can flow from the wick assembly to the mouthpiece opening.

7. The apparatus of claim 1, further comprising:
    a processor and a battery, the processor configured to apply a current to the heating element, the mouthpiece and the housing being integrally formed.

8. The apparatus of claim 1, wherein the wick component includes a ceramic cylinder defining a central passageway.

9. The apparatus of claim 8, wherein the heating element is at least partially embedded within the wick component.

10. The apparatus of claim 1, further comprising:
    a chimney component defining a passageway via which the vapor can travel from the wick assembly to the space between the first filter portion and the second filter portion, the passageway having a central axis that is offset from a central axis of the mouthpiece opening.

11. The apparatus of claim 10, wherein the housing includes an inner tubular portion coupled to the chimney component via a sealing cap.

12. The apparatus of claim 10, wherein a first surface of the first filter portion faces and is spaced from a second surface of the second filter portion, the first surface and the second surface each forming a boundary of a passageway via which the vapor can travel from the passageway of the chimney component to the mouthpiece opening.

13. The apparatus of claim 10, wherein the upper surface of the housing defines a recess configured to receive the second filter portion.

14. The apparatus of claim 10, wherein the upper surface of the housing defines a recess configured to receive a portion of the first filter portion.

15. The apparatus of claim 10, wherein the lower surface of the mouthpiece defines a recess configured to receive at least a portion of the first filter portion.

16. The apparatus of claim 10, wherein the portion of the passageway defined by the first filter portion and the second filter portion via which the vapor can travel from the passageway of the chimney component to the mouthpiece opening is wider than the passageway of the chimney component.

17. The apparatus of claim 10, wherein the second filter portion defines an opening through which the vapor can pass.

18. The apparatus of claim 10, wherein the first filter portion defines an opening through which the vapor can pass.

19. The apparatus of claim 1, wherein the mouthpiece has an upper surface and a lower surface, and further comprising:
- a chimney component defining a passageway via which the vapor can travel from the wick assembly to the mouthpiece opening, the passageway having a central axis that is not coaxial with a central axis of the mouthpiece opening, and
- the housing defining a portion of a passageway between the chimney component and the mouthpiece opening, the portion of the passageway being wider than the chimney passageway such that the vapor can expand as the vapor flows into the portion of the passageway.

20. The apparatus of claim 19, wherein the portion of the passageway defined by the housing increases in width from a portion closer to the chimney component toward the mouthpiece opening.

21. The apparatus of claim 19, wherein the central axis of the passageway of the chimney component is disposed parallel to the central axis of the mouthpiece opening.

22. The apparatus of claim 19, wherein the housing has an upper surface facing and spaced from the lower surface of the mouthpiece, the upper surface of the housing and the lower surface of the mouthpiece defining an expansion chamber, the expansion chamber including the portion of the passageway between the chimney component and the mouthpiece opening.

23. The apparatus of claim 1, further comprising:
- a tracking component disposed within the housing.

24. The apparatus of claim 23, further comprising:
- a lower subassembly, an upper portion of the lower subassembly forming a seal between the housing and the chimney component, the tracking component disposed between the lower portion and the upper portion of the lower subassembly and accessible by an electrical connection of a vaporizer pen via an opening in a lower portion of the lower subassembly.

25. The apparatus of claim 23, wherein the tracking component stores information associated with a fluid disposed in the reservoir.

26. The apparatus of claim 25, wherein the information includes characteristics of the fluid disposed in the reservoir.

27. An apparatus, comprising:
- a housing defining a reservoir and an opening in a sidewall of the housing;
- a resealable membrane disposed within the opening, the resealable membrane configured to be pierced by a needle such that the reservoir can receive fluid via the needle and to seal the opening upon removal of the needle from the resealable membrane;
- a wick assembly including a wick component and a heating element, the wick component configured to transport fluid from the reservoir toward the heating element such that the fluid can be transitioned into vapor by the heating element; and
- a mouthpiece defining a mouthpiece opening such that the vapor can be drawn from the wick assembly through the mouthpiece opening, wherein a portion a passageway between the wick assembly and the mouthpiece opening is partially defined by the sidewall of the housing and is U-shaped.

28. The apparatus of claim 27, wherein the central axis of the passageway of the chimney component is disposed perpendicular to the central axis of the mouthpiece opening.

* * * * *